US011918647B2

(12) United States Patent
Hasler et al.

(10) Patent No.: US 11,918,647 B2
(45) Date of Patent: Mar. 5, 2024

(54) TFR SELECTIVE BINDING COMPOUNDS AND RELATED METHODS

(71) Applicant: Ossianix, Inc., Philadelphia, PA (US)

(72) Inventors: Julien Hasler, Hoogstraten (BE); Julia Lynn Rutkowski, Bryn Mawr, PA (US); Krzysztof Bartlomiej Wicher, Cambridge (GB)

(73) Assignee: OSSIANIX, INC., Philadelphia, PA (US)

( * ) Notice: Subject to any disclaimer, the term of this patent is extended or adjusted under 35 U.S.C. 154(b) by 783 days.

(21) Appl. No.: 16/946,524

(22) Filed: Jun. 25, 2020

(65) Prior Publication Data

US 2020/0316195 A1    Oct. 8, 2020

Related U.S. Application Data

(60) Division of application No. 15/594,632, filed on May 14, 2017, now Pat. No. 10,722,576, which is a continuation of application No. PCT/US2015/060948, filed on Nov. 14, 2015.

(60) Provisional application No. 62/141,773, filed on Apr. 1, 2015, provisional application No. 62/080,112, filed on Nov. 14, 2014.

(51) Int. Cl.
  *C07K 14/705*  (2006.01)
  *A61K 39/395*  (2006.01)
  *C07K 16/40*  (2006.01)
  *C07K 16/28*  (2006.01)
  *C07K 16/46*  (2006.01)
  *C12N 15/85*  (2006.01)
  *A61K 39/00*  (2006.01)
  *G01N 33/53*  (2006.01)

(52) U.S. Cl.
  CPC ........ *A61K 39/395* (2013.01); *C07K 16/2881* (2013.01); *C07K 16/40* (2013.01); *C07K 16/464* (2013.01); *C12N 15/85* (2013.01); *A61K 2039/505* (2013.01); *C07K 2317/20* (2013.01); *C07K 2317/24* (2013.01); *C07K 2317/31* (2013.01); *C07K 2317/32* (2013.01); *C07K 2317/33* (2013.01); *C07K 2317/34* (2013.01); *C07K 2317/35* (2013.01); *C07K 2317/52* (2013.01); *C07K 2317/569* (2013.01); *C07K 2317/622* (2013.01); *C07K 2317/64* (2013.01); *C07K 2317/76* (2013.01); *C07K 2317/77* (2013.01); *C07K 2317/92* (2013.01); *C07K 2318/10* (2013.01); *G01N 33/53* (2013.01)

(58) Field of Classification Search
None
See application file for complete search history.

(56) References Cited

U.S. PATENT DOCUMENTS

| | | |
|---|---|---|
| 2016/0333103 A1 | 11/2016 | Häsler |
| 2017/0198281 A1 | 7/2017 | Häsler |
| 2017/0348416 A1 | 12/2017 | Häsler |
| 2019/0175746 A1 | 6/2019 | Stocki |
| 2020/0024354 A1 | 1/2020 | Häsler |
| 2020/0115702 A1 | 4/2020 | Häsler |

FOREIGN PATENT DOCUMENTS

| | | |
|---|---|---|
| WO | WO2002/057445 A1 | 7/2002 |
| WO | WO2003/014161 A2 | 2/2003 |
| WO | WO2005/118629 A1 | 12/2005 |
| WO | WO2007/036021 A1 | 4/2007 |
| WO | WO2007/140371 A2 | 12/2007 |
| WO | WO2010/033913 A1 | 3/2010 |
| WO | WO2012/075037 A1 | 6/2012 |
| WO | WO2013/177062 A2 | 11/2013 |
| WO | WO2014/173959 A2 | 10/2014 |
| WO | WO2014/189973 A2 | 11/2014 |
| WO | WO2015/100246 A1 | 7/2015 |
| WO | WO2015/200883 A2 | 12/2015 |

(Continued)

OTHER PUBLICATIONS

Abbott et al. (2010) "Structure and function of the blood-brain barrier," Neurobiol. Dis. 37:13-25.

(Continued)

*Primary Examiner* — Michael D Pak
(74) *Attorney, Agent, or Firm* — KDW Firm PLLC

(57) ABSTRACT

The present invention relates to peptides that bind with high specificity and which functionally interact with the transferrin receptor ("TfR") and which may be used in making molecular vehicles that carry biomolecules across membranes, including, e.g., across the blood brain barrier or the gastrointestinal tract. TfR specific binding moieties may also be used alone or as components in specific molecules that target the transferrin/transferrin receptor transport system. The invention relates more specifically to VNAR single chain antibodies derived from nurse shark that bind to TfR, compounds and compositions comprising a TfR specific VNAR binding moiety, methods for preparing them, diagnostic and therapeutic methods of use in vitro or in vivo, e.g., to diagnose, treat and/or prevent a pathological condition, disorder or disease in which it is beneficial to deliver a heterologous biomolecule across the blood brain barrier by association with a TfR specific VNAR binding moiety. Other uses for TfR specific VNAR binding moieties of the invention include, e.g., regulating the interaction of iron-charged transferrin with TfR (receptor cycling or cell surface presentation), such as may be therapeutic in treatment of certain cancer cells and tumors of various tissue types.

13 Claims, 20 Drawing Sheets

Specification includes a Sequence Listing.

(56) References Cited

FOREIGN PATENT DOCUMENTS

| WO | WO2016/094566 A2 | 6/2016 |
|---|---|---|
| WO | WO2016/097315 A2 | 6/2016 |

OTHER PUBLICATIONS

Ahmad et al. (2012) "scFv Antibody: Principles and Clinical Application," Clin. Dev. Immunol. 2012: 980250, 15 pages.
Alata et al. (2014) "Brain uptake of a fluorescent vector targeting the transferrin receptor: a novel application of in situ brain perfusion," Mol. Pharm 11: 243-253.
Arap et al. (1998) "Cancer Treatment by Targeted Drug Delivery to Tumor Vasculature in a Mouse Model," Science 279:377-380.
Bien-Ly et al. (2014) " Transferrin receptor (TfR) trafficking determines brain uptake of TfR antibody affinity variants," J. Exp. Med. 211:233-44.
Boado et al.(2009) "Engineering and Expression of a Chimeric Transferrin Receptor Monoclonal Antibody for Blood- Brain Barrier Delivery in the Mouse," Biotechnol. Bioeng. 102:1251-8.
Calzolari et al. (2007) "Transferrin receptor 2 is frequently expressed in human cancer cell lines," Blood Cells Mol. Dis. 39:82-91.
Couch et al. (2013) "Addressing Safety Liabilities of TfR Bispecific Antibodies That Cross the Blood-Brain Barrier," Sci. Transl. Med. 5:183ra57, 12 pages.
Crepin et al. (2010) "Development of Human Single-Chain Antibodies to the Transferrin Receptor that Effectively Antagonize the Growth of Leukemias and Lymphomas," Cancer Res. 70:5497-506.
Diaz et al. (2002) "Structural analysis, selection, and ontogeny of the shark new antigen receptor (IgNAR): dentification of a new locus preferentially expressed in early development," Immunogenetics 54:501-512.
Dooley et al. (2003) "Selection and characterization of naturally occurring single-domain (IgNAR) antibody fragments from immunized sharks by phage display," Mol. Immunol. 40:25-33.
Fennell et al. (2010) "Dissection of the IgNAR V Domain: Molecular Scanning and Orthologue Database Mining Define Novel IgNAR Hallmarks and Affinity Maturation Mechanisms," J. Mol. Biol. 400:155-170.
Forejtnikova et al. (2010) "Transferrin receptor 2 is a component of the erythropoietin receptor complex and is required for efficient erythropoiesis," Blood 116:5357-67.
Friden et al. (1991) "Anti-transferrin receptor antibody and antibody-drug conjugates cross the blood-brain barrier," Proc. Natl. Acad. Sci. USA 88:4771-5.
Griffiths et al. (1994) "Isolation of high affinity human antibodies directly from large synthetic repertoires," EMBO J. 13:3245-3260.
Häsler et al. (2015) "Species cross-reactive single domain antibodies (VNARs) to the transferrin receptor 1 (TfR-1) that cross the BBB", Poster presentation at Cold Spring Harbor Laboratory Blood Brain Barrier meeting, Dec. 10-13, 2014.
Jefferies et al. et al. (1985) "Analysis of lymphopoietic stem cells with a monoclonal antibody to the rat transferrin receptor," Immunology 54:333-341.
Jones et al. (2007) "Blood-Brain Barrier Transport of Therapeutics via Receptor-Mediation," Pharm. Res. 24:1759-71.
Jones et al. (2014) "Identifying Blood-Brain Barrier Selective Single-Chain Antibody Fragments," Biotechnopl. J. 9:664-674.
Kovaleva et al. (2014) "Shark variable new antigen receptor biologics - a novel technology platform for therapeutic drug development," Expert Opin. Biol. Ther. 14:1527-1539.
Moos et al. (2002) "Restricted transport of anti-transferrin receptor antibody (OX26) through the blood+brain barrier in the rat," J. Neurochem. 79:119-129.
NCBI human TfR1 isoform 1 sequence, NP_001121620.
Ng et al. (2006) "Molecular events contributing to cell death in malignant human hematopoietic cells elicited by an lgG3-avidin fusion protein targeting the transferrin receptor," Blood 108:2745-54.
Niewoehner et al. (2014) "Increased Brain Penetration and Potency of a Therapeutic Antibody Using a Monovalent Molecular Shuttle," Neuron 81:49-60.
Nuttall et al. (2001) "Isolation of the new antigen receptor from wobbegong sharks, and use as a scaffold for the display of protein loop libraries," Mol. Immunol. 38:313-26.
Pardridge (2002) "Drug and gene targeting to the brain with molecular Trojan horses," Nat. Rev. Drug Discov. 1:131-9.
Pardridge (2012a) "Drug transport across the blood-brain barrier," J. Cereb. Blood Flow Metab. 32:1959-72.
Pardridge et al. (2012b) "Reengineering Biopharmaceuticals for Targeted Delivery Across the Blood-Brain Barrier," Methods Enzymol. 503:269-92.
Poul et al. (2000) "Selection of Tumor-Specific Internalizing Human Antibodies from Phage Libraries," J. Mol. Biol. 301:1149-61.
Ravn et al. (2010) "By-passing in vitro screening—next generation sequencing technologies applied to antibody display and in silico candidate selection," Nucleic Acids Res. 38:e193, 11 pages.
Shao et al. (2007) "Rapid isolation of IgNAR variable single-domain antibody fragments from a shark synthetic library," Mol. Immunol. 44:656-665.
Silvestri et al. (2014) "The extrahepatic role of TFR2 in iron homeostasis," Front. Pharmacol. 5:93, 6 pages.
Stanfield et al. (2004) "Crystal Structure of a Shark Single-Domain Antibody V Region in Complex with Lysozyme," Science 305:1770-3.
Triguero et al. (1990) "Capillary Depletion Method for Quantification of Blood-Brain Barrier Transport of Circulating Peptides and Plasma Proteins," J. Neurochem. 54:1882-8.
Tuma et al. (2003) "Transcytosis: Crossing Cellular Barriers," Physiol. Rev. 83:871-932.
Weiner et al. (2012) "Antibody-based immunotherapy of cancer: New insights, new targets," Cell 148:1081-4.
Wesolowski et al. (2009) "Single domain antibodies: promising experimental and therapeutic tools in infection and Immunity," Med. Microbiol. Immunol. 198:157-74.
Yu et al. (2011) "Boosting Brain Uptake of a Therapeutic Antibody by Reducing Its Affinity for a Transcytosis Target," Sci. Transl. Med. 6:261ra154, 8 pages.
Yu et al. (2014) "Therapeutic bispecific antibodies cross the blood-brain barrier in nonhuman primates," Sci. Transl. Med. 3:84ra44, 10 pages.
Friden et al. (1996) "Characterization, Receptor Mapping and Blood-Brain Barrier Transcytosis of Antibodies to the Human Transferrin Receptorer," J. Pharm. Exp. Therap. 278:1491-98.
Helguera et al. (2012) "An Antibody Recognizing the Apical Domain of Human Transferrin Receptor Efficiently Inhibits the Entry of All New World Hemorrhagic Fever Arenaviruses," J. Virol. 86:4024-4028.
Pardridge (2015) "Blood-brain barrier drug delivery of IgG fusion proteins with a transferrin receptor monoclonal antibody," Expert Opin. Drug Deliv. 12:207-222.
U.S. Appl. No. 16/761,190, filed May 1, 2020; "Improved TfR-Selective Binding Peptides Capable of Crossing the Blood Brain Barrier."

ND RELATED METHODS

TFR SELECTIVE BINDING COMPOUNDS AND RELATED METHODS

CROSS REFERENCE TO RELATED APPLICATION

This application is a divisional application of U.S. Ser. No. 15/594,632, filed May 14, 2017, which is a continuation of Intl. Appln. No. PCT/2015/060948, filed Nov. 16, 2015 and which claims the benefit of provisional application U.S. Ser. No. 62/080,112, filed on Nov. 14, 2014 and U.S. Ser. No. 62/141,773, filed on Apr. 1, 2015, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 12, 2016, is named OSX1402-WO1_SL.txt and is 291,569 bytes in size.

FIELD OF THE INVENTION

The present invention relates to peptides that bind with high specificity and which functionally interact with the transferrin receptor ("TfR") and which may be used in making chimeric molecular vehicles that carry biomolecules such as therapeutic or diagnostic agents across TfR-positive membranes, including, e.g., across the blood brain barrier or the gastrointestinal tract using TfR-specific binding moieties of the invention. Such moieties may be used alone or as components in specific conjugates that target the transferrin/transferrin receptor transport system. The invention relates more specifically to VNAR single chain antibodies derived from nurse shark that bind to TfR, compounds and compositions comprising a TfR-specific binding moiety, methods for preparing them, diagnostic and therapeutic methods of use in vitro or in vivo, e.g., to diagnose, treat and/or prevent a pathological condition, disorder or disease in which it is beneficial to deliver a heterologous biomolecule across the blood brain barrier by association with a TfR specific VNAR binding moiety. Other uses for TfR-specific binding moieties of the invention include, e.g., regulating the interaction of iron-charged transferrin with TfR (receptor cycling or cell surface presentation), such as may be therapeutic in treatment of certain cancer cells and tumors of various tissue types.

BACKGROUND OF THE INVENTION

The blood-brain barrier (BBB) is the principal interface between blood and the interstitial fluid that bathes neurons within the brain parenchyma (Abbott et al., Neurobiol Dis. 2010 January; 37(1):13-25). The BBB is formed by highly specialized endothelial cells that maintain an optimal environment for neuronal function by eliminating toxic substances and supplying the brain with nutrients and other metabolic requirements. The BBB likewise presents a formidable obstacle for the systemic delivery of many potentially important therapeutic and diagnostics agents. With the exception of small, lipophilic molecules (MW less than 500 Daltons), which can cross the BBB by transmembrane diffusion, nearly all hydrophilic small molecules, peptides, proteins, RNAs and genetic vectors that could be of therapeutic value are excluded (Pardridge, J Cereb Blood Flow Metab. 2012 November; 32(11):1959-72.). Many of the antibodies designed to treat a variety of neurodegenerative disorders including Alzheimer's disease, Parkinson's disease, Huntington's disease and frontotemporal dementia will be limited by their inability to reach the pathological target within the brain. Thus, despite tremendous progress in the discovery of potential therapeutics for CNS diseases, very few will be successfully developed without an effective means of delivery across the BBB.

Although the BBB restricts the passage of many substances, brain capillaries use membrane transport systems to deliver important nutrients and macromolecules important for normal brain function. The main route whereby large molecules, such as proteins and peptides, enter the CNS is by the receptor-mediated transcytosis (RMT) which might also be used to shuttle a wide range of therapeutics into the brain in a non-invasive manner (Jones and Shusta, Pharm Res. 2007 September; 24(9):1759-71). Circulating ligands such as transferrin, insulin and leptin interact with specific receptors concentrated on the luminal side of the brain capillary endothelial cells. Once bound to the receptor, the process of endocytosis is initiated as the receptor-ligand complexes cluster and intracellular transport vesicles detach from the membrane (Tuma and Hubbard, Physiol Rev. 2003 July; 83(3):871-932). The transport vesicles containing receptor-ligand complexes or dissociated ligands are directed away from the lysosomal compartment and trancytosed to the brain interstitial side of the endothelial cell, where they are released without disrupting the BBB.

One way to exploit endogenous RMT systems for drug delivery is to couple the drug therapeutic of interest to a vector such as an antibody or ligand that targets a particular RMT system. The drug cargo gains access to the brain parenchyma by "piggybacking" on the delivery vector (i.e., a type of "molecular vehicle" and also described as a molecular Trojan horse), which carries it across the BBB (Pardridge, Nat Rev Drug Discov. 2002 February; 1(2):131-9). The transferrin receptor 1 (TfR-1) endocytotic pathway for iron homeostasis has been one of the most extensively characterized systems for drug delivery across the BBB. TfR-1 mediates influx of iron-loaded transferrin from blood to brain in addition to the transcytosis of iron-depleted transferrin in the reverse direction. Transferrin itself has been used as a vehicle for brain delivery, but transferrin conjugates have to compete for the receptor with the high plasma concentration of the endogenous ligand. The OX-26 mouse monoclonal antibody, which specifically binds the rat transferrin receptor in brain capillaries without blocking the binding of transferrin (Jefferies et al., 1985), was the first antibody used to carry a drug cross the BBB (Freiden et al., Proc Natl Acad Sci USA. 1991 Jun. 1; 88(11):4771-5).

Anti-TfR antibodies have since been modified in a several different ways to deliver heterologous biomolecules, e.g., drug cargo, to the brain. Potential biotechnology products, including lysosomal enzymes, neurotrophins, decoy receptors, antibody fragments have been fused to the carboxyl terminus of the Fc domain of TfR for CNS delivery (Pardrige and Boado, Methods Enzymol. 2012; 503:269-92). More recently, bispecific antibodies have been produced by knobs-into-holes technology whereby one half of the antibody binds the CNS target and the other binds the TfR-1 (Yu et al., Sci Transl Med. 2011 May 25; 3(84):84ra44). Bispecific antibodies have also been generated by fusing the ScFv portion of a TfR-1 antibody to the carboxyl terminus of a therapeutic antibody (Niewoehner et al., Neuron. 2014 Jan. 8; 81(1):49-60) which maintains avid binding to the target. Each of these approaches has provided evidence of CNS activity in animal models following the intravenous injection, indicating that TfR-1 antibodies as therapeutic carriers hold significant promise for the non-invasive treatment of CNS disorders.

Despite these advances, several features of monoclonal antibodies as BBB carriers have hampered their translation from animal to humans. Antibodies are large molecules composed of 4 disulfide-linked subunits that are challenging to format as bispecific molecules. Moreover, functional components outside the antigen recognition domain can lead to off-mechanism toxicity, and complement-mediated lysis of TfR-rich reticulocytes has been reported (Couch et al., Sci Transl Med. 2013 May 1; 5(183):183ra57, 1-12). Another drawback is that TfR antibodies used to date are species-specific, which is problematic for preclinical safety testing of potential therapeutic molecules. Surrogate antibodies to the TfR-1 with the same biochemical properties (binding epitope, affinity, avidity and pH sensitivity) and transcytosis activity will be difficult to identify and antibodies that block ligand binding (Crepin et al., Cancer Res. 2010 Jul. 1; 70(13):5497-506) or inhibit transcytosis and deplete surface receptors (Bien-Ly et al., J Exp Med. 2014 Feb. 10; 211(2): 233-44) would be unsuitable as BBB carriers due to potential iron deprivation.

To address the drawbacks inherent in full size antibodies as BBB carriers, a panel of species cross-reactive VNARs to TfR-1 have been identified by phage display and selected for brain uptake. VNARs are isolated variable domains derived from the naturally-occurring single chain antibodies found in the shark (Stanfiled et al., Science. 2004 Sep. 17; 305 (5691):1770-3.). Their small size (~12 kDa), high solubility, thermal stability and refolding capacity (Wesolowski et al., Med Microbiol Immunol. 2009 August; 198(3):157-74) simplifies coupling to a monoclonal antibody or other pharmaceutical. Their modularity offers a wide range of therapeutic design and their species cross-reactivity can facilitate the development and clinical translation of brain penetrant therapeutics to treat a broad spectrum of CNS disorders.

Similar problems are encountered in transporting molecules, such as drug substances, across intestinal epithelium of the gut, where transcellular and paracellular routes of transport exist for water and ions but where larger molecules are transported exclusively by transporter molecules in epithelial cell plasma membranes.

Hence, it is desirable to have new molecular tools for efficient and selective delivery of compounds such as biomolecules (e.g., therapeutics and diagnostics) across the BBB to avoid some or all of the problems discussed above. It would thus also be desirable to have new molecular tools for efficient and selective delivery of compounds biomolecules across the cells of the gastrointestinal (GI) tract thereby increasing the oral bioavailability of certain molecules, e.g., drugs, which do not naturally cross the GI tract when delivered in oral form. Moreover, it would be advantageous to have new selective TfR-specific binding compounds, especially ones having one or more advantageous biological properties with therapeutic and/or diagnostic benefit over current anti-TfR antibodies and other regulators of iron transport systems.

SUMMARY OF THE INVENTION

The present invention addresses the needs described above by providing specific binding moieties which bind selectively to a mammalian transferrin receptor (TfR), especially to a human Transferrin Receptor. The invention provides TfR specific binding moieties of general motif structure (FW1-CDR1-FW2-3-CDR3-FW4) derived from sequences obtained from a shark semi-synthetic VNAR library. The invention provides a TfR specific binding moiety comprising a CDR 1 region and CDR3 region inserted into a semisynthetic scaffold comprising VNAR framework and hypervariable regions, wherein the CDR 1 region comprises or consists essentially of a peptide having an amino acid sequence of formula: $D-X_2-X_3-X_4-X_5-X_6-X_7$ (SEQ ID NO: 482) wherein $X_2$ is A, K, N, R, S or T; $X_3$ is A, D, I, N, S, V or Y; $X_3$ is A, D, I, N, S, V or Y; $X_4$ is C or Y; $X_5$ is A, D, P, R or T; $X_6$ is A or L; and $X_7$ is D, G, L, S, P or T. Exemplary CDR1 and CDR3 regions which may be used in various combinations, surrounding framework regions FW1 and FW4 and interspersing framework regions FW2-3, are also provided. Specific exemplary hTfR specific binding moieties are provided.

In a specific embodiment, the invention provides an isolated TfR-specific binding moiety comprising a VNAR represented by the formula, from N to C terminus,

FW1-CDR1-FW2-HV2-FW2'-HV4-FW3-CDR3-FW4, wherein the CDR 1 region comprises or consists essentially of a peptide having an amino acid sequence of formula: $D-X_2-X_3-X_4-X_5-X_6-X_7$ (SEQ ID NO: 482)
wherein $X_2$ is A, K, N, R, S or T;
$X_3$ is A, D, I, N, S, V or Y;
$X_4$ is C or Y;
$X_5$ is A, D, P, R or T
$X_6$ is A or L; and
$X_7$ is D, G, L, S, P or T;
wherein the CDR3 region comprises or consists essentially of a peptide having an amino acid sequence of any one of SEQ ID NOS. 185-368 in Table 1; and wherein the moiety is specific for human TfR-1.

In further embodiments, optionally, the TfR-specific binding moiety has an EC50 for human Tfr-1 ranging from about 0.1 nM to about 10 µM and preferably ranging from about 1 nM to about 800 nM; does not substantially bind to human TfR-2 and/or is capable of cross reacting with mouse TfR-1. In other embodiments, optionally, the binding of the TfR-specific binding moiety to TfR-1 does not inhibit transferrin binding to and/or transport by TfR-1, induces endocytosis of the moiety in a TfR-positive cell and/or is reversibly pH dependent.

In some embodiments the TfR-specific binding has a CDR 1 region is selected from the group consisting of peptides DASYALG (SEQ ID NO: 425), DKDCALS (SEQ ID NO: 434), DNDCALS (SEQ ID NO: 426), DNDCTLS (SEQ ID NO: 429) DNNCALS (SEQ ID NO: 431), DNYCPLS (SEQ ID NO: 476), DRACALL (SEQ ID NO: 477), DRDCALS (SEQ ID NO: 427), DSDCALS (SEQ ID NO: 433), DSNCAAT (SEQ ID NO: 435), DSNCALS (SEQ ID NO: 423), DSNCALP (SEQ ID NO: 419), DSNCDLS (SEQ ID NO: 416), DSNCPLS (SEQ ID NO: 432), DSNCRLS (SEQ ID NO: 442), DSICALS (SEQ ID NO: 424), DSVCALS (SEQ ID NO: 478), DTACALD (SEQ ID NO: 479) and RACALLN (SEQ ID NO: 480). In some embodiments, the TfR-specific binding moiety has one or more of FW1, FW2, FW2', FW3 or FW4 are selected from peptide sequences set forth in Table 1.

In further embodiments, the invention provides isolated VNAR domains comprising or consisting essentially of an amino acid sequence of any one of SEQ. ID NOS. 1-184. In other embodiments the isolated TfR-specific binding moiety comprising or consisting essentially of a VNAR scaffold with any one CDR1 peptide in Table 1 in combination with any one CDR3 peptide in Table 1.

In some embodiments, the invention provides an isolated TfR-specific binding moiety comprising a VNAR domain capable of specifically binding to human TfR-1 without substantially interfering with transferrin binding to and/or transport by said human TfR-1. Such moieties are capable of binding to the apical domain of human TfR-1, generally within amino acids 215 to 380 of human TfR-1. For certain embodiments, TfR-specific binding moieties are provided that bind to epitopes comprising one or more sequences selected from the group consisting of (i) KAATVT (SEQ ID NO: 413), (ii) SGLPNIPVQTISRAAAEK (SEQ ID NO: 411), (iii) KLFGNMEGDCPS (SEQ ID NO: 414), (iv) SDWKTDS (SEQ ID NO: 415) and (v) STCRMVTSES (SEQ ID NO: 412). Examples of TfR-specific binding moieties that bind these epitopes are those in which the VNAR domain F02, A07 or H01. Further, optionally, for these embodiments, the TfR-specific binding moiety can have an EC50 for human Tfr-1 ranging from about 0.1 nM to about 10 μM and preferably ranging from about 1 nM to about 800 nM; does not substantially bind to human TfR-2 and/or is capable of cross reacting with mouse TfR-1. In other embodiments, optionally, the binding of the TfR-specific binding moiety to TfR-1 does not inhibit transferrin binding to and/or transport by TfR-1, induces endocytosis of the moiety in a TfR-positive cell and/or is reversibly pH dependent.

In some aspects of the invention, the TfR-specific binding moieties of the invention form all or part of the variable domain of a single variable domain antibody, a bi- or tri-functional VNAR, a conventional antibody, or any fragment or fusion protein of said antibody. Examples of single variable domain antibody include, but are not limited to, is a shark antibody, a camelid antibody or a nanobody. Examples of a conventional antibody include, but are not limited to, an immunoglobin having both heavy and light chains such as IgM, IgA, IgG or IgE, a single chain Fv, an Fab fragment, or any fragment or fusion protein of said antibody or fragment.

Yet another aspect of the invention relates to variants of the TfR-specific binding moieties of the invention, wherein the variant (i) differs by 1 to 10 amino acid residues from a recited amino acid sequence and/or (ii) retains human TfR-1-binding activity of at least half of the activity of a non-variant binding moiety.

Still a further aspect of the invention provides TfR-specific conjugate comprising a TfR-specific binding moiety of the invention operably linked to a heterologous molecule which differs in biological activity from said moiety. Such linkages may be covalent or non-covalent. Examples of a heterologous molecule include, but are not limited to, a growth factor, cytokine, lymphokine, cell surface antigen or an antibody or antibody fragment which binds to any of the foregoing; a chimeric antigen receptor; a cytotoxic small molecule; a biochemical pathway agonist or antagonist; a therapeutic agent or drug; a diagnostic agent such as a fluorescent molecule or other molecular marker; or a nucleic acid molecule with regulatory properties or which encodes a regulatory molecule for a cell.

The present invention also provides pharmaceutical compositions comprising one or more of any one of the TfR-specific binding moieties or any one of the TfR conjugates of the invention, optionally in formulation with the preceding claims one or more additional therapeutic agents.

Further, the instant invention provides a nucleic acid molecule encoding at least one TfR-specific binding moiety or a TfR-specific conjugate of the invention, vectors containing that nucleic acid, host cells containing those vectors and methods of producing at least one TfR-specific binding moiety or TfR-specific conjugate by culturing those host cells for a time and under conditions in a growth medium to enable the host cells to express the at least one TfR-specific binding moiety or TfR-specific conjugate. In some embodiments, the expression systems are such that the at least one TfR-specific binding moiety or TfR-specific conjugate produced by the host cell is secreted into the growth medium.

In other aspects, the invention relates to a method of delivering a therapeutic or diagnostic molecule across the blood brain barrier which comprises administering a TfR-specific binding moiety comprising a VNAR domain capable of specifically binding to human TfR-1 without substantially binding to human TfR-2, wherein said therapeutic molecule is conjugated to said moiety, to a subject for a time and in an amount effective to treat or diagnose a CNS disease or condition.

In yet other aspects, the invention relates to a method of delivering a therapeutic or diagnostic molecule to the gastrointestinal (GI) tract which comprises administering a TfR-specific binding moiety comprising a VNAR domain capable of specifically binding to human TfR-1 without substantially binding to human TfR-2, wherein said therapeutic molecule is conjugated to said moiety, to a subject for a time and in an amount effective to treat or diagnose a GI disease or condition.

Additional embodiments of the invention are directed to methods of treatment which comprises administering to a subject in need thereof a compound or composition comprising a TfR-specific binding moiety of the invention. In some embodiments, the disease or condition is ameliorated upon transport of a heterologous molecule across a cell membrane of a TfR-positive cell, wherein said heterologous molecule comprises or is associated with a TfR-specific binding moiety of the invention. In some cases, the TfR-specific binding moiety can be internalized by a TfR in a cell membrane associated with the blood brain barrier or the gastrointestinal (GI) tract. In some embodiments, the disease or condition is a central nervous system disease or condition.

Still a further aspect of the invention provides a method of identifying, quantifying or localizing a TfR-containing biological sample or cell by contacting a test sample in vitro or in vivo with any one of the TfR-specific binding moiety of the invention, and directly or indirectly measuring the TfR-specific binding in or to said sample.

The invention also provides several additional methods including a method of targeting delivery of a heterologous molecule to a TfR-expressing cell by delivering a TfR-specific conjugate of any the invention to the target and a method of increasing the oral bioavailability of a drug which comprises associating the drug with a TfR-specific-binding moiety of the invention.

A yet further aspect of the invention provides kits for detecting or quantifying TfR-1 in a sample which comprises at least one TfR-specific binding moiety or conjugate of the invention.

In summary, complex phage libraries have been generated using a shark VNAR derived scaffold which enables the generation of novel therapeutic products, in particular, specific binding moieties which bind selectively and with high affinity to human TfR, thereby producing a TfR specific binding moiety. As described in detail herein, the present invention thus provides VNAR derived TfR specific binding moieties, and TfR mediated vehicles (e.g., BBB vehicles) and TfR antagonist compounds comprising them. TfR specific binding moieties of the invention comprise a shark VNAR derived CDR1 region and a CDR3 region interspersed by a framework region FW2-3. CDR1 and CDR3 regions are also bordered by VNAR framework regions FW1 and FW4, respectively. TfR mediated vehicles are capable of transporting one or more associated (e.g., covalently or non-covalently) heterologous molecules across the cell membrane of a TfR-positive cell by means of binding to cell surface TfR. Any non-polarized cell which expressed TfR may be used as a target for transport of a heterologous molecule using a TfR specific binding moiety of the invention. In certain embodiments, TfR expression on gut epithelial cells may advantageously be used for oral drug delivery of otherwise non-orally bioavailable drugs or compounds. In certain embodiments, TfR expression on cells of the blood brain barrier may advantageously be used for drug or compound delivery across the blood brain barrier. In yet other embodiments, TfR antagonist compounds comprising a TfR specific binding moiety of the invention compete with or inhibit one or more bioactivities of a native TfR ligand in vitro or in vivo and may be useful for antagonizing TfR bioactivity in, e.g., cancer diagnostics and therapeutics. Nucleic acid sequences encoding one or more TfR specific binding moieties, vectors comprising nucleic acid sequences, and host cells comprising them are also provided, as are related methods for producing a TfR mediated drug delivery vehicle and a TfR antagonist compound.

TfR specific binding moieties, and vehicles and TfR antagonist compounds comprising such moieties, may be used to produce variants and derivatives, including conjugates, e.g., immunoconjugates, and multimers having multiple binding specificities built into a single molecule, such as bispecific binding molecules specific for two heterologous targets, multimers thereof, or heterospecific binding molecules specific for more than two heterologous targets. Moreover, TfR specific compounds of the invention, and variants or derivatives thereof, may be combined with other therapeutic agents in compositions for use in related therapeutic, prophylactic and diagnostic methods. Therapeutic methods are provided for treating diseases, disorders and conditions which benefit from the TfR vehicles or antagonists of the invention. In particular, compositions and methods for treating diseases, disorders and conditions of the brain and spinal cord (central nervous system) are provided, where the ability to transport heterologous molecules across the BBB may be particularly beneficial. A method for increasing the oral bioavailability of a drug by complexing or conjugating it with a TfR specific binding moiety of the invention is also provided. Methods and kits for identifying, quantifying or localizing a TfR-containing biological sample are also provided, as are methods for the targeted delivery of a payload to a TfR expressing cell using a TfR specific binding moiety-payload conjugate.

BRIEF DESCRIPTION OF THE DRAWINGS

FIG. 7B shows little if any capillary contamination in the brain parenchymal fraction based on alkaline phosphatase assays (Example 7).

DETAILED DESCRIPTION OF THE INVENTION

Figure 1:
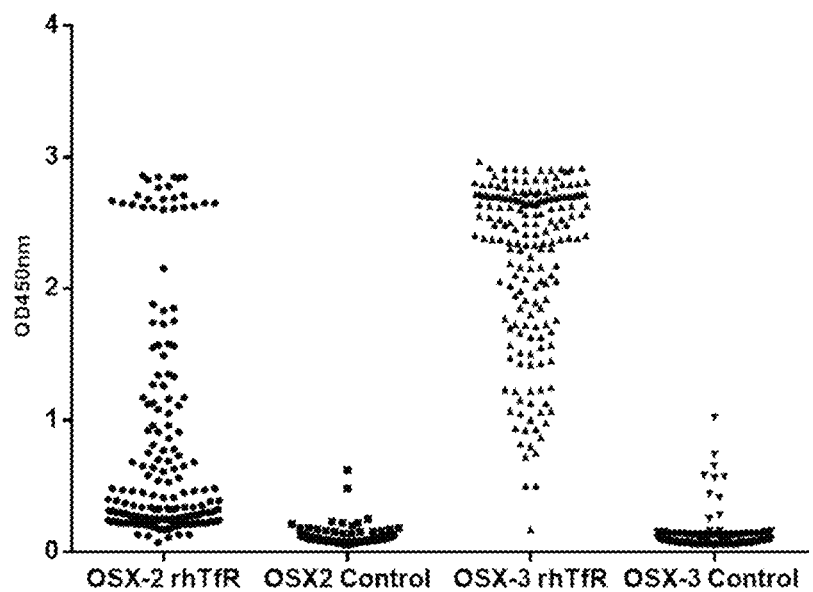
FIG. 1: Specific binding of individual clones to human TfR-1. Individual phage clones were isolated and tested for binding human TfR-1 (wells coated at 1 µg/ml) relative to a negative control (HEL or HSA) after 3 rounds of panning. Phage binding was measured by ELISA using an HRP-conjugated anti-M13 antibody.

In order that the present invention may be more readily understood, certain terms are defined below. Additional definitions may be found within the detailed description of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

As used herein, the term "TfR" or "TfR-1" refers to a mammalian transferrin receptor-1 (in context as a protein or a nucleic acid), unless the context indicates that it refers specifically to human TfR-1 (see, e.g., UniProt P02786 TFR1_Human) or mouse TfR-1.

VNAR Semi-Synthetic Library Construction and Screening

A Type 2 nurse shark VNAR semi-synthetic library was constructed by a rationale design based on sequence analysis of 188 Type 2 VNAR sequences containing a single cysteine in their CDR3 region (see M. Diaz, et al., *Immunogenetics* 54 (2002) pp. 501-512) as described in Intl. Appln. No. PCT/US2015/038166, filed 26 Jun. 2015 (hereafter the "PCT '166 appln."). These sequences were obtained by randomly sequencing clones in naïve VNAR libraries built from two different adult nurse sharks. Information obtained by alignment of the 188 protein sequences was used to design a new semi-synthetic library including sequence variation in both the CDR3 and the framework regions.

The VNAR library was generated by overlap PCR as described in the PCT '166 appln. A mixture of the ten selected templates was used to introduce framework mutations, while a mixture of oligonucleotides was used to incorporate both randomization of the CDR3 by NNK codons, fixed and loose cysteines by use of TGC and DRY codons, and sequence variability on both edges of the CDR.

A Type 1 nurse shark VNAR semi-synthetic library was built from three specific clones identified by randomly sequencing VNARs in naïve libraries built from two different adult nurse sharks. These clones harboured unusually long CDR3 regions of 26 and 32 amino acids and had very few framework mutations. In order to generate a semi-synthetic library specifically enriched for clones harbouring long CDR3s, the CDR3 of these 3 clones was randomized, as previously described, by overlap PCR, keeping only the two cysteines unchanged in order to preserve the structural integrity of the molecule.

Sequence analysis and further characterization of the resulting VNAR Type 2 (OsX-3) and Type 1 (OsX-4) semi-synthetic libraries was also performed as further described in the PCT '166 appln.

Selection of VNARs having particular binding specificities to TfR target proteins was performed as described in Example 1. The Tfr target protein binding moieties were selected for further expression and monomeric VNARs purified. Selected VNARs were produced in CHO cells as fusions to the N-terminus of the IgG-Fc fragment, as described in Example 1.

Isolating TfR-1 Binding VNARs

VNARs that bind specifically to human TfR-1 were isolated from semi-synthetic phage display libraries by three rounds of panning and amplification on immobilized recombinant human TfR-1 (rhTfR-1) (Examples 2 and 3). The stringency of selection was increased at each round by decreasing hTfR-1 concentration and increasing the number of washing steps and the efficiency and specificity of the selection procedure of eluted polyclonal phage was monitored by ELISA after each round of selection. Clones were enriched for binding to human and mouse rTfR-1 but not HSA. Approximately 200 clones from each library were randomly selected from round three and binding ELISAs were performed with phage. The results show that more than 90% of the clones appeared specific for TfR-1 relative to HSA or HEL controls (FIG. 1).

DNA Sequence Analysis

The DNA sequence of positive clones was determined and the unique VNARs identified by their CDR3 and CDR1 regions (Example 3). The OSX-3 library returned 137 unique VNARs based on their CDR3/CDR1 combination and 70 unique clones displayed TfR-binding at least 3-fold above background HSA binding were isolated for further analyses. The deduced amino acid sequences with specific CDR3 and CDR1 regions for the VNARs selected for functional binding activity after further characterization are shown in Table 1. Unique CDR3 sequences of Table 1 may be grouped into 38 separate genera, as shown in Table 2, based on sequence similarity.

Next Generation Screening to Identify TfR-1 Binding VNARs

Mouse- and human-species cross-reactive VNAR were identified directly by next generation sequencing (NGS) of lymphocytes after alternate immunization with recombinant mouse and human TfR-1 ectodomains (Ravn et al., Nucleic Acids Res. 2010 November; 38(21):e193). VNARs were selected which fulfilled all of the following three criteria: a) their abundance determined in the Week 4 sample had to be at least 10 higher than abundance determined in sample before the boost; b) the relative abundance score in Week 4 had to be at least 100; and c) the sequence did not contain any stop codons. The deduced amino acid sequences of the VNARs selected by this method are grouped by genus and listed in Table 1.

Species Cross-Reactivity and Cell Surface Binding of Phage Clones

Figure 2:
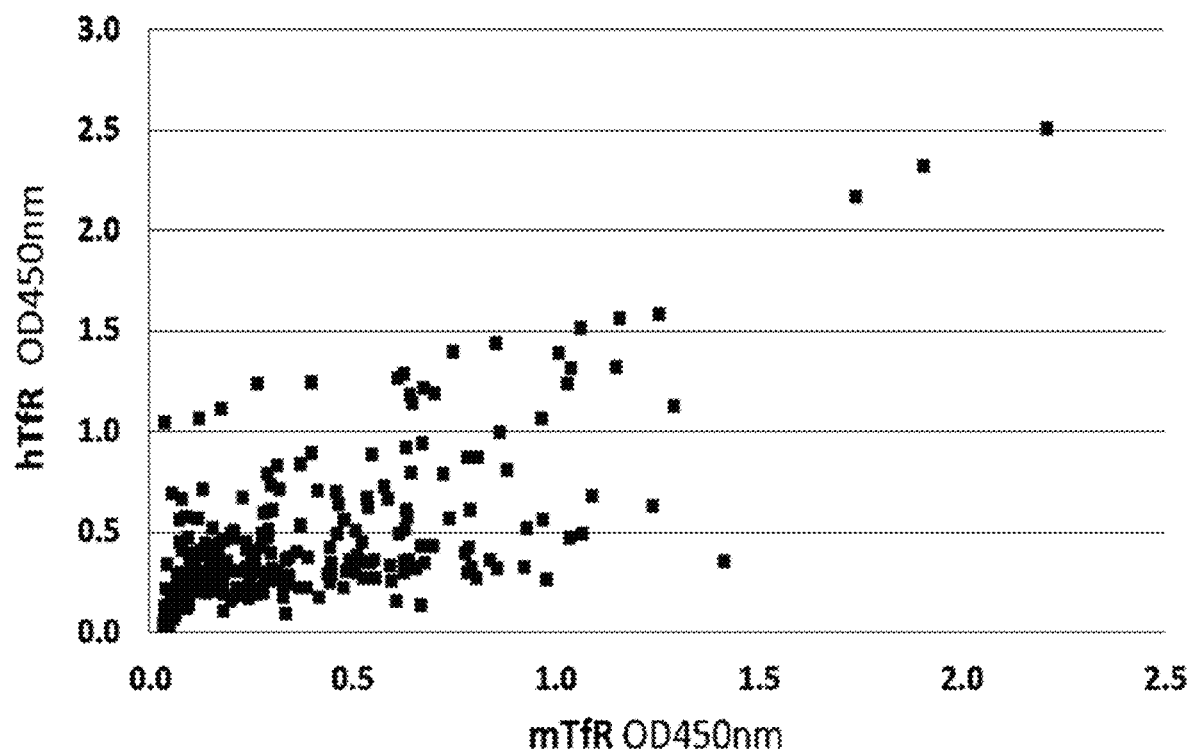
FIG. 2: Human-mouse cross reactivity of TfR-binding of clones. The binding of individual phage clones to either human TfR-1 or mouse TfR-1 (1 µg/ml) was initially assessed by phage ELISA. Phage binding was measured by ELISA using anti-M13-HRP-conjugated antibody.
Figure 3:
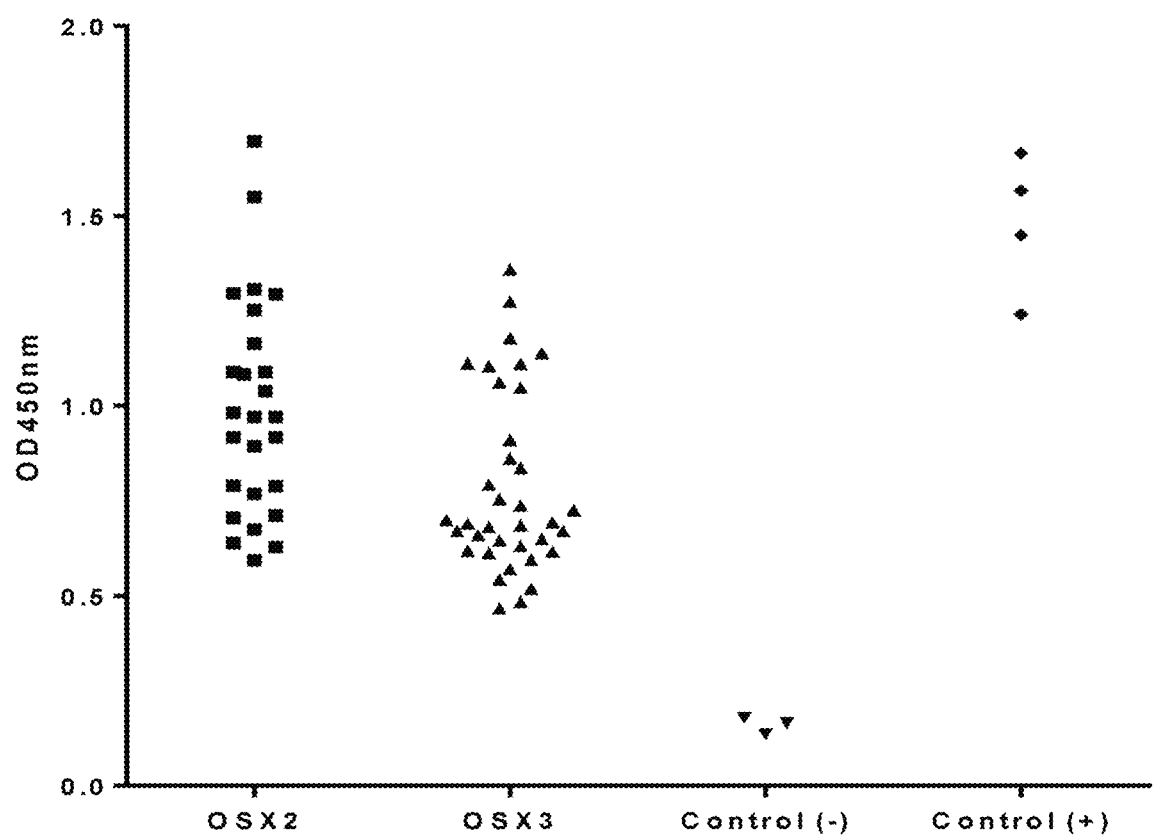
FIG. 3: Phage binding to human SKOV3 cells expressing the TfR-1. After sequence analysis, unique VNAR-expressing clones were assessed for cell-surface binding to human TfR-1. SKOV3 human ovarian carcinoma cells were seeded in 96-well plates and phage binding was measured by ELISA using anti-M13-HRP conjugated antibody. The OD450 nm for each clone is presented relative to a positive (OKT9 anti-TfR antibody) and negative VNAR (anti-HEL) controls.

The cross-reactivity of individual clones to recombinant human and mouse TfR-1 was initially assessed by phage ELISA (Example 4). Although some clones appeared to be species specific, the majority bound to both human and mouse TfR-1 (FIG. 2). Clones selected based on binding to the extracellular domain of TfR-1 adsorbed to plastic were subsequently tested for their ability to recognize the native transmembrane receptor on the cell surface. Of the rhTfR-1 binding clones identified by phage ELISA, over 50% also bound to membrane associated TfR-1 in human SKOV3 cells (FIG. 3), which exclusively express TfR-1 and not the related TfR-2 (Calzolari et al., Blood Cells Mol Dis. 2007 July-August; 39(1):82-91).

Species Cross-Reactivity and pH-Sensitivity of Purified VNARs

Figure 4:
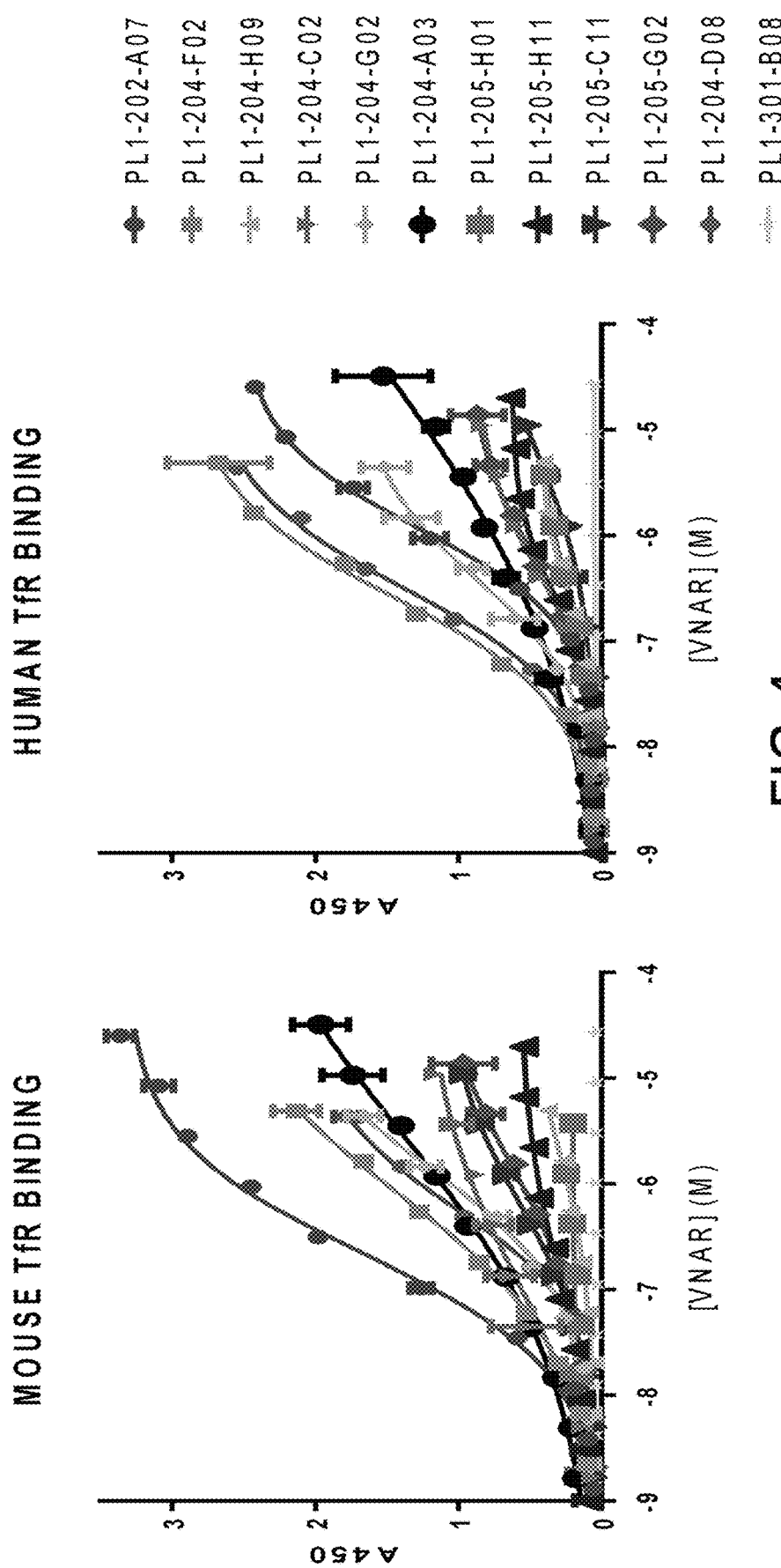
FIG. 4: EC50 binding curves of VNAR monomers to human or mouse TfR-1. VNAR monomers were purified by nickel affinity purified and titred against either rhTfR-1 (upper) or rmTfR-1 (lower) adsorbed to the solid phase of an ELISA plate. Binding was measured with an HRP-labelled anti-FLAG tag antibody and cross-reactive VNARs with different binding potency were selected for further characterization.
Figure 5:
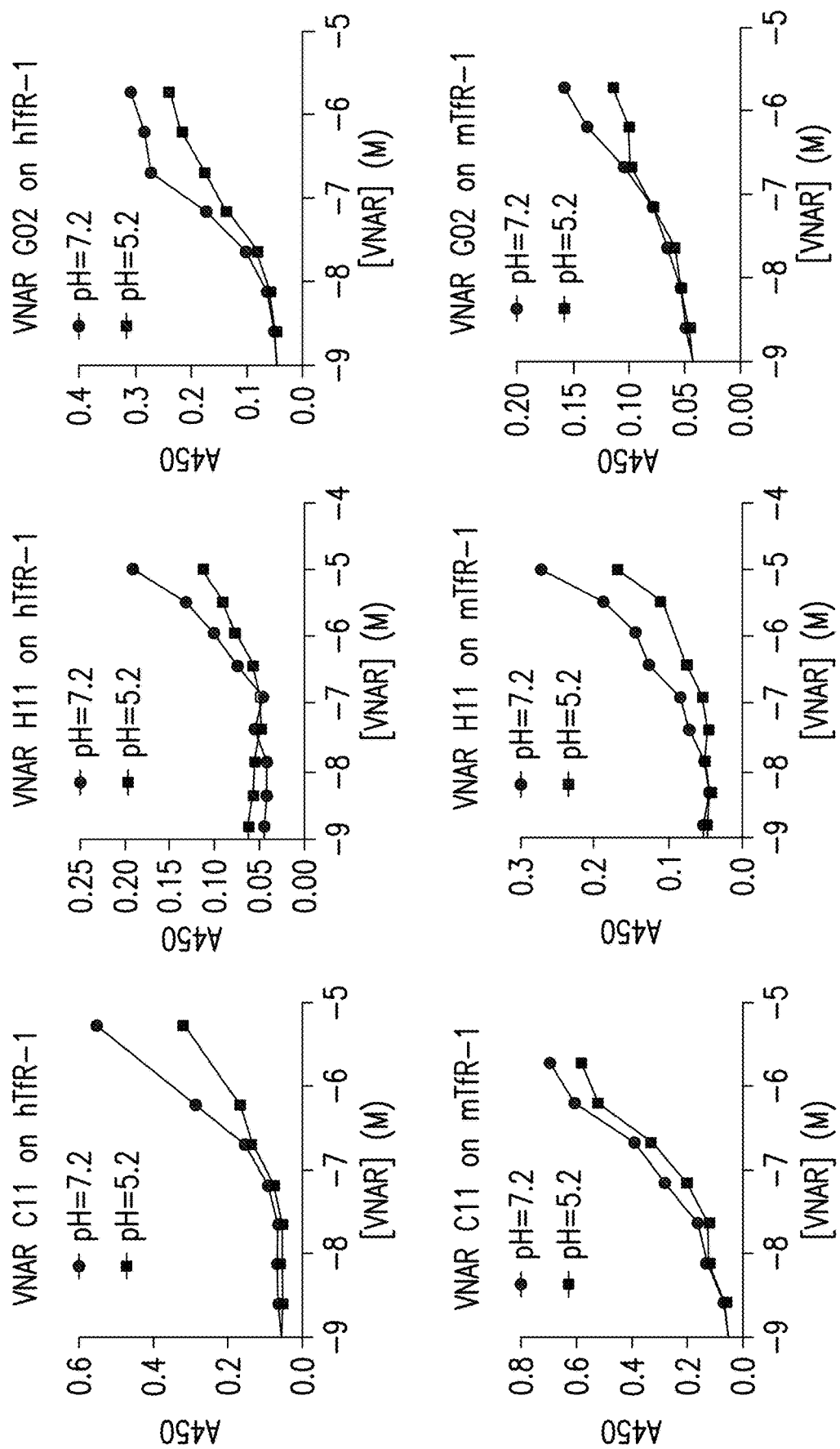
FIG. 5: pH sensitive binding of VNAR monomers to human and mouse TfR-1. Purified VNAR monomers were bound at pH7 to either rhTfR-1 (upper row) or rmTfR-1 (lower row) adsorbed to the solid phase of an ELISA plate. The plates were then washed 3 times for 3 min at either pH5.2 or pH7.2 and binding was measured with an RP-labelled anti-FLAG tag antibody.
Figure 6:
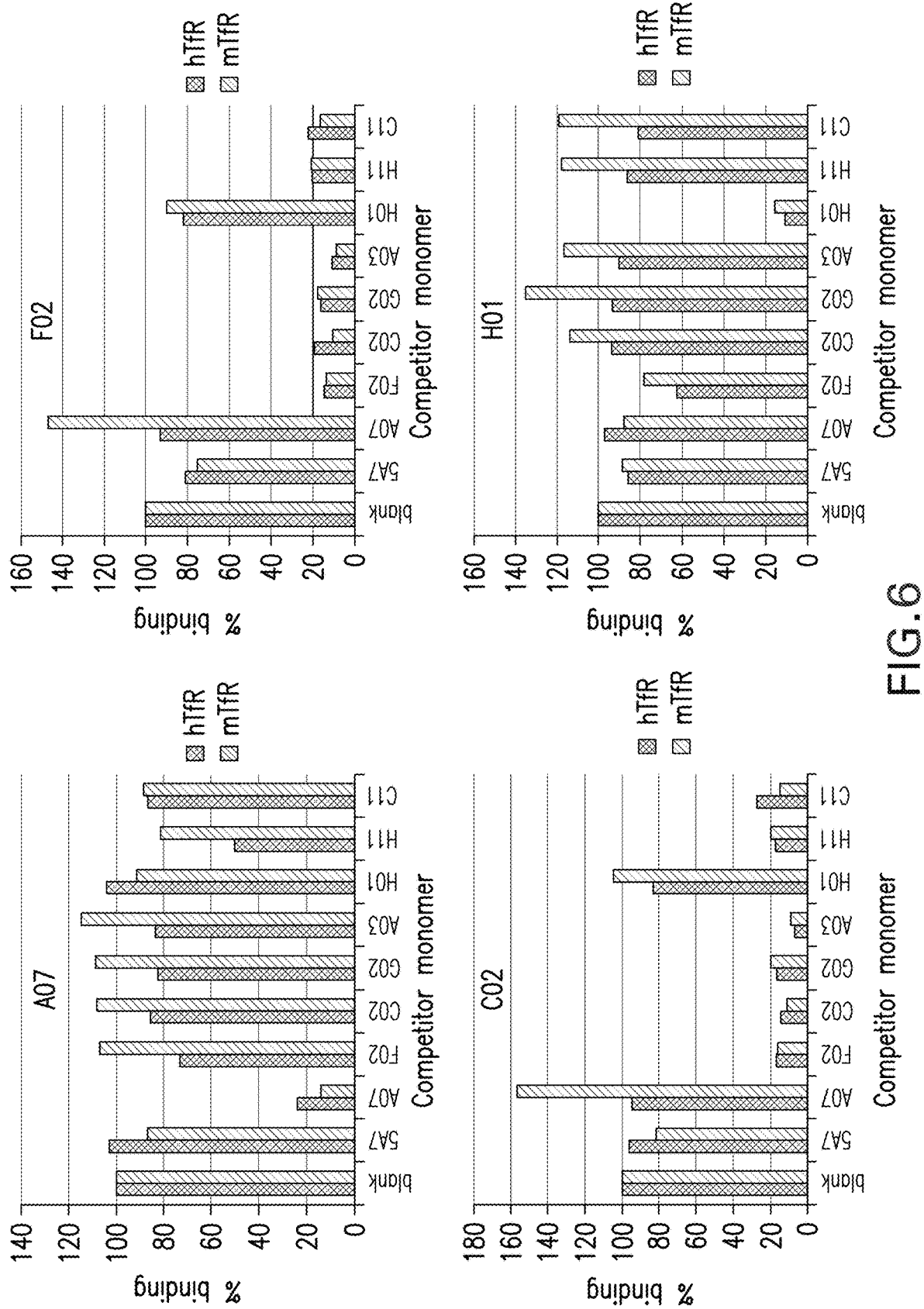
FIG. 6: Competition binding between VNAR for human and mouse TfR-1. The binding of a panel of phage clones to human and mouse TfR-1 the presence of purified VNAR monomers (2 µM) was measured by ELISA using anti-M13-RP conjugated antibody. The % binding of each TfR-1 clone against the panel was compared to the positive phage control (blank) and negative control (VNAR-5A7).

Selected VNARs were purified from *E. coli* periplasmic extracts by nickel affinity chromatography to assess monomeric binding and functional activity (Example 4). Binding curves indicate a range of EC50s from approximately 150 nM to 1.5 µM (Example 5; FIG. 4), and although there was no linear correlation between human and mouse receptor binding, some VNARs bound both species with similar potency. Eight clones were further characterized for pH-sensitive binding to human and mouse TfR-1. Although most were pH-sensitive binders, overall the binding of individual monomers appeared more pH-sensitive to human TfR-1 compared to mouse TfR-1 (FIG. 5). The pH-sensitive VNARs facilitates its binding to the receptor at neutral pH in plasma, followed by dissociation from the receptor at at acidic pH in the endosome and release into the brain parenchyma following transcytosis.

TfR-1 Binding Epitopes of Species Cross-Reactive VNARs

A panel of VNARs was analysed in a competitive immunoassay for cross blocking in a pairwise, combinatorial manner against both mouse and human TfR-1. Three distinct groups were identified; the first is represented by clone A07, the second by a group of clones that share a similar or overlapping epitope (F02, G02, C02, A03, H11, C11) and third by H01 (FIG. 6). Each VNAR recognized the same epitope in both mouse and human TfR-1 in agreement with their species cross reactivity in other assays. However, not all of the VNARs that recognize a similar epitope were endocytosed in vitro, suggesting that other properties of the VNAR molecule are important for functional activity.

The VNAR Domain Amino Acid Sequence have SEQ ID NOS. 1-184; the CDR3 regions listed above in Table 1 have SEQ ID NOS. 185-368; and because so many of the above CDR1 regions have the same sequence, only the unique CDR1 regions in Table 1 has been assigned a sequence identification number (SEQ ID NOS. 416-475).

TABLE 1

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 1 | | ARVDQTPQTITKETGESLTINCVLRDSNCDLSSTYWYRKKS<br>GSTNEESISKGGRYVETVNSGSKSFSLRINDLTVEDSGTYRS<br>NVFCIIDGELEDVYGGGTVVTVNAASGA | DSNCDLS | 416 | FCIIDGELEDV | 185 | 1 |
| 2 | | ARVDQTPQTIIKETGESLTINCVLRDNNCDLSSTYWYRKKS<br>GSTNEESISKGGRYVETVNSGSKSFSLRINDLTVEDSGTYRS<br>NVFCIIDGELEDVYGGGTVVTVNAASGA | DNNCDLS | 417 | VFCIIDGELEDV | 186 | 1 |
| 3 | | MAQAARVDQTPRIATKETGESLTINCVLRDNNCALPSTNW<br>YRTKLGSTKEQTISIGGRYSETVDEGSNSASLTIRDLRVEDS<br>GTYKCKADYWCDPMRAPGLFGRKEGAGTVLTVKEASGA | DNNCALP | 418 | DYWCDPMRAPGL<br>FGRK | 187 | 2 |
| 4 | | MAQAARVDQTPRIATKETGESLTINCVLRDSNCALPSTNW<br>YRTKLGSTKEQTISIGGRYSETVDEGSNSASLTIRDLRVEDS<br>GTYKCKAETNCHIFYQFPKDEGAGTVLTVKEASGA | DSNCALP | 419 | ETNCHIFYQFPK<br>D | 188 | 3 |
| 5 | | ARVDQTPQTITKETGESLTINCVLRDSNCAAGSTYWYRKKS<br>GSTNEVRISKGGRYVETVNSGSKSFSLRINDLTVEDSGTYRC<br>HVETPYDCPELNWWDVYGGGTVVTVNAASGA | DSNCAAG | 420 | ETPYDCPELNWW<br>DV | 189 | 4 |
| 6 | | ARVDQTPQTITKETGESLTINCVLRDSNCAASSRYWYRKKS<br>GSTNEESISKGGRYVETVNSGSKSFSLRINDLTVEDSGTYRC<br>HVETPYDCPELNWWDVYGGGTVVTVNAASGA | DSNCAAS | 421 | ETPYDCPELNWW<br>DV | 190 | 4 |
| 7 | "E04" | ARVDQTPQTITKETGESLTINCVLRDSRCAASSRYWYRKKS<br>GSTNEENISKGGRYVETVNSGSKSFSLRINDLTVEDSGTYRC<br>HVETPYDCPELNWWDVYGGGTVVTVNAASGA | DSRCAAS | 422 | ETPYDCPELNWW<br>DV | 191 | 4 |
| 8 | | ARVDQTPQTITKETGESLTINCVLRDSNCAASSTYWYRKKS<br>GSTNEESISKGGRYVETVNSGSKSFSLRINDLTVEDSGTYRC<br>HVQTPYDCPELNWWDVYGGGTVVTVNAASGA | DSNCAAS | 421 | QTPYDCPELNWW<br>DV | 192 | 4 |
| 9 | | ARVDQTPQTITKETGESLTINCVLRDSNCALSSTYWYRKKS<br>GSTNEESISKGGRYVETVNSGSKSFSLRINDLTVEDSGTYRC<br>HVRTPYDCPELNWWDVYGGGTVVTVNAASGA | DSNCALS | 423 | RTPYDCPELNWW<br>DV | 193 | 4 |
| 10 | | ARVDQTPQTITKETGESLTINCVLRDSNCALSSTYWYRKKS<br>GSTNEESISKGGRYVETVNSGSKSFSLRINDLTVEDSGTYRC<br>HVTTPYDCPELNWWDVYGGGTAVTVNAASGA | DSNCALS | 423 | TTPYDCPELNWW<br>DV | 194 | 4 |
| 11 | | ARVDQTPRIATKETGESLTINCVLRDSNCALPSTNWYRTKL<br>GSTKEQTISIGGRYSETVDEGSNSASLTIRDLRVEDSGTYKC<br>KAICDIFTYYYGTSWEGAGTVLTVKEASGA | DSNCALP | 419 | ICDIFTYYYGTS<br>W | 195 | 5 |
| 12 | | ARVDQTPRIATKETGESLTINCVLRDNNCALPSTNWYRTK<br>LGSTKEQTISIGGRYSETVDEGSNSASLTIRDLRVEDSGTYK<br>CKAIDYCLSWYRSINLEGAGTVLTVKEASGA | DNNCALP | 418 | IDYCLSWYRSIN<br>L | 196 | 6 |
| 13 | | ARVDQTPRIATKETGESLTINCVLRDNNCALPSTNWYRTK<br>LGSTKEQTISIGGRYSETVDEGSNSASLTIRDLRVEDSGTYK<br>CKAPSFDPLNYCYIWRRTTEGAGTVLTVKEASGA | DNNCALP | 418 | PSFDPLNYCYIW<br>RRTT | 197 | 7 |
| 14 | | ARVDQTPQTITKETGESLTINCVLRDSICALSSTYWYRKKS<br>GSTNEERISAGGRYVETVNSRSKSFSLRINDLTVEDSGTYRC<br>NVSPPLVAGVLNCYDIYGGGTAVTVNAASGA | DSICALS | 424 | SPPLVAGVLNCY<br>DI | 198 | 8 |
| 15 | | ARVDQTPQTITKETGESLTINCVLRDNNCALPNTYWYRKK<br>SGSTNEESISKGGRYVETVNSGSKSFSLRINDLTVEDSGTYR<br>CNVYSSPQLGFYDCGHWIDVYGGGTVVTVNAASGA | DNNCALP | 418 | SSPQLGFYDCGH<br>WIDV | 199 | 9 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 16 | | ARVDQTPQTITKETGESLTINCVLRDASYALGSAYWYRKKS GSTNEESILKGGRYVETVNSGSKSFSLRINDLTVEDSGTYRC NVFHIAGTDMAELVYDVYGGGTVVTVNAASGA | DASYALG | 425 | VFHIAGTDMAEL VYDV | 200 | 10 |
| 17 | | ARVDQTPRIATKETGESLTINCVLRDSNCALPSTNWYRTKL GSTKEQTISIGGRYSETVDEGSNSASLTIRDLRVEDSGTYKC KAVLVPAHGDCSAWSLWVGVEGAGTVLTVKEASGA | DSNCALP | 419 | VLVPAHGDCSAW SLWVGV | 201 | 11 |
| 18 | | ARVDQTPQTITKETGESLTMYCVLRDSNCALSSTYWYRKK SGSTNEESISSGGRYVETVNSGSKSFSLRINDLTVEDSGTYR CLVRLGVVYEYCPVLGGVYDVYGGGTAVTVNAASGA | DSNCALS | 423 | VRLGWYEYCPV LGGVYDV | 202 | 12 |
| 19 | | ARVDQTPRIATKETGESLTINCVLRDNNCALPSTNWYRTK LGSTKEQTISIGGRYSETVDEGSNSASLTIRDLRVEDSGTYK CKAVSWCTRHTMWNVVYTVHEGAGTVLTVKEASGA | DNNCALP | 418 | VSWCTRHTMWNV VYTVH | 203 | 13 |
| 20 | | ARVDQTPRIATKETGESLTINCVLRDNNCALPSTNWYRTK LGSTKEQTISIGGRYSETVDEGSNSASLTIRDLRVEDSGTYK CKAVVYHMSSSDCLSGYSYEGAGTVLTVKEASGA | DNNCALP SY | 418 | WYWHMSSSDCL SGY | 204 | 14 |
| 21 | | ARVDQTPQTITKETGESLTINCVLRDNDCALSSTHWYRKK SGSTNEESISKGGRYVETVNSGSKSFSLRINDLTVEDSGTYR CNVYAMTANWWCDVYGGGTVVTVNAASGA | DNDCALS | 426 | YAMTANWWCDV | 205 | 15 |
| 22 | | ARVDQTPQTITKETGESLTINCVLRDNDCALSSTHWYRKK SGSTNEESIWKGGRYVETVNSGSKSFSLRINDLTVEDSGTY RCNVYAMTANWWCDVYGGGTVVTVNAASGA | DNDCALS | 426 | YAMTANWWCDV | 206 | 15 |
| 23 | | ARVDQTPQTITKETGESLTINCVLRDRDCALSSTHWYRKK SGSTNEESISKGGRYVETVNSGSKSFSLRINDLTTEDSGTYR CNVYAMTANWWCDVYGGGTVVTVNAASGA | DRDCALS | 427 | YAMTANWWCDV | 207 | 15 |
| 24 | | ARVDQTPQTITKETGESLTINCVLRDRDCALSSTYWYRKKS GSSNEESISKGGRYVETVNSGSKSFSLRINDLTVEDSGTYRC NVYAMTANWWCDVYGGGTAVTVNAASGA | DRDCALS | 427 | YAMTANWWCDV | 208 | 15 |
| 25 | | ARVDQTPQTITKETGESLTINCVLRDRDCALSSTYWYRKKS GSSNEESISKGGRYVETVNSGSKSFSLRINDLTVEDSGTYRC NVYAMTANWWCDVYGGGTVVTVNAASGA | DRDCALS | 427 | YAMTANWWCDV | 209 | 15 |
| 26 | | ARVDQTPQTITKETGESLTINCVLRDEDCALSSTYWYHKKS GSTNEESISKGGRYVETVNSGSKSFSLRINDLTVEDSGTYRC NIYGLTANWWCDVYGGGTVVTVNAASGA | DEDCALS | 428 | YGLTANWWCDV | 210 | 15 |
| 27 | | ARVDQTPQTITKETGESLTINCVLRDNDCTLSSTYWYRKKS GSTNEERISKGGRYVETVNSGSKSFSLRINDLTVEDSGTYRC NVYAMTRNWWCDVYGDGTAVTVNAASGA | DNDCTLS | 429 | YAMTRNWWCDV | 211 | 15 |
| 28 | | ARVDQTPQTITKETGESLTINCVLRDNDCTLSSTYWYRKKS GSTNEERISKGGRYVETVNSGSKSFSLRINDLTVEDSGTYRC NVYAMTRNWWCDVYGGGTVVTVNAASGA | DNDCTLS | 429 | YAMTRNWWCDV | 212 | 15 |
| 29 | | ARVDQTPQTITKETGESLTINCVLRDRDCALSSTHWYRKK SGSTNEESISKGGRYVETVNSGSKSFSLRINDLTVEDSGTYR CNVYSMTANWWCDVYGGGTVVTVNAASGA | DRDCALS | 427 | YSMTANWWCDV | 213 | 15 |
| 30 | "F02" | ARVDQTPQTITKETGESLTINCVLRDNDCTLSSTHWYRKK SGSTNEERISKGGRYVETVNSGSKSFSLRINDLTVEDSGTYR CNVYAMTRNWWCDVYGGGTVVTVNAASGA | DNDCTLS | 429 | YAMTRNWWCDV | 214 | 15 |
| 31 | "A03" | ARVDQTPQTITKETGESLTINCVLRDRDCALSSTHWYRKK SGSTNEESIPKGGRYVETVNSGSKSFSLRINDLTVEDSGTYR CNVYSLTANWWCDVYGGGTVVTVNAASGA | DRDCALS | 427 | YSLTANWWCDV | 215 | 15 |
| 32 | | ARVDQTPQTITKETGESLTINCVLRDSNCALSSAYWYRKKS GSTNEESISAGGRYVETVNKGSKSFSLTINDLTVEDNGTYR CNIYAREDTWYGSRDCGLGDVYGGGTVVTVNAASGA | DSNCALS | 423 | YAREDTVVYGS RDCGLGDV | 216 | 16 |
| 33 | | ARVDQTPRIATKETGESLTINCVLRDSNCALPSTNWYRTKL GSTKEQTISIGGRYSETVDEGSNSASLTIRDLRVEDSGTYKC KAYDYCLHWFHPYVIEGAGTVLTVKEASGA | DSNCALP | 419 | YDYCLHWFHPY VI | 217 | 17 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 34 | "H11" | ARVDQTPQTITKETGESLTINCVLRDNDCALSSTYWYRKKS GSTNEERMTKGGRYVETVNSGSKSFSLRINDLTVEDSGTYR CNVYGLVDCASGMNWIDVYGGGTVVTVNAASGA | DNDCALS | 426 | VYGLVDCASGM NWIDV | 218 | 18 |
| 35 | | ARVDQTPQTITKETGESLTINCVLRDNNCPLSSTYWYRKKS GSTNEESISKGGRYVETVNSGSKSFSLRINDLTVEDSGTYRC NVYGLVDCGSGMNWIDVYGGGTAVTVNAASGA | DNNCPLS | 430 | YGLVDCGSGMN WIDV | 219 | 18 |
| 36 | | ARVDQTPQTITKETGESLTINCVLRDNNCPLSSTYWYRKKS GSTNEESISKGGRYVETVNSGSKSFSLRINDLTVEDSGTYRC NVYGLVDCGSGMNWIDVYGGGTVVTVNAASGA | DNNCALS | 431 | YGLVDCGSGMN WIDV | 220 | 18 |
| 37 | | ARVDQTPQTITKETGESLTINCVLRDNDCALSSTYWYRKKS GSTNEERMTKGGRYVETVNSGSKSFSLRINDLTVEDSGTYR CNVYGLVDCASGMNWIDVYGGGTVVTVNAASGA | DNDCALS | 426 | YGLVDCASGMN WIDV | 221 | 18 |
| 38 | | ARVDQTPQTITKETGESLTINCVLRDSNCALSNTYWYRKK QGSHHEESISKGGRYVETVNSGSKSFSLRINDLTVEDSGTYR CNVYGVIECRYEGMNWFDVYGDGTAVTVNAASGA | DSNCALS | 423 | YGVIECRYEGM NWFDV | 222 | 19 |
| 39 | | ARVDQTPQTITKETGESLTINCVLRDSNCALSNTYWYRKKS GSHHEESISKGGRYVETVNSGSKSFSLRINDLTVEDSGTYRC NVYGVIECRYEGMNWFDVYGDGTAVTVNAASGA | DSNCALS | 423 | YGVIECRYEGM NWFDV | 223 | 19 |
| 40 | | ARVDQTPQTITKETGESLTINCVLRDSNCALSNTYWYRKKS GSHHEESISKGGRYVETVNSGSKSFSLRINDLTVEDSGTYRC NVYGVIECRYEGMNWFDVYGGGTVVTVNAASGA | DSNCALS | 423 | YGVIECRYEGM NWFDV | 224 | 19 |
| 41 | | ARVDQTPQTITKETGESLTINCVLRDSNCPLSSTYWYRKKS GSTNEESISKGGRYVETVNSGSKSFSLRINDLTVEDSGTYRC NVYNIAVMCNDYVRYWTDVYGGGTVVTVNAASGA | DSNCPLS | 432 | YNIAVMCNDYV RYWTDV | 225 | 20 |
| 42 | "C02" | ARVDQTPQTITKETGESLTINCVLRDNDCALSSTYWYRKKS GSTNEESISKGGRYVETVNSGSKSFSLRINDLTVEDSGTYRC NVYQPPSTESLYWCDVYGGGTAVTVNAASGA | DNDCALS | 426 | YQPPSTESLYW CDV | 226 | 21 |
| 43 | | ARVDQTPQTITKETGESLTINCVLRDSDCALSSTYWYRKKS GSTNEESISKGGRYVETVNSGSKSFSLRINDLTVLDSGTYRC NVYQPPSTESLYWCDVYGGGTVVTVNAASGA | DSDCALS | 433 | YQPPSTESLYW CDV | 227 | 21 |
| 44 | | ARVDQTPQTITKETGESLTINCVLRDSDCALSSTHWYRKKS GSTNEESISKGGRYVETVNSGSKSFSLRINDLTVEDSGTYRC NVYSGPSYDQLFWCDVYGDGTAVTVNAASGA | DSDCALS | 433 | YSGPSYDQLFW CDV | 228 | 22 |
| 45 | | ARVDQTPQTITKETGESLTINCVLRDSDCALSSTHWYRKKS GSTNEESISKGGRYVETVNSGSKSFSLRINDLTVEDSGTYRC NVYSGPSYDQLFWCDVYGGGTVVTVNAASGA | DSDCALS | 433 | YSGPSYDQLFW CDV | 229 | 22 |
| 46 | | ARVDQTPQTITKETGESLTINCVLRDSDCALSSTHWYRKKS GSTNEESISKGGRYVETVNSGSKSFSLRINDLTVEDSGTYRC NVYSGPSYDQLFWCDVYGGGTVVTVNAASGA | DSDCALS | 433 | YSGPSYDQLFW CDV | 230 | 22 |
| 47 | | ARVDQTPQTITKETGESLTINCVLRDSNCALSSTYWYRKKS GSTNEESISKGGRYVETVNSGSKSFSLRINDLTVEDSGTYRC NVYSGPSYDQLFWCDVYGDGTAVTVNAASGA | DSNCALS | 423 | YSGPSYDQLFW CDV | 231 | 22 |
| 48 | | ARVDQTPQTITKETGESLTINCVLRDSNCALSSTYWYRKKS GSTNEESISKGGRYVETVNSGSKSFSLRINDLTVEDSGTYRC NVYSTPSYDQLYWCDVYGDGTAVTVNAASGA | DSNCALS | 423 | YSTPSYDQLYW CDV | 232 | 22 |
| 49 | | ARVDQTPQTITKETGESLTINCVLRDSNCALSSTYWYRKKS GSTNEESISKGGRYVETVNSGSKSFSLRINDLTVEDSGTYRC NVYSTPSYDQLYWCDVYGGGTAVTVNAASGA | DSNCALS | 423 | YSTPSYDQLYW CDV | 233 | 22 |
| 50 | | ARVDQTPQTITKETGESLTINCVLRDNNCALSSTHWYRKK SGSTNEESISKGGRYVETVNVGSKSFSLRINDLTVEDSGTYR CNVYVPPGYDCNYWMDVYGGGTVVTVNAASGA | DNNCALS | 431 | YVPPGYDCNYW MDV | 234 | 23 |
| 51 | "H01" | ARVDQTPQTITKETGESLTINCVLRDSNCALSSTYWYRKKS GSTKEESISKGGRYVETVNSGSKSFSLRINDLTVEDSGTYRC NVWHDLVWSVCTTDVYGGGTVVTVNAASGA | DSNCALS | 423 | WHDLVWSVCTT DV | 235 | 24 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 52 | | ARVDQTPQTITKETGESLTINCVLRDSDCALSSTYWYRKKS GSTKEESISKGGRYVETVNSGSKSFSLRINDLTVEDSGTYRC NVWHDLVWSVCTTDVYGGGTVVTVNAASGA | DSDCALS | 433 | WHDLVWSVCTTDV | 236 | 24 |
| 53 | "C11" | ARVDQTPQTITKETGESLTINCVLRDKDCALSSTYWYRKKS GSTNEESISKGGRYVETVNSGSKSFSLRINDLTVEDSGTYRC NVYARPRPDNLNWCDVYGGGTAVTVNAASGA | DKDCALS | 434 | YARPRPDNLNWCDV | 237 | 25 |
| 54 | | ARVDQTPQTITKETGESLTINCVLRDSDCALSSTYWYRKKS GSTNEESISKGGRYVETVNSGSKSFSLRINDLTVEDSGTYRC NVYARPRPDNLNWCDVYGGGTAVTVNAASGA | DNDCALS | 426 | YARPRPDNLNWCDV | 238 | 25 |
| 55 | | ARVDQTPQTITKETGESLTINCVLRDSNCAATVTYWYRKT SGSTHEEMISKGGRYVETFSSGSKSFSLRINELTVEDSGXYR CNVLRDSCYDVTNWLERYGGGTVVTVNAASGA | DSNCAAT | 435 | LRDSCYDVTNWLER | 239 | 26 |
| 56 | "G04" | ARVDQTPQTITKETGESLTINCVLRDSICALSSTHWYRKKS GSTNEESISKGGRYVETVNSGSKSFSLRINDLTVEDSGTYRC NVENFLLDCYDWLDVYGGGTVVTVNAASGA | DSICALS | 424 | ENFLLDCYDWLDV | 240 | 27 |
| 57 | | ARVDQTPQTITKETGESLTINCVLRDSNCALSNLYWYRKKS GSTNEESISLGGRYVETVNSGSKSFSLRINDLTVEDSGTYRC NVERHWRSRCQRAVDVYGGGTAVTVNAASGA | DSNCALS | 423 | ERHWRSRCQRAVDV | 241 | 28 |
| 58 | | ARVDQTPQTITKETGESLTINCVLRDSNCALSSTYWYRKKS GSTNEESISKGGRYVETVNSGSKSFSLRINDLVVEDSGTYRC KVBLWCLCPCTVWVLGDVYGGGTVVTVNAASGA | DSNCALS | 423 | BLWCLCPCTWVVLGDV | 242 | 29 |
| 59 | | ARVDQTPRSVTKETGESLTINCVLRDSICALSSTHVVYRKKS GSTNEESISKGGRYVETVNSGSKSFSLRINDLVVEDSGTYRC NVCGILCCFBFDVYGGGTVVTVNAASGA | DSICALS | 424 | CGILCCFBFDV | 243 | 30 |
| 60 | | ARVDQTPQTITKETGESLTINCVLRDSNCDLSRTYVVYRKKS GSTNEESISKGGRYVETVNSGSKSFSLRINDLVVEDSGTYRC NVTAILSBDCGAFADVYGDGTAVTVNAASGA | DSNCDLS | 416 | TAILSBDCGAFADV | 244 | 31 |
| 61 | | ARVDQTPQTITKETGESLTINCVLRDSNCALSSTYWYRKKS GSTNEENISKGGRYVETVNSGSKSFSLRINDLTVEDSGTYRC NVTGLRYHSGCRTGDVYGGGTAVTVNAASGA | DSNCALS | 423 | TGLRYHSGCRTGDV | 245 | 33 |
| 62 | | ARVDQTPQTITKETGESLTINCVLRDSNCALSSTYWYRKKS GSTNEESISKGGRYVETVNSGSKSFSLRINDLTVEDSGTYRC NVCFGBCVNSCGESMDVYGDGTAVTVNAASGA | DSNCALS | 423 | CFGBCVNSCGESMDV | 246 | 34 |
| 63 | | ARVDQTPQTITKETGESLTINCVLRDSNCALPSTYWYRKKS GSTNEESISKGGRYVETVNSGSKSFSLRINDLTVKDSGTYRC NVLRFBCVFHWDVYGGGTVVTVNAASGA | DSNCALP | 419 | LRFBCVFHWDV | 247 | 35 |
| 64 | | ARVDQTPQTITKETGESLTINCVLRDSNCALPSTYVVYRKKS GSTNEESISKGGRYVETVNSGSKSFSLRINDLTVKDSGTYRC KVRDVVLVBYGYCLVDGQDVYGGGTVVTVNAASGA | DSNCALP | 419 | RDVVLVBYGYCLVDGQDV | 248 | 36 |
| 65 | "A07" | ARVDQTPQTITKEEGESLTINCVLRDSSSALASTSWYRKKS GSTREETISKGGRYVETVNSGSKSFSLRINDLTVEDSGTYRC NVYELVEDTSAYEIGVDVYGDGTAVTVNAASGA | DSSSALAS | 436 | YELVEDTSAYEIGVDV | 249 | 37 |
| 66 | "G02" | ARVDQTPQTITKETGESLTINCVLRDRDCALSSTHVVYRKK SGSTNEESISKGGRYVETVDSGSKSFSLRINDLTVEDSGTYR CNVYQSPVGRRWCDVYGGGTVVTVNAASGA | DRDCALS | 427 | YQSPVGRRWCDV | 250 | 38 |
| 67 | | ARVDQTPQTITKETGESSTINCVSRDSNCELSLTYWYRKKS GSTLEESIAKGGRYVETVNSKSKSFSLRINDLTVEDSGTYRC NLWYRPDCEEEFDVYGGGTAVTVNA | DSNCELS | 437 | WYRPDCEEEFDV | 251 | 39 |
| 68 | | ARVDQTPQTITKETGESSTINCVSRDSNCELSLTYWYRKKS GSTLEESIAKGGRYVETVNSKSKSFSLRINDLTVEDSGTYRC NLWYRPDCEEEFDVYGGGTVVTVNA | DSNCELS | 437 | WYRPDCEEEFDV | 252 | 39 |
| 69 | | ARVDQTPQTITKETGESSTINCVSRDSNCELSLTYWYRKKS GSTLEESIAKGGRYVETVNSKSKSFSLRINDLTVEDSGTYRC NLWYRPDCEEEFDVYGDGTAVTVNA | DSNCELS | 437 | WYRPDCEEEFDV | 253 | 39 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 70 | | ARVDQXPQTITKETGESSTINCVSRDSNCELSLTYWYRKKS GSTLEESIAKGGRYVETVNSKSKSFSLRINDLTVEDSGTYRC NLWYRPDCEEEFDVYGGGTVVTVNA | DSNCELS | 437 | WYRPDCEEEFDV | 254 | 39 |
| 71 | | ARVDQTPQTITKETGESSTINCISLDSNCELSLTYWYRKKT GSTFEENIAKGGRYVETVNSKSKSFSLRINDLTVEDSGTYRC NLWYRPDCEEEFDVYGGGTAVTVNA | DSNCELS | 437 | WYRPDCEEEFDV | 255 | 39 |
| 72 | | ARVDQTPQTITKETGESSTINCISLDSNCELSLTYWYRKKT GSTFEENIAKGGRYVETVNSKSKSFSLRINDLTVEDSGTYRC NLWYRPDCEEEFDVYGGGTVVTVNA | DSNCELS | 437 | WYRPDCEEEFDV | 256 | 39 |
| 73 | | ARVDQXPQTITKETGESSTINCVLRDSNCALSLTYWYRKKS GSTNEESISKGGRYVETVNSGSKSFSLRINDLIVEDSGTYRC NAWYRPDCELDYDVYGGGTVVTVNA | DSNCALS | 423 | WYRPDCELDYDV | 257 | 40 |
| 74 | | ARVDQTPQTITKETGESSTINCVLRDSNCALSLTYWYRKKS GSTNEESISKGGRYVETVNSGSKSFSLRINDLIVEDSGTYRC NAWYRPDCELDYDVYGGGTAVTVNA | DSNCALS | 423 | WYRPDCELDYDV | 258 | 40 |
| 75 | | ARVDQTPQTITKETGESSTINCVLRDSNCALSLTYWYRKKS GSTNEESISKGGRYVETVNSGSKSFSLRINDLIVEDSGTYRC NAWYRPDCELDYDVYGGGTVVTVNA | DSNCALS | 423 | WYRPDCELDYDV | 259 | 40 |
| 76 | | ARVDQTPQTITKETGESSTINCVLRDSNCALSLTYWYRKKS GSTNEESISKGGRYVETVNSGSKSFSLRINDLIVEDSGTYRC NAWYRPDCELDYDVYGDGTAVTVNA | DSNCALS | 423 | WYRPDCELDYDV | 260 | 40 |
| 77 | | ARVDQTPQSITKDAGESSTINCVLLDSNCALESTYWYRKKS GSSNEETEISKGGRYVETVNSGSKSFSLKINDLTIEDSGTFRC NANTWQARHPYDCAESLRVYGDGTAVTVNA | DSNCALE | 438 | NTWQARHPYDCAESLRV | 261 | 41 |
| 78 | | ARVDQTPQSITKDAGESSTINCVLLDSNCALESTYWYRKKS GSSNEETEISKGGRYVETVNSGSKSFSLKINDLTIEDSGTFRC NANTWQARHPYDCAESLRVYGGGTAVTVNA | DSNCALES | 439 | NTWQARHPYDCAESLRV | 262 | 42 |
| 79 | | ARVDQTPQSITKDAGESSTINCVLLDSNCALESTYWYRKKS GSSNEETEISKGGRYVETVNSGSKSFSLKINDLTIEDSGTFRC NANTWQARHPYDCAESLRVYGGGTVVTVNA | DSNCALE | 438 | NTWQARHPYDCAESLRV | 263 | 43 |
| 80 | | ARVDQTPQTITKETGESSTINCVLRDTNCALSSTYWYRQNS GSRREESIPKGGRYKETLNSGSKSFSLRINDLRIEDTGTYLC KADNFACEMAYNVYGGGTVVTVNA | DTNCALS | 440 | DNFACEMAYNV | 264 | 44 |
| 81 | | ARVDQTPQTITKETGESSTLNCVLRDINCALQVTYWIRKKS GSTNEESISKGGRYVETVNSGSKSFSLRINDLTVEDSGTYRC NVLWGSYPCDEIMHGTAVYGGGTVVTVNA | DINCALQ | 441 | LWGSYPCDEIMHGTAV | 265 | 45 |
| 82 | | ARVDQTPQTITKETGESSTINCVLRDSNCRLSKTYWLRKKS GSLNEENISLGGRYVETVNSGSKSFSLRINDSTVEDSGTYRC NALPRPISWINCDDSHAYGGGTVVTVNA | DSNCRLS | 442 | LPRPISWINCDDSHA | 266 | 46 |
| 83 | | ARVDQTPQTITKETGESSTINCVLRDSNCGFSSTYWYRKTA TSRGEELIKRGGRYVETINSESKSFSLRITDLTVEDSGTYRC NLVWGWSCDVYGGGTVVTVNA | DSNCGFS | 443 | VWGWSCDV | 267 | 47 |
| 84 | | ARVDQTPQTITKETGESSTINCVLRDSNCGFSSTYWYRKTA TSRGEELIKRGGRYVETINSESKSFSLRITDLTVEDSGTYRC NLVWGWSCDVYGGGTAVTVNA | DSNCGFS | 443 | VWGWSCDV | 268 | 47 |
| 85 | | ARVDQTPQTITKETGESSTINCVLRDSNCGFSSTYWYRKTA TSRGEELIKRGGRYVETINSESKSFSLRITDLTVEDSGTYRC NLVWGWSCDVYGDGTAVTVNA | DSNCGFS | 443 | VWGWSCDV | 269 | 47 |
| 86 | | ARVDQTPQTITKETGESSTINCVLRDSNCALSSTYWYRKKS GSTNEESISKGGRYVETVNKGAKSFSLRINDLTVEDSGTYRC NKGAGFFALMNCNYDVYGGGTVVTVNA | DSNCALS | 423 | GAGFFALMNCNYDV | 270 | 48 |
| 87 | | ARVDQTPQTITKETGESSTINCVLRDSNCALSSTYWYRKKS GSTREEIISKGGRYVETVNSGSKSFSLRINDLTVEDSGTYQC NAYHDRHITKNWRCPNLDVYGGGTVVTVNA | DSNCALSLDV | 423 | YHDRHITKNWRCPN | 271 | 49 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 88 | | ARVDQTPQTITKETGESSTINCVLRDSNCALSSTYWYRKKS GSTNEENISKGGRYVETVNSGSKSFSLRINDLTVEDSGTYRC MTWYGYDCGAMNRDVYGGGTVVTVNA | DSNCALS | 423 | WYGYDCGAMNRDV | 272 | 50 |
| 89 | | ARVDQTPQTITKETGESSTINCVLRDSNCALSTTYWYRKTS GSANDQSISKGGRYVETVDYGSKSFSLRINDLTVEDSGTYRC KKWGPDIDGAGYGTHGCYDVYGGGTVVTVNA | DSNCALS | 423 | WGPDIDGAGYGTHGCYDV | 273 | 51 |
| 90 | | ARVDQTPQTITKETGESSTINCVARDSNCALSRTYWYRKKS GSTNEESISKGGRYVETVNSGSKSFSLRINDLTVEDSGTYRC NAWYRPDCESDYDVYGGGTVVTVNA | DSNCALS | 423 | VVYRPDCESDYDV | 274 | 52 |
| 91 | | ARVDQTPQTITKETGESSTINCVARDSNCALSRTYWYRKKS GSTNEESISKGGRYVETVNSGSKSFSLRINDLTVEDSGTYRC NAWYRPDCESDYDVYGGGTAVTVNA | DSNCALS | 423 | WYRPDCESDYDV | 275 | 52 |
| 92 | | ARVDQTPQTITKETGESSTINCVLRDSNCALSSTYWYRKKS GSTNEESISKGGRYVETVNSGSKSFSLRINDLTVEDSGTYRC NVFGRYGWYHDCIDTGEAYGGGTAVTVNA | DSNCALS | 423 | FGRYGVVYHDCIDTGEA | 276 | 53 |
| 93 | | ARVDQTPQTITKETGESSTINCVLRDSNCALSSTYWYRKKS GSTNEESISKGGRYVETVNSGSKSFSLRINDLTVEDSGTYRC NVFGRYGWYHDCIDTGEAYGGGTVVTVNA | DSNCALS | 423 | FGRYGWYHDCIDTGEA | 277 | 53 |
| 94 | | ARVDQTPQTITKETGESSTINCVLRDSNCALSSTYWYRKKS GSTNEESISKGGRYVETVNSGSKSFSLRINDLTVEDSGTYRC NVFGRYGWYHDCIDTGEAYGDGTAVTVNA | DSNCALS | 423 | FGRYGWYHDCIDTGEA | 278 | 53 |
| 95 | | ARVDQTPQTITKETGESSTINCVLRDSNCALSSTYWYRKKS GSTNEENISKGGRYVETVNSGSKSFSLRINDLTVEDSGTYRC NVFGRYGWYHDCIDTGEAYGGGTVVTVNA | DSNCALS | 423 | FGRYGWYHDCIDTGEA | 279 | 53 |
| 96 | | ARVDQTPQTITKETGESSTINCVLRASNCALSSTYWYRKKS GSTNEESISKGGRYVETVNSGSKSFSSRINDLTVEDSGTYRC NVFGRYGWYHDCIDTGEASGGGTVVTVNA | ASNCALS | 444 | FGRYGWYHDCIDTGEA | 280 | 53 |
| 97 | | ARVDQTPQTITKETGESSTINCVLRASNCALSSTYWYRKKS GSTNEESISKGGRYVETVNSGSKSFSSRINDLTVEDSGTYRC NVFGRYGWYHDCIDTGEASGGGTAVTVNA | ASNCALS | 444 | FGRYGWYHDCIDTGEA | 281 | 53 |
| 98 | | ARVDQTPQTITKETGESSTINCVLRDSNCALSSTYVVYRKRT GSTNEESISKGGRYVETVNSGSKSFSLRINDLTVEDSGTYRC NVFGRYGWYHDCIDTGEAYGGGTVVTVNA | DSNCALS | 423 | FGRYGWYHDCIDTGEA | 282 | 53 |
| 99 | | ARVDQTPQTITKETGESSTINCVLRDSNCALSSTYWYRKKS GSTNEESISKGGRYVETVNSGSKSFSLRINDLRVEDSGTYRC NVFGRYGWYHDCIDTGEAYGGGTVVTVNA | DSNCALS | 423 | FGRYGWYHDCIDTGEA | 283 | 53 |
| 100 | | ARVDQTPRSVTKETGESSTINCVLRDANYALGSTCWYRKN SGSTNLESISKGGRYVETVNSGSKSFSLRINDLTVEDGGTYR CGVCTRWCPSCDESCSRNFAACGDGTAVTVNA | DANYALG | 445 | CTRWCPSCDESCSRNFAAC | 284 | 54 |
| 101 | | ARVDQTPQTITKETGESSTINCVLSDSRCELSNTYWYREKS GSRNEESISKGGRYVETVNSGSKSFSLRINDLTVEDSGTYRC KANSFSCESAYNVYGGGTVVTVNA | DSRCELS | 446 | NSFSCESAYNV | 285 | 55 |
| 102 | | ARVDQTPQTITKETGESSTINCVLSDSRCELSNTYWYREKS GSRNEESISKGGRYVETVNSGSKSFSLRINDLTVEDSGTYRC KANSFSCESAYNVYGGGTAVTVNA | DSRCELS | 446 | NSFSCESAYNV | 286 | 55 |
| 103 | | ARVDQTPQTITKDAGESSTINCVLRDSNCALDHTFWYRKK PGSRNEESISKGGRYVETVYSGSKSFSLRINDLTVEDSGVFR CQVNNFACESAYNVYGGGTVVTVNA | DSNCALD | 447 | NNFACESAYNV | 287 | 55 |
| 104 | | ARVDQTPQTITKDAGESSTINCVLRDSNCALDHTFWYRKK PGSRNEESISKGGRYVETVYSGSKSFSLRINDLTVEDSGVFR CQVNNFACESAYNVYGGGTAVTVNA | DSNCALD | 447 | NNFACESAYNV | 288 | 55 |
| 105 | | ARVDQTPQTITKETGESSTINCILSDSNCALSTTHWHRQKP GSRNEENIPKGGRYVETVNYRSKSFSLTINDLTVEDADTYR CRASSFSCEMAYNVYGGGTAVTVNA | DSNCALS | 423 | SSFSCEMAYNV | 289 | 56 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 106 | | ARVDQTPQTITKETGESSTINCILSDSNCALSTTHWHRQKPGSRNEENIPKGGRYVETVNYRSKSFSLTINDLTVEDADTYRCRASSFSCEMAYNVYGGGTVVTVNA | DSNCALS | 423 | SSFSCEMAYNV | 290 | 56 |
| 107 | | ARVDQTPQTITKETGESSTINCILSDSNCALSTTHWHRQKPGSRNEENIPKGGRYVETVNYRSKSFSLTINDLTVEDADTYRCRASSFSCEMAYNVYGDGTAVTVNA | DSNCALS | 423 | SSFSCEMAYNV | 291 | 56 |
| 108 | | ARVDQTPQTITKETGESSTINCILRDSNCALSTTYWYRQKPGSRNEENIPKGGRYVETVNNRSKSFSLTINDLTVEDADTYRCRASSFSCESAYNVYGGGTVVTVNA | DSNCALS | 423 | SSFSCESAYNV | 292 | 56 |
| 109 | | ARVDQTPQTITKETGESSTINCVLRDSNCALSSTYWYRKKSGSTNEESISKGGRYVETVNSGSKSFSLRINDLTVEDSGTYRCNVWAPYDCENWRDVYGGGTVVTVNA | DSNCALS | 423 | WAPYDCENWRDV | 293 | 57 |
| 110 | | ARVDQTPQTITKETGESSTINCVLRDSNCALSNTYWYRLFSGSRREERISKGGRYVETVNSGSKSFSLRINDLRIEDTGTYKCKATNFACESAYNVYGGGTAVTVNA | DSNCALS | 423 | TNFACESAYNV | 294 | 58 |
| 111 | | ARVDQTPQTITKETGESSTINCVLRDSNCALSNTYWYRLFSGSRREERISKGGRYVETVNSGSKSFSLRINDLRIEDTGTYKCKATNFACESAYNVYGGGTAVTVNA | DSNCALS | 423 | TNFACESAYNV | 295 | 58 |
| 112 | | ARVDQTPQTITKETGESSTINCILRDSNCRLSSTYWYRKKSGSTNEESISKGGRYVETVNSGSKSFSLRINDLTVEDSGTYRCNVAGMDARYDCGSNWTVYGGGTVVTVNA | DSNCRLS | 442 | VAGMDARYDCGSNWTV | 296 | 59 |
| 113 | | ARVDQTPRSVTKETGESSTINCVLRDASYALGSTCWYRKKSGSTNEERISKGGRYVETVNSGSKSFSLRINDLTVEDGGTYRCASSSWCTSLTVTCGVDPYAVCGDGTAVTVNA | DASYALG | 425 | SSWCTSLTVTCGVDPYAVC | 297 | 60 |
| 114 | | ARVDQTPQTITKETGESSTISCVLRDSPCALTSVYWYRKKSGSTNEESISKGGRYVETVNTGSKSFSLRINDLTVEDSGTYRCRNLGFNARAFSEAGCEQYGGGTVVTVNA | DSPCALT | 448 | GFNARAFSEAGCEQ | 298 | 61 |
| 115 | | ARVDQTPQTITKETGESSTINCVLRDSDCADVSAHWRRKKSASTREEVISQDGRYVETVNSGSKSFSLRINDLRFEDSGTYRCNVRASWDLESYCTGLDVYGGGTVVTVNA | DSDCADV | 449 | RASWDLESYCTGLDV | 299 | 62 |
| 116 | | ARVDQTPQTITKETGESSTINCVLRDSNCAFSSTYWYRKKSGSTNEESISKGGRYVETVNSGSKSFSLRINDLTVEDSGTYRCNWYSICIETVDVYGGGTVVTVNA | DSNCAFS | 450 | WYSICIETVDV | 300 | 63 |
| 117 | | ARVDQTPQTITKETGESSTINCVLRDSNCAWSSTYWYRKKSGSTNEESISKGGRYVETVNSGSKSFSLRINDLTVEDSGTYRCNWYSICIETVDVYGDGTAVTVNA | DSNCAWS | 451 | YSICIETVDV | 301 | 63 |
| 118 | | ARVDQTPQTITKETGESSTINCVLRDSNCAWSSTYWYRKKSGSTNEESISKGGRYVETVNSGSKSFSLRINDLTVEDSGTYRCNWYSICIETVDVYGGGTVVTVNA | DSNCAWS | 451 | YSICIETVDV | 302 | 63 |
| 119 | | ARVDQTPQTITKETGESSTINCVLRDSNCAWSSTYWYRKKSGSTNEESISKGGRYVETVNSGSKSFSLRINDLTVEDSGTYRCNWYSICIETVDVYGGGTVVTVNA | DSNCAWS | 451 | YSICIETVDV | 303 | 63 |
| 120 | | ARVDQTPQTITKETGESSTINCVLRDTSCALGTTYWTYKESGSTNEENISVGGRYVETINSGSKSFSLRINDLTLEDSGTYRCKNWFDCGSGTGRLVYGGGTVVTVNA | DTSCALG | 452 | WFDCGSGTGRLV | 304 | 64 |
| 121 | | ARVDQTPQTITKSTGESSTINCVLRDTYCALSNTNWYHKKSGSTHEESISKGGRYVETLNTDSKSFSLRITDLTIEDSGLYRCNIYQLPPSRWTTECLLDLYGGGTVVTVNA | DTYCALS | 453 | YQLPPSRWTTECLLDL | 305 | 65 |
| 122 | | ARVDQTPQTITKSTGESSTINCVLRDTYCALSNTNWYHKKSGSTHEESISKGGRYVETLNTDSKSFSLRITDLTIEDSGLYRCNIYQLPPSRWTTECLLDLYGDGTAVTVNA | DTYCALS | 453 | YQLPPSRWTTECLLDL | 306 | 65 |
| 123 | | ARVDQTPQTITKSTGESSTINCVLRDTYCALSNTNWYHKKSGSTHEESISKGGRYVETLNTDSKSFSLRITDLTIEDSGLYRCNIYQLPPSRWTTECLLDLYGGGTVVTVNA | DTYCALS | 453 | YQLPPSRWTTECLLDL | 307 | 65 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 124 | | ARVDQTPKTITKETGESSTINCVLVESKYPLGSTCWFRKRS GSTSEEIISKGGRYVETVNSGSKSFSLRINDLTDEDGGTYRC GGSVLVAEKSCNCTSAYTECGDGTAVTVNA | ESKYPLG | 454 | SVLVAEKSCN CTSAYTEC | 308 | 66 |
| 125 | | ARVDQTPRSVTKETGESSTINCVLRDASYSLGTTCWYRKKS GSTNEENISKGGRYVETVNSGSKSFSLRINDLTVEDGGTYR CGASPPDWSCDGSCRLDAACGDGTAVTVNA | DASYSLG | 455 | SPPDWSCDGS CRLDAAC | 309 | 67 |
| 126 | | ARVDQTPRSVTKETGESSTINCVLRDASYGLVETCWYRKK SDSTYEETISKGGRYVETVVSGSKSFSLRINDLTVEDGGTYR CGVRCAVRLGYSGCSGTYATCGDGTAVTVNA | DASYGLV | 456 | RCAVRLGYSG CSGTYATC | 310 | 68 |
| 127 | | ARVDQTPQTITKLEGESSTINCVLRDNNCGLSDTHWFYKR SGSVHEEKISKGGRYVETVNSRSKSFSLRINDLTVEDSGTYR CNGKGQCFVSGGSTLPYNEYGGGTAVTVNA | DNNCGLS | 457 | KGQCFVSGGS TLPYNE | 311 | 69 |
| 128 | | ARVDQTPQTITKLEGESSTINCVLRDNNCGLSDTHWFYKR SGSVHEEKISKGGRYVETVNSRSKSFSLRINDLTVEDSGTYR CNGKGQCFVSGGSTLPYNEYGGGTVVTVNA | DNNCGLS | 457 | KGQCFVSGGS TLPYNE | 312 | 69 |
| 129 | | ARVDQTPQTITKETGESSTINCVLRDSNCALSSTYWYRKKS GPTNEESISKGGRYVETVNSGSKSFSLRINDLTVEDSGTYRC NVFESVCRYRGESEVDVYGGGTVVTVNA | DSNCALS | 423 | FESVCRYRGE SEVDV | 313 | 70 |
| 130 | | ARVDQTPQTITKETGESSTINCVLRDSNCALSSTYWYRKKS GPTNEESISKGGRYVETVNSGSKSFSLRINDLTVEDSGTYRC NVFESVCRYRGESEVDVYGGGTVVTVNA | DSNCALS | 423 | FESVCRYRGE SEVDV | 314 | 70 |
| 131 | | ARVDQTPQTITKETGESSTINCVLRDSNCALSSTYWYRKKS GPTNEESISKGGRYVETVNSGSKSFSLRINDLTVEDSGTYRC NVFESVCRYRGESEVDVYGDGTAVTVNA | DSNCALS | 423 | FESVCRYRGE SEVDV | 315 | 70 |
| 132 | | ARVDQTPQTITKETGESSTINCVLRDTNCALSPTNWYRKK SGSTNEESISKGGRYVETVNSGSKSFSLRINDLTVEDRGTYR CNVYSPDDCTDYNYDVYGGGTAVTVNA | DTNCALS | 440 | YSPDDCTDYN YDV | 316 | 71 |
| 133 | | ARVDQTPQTITKETGESSTINCVLRDTNCALSPTNWYRKK SGSTNEESISKGGRYVETVNSGSKSFSLRINDLTVEDRGTYR CNVYSPDDCTDYNYDVYGGGTVVTVNA | DTNCALS | 440 | YSPDDCTDYN YDV | 317 | 71 |
| 134 | | ARVDQTPRSVTKETGESSTINCVLRDASYALGSTCWYRKKS GSTNEESISKGGRYVETVNSGSKSFSLRINDLTVEDGGTYRC GVWCGLPDYRSWGARAACGDGTAVTVNA | DASYALG | 425 | WCGLPDYRSW GARAAC | 318 | 72 |
| 135 | | ARVDQTPQTITKETGESSTINCVIRDGTCAFASTFWYRNKQ GSTNEENISKGGRYVETVNKGSKSFSLRINDLTVEDSGTYR CKAASVCAPRLFETKDVIGGGTAVTVNA | DGTCAFA | 458 | ASVCAPRLFE TKDV | 319 | 73 |
| 136 | | ARVDQTPQTITKETGESSTINCVIRDGTCAFASTFWYRNKQ GSTNEENISKGGRYVETVNKGSKSFSLRINDLTVEDSGTYR CKAASVCAPRLFETKDVIGGGTVVTVNA | DGTCAFA | 458 | ASVCAPRLFE TKDV | 320 | 73 |
| 137 | | ARVDQTPQTITKETGESSTINCVLRDSNCALSSTFWYRKIS GSRNEDLISKSGRYVETVNSVAKSFSLRINDLTVKDTGTYR CNVFSWCDDSSDLDVYGGGTVVTVNA | DSNCALS | 423 | FSWCDDSSDL DV | 321 | 74 |
| 138 | | ARVDQTPRSVTKETGESSTINCVLRDAGWRSGSTCWYRKK SDSTNEESISEGGRYVETVNSGSNTFSLRINDLTVEDGTYL CGASLPEWGCSVYCRLDAACGDGTAVTVNA | DAGWRSG | 459 | SLPEWGCSVY CRLDAAC | 322 | 75 |
| 139 | | ARVDQTPQTITKETGESSTINCVLRDSECALSSTYWYRKKS GSTSEENISKGGRYVETVNSGSKSFSLRINDLTVEDSGTYRC NVANYDCFRRIELRNFYDRYGGGTVVTVNA | DSECALS | 460 | ANYDCFRRIE LRNFYDR | 323 | 76 |
| 140 | | ARVDQTPQTITKETGDSSTINCVLRDSNCDLTSTYWYRKKS GSTNEESISKGGRYVETVNSGSKSFSLRIDDLRVEDSGTYRC AVYGSVCYEIRTGQFGDGTAVTVNA | DSNCDLT | 461 | YGSVCYEIRT GQ | 324 | 77 |
| 141 | | ARVDQTPQTITKETGDSSTINCVLRDSNCDLTSTYWYRKKS GSTNEESISKGGRYVETVNSGSKSFSLRIDDLRVEDSGTYRC AVYGSVCYEIRTGQFGGGTVVTVNA | DSNCDLT | 461 | YGSVCYEIRT GQ | 325 | 77 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 142 | | ARVDQTPQTITKETGDSSTINCVLRDSNCDLTSTYWYRKKS GSTNEESISKGGRYVETVNSGSKSFSLRIDDLRVEDSGTYRC AVYGSVCYEIRTGQFGGGTAVTVNA | DSNCDLT | 461 | YGSVCYEIRTGQ | 326 | 77 |
| 143 | | ARVDQTPQTITKETGESSTINCVLRDSNCALSNTYWYRKKS GSTNEENISKAGRYARYVETGDSGSKSFSLRINDLTVEDSGT FRCNAFSWGGCPNPFDIYGGGTAVTVNA | DSNCALS | 423 | FSWGGCPNPFDI | 327 | 78 |
| 144 | | ARVDQTPQTITKETGESSTINCVLRDSNCALSNTYWYRKKS GSTNEENISKAGRYARYVETGDSGSKSFSLRINDLTVESGTF RCNAFSWGGCPNPFDIYGGGTVVTVNA | DSNCALS | 423 | FSWGGCPNPFDI | 328 | 78 |
| 145 | | ARVDQTPQRITKETGESSTINCVLRDSKCALSDTYWYRKKS GSTNEEKISKGGRYVETTISGRSSFSLRIYDLTVEDSGTYRC NTVYVWRGSHYHQELACDYDVSGGGTVVTVNA | DSKCALS | 462 | VYVWRGSHYHQELACDYDV | 329 | 79 |
| 146 | | ARVDQTPQRITKETGESSTINCVLRDSKCALSDTYWYRKKS GSTNEEKISKGGRYVETTISGRSSFSLRIYDLTVEDSGTYRC NTVYVWRGSHYHQELACDYDVSGGGTVVTVNA | DSKCALS | 462 | VYVWRGSHYHQELACDYDV | 330 | 79 |
| 147 | | ARVDQTPRSVTKETGESSTINCVLRDASYALGSTCWYRKKS GSTNEESISKGGRYVETVNSGSKSFSLRINDLTVEDGGTYRC GHSWLESCDYRPCSDYAACGDGTAVTVNA | DASYALG | 425 | SWLESCDYRPCSDYAAC | 331 | 80 |
| 148 | | ARVDQTPQTITKETGESSTINCVLRDSDCALSSTYWYRKVS GSTNEESISIGGRYVETVNSGSKSFSLRINDLTVEDSGTYRC NTLVWCGMAGMGWSPDVSGGGTVVTVNA | DSDCALS | 433 | LVWCGMAGMGWSPDV | 332 | 81 |
| 149 | | ARVDQTPQTITKETGESSTINCVLVDTDCALAVTYWHRKK LGSTNEESISKGGRYVETVNSGSKSFSLRINDLTVEDNGTYR CAVRRAEKKGGDCTLNYHAFGGGTVVTVNA | DTDCALA | 463 | RRAEKKGGDCTLNYHA | 333 | 82 |
| 150 | | ARVDQTPQTITKETGESSTINCVLLDTNCPMPVAYWYRKK AGSRREERISKGGRYVETVNSGRLSFSLRINDLTVEDSGKYR CNAYSFIGVDSCDWDIYGDGTAVTVNA | DTNCPMP | 464 | YSFIGVDSCDWDI | 334 | 83 |
| 151 | | ARVDQTPQTITKETGESSTINCVLRDSNCALSSTYWYRKKS GSTNEESISKGGRYVETVNSGSKSFSLRINDLTVEDSGTYRC NVWGIAGVVCREVNWGGQYDVYGGGTVVTVNA | DSNCALS | 423 | WGIAGVVCREVNWGGQYDV | 335 | 84 |
| 152 | | ARVDQTPQTITKETGESSTINCVLLDTNCPMPVAYWYRKK AGSRREERISKGGRYVETVNSGRLSFSLRINDLTVEDSGKYR CNAYSFIGVDSCDWDIYGDGTVVTVNAVKGGGTVVTVNA | DTNCPMP | 464 | YSFIGVDSCDWDIYGDGTVVTVNAVK | 336 | 85 |
| 153 | | ARVDQTPQTITKETGESSTINCVLRARDCGLSSTYWYRKKS GSTNEESISKGGRYVETVNIGSKSFSLRINDLTSEDSGTYRC NVFGYCPVSGVEIVGVYGGGTVVTVNA | ARDCGLS | 465 | FGYCPVSGVEIVGV | 337 | 86 |
| 154 | | ARVDQTPQTITKETGESSTINCVLRARDCGLSSTYWYRKKS GSTNEESISKGGRYVETVNIGSKSFSLRINDLTSEDSGTYRC NVFGYCPVSGVEIVGVYGGGTAVTVNA | ARDCGLS | 465 | FGYCPVSGVEIVGV | 338 | 86 |
| 155 | | ARVDQTPQTITKETGESSTINCVLRDSNCALSSTYWLRKKS GSTNEESISKGGRYVETVNSGSKSFSLRINDLTVEDSGTYRC NVYHRWCTMGTGGPGYDVYGGGTVVTVNA | DSNCALS | 423 | YHRWCTMGTGGPGYDV | 339 | 87 |
| 156 | | ARVDQTPQTITKETGESSTINCVLRDSNCALSSTYWLRKKS GSTNEESISKGGRYVETVNSGSKSFSLRINDLTVEDSGTYRC NVYHRWCTMGTGGPGYDVYGGGTVVTVNA | DSNCALS | 423 | YHRWCTMGTGGPGYDV | 340 | 87 |
| 157 | | ARVDQTPQTITKQTGESSTINCVLRDRNCAFMSTDWYRKK SGSTHEESISKGGRYVETVVRESKSGSLRITDLTVEDSGNYR CKIYSRTGDLEGPLNWCPEIYGGGTVVTVNA | DRNCAFM | 466 | YSRTGDLEGPLNWCPEI | 341 | 88 |
| 158 | | ARVDQTPQTITKETGESSTINCVLRDTNCALSSTYWYRKKS GSTNEESISKGGRYVETVNSGSKSFSLRINDLTVEDSGTYRC NVYRNSSTKDCASNWNYDVRGGGTVVTVNA | DTNCALSYDV | 440 | YRNSSTKDCASNWN | 342 | 89 |
| 159 | | ARVDQTPQTITKETGESSTINCVLRDTNCALSSTYWYRKKS GSTNEESISKGGRYVETVNSGSKSFSLRINDLTVEDSGTYRC NVYRNSSTKDCASNWNYDVRGGGTAVTVNA | DTNCALS | 440 | YRNSSTKDCASNWNYDV | 343 | 89 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 160 | | ARVDQTPQTITKETGESSTINCVLRDSNCALSSTYWYRKKS GSTNEESISKGGRYVETVNSGSKSFSLRINDLTVEDSGTYRC NVFPLSVPDCGTGPDVYGGGTVVTVNA | DSNCALS | 423 | FPLSVPDCGTG PDV | 344 | 90 |
| 161 | | ARVDQTPQTITKETGESSTVNCVLRDSGCALSSTYWYRKSS GSTNEESIPKGGRYVETVNSGSKSFSLRINDLTVEDSGTYRC NVAKSLYYPDCNDVYGGGTVVTVNA | DSGCALS | 467 | AKSLYYPDCND V | 345 | 91 |
| 162 | | ARVDQTPQTITKETGESSTINCVLRDTNCASSLTYWGRKKS GSRREENISKTGRYVETVNSGEKSFSLTINDLTVEDSSTYRC NVYFNDCPLRNWERIYGGGTVVTVNA | DTNCASS | 468 | YFNDCPLRNWE RI | 346 | 92 |
| 163 | | ARVDQTPQTITKETGESSTINCVLRDSNCALSSTYWYRKKS GSTNEESISKGGRYVETVNSGSKSFSLRINDLTVEDSGTYRC NCVAGGCTRIIDVYGGGTVVTVNA | DSNCALS | 423 | CVAGGCTRIID V | 347 | 93 |
| 164 | | ARVDQTPQTITKETGESSTINCVLRDSNCEMSSTDWYRKK SGSTSEESISKGGRYNETVNTGSKSSSLRINDLLVEDSGTYR CTVKEAGGLCRKNTWVHSGGGTVVTVNA | DSNCEMS | 469 | KEAGGLCRKNT WVH | 348 | 94 |
| 165 | | ARVDQTPRSVTKETGESSTINCVLRDAVYALGNTCWYRKK SGSTFEESISKGGRYVETVNSGSKSFSLRINDLTVEDGGTYR CGVATPTGPSCSCIWDYGICGDGTAVTVNA | DAVYALG | 470 | ATPTGPSCSCI WDYGIC | 349 | 95 |
| 166 | | ARVDQTPQTITKETGESSTINCVIRDGTCAFASTFWYRNKQ GSTNEENISKGGRYVETVNKGSKSFSLRINDLTVEDSGTYR CKAASVCAPRLFTTKDVYGGGTAVTVNA | DGTCAFA | 458 | ASVCAPRLFTT KDV | 350 | 96 |
| 167 | | ARVDQTPQTITKETGESSTINCVIRDGTCAFASTFWYRNKQ GSTNEENISKGGRYVETVNKGSKSFSLRINDLTVEDSGTYR CKAASVCAPRLFTTKDVYGGGTAVTVNA | DGTCAFA | 458 | ASVCAPRLFTT KDV | 351 | 96 |
| 168 | | ARVDQTPQTITKETGESSTINCVLRDSNCALSNTYWYRKKS GSTNEERISKGGRYVETVNSGSSSFSLRINDLTVEDSGTYRC NTKYVWYGSRYHQESACDYDVSGGGTAVTVNA | DSNCALS | 423 | KYVWYGSRYH QESACDYDV | 352 | 97 |
| 169 | | ARVDQTPQTITKETGESSTINCVLRDSNCALSNTYWYRKKS GSTNEERISKGGRYVETVNSGSSSFSLRINDLTVEDSGTYRC NTKYVWYGSRYHQESACDYDVSGGGTAVTVNA | DSNCALS | 423 | KYVWYGSRYH QESACDYDV | 353 | 97 |
| 170 | | ARVDQTPQTITKETGESSTINCVLRDSSCDSSRTYWYRKKS GSTKEESISKGGRYVETVNSGLKSFSLRINDLTVEDSGTYRC NAFNTGVRCDRAPVDVYGGGTAVTVNA | DSSCDS | 471 | FNTGVRCDRAP VDV | 354 | 98 |
| 171 | | ARVDQTPQTITKETGESSTINCVLRDSSCDSSRTYWYRKKS GSTKEESISKGGRYVETVNSGLKSFSLRINDLTVEDSGTYRC NAFNTGVRCDRAPVDVYGGGTAVTVNA | DSSCDS | 471 | FNTGVRCDRAP VDV | 355 | 98 |
| 172 | | ARVDQTPQTITKETGESLTINCVLLDSNCALSSAYWYRKKS GSTNEENISKAGRYPRYVETVNSGSKSFSLRINDLTVEDAG TYRCNVFSWGGCPTAFDVYGGGTAVTVNA | DSNCALS | 423 | FSWGGCPTAFD V | 356 | 99 |
| 173 | | ARVDQTPQTITKETGESLTINCVLLDSNCALSSAYWYRKKS GSTNEENISKAGRYPRYVETVNSGSKSFSLRINDLTVEDAG TYRCNVFSWGGCPTAFDVYGGGTAVTVNA | DSNCALS | 423 | FSWGGCPTAFD V | 357 | 99 |
| 174 | | ARVDQTPQTIRKVTGESSTINCVIQDSKCRLSDTHWWRKA PGSTNEERISKGGRYIETVNSALKSFSSRINDLRVEDSGTYR CNVLSWRDAVSNCDVAGGGTVVTVNA | DSKCRLS | 472 | LSWRDAVSNCD V | 358 | 100 |
| 175 | | ARVDQTPQTIRKVTGESSTINCVIQDSKCRLSDTHWWRKA PGSTNEERISKGGRYIETVNSALKSFSSRINDLRVEDSGTYR CNVLSWRDAVSNCDVAGGGTVVTVNA | DSKCRLS | 472 | LSWRDAVSNCD V | 359 | 100 |
| 176 | | ARVDQTPRSVTKETGESSTINCVLRDASYALGSTCWYRKS GSTNEESISKGGRYVETVNSGSKSFSLRINDLTVEDGGTYRC GVPHWLKGCRVCSWNGAAACGDGTAVTVNA | DASYALG | 425 | PHWLKGCRVCS WNGAAAC | 360 | 101 |
| 177 | | ARVDQTPQTITKETGESSTINCVLRDSKCALSDTYWYRKKS GSTNEESISRGGRYVETVNSGSKSFSLRINDLTVEDSGTYRC NTGGFCLSGFALYGGGTVVTVNA | DSKCALS | 462 | GGFCLSGFAL | 361 | 102 |

TABLE 1-continued

Amino acid sequence of VNARs binding the TfR1 receptor

| Seq. ID No. | VNAR name | VNAR Domain Amino Acid Sequence | CDR1 | SEQ ID NO: | CDR3 | SEQ ID NO: | Genus |
|---|---|---|---|---|---|---|---|
| 178 | | ARVDQTPQTITKETGESSTINCVLRESKCALSTTYWHRKKS GSRDEESISLGGRYVETVNRGSKSFSLRINGLTVEDSGTYRC NIFNDCATTVYESDAFGGGTVVTVNA | ESKCALS | 473 | FNDCATTVYES DA | 362 | 103 |
| 179 | | ARVDQTPQTITKETGESSTINCVLRDSNCALSSTYWYRKKS GSTNEESISKGGRYVETVNSGSKSFSLRINDLTVEDSGTYRC NVSPNCWLTKRTGSYVYGGGTVVTVNA | DSNCALS | 423 | SPNCWLTKRTG SYV | 363 | 104 |
| 180 | | ARVDQTPQTITKETGESSTINCVLRDSNCALSSTYWYRKKS GSTNEESISKGGRYVETVNSGSKSFSLRINDLTVEDSGTYRC NPQQVYCRHEQDWHDVYGGGTVVTVNA | DSNCALS | 423 | QQVYCRHEQDW HDV | 364 | 105 |
| 181 | | ARVDQTPQTITKETGESSTINCVLRDSNCALSKTYWYRKKS GSTNEESISKGGRYVETVNSGSKSFSLRINDLTVEDSGTYRC KTAYDCSHWRSIGVYGGGTVVTVNA | DSNCALS | 423 | AYDCSHWRSIG V | 365 | 106 |
| 182 | | ARVDQTPQTITKETGESSTINCVLSDSNCALASTYWYRKKS GSTNEESISKGGRYVETVASGSKSFSLRINDLTVEDSGTYRC NPQTEYCRHEQDFYDVYGGGTVVTVNA | DSNCALA | 474 | QTEYCRHEQDF YDV | 366 | 107 |
| 183 | | ARVDQTPQTITKETGESSTINCVLRDSNCALASTYWYRKKS GSTNEENISKGGRYVETVNSGSKSFSLRINDLTVEDSGTYRC NVANYDCFRRIELWNFYDRYGGGTVVTVNA | DSNCALA | 474 | ANYDCFRRIEL WNFYDR | 367 | 108 |
| 184 | | ARVDQTPQTITQETGESSTINCVLRDSKCVFASTYWHRNKS GSTNEESISKGGRYVETVNKGSKSFSLRINDLTVEDSGTYRC SLASVCPPRLFESEYVYGGGTVVTVNA | DSKCVFA | 475 | ASVCPPRLFES EYV | 368 | 109 |

TABLE 2

Unique CDR3 sequences constituting 36 separated genera

| SEQ ID NO. | Genus | CDR3 genus |
|---|---|---|
| 369 | 1 | FCIIDGELEDV |
| 370 | 2 | DYWCDPMRAPGLFGRK |
| 371 | 3 | ETNCHIFYQFPKD |
| 372 | 4 | ETPYDCPELNWWDV |
| 373 | 5 | ICDIFTYYYGTSW |
| 374 | 6 | IDYCLSWYRSINL |
| 375 | 7 | PSFDPLNYCYIWRRTT |
| 376 | 8 | SPPLVAGVLNCYDI |
| 377 | 9 | SSPQLGFYDCGHWIDV |
| 378 | 10 | VFHIAGTDMAELVYDV |
| 379 | 11 | VLVPAHGDCSAWSLWVGV |
| 380 | 12 | VRLGWYEYCPVLGGVYDV |
| 381 | 13 | VSWCTRHTMWNWYTVH |
| 382 | 14 | WYWHMSSSDCLSGYSY |
| 383 | 15 | YAMTANWWCDV |
| 384 | 16 | YAREDTWYGSRDCGLGDV |
| 385 | 17 | YDYCLHWFHPYVI |
| 386 | 18 | YGLVDCGSGMNWIDV |
| 387 | 19 | YGVIECRYEGMNWFDV |
| 388 | 20 | YNIAVMCNDYVRYWTDV |
| 389 | 21 | YQKPSFESLYWCDV |
| 390 | 22 | YSGPSYDQLFWCDV |
| 391 | 23 | YVPPGYDCNYWMDV |
| 392 | 24 | WHDLVWSVCTTDV |
| 393 | 25 | YARPRPDNLNWCDV |
| 394 | 26 | LRDSCYDVTNWLER |
| 395 | 27 | ENFLLDCYDWLDV |
| 396 | 28 | ERHWRSRCQRAVDV |
| 397 | 29 | BLWCLCPCTVWVLGDV |
| 398 | 30 | CGILCCFBFDV |
| 399 | 31 | TAILSBDCGAFADV |
| 400 | 33 | TGLRYHSGCRTGDV |
| 401 | 34 | CFGBCVNSCGESMDV |
| 402 | 35 | LRFBCVFHWDV |
| 403 | 36 | RDVVLVBYGYCLVDGQDV |

TABLE 2 -continued

Unique CDR3 sequences constituting
36 separated genera

| SEQ ID NO. | Genus | CDR3 genus |
|---|---|---|
| 404 | 37 | YELVEDTSAYEIGVDV |
| 405 | 38 | YQSPVGRRWWCDV |

Species Cross-Reactivity and Endocytosis of Mono- and Bivalent VNARs to TfR-1

Purified VNAR monomers were further screened for endocytosis by incubating with CHO cells transfected with rhTfR-1 using confocal microscopy (Example 6). Dispersed surface staining was observed when cellular metabolism was arrested on ice, whereas clustered 'hot spots', characteristic of endocytosis, were seen with incubation at 37° C. The negative control VNAR 5A7 specific for HEL failed to show any surface binding or internalisation. VNARs that endocytosed as monomers were subcloned into a modified pFUSE vector to produce bivalent VNAR antibodies (MW~75 kDa). All but one Fc fusion tested retained binding to immobilized recombinant protein. Cellular binding and endocytosis was then tested both in mouse bEnd.3 cells and human SKOV3 cells that express TfR-1 receptors. Bivalent VNAR-Fc retained species cross-reactivity for TfR-1 as shown by fluorescence microscopy. Cell surface and internalized staining was observed in both mouse and human cells whereas staining monoclonal antibodies to mouse (RI7217) and human TfR (OKT9) are species specific. TfR-1 receptor binding is required for VNAR internalization as the VNAR-Fc to HEL failed to show any cellular reactivity.

Brain Uptake of VNAR-Fc Fusions to TfR-1

Figure 7B:
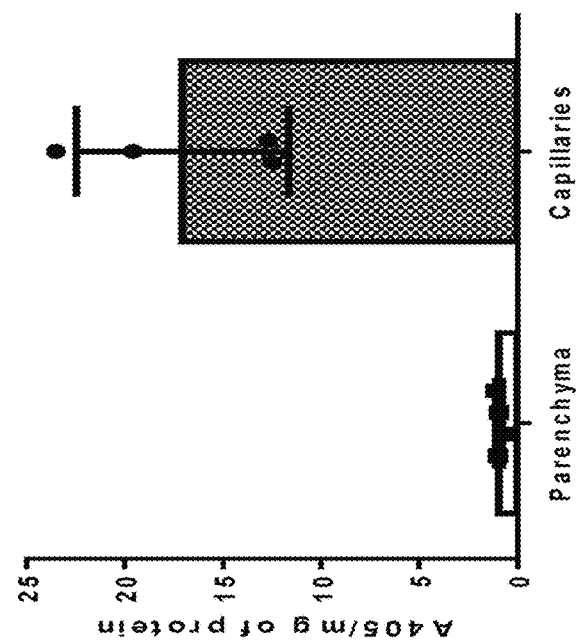
FIGS. 7A and 7B: In vivo brain uptake of VNAR-Fc fusions to TfR-1. VNAR-Fc fusion proteins were injected into tail vein at 10 mg/mg and the mice were perfused with saline at either 2 or 18 hours (hrs) later. The brains were homogenized and fractionated to separately measure the amount of VNAR-Fcs in the brain parenchyma and capillary compartments by ELISA (Example 7). Enrichment of the VNAR-Fc fusions in the parenchyma after fractionation is shown in FIG. 7A.
Figure 7A:
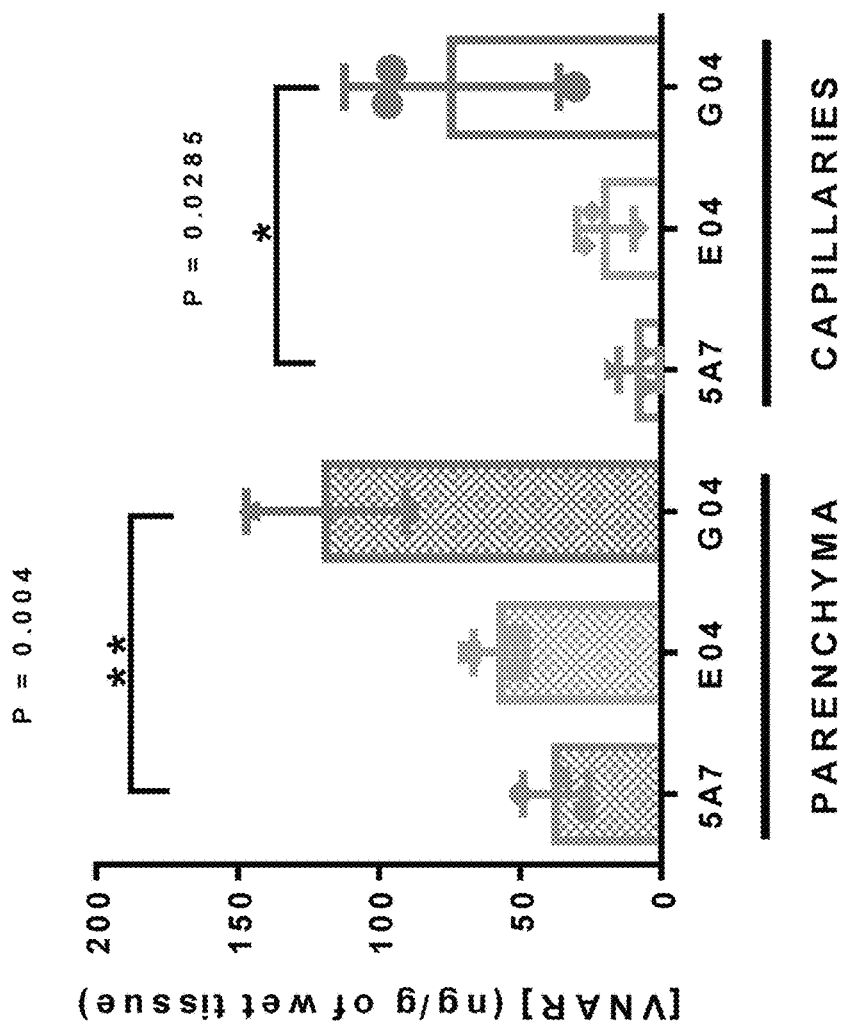

VNAR-Fc fusion proteins were injected into tail veins at 10 mg/kg and the mice were perfused with saline 18-24 hours later. To assess how much antibody was in the brain parenchyma compared to capillary endothelium, brain homogenates were fractionated by density gradient centrifugation and the VNAR-Fc concentration in each brain compartment was determined by ELISA (Example 7). VNAR-Fcs that were taken up by the parenchyma to a significantly greater extent than control were selected as leads (FIG. 7). Since capillary contamination was less than 1% based on alkaline phosphatase activity, the amount of VNAR-Fcs measured in brain parenchyma represents the amount trancytosed through the blood-brain barrier into the brain.

Figure 8:
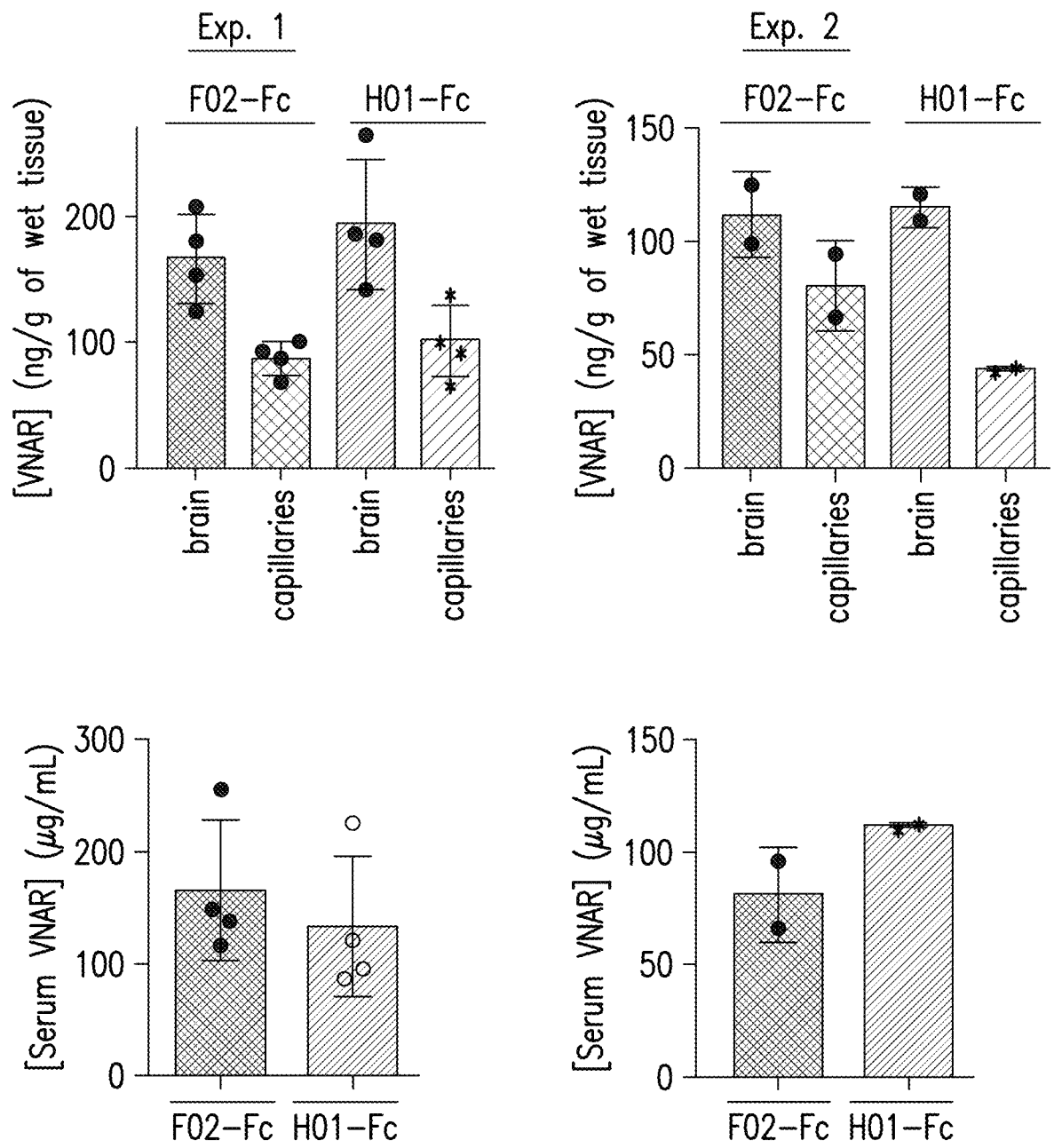
FIG. 8: Brain uptake of VNARs to different TfR-1 epitopes. Uptake of VNAR-Fc constructs F02-Fc and H01-Fc. The concentration of VNAR-Fc (ng/gram of wet tissue) in brain and capillaries (above) and in serum (below) is shown from two separate experiments.
Figure 9:
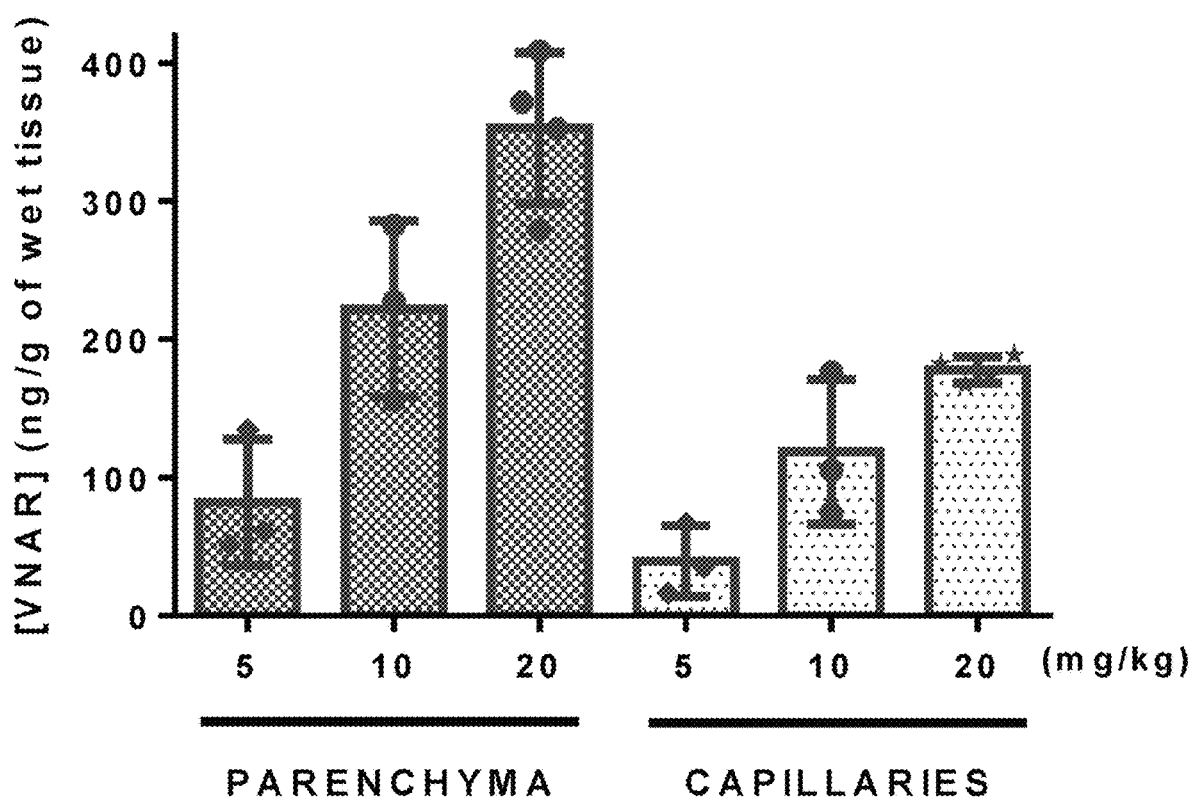
FIG. 9: Dose-response of anti-TfR-1 VNAR-Fc is 18 hours after IV injection of 10 mg/kg. Brain parenchyma and capillaries were separated by density gradient centrifugation and the amount of VNAR-Fc was measured by ELISA. The concentration of VNAR-Fc (ng/gram of wet tissue) in parenchyma and capillaries after 5, 10 or 20 mg/kg dosing is shown.

Additional VNAR clones against TfR-1 were formatted as Fc-fusion proteins for in vivo characterization in mice. In two separate experiments, VNAR clones H01 and F02 which bind non-competing epitopes on the TfR-1, when formatted as Fc fusions (H01-Fc and F02-Fc), were equally able to penetrate the BBB into the brain parenchyma (FIG. 8). Although the total amount of VNAR-Fc fusion proteins in the brain varied between experiments, it was consistently proportional to the plasma concentration. In addition, varying doses of H01-Fc were administered systemically and transport across the BBB was measured. The amount of VNAR-Fc transported into the brain was linear and dose-dependent with preferential accumulation in brain parenchyma over the brain capillaries (FIG. 9). This experiment confirms that bivalent VNAR antibody to TfR-1 (H01) can readily pass through the capillary endothelium in vivo.

Figure 10:
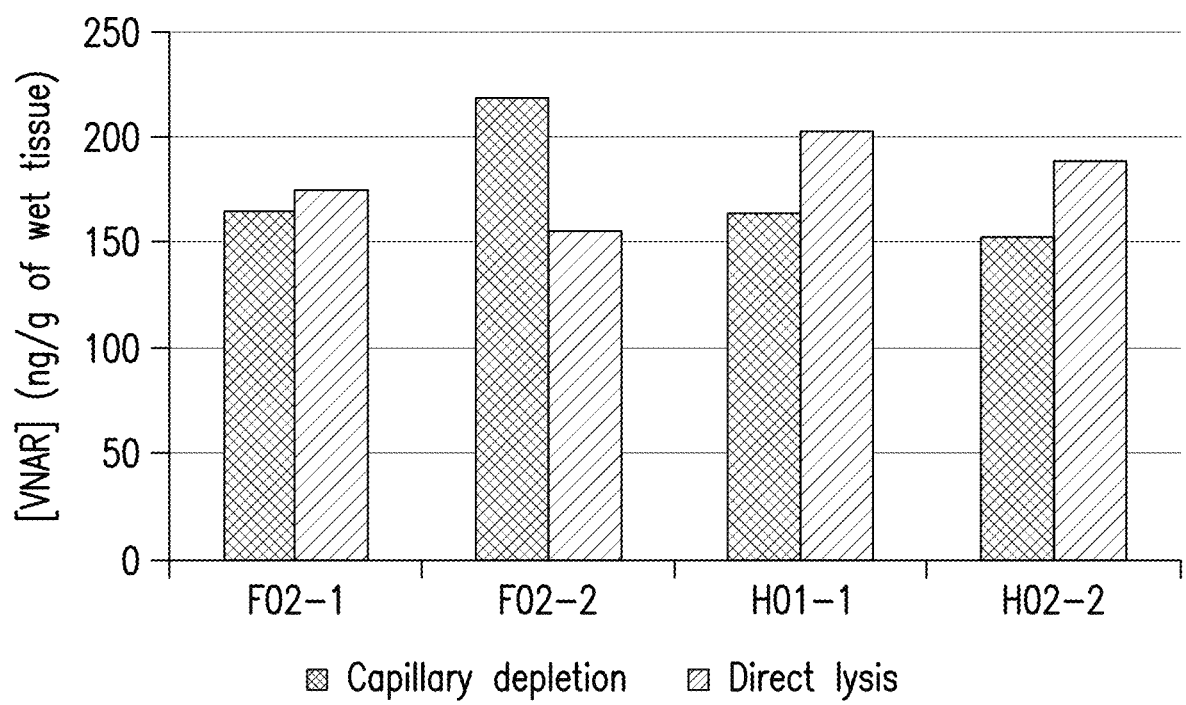
FIG. 10: Comparison of total brain level of VNAR-Fc after direct lysis or capillary depletion. Mice were administered 10 mg/kg IV of either F02-Fc or H01-Fc and perfused 18 hours later. One hemisphere was processed by the capillary depletion method while the other half was lysed directly. The concentration of VNAR-Fc (ng/gram of wet tissue) for each construct comparing the two methods in two experiments is shown.
Figure 11:
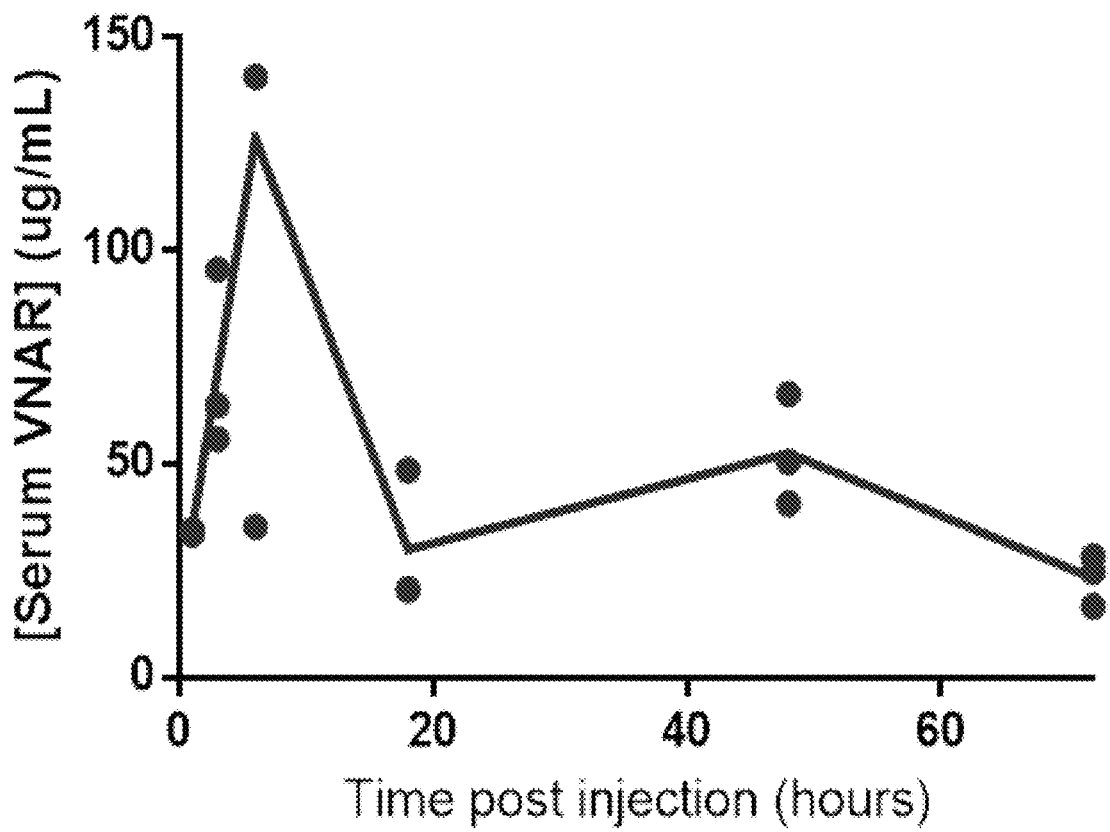
FIG. 11: Time course of brain exposure after a single 10 mg/kg dose of anti-TfR-1 VNAR-Fc to TfR-11. The concentration of VNAR-Fc (ng/gram of wet tissue; bottom) or in serum; top) as a function of time after injection (hours) is shown. The peak plasma concentration of a bivalent F02 VNAR-hFc fusion protein to TfR-1 occurred approximately 6 hours after IV injection (top). The peak brain concentration measured after brain perfusion and direct lysis occurred at approximately 18 hours and declined slowly with a half-life of more that 72 hours (bottom).
Figure 11:
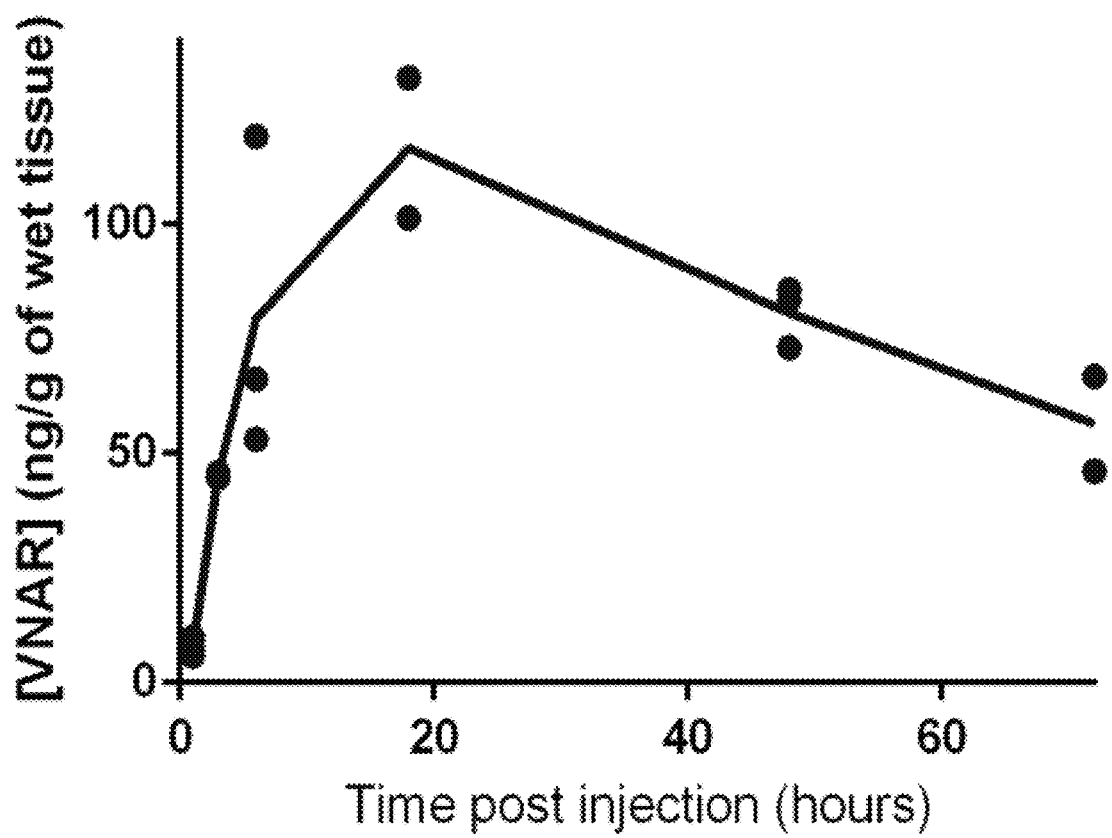

In order to test whether the total brain uptake of VNAR-Fc could be measured after capillary fractionation, one brain hemisphere was fractionated and the amount in each compartment was combined, while the other hemisphere lysed and the amount of VNAR-Fc directly measured. The total brain levels measured by either method were comparable, demonstrating that material was not lost during tissue processing (FIG. 10). The direct lysis method was then used to determine the time-course of anti-TfR-1 VNAR-Fc binding to TfR-1 after systemic administration. The brain concentration of F02-Fc peaked at approximately 18 hours and declined slowly with an approximate half-life in the brain of 72 hours (FIG. 11). The peak plasma concentration of a bivalent F02 VNAR-hFc fusion protein to TfR-1 occurred approximately 6 hours after IV injection (top). The peak brain concentration measured after brain perfusion and direct lysis occurred at approximately 18 hours and declined slowly with a half-life of more that 72 hours (bottom). The brain PK results indicate that a therapeutic dose (10 mg/kg) of a VNAR-Fc is suitable for a once weekly dosing schedule in mice.

The observed plasma half-life of various VNAR-Fcs was consistent with the long half-life of IgG. There was no evidence of rapid clearance by the liver due to cross-reactivity with TfR-2, which is highly expressed by hepatocytes (Silvestri et al., Front Pharmacol. 2014 May 7; 5:93) as has been reported for another TfR-1 antibody (Boado et al., Biotechnol Bioeng. 2009 Mar. 1; 102(4):1251-8). For example, directly testing the binding specificity of of the VNAR-Fcs for TfR-2 binding using an ELISA (FIG. 18) confirmed that H01-Fc and F02-Fc bound specifically to hTfR-1 and not hTfR-2.

This series of studies demonstrates that VNARs to TfR-1 with a wide range of affinities can function as Trojan horses to ferry molecules (e.g., "payloads") across the BBB. In similar fashion, VNARs can be genetically fused or chemically conjugated to other molecules to facilitate their transport across the BBB into the brain. We have further demonstrated the more than one site on TfR-1 is accessible to VNARs and that bivalent TfR-1 binding molecules are not necessarily trapped in the brain capillaries.

Bispecific Anti-TfR1 VNAR Fusions

Figure 12:
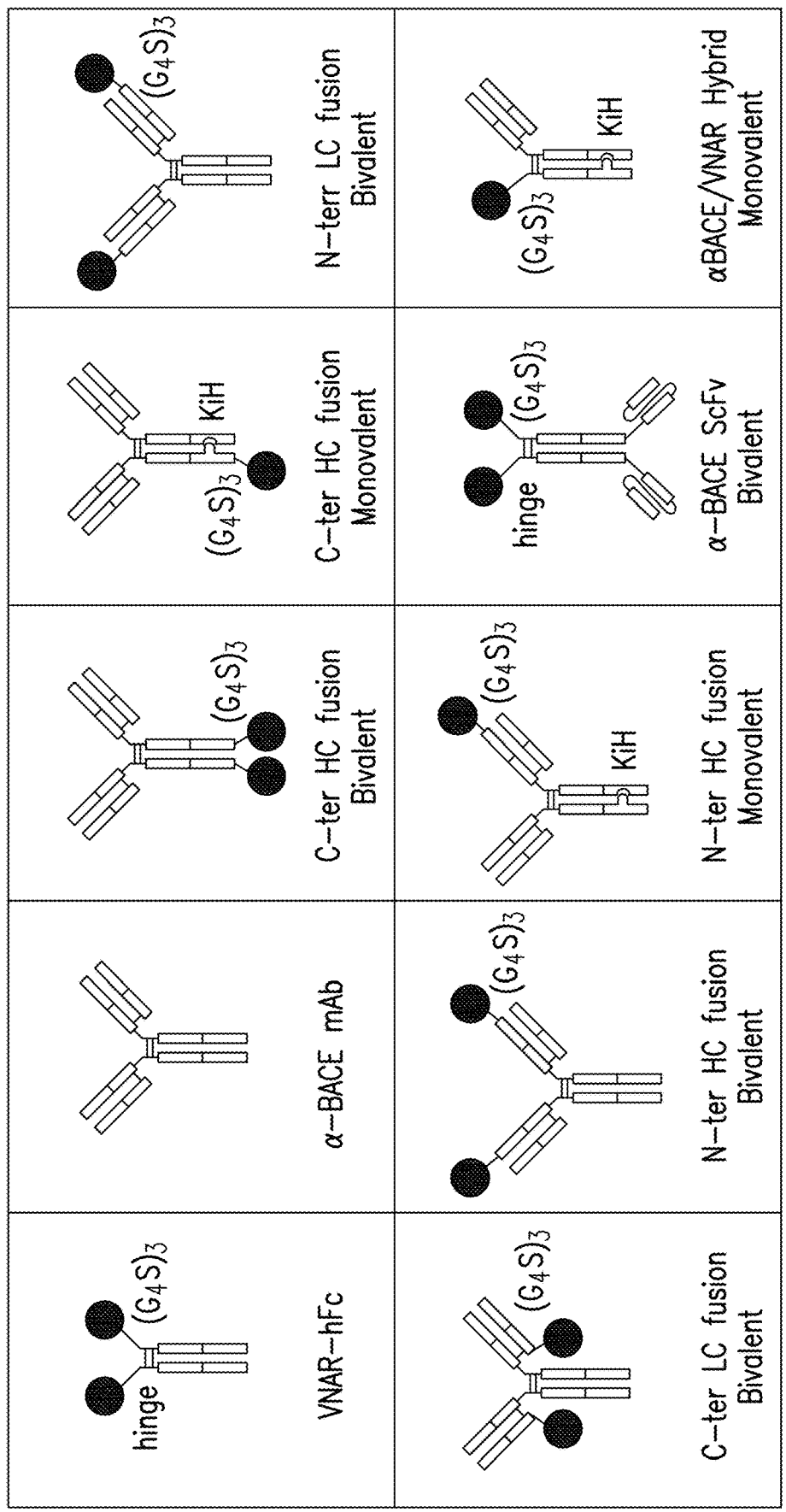
FIG. 12: Combining VNARs to TfR-1 with a monoclonal antibody to BACE to create eight different bispecifics formats. VNAR F02 was fused to the N- or C terminus of light chain (LC) or heavy (HC) of a monoclonal antibody to BACE using a triple G4S linker (SEQ IDNO: 481). Monovalent molecules were created using 'knobs-into-holes' technology (see Example 14).
Figure 13:
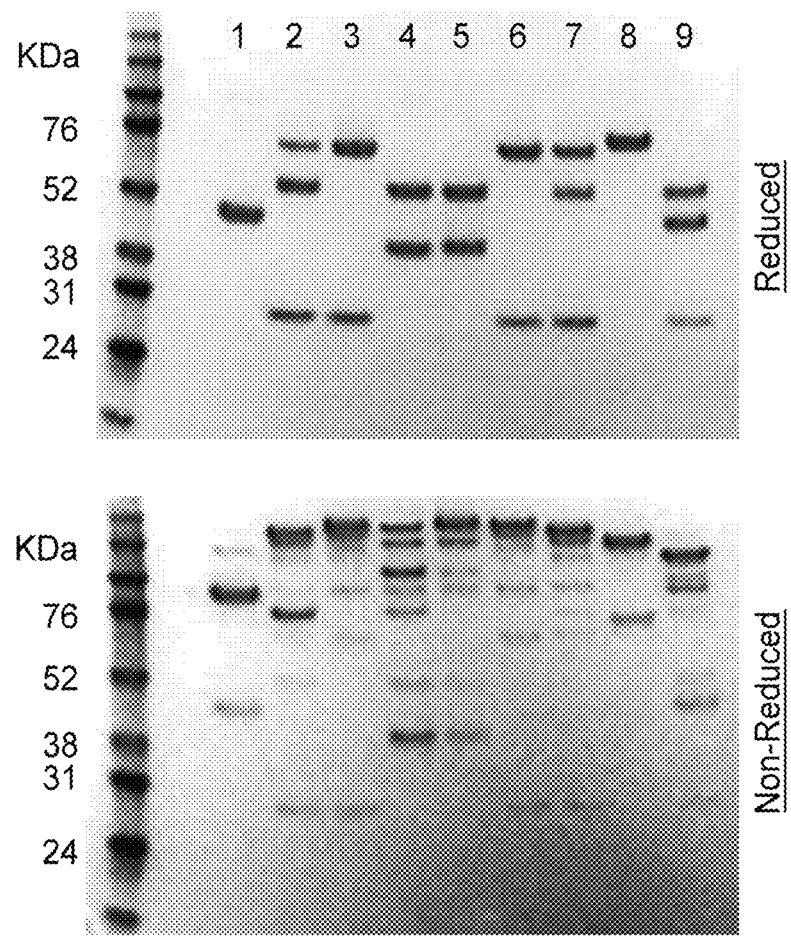
FIG. 13: Expression and purification of TfR-1/BACE bispecific molecules. Proteins were cloned and expressed in CHO cells. Gel electrophoresis of the purified proteins revealed that the samples displayed the expected band pattern in reducing condition, and that no aberrant migration was observed in non-reducing conditions, suggesting that the bispecific molecules were correctly assembled.

To test the ability of the anti-TfR1 VNARs to increase the brain penetration of a monoclonal antibody, we generated a series of fusion molecules using an anti-BACE1 antibody. BACE1 (beta-secretase 1, also known as beta-site amyloid precursor protein (APP) cleaving enzyme) is an aspartic acid protease enzyme known to cleave the extracellular portion of APP in one step of a process that produces amyloid-beta. Anti-BACE 1 antibodies can inhibit BACE1 enzymatic activity. A VNAR to TfR-1 (clone F02) was fused to different parts of the antibody molecule to create a series of bispecific molecules as shown in FIG. 12 (see also Example 8). Fusion proteins cloned and expressed in CHO cells were further characterized (Example 8; FIG. 13).

A. Binding of Bi-Specific Molecules to TfR1 and BACE1.

To test whether the bispecific molecules retained binding to both transferrin receptor and BACE1, the purified proteins were titrated against either hTfR, mTfR, or BACE1 adsorbed to the solid phase of an ELISA plate. Binding was measured with an RP-labelled anti-human-Fc antibody (Example 8; Table 3). Results showed that all molecules retained efficient binding to both TfR and BACE1. Only the scFv had a significantly decreased potency.

B. Brain Uptake of Bi-Specific Molecules to TfR1 and BACE1.

Figure 14:
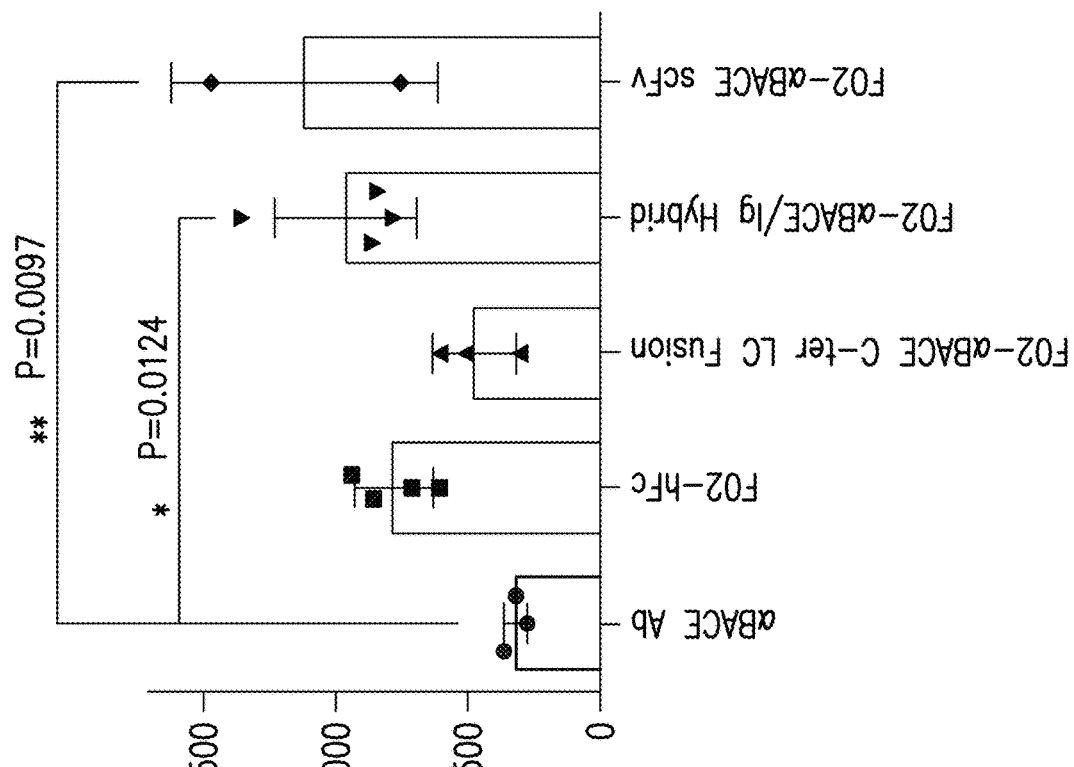
FIG. 14. Brain uptake of bispecific TfR-1/BACE bispecific molecules compared to the parental monoclonal antibody. The brain concentration of antibody (ng/gram of wet tissue) measured after direct lysis 18 hours after a single 10-mg/kg dose. Brain uptake of the BACE/Ig hybrid and the BACE/scFv bispecifics relative to the parental antibody (BACE Ab) at this time point from two separate experiments is shown.
Figure 14:
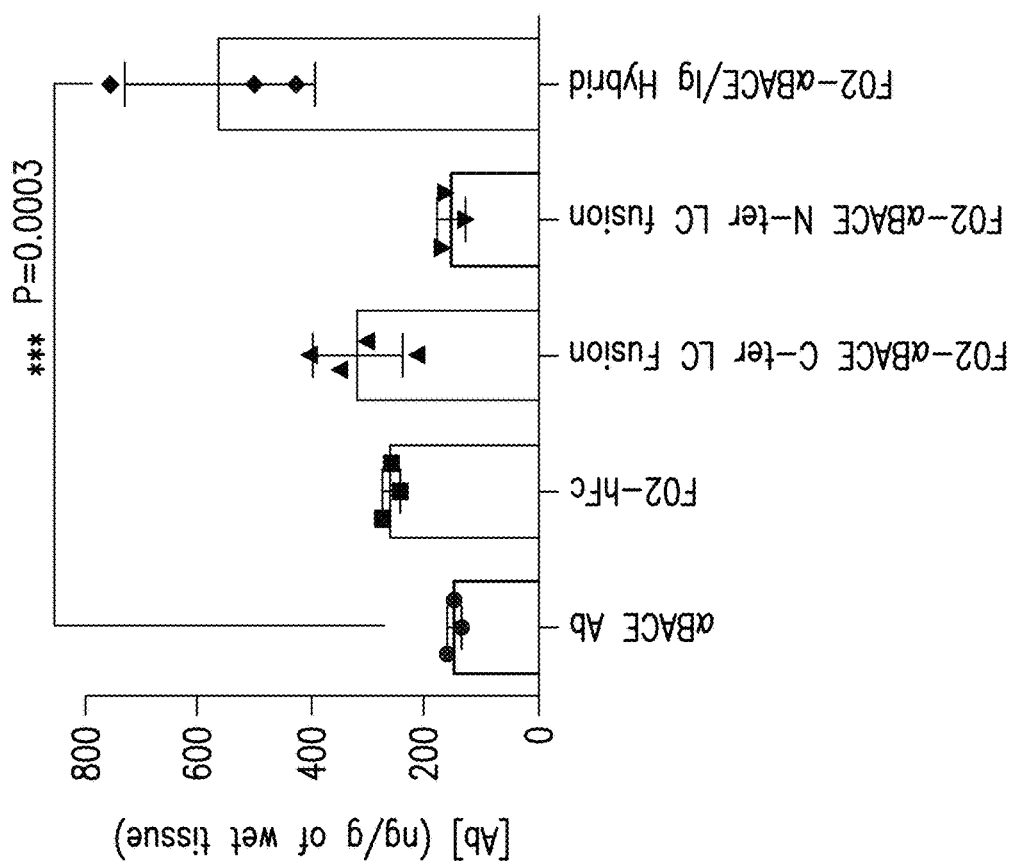

The purified bispecific molecules were injected into tail veins of female BALB-c mice, mice were perfused with saline for 18 hours and brain homogenates prepared (Example 8). The amount of antibody that had been transported into the brain was determined by Fc-capture ELISA. As shown in FIG. 14, the brain penetration of different bi-specific molecules was not equivalent. Three molecules (hFc-α-BACE-ScFv, αBACE/Ig Hybrid, and α-BACE C-ter LC fusion) showed a significantly increased brain uptake (three- to five-fold) as compared to the anti-BACE1 antibody.

C. Bispecific Anti-TfR1 VNAR Fusions have Functional Activity in the Brain.

Figure 15:
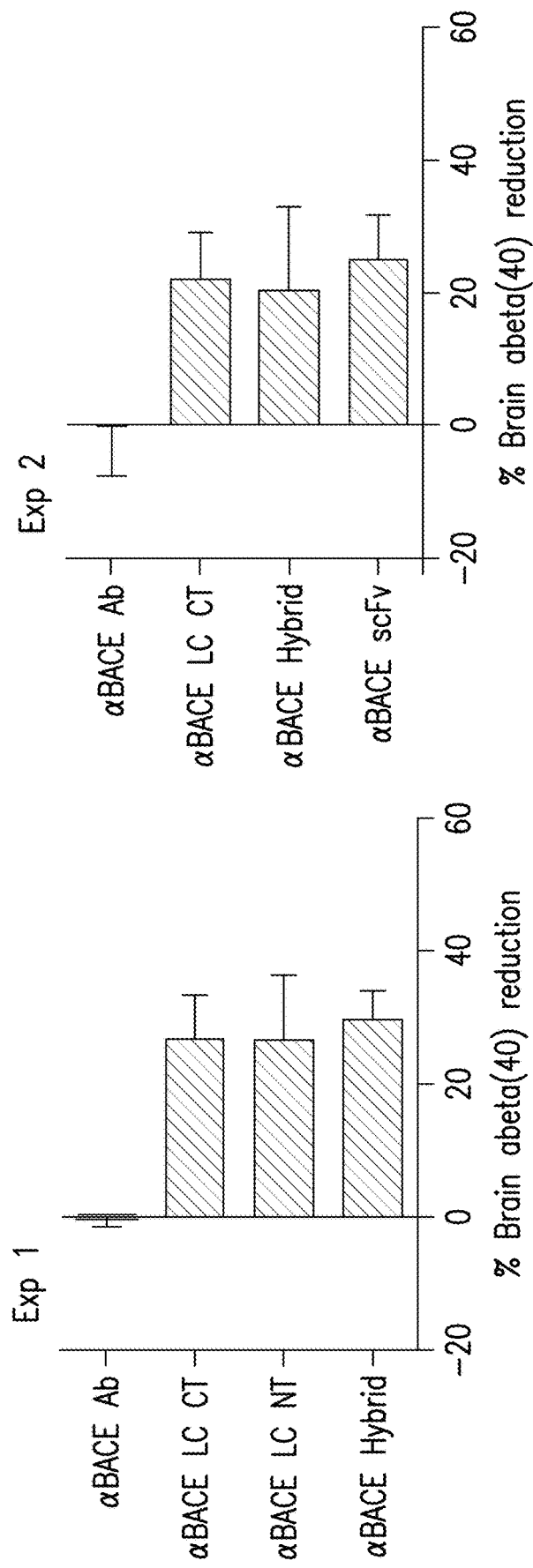
FIG. 15. Abeta (40) level in the brain of mice treated with TfR-1/BACE bispecific molecules compared to the parental monoclonal antibody. Shown is percent reduction of brain Abeta (40) after treatment with the parental monoclonal antibody (BACE Ab) compared to BACE/scFv bispecifics and the BACE LC N-terminal and C-terminal fusions.

In order to demonstrate that the three anti-TfR VNAR bi-specific molecules shown to penetrate the BBB also deliver functional activity of a conjugate payload molecule (here, BACE1), the level of Abeta (40) was measured in the brain lysate of the same bispecific molecule-treated mice (Example 8). Results from two independent experiments showed that the anti-TfR VNAR-Fc fusion molecule or the BACE1 antibody alone did not reduce the brain Abeta levels, whereas both N- and C-terminal light chain fusions, and the Ig/hybrid and the scFv-fusions of anti-TfR VNAR with anti-BACE1 moieties had a significant effect on the Abeta (40) level, reducing it by 20-30% (FIG. 15).

This series of studies demonstrated that a VNAR to TfR-1 can be fused to a monoclonal antibody in either a monovalent or bivalent format to carry it into the brain. Using an antibody to BACE1 to block the cleavage of the Abeta precursor protein (APP), it has been further demonstrated that the antibody reaches its target, which is expressed predominantly by neurons. Based on the degree of inhibition, the antibody appears to inhibit BACE1 on neuronal membranes but does not access the intracellular pool after a single systemic administration. A multiple dosing schedule may reach intracellular pools through endocytosis, however, sifting the balance of APP processing toward a non-amyloidogenic pathway at the plasma membrane could provide significant therapeutic benefit.

While the particular series of anti-TfR VNAR conjugates disclosed herein to establish utility are useful to exemplify the invention, it is envisioned that TfR-specific binding moieties of the invention, and polypeptides, compositions and vehicles comprising a TfR binding VNAR, may be used to carry a wide variety of active molecules across the BBB for therapeutic and/or diagnostic benefit in the brain and/or central nervous system, or across other TfR-positive membranes to deliver a therapeutic and/or diagnostic agent.

Polypeptide Sequences and Compounds Comprising a TfR Specific VNAR

The present invention provides a TfR-specific binding moiety, e.g., a polypeptide comprising a TfR-binding VNAR; TfR mediated drug vehicles that can carry heterologous molecules across the membrane of a TfR-positive cell; and TfR antagonist compounds comprising at least one TfR-specific binding moiety. Isolated TfR-binding VNARs are also provided. In certain embodiments, the TfR-specific binding moiety is specific for a mammalian TfR. In certain embodiments, the TfR-binding moiety is specific for human TfR. In certain embodiments, the TfR-specific binding moiety is a component of a BBB vehicle and mediates endocytosis of an associated heterologous molecule across a cell membrane, and in particular, across the BBB. In certain embodiments, the TfR-specific binding moiety is itself or is a component of a TfR antagonist compound which blocks the interaction between TfR, such as hTfR, and one or more of its ligands in vivo. In certain embodiments, the TfR-specific binding moiety mediates endocytosis without blocking ligand binding.

Hence, in accordance with the invention, certain embodiments of TfR-specific binding moieties comprise a VNAR scaffold represented by the formula, from N to C terminus, FW1-CDR1-FW2-HV2-FW2'-HV4-FW3-CDR3-FW4, wherein the CDR 1 region comprises or consists essentially of a peptide having an amino acid sequence of formula: D-$X_2$-$X_3$-$X_4$-$X_5$-$X_6$-$X_7$ (SEQ ID NO: 482)

wherein $X_2$ is A, K, N, R, S or T;
$X_3$ is A, D, I, N, S, V or Y;
$X_4$ is C or Y;
$X_5$ is A, D, P, R or T
$X_6$ is A or L; and
$X_7$ is D, G, L, S, P or T;

wherein the CDR3 region comprises or consists essentially of a peptide having an amino acid sequence from any of the CDR3 regions of Table 1; and wherein the moiety is specific for human TfR-1. In some embodiments, the TfR-specific binding moiety has an EC50 for human Tfr-1 ranging from about 0.1 nM to about 10 μM and more preferably ranging from about 1 nM to about 800 nM. In some embodiments, the TfR-specific binding moiety does not substantially bind to human TfR 2. In some embodiments, the TfR-specific binding moiety is capable of cross reacting with mouse TfR-1. In some embodiments, binding of the TfR-specific binding moiety to TfR-1 does not inhibit transferrin binding to and/or transport by TfR-1. In some embodiments, binding of the TfR-specific binding moiety to TfR-1 induces endocytosis of said moiety in a TfR-positive cell. In some embodiments, binding of the TfR-specific binding moiety to TfR-1 is reversibly pH dependent.

As used herein, a "VNAR scaffold" has the general structure, from N to C terminus, given by the formula FW1-CDR1-FW2-HV2-FW2'-HV4-FW3-CDR3-FW4, wherein the FWs are framework regions, CDRs are complementarity determining regions and HVs are hypervariable regions that form the variable domain of a shark IgNAR ("VNAR"). VNAR scaffolds of the invention where the FW1, FW2, FW2', FW3 and FW4 regions have naturally occurring VNAR sequences or altered VNAR sequences with amino acid substitutions, insertions or deletions (typically, but not limited to, no more than 1-10 amino acids a changes) provided that such changes maintain the overall primary and tertiary structure of the VNAR. Those of skill in the art can identify and ascertain the effect of such alterations. In addition, the FW1, FW2, FW2', FW3 and FW4 regions can have any of the sequences shown in Table 1 for these regions under the VNAR Domain Amino Acid Sequence column.

As used herein a "VNAR domain" means a naturally-occurring VNAR, an altered VNAR (such as those described in the paragraph above), a variable domain of a camelid antibody (known as a VHH) or the variable domain of any single chain antibody, whether such domains are naturally occurring, selected or engineered.

The VNARs, the VNAR scaffolds and the VNAR domains of the invention can optionally have a His-Tag (or other convenient tag for purification purposes). In some cases, such tags are removable.

In certain aspects of the embodiments with TfR-specific binding moieties comprising a VNAR scaffold, the CDR 1 region, which in naturally-occurring VNARs is a conserved seven amino acid residue stretch, comprises or consists essentially of a peptide selected from DASYALG (SEQ ID NO: 425), DKDCALS (SEQ ID NO: 434), DNDCALS (SEQ ID NO: 426), DNDCTLS (SEQ ID NO: 429) DNNCALS (SEQ ID NO: 431), DNYCPLS (SEQ ID NO: 476), DRACALL (SEQ ID NO: 477), DRDCALS (SEQ ID NO:

427), DSDCALS (SEQ ID NO: 433), DSNCAAT (SEQ ID NO: 435), DSNCALS (SEQ ID NO: 423), DSNCALP (SEQ ID NO: 419), DSNCDLS (SEQ ID NO: 416), DSNCPLS (SEQ ID NO: 432), DSNCRLS (SEQ ID NO: 442), DSICALS (SEQ ID NO: 424), DSVCALS (SEQ ID NO: 478) or DTACALD (SEQ ID NO: 479) (Table 1) or any other CDR1 shown in Table 1.

The CDR3 region in naturally-occurring VNARs is of heterogeneous size, ranging from about 7 to about 32 amino acid residues in length. In synthetic VNAR libraries exemplifying the present invention, CDR3 regions of 11 to 18 residues were constructed. In certain embodiments, the TfR-specific binding moiety comprises a [XDV] motif at the C terminus of the CDR3 region wherein X is an amino acid residue selected from A, C, E, I, F, G, L, M, Q, T, V, W or Y (see, e.g., Table 2). In certain embodiments, the TfR-specific binding moiety of the invention comprises a CDR3 region selected from a peptide consisting essentially of or comprising an amino acid sequence of any one of the CDR3 sequences shown in Table 1 (as well as those shown in Table 2).

In certain embodiments, the framework region interspersed between CDR1 and CDR3 comprises any one of the FW2-3 amino acid sequences shown in Table 1. The FW2-3 region in naturally-occurring VNARs is 53 amino acids in length, with insertions and deletions rarely observed. The FW2-3 region comprises hypervariable regions HV2 and HV4 (see B. J. Fennell et al., *J Mol Biol.* 400 (2010) pp. 155-170) which display some sequence variability and hence which can be suitable regions in which amino acid residues may be modified to create a variant of the TfR specific binding moiety of the invention.

As shown by the sequences in Table 1, The VNAR scaffold consists of amino acid residues (aa) 1-25 of the framework 1 (FW1) region; aa 26-32 of the complimentary determining region 1 (CDR1); aa 33-43 of FW2; aa 44-52 of the hypervariable 2 region (HV2); aa 53-85 of FW3; aa 61-65 of HV4; the CDR3 region (of variable length) and FW4 (11 residues starting at XGXG).

In any one of the individual embodiments described above, the TfR-specific binding moiety may further comprise one or more of the FW1, FW2-3 or FW4 amino acid sequences shown in Table 1, in any functional combination. The present invention further provides a TfR-specific binding moiety comprising one of the cloned VNAR peptide sequences shown in Table 1, that is, in some embodiments a TfR-specific binding moiety of the invention comprises or consists essentially of an amino acid sequence of any one of SEQ. ID NOS. 1-184 (i.e., the VNAR Domain Amino Acid Sequence of any one of the clones of Table 1).

In certain other embodiments of the invention, the present invention further provides a TfR-specific binding moiety comprising a CDR1 region comprising any one of the CDR1 peptide sequences shown in Table 1 in combination with a CDR3 region comprising any one of the CDR3 peptides shown in Table 1. These CDR regions are separated by a framework region (see, e.g., exemplary framework regions separating CDR1 and CDR3 regions as shown in Table 1), each considered to be an independent embodiment of the invention.

Further, in accordance with the invention, certain embodiments of TfR-specific binding moieties are directed to isolated TfR-specific binding moieties which comprise a VNAR domain capable of specifically binding to human TfR-1 without substantially interfering with transferrin binding to and/or transport by said human TfR-1. In some embodiments, such antibodies bind to the apical domain of human TfR-1. In some embodiments, such antibodies bind to the apical domain of human TfR-1 to at least one epitope within amino acids 215 to 380 of human TfR-1. The epitopes may be continuous or discontinuous epitopes. In some embodiments, the TfR-specific binding moiety binds to an epitope which comprises one or more sequences selected from the group consisting of (i) KAATVT (SEQ ID NO: 413), (ii) SGLPNIPVQTISRAAAEK (SEQ ID NO: 411), (iii) KLFGNMEGDCPS (SEQ ID NO: 414), (iv) SDWKTDS (SEQ ID NO: 415) and (v) STCRMVTSES (SEQ ID NO: 412). Examples of specific VNAR domains that bind these epitopes are A07, F02 and H01 as well as the family of F02 binding domains (discussed below).

For some embodiments in the immediately foregoing paragraph, the TfR-specific binding moiety does not substantially bind to human TfR-2. For some embodiments in the immediately foregoing paragraph, the TfR-specific binding moiety has an EC50 for human Tfr-1 ranging from about 0.1 nM to about 10 μM, and preferably ranging from about 1 nM to about 800 nM. For some embodiments in the immediately foregoing paragraph, the TfR-specific binding moiety is capable of cross reacting with mouse TfR-1. For some embodiments in the immediately foregoing paragraph, binding of the TfR-specific binding moiety to TfR-1 does not inhibit transferrin binding to and/or transport by TfR-1. For some embodiments in the immediately foregoing paragraph, binding of the TfR-specific binding moiety to TfR-1 induces endocytosis of said moiety in a TfR-positive cell. For some embodiments in the immediately foregoing paragraph, binding of the TfR-specific binding moiety to TfR-1 is reversibly pH dependent. In yet further embodiments, the TfR-specific binding moiety may have any or all such activity combinations.

Another aspect of the invention is directed to variants of TfR-specific binding moieties of the invention. Such variants differ by 1 to 10 amino acid residues from a recited amino acid sequence and/or retains human TfR-1-binding activity of at least half of the activity of the corresponding non-variant binding moiety. Those of skill in the art can readily identify and characterize variants of the invention using methods known in the art.

In yet another aspect of the invention, any of the TfR-specific binding moieties can form all or part of the variable domain of a single variable domain antibody, a bi- or tri-functional VNAR, a conventional antibody, or any fragment or fusion protein of said antibody as well as variable domains with antibody-like backbones.

Examples of single variable domain antibodies include, but are not limited to, a shark or other cartilaginous fish antibodies, camelid antibodies and nanobodies. Examples conventional antibodies include, but are not limited to, immunoglobins having both heavy and light chains, such as IgM's, IgA's, IgG's, IgE's, single chain Fv's, Fab fragments, or any fragment or fusion protein of such antibodies or fragments.

Non-limiting examples of antibody-like backbones that may be used according to the invention include monospecific and bispecific such as multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, $C_L$ and $C_H$1 domains, bivalent F(ab')2 fragments, Fd fragments consisting of the heavy chain and $C_H$1 domains, dimeric $C_H$2 domain fragments ($C_H$2D), Fc antigen binding domains (Fcabs), single chain Fv-$C_H$3 minibodies, bispecific minibodies, isolated complementary determining region 3 (CDR3) fragments, constrained FR3-CDR3-FR4 polypeptides, SMIP domains, and any genetically manipulated counterparts of the foregoing that retain TfR-1 binding function (see e.g., Weiner L, Cell 148: 1081-4 (2012); Ahmad Z et al., Clin Dev Immunol 2012: 980250 (2012) for reviews).

Therefore, in one aspect, the invention provides a TfR-selective compound comprising or consisting essentially of a VNAR derived TfR-specific binding moiety which binds selectively to a TfR polypeptide, preferably to human TfR (see e.g., UniProt P02786 TFR1_Human) or to a TfR, e.g., human TfR epitope-containing polypeptide.

In certain embodiments, a TfR specific binding moiety of the invention binds to a transferrin receptor (TfR) on the membrane of a mammalian cell and TfR specific binding mediates transport of the TfR specific binding moiety and at least one associated heterologous molecule across the cell membrane. Any TfR-positive cell or cell type (i.e., one with the transferrin receptor localized at the cell membrane) may thus be used to target delivery of heterologous molecules across its membrane by association (e.g., a complex or conjugate) with a TfR specific binding moiety of the invention. As described in more detail below, heterologous molecules may be selected from an enormously wide variety of agents, limited only by the target cell requiring a cell surface TfR which can internalize upon binding.

In certain embodiments of the invention, the cell membrane is part of the blood brain barrier (BBB) and TfR-mediated transport across the BBB of a heterologous molecule may be accomplished. In certain other embodiments of the invention, the cell membrane is part of the GI tract and TfR-mediated transport of a heterologous molecule may be accomplished, enabling oral drug delivery routes, especially advantageous for previously non-orally bioavailable drugs or molecules for therapeutics and/or diagnostics.

Associated heterologous molecules which may be used in conjunction with any one of the above embodiments may comprise, e.g., one or more biologically active molecules and/or imaging agents. Exemplary biologically active molecules which may be transported into a TfR-positive cell in association with a TfR-specific binding moiety of the invention include, e.g., toxins for targeted TfR-positive cell death (useful e.g., in certain hyperproliferative diseases or disorders such as cancers or aberrant proliferative conditions). Other exemplary biologically active molecules which may be transported in association with a TfR specific binding moiety include, e.g., polypeptides, such as an antibody or antibody fragment; a therapeutic peptide such as a hormone, cytokine, growth factor, enzyme, antigen or antigenic peptide, transcription factor, or any functional domain thereof. Other exemplary biologically active molecules which may be transported into a TfR-positive cell in association with a TfR specific binding moiety include, e.g., nucleic acid molecules, such as an oligonucleotide (e.g., single, double or more stranded RNA and/or DNA molecules, and analogs and derivatives thereof); small regulatory RNA such as shRNA, miRNA, siRNA and the like; and a plasmid or fragment thereof.

Exemplary polypeptides which may be therapeutically beneficial when administered as a heterologous molecule for TfR-mediated transport across the BBB or other TfR-containing cell membrane include but are not limited to: a brain derived neurotrophic factor (BDNF), a bone morphogenic protein (e.g., BMP-1 through BMP-7, BMP8a, BMP8b, BMP10 and BMP15), a ciliary neurotrophic factor (CNF), an epidermal growth factor (EGF), erythropoietin, a fibroblast growth factor (FGF), a glial derived neurotrophic factor (GDNF), a heptocyte growth factor, an interleukin (e.g., IL-1, IL-4, IL-6, IL-10, IL-12, IL-13, IL-17), a nerve growth factor (NGF), a neurotrophin (e.g., NT-3 and NT-4/5), a neurturin, a neuregulin, a platelet derived growth factor (PDGF), a transforming growth factor (e.g., TGF-alpha and TGF-beta), a vasoactive intestinal peptide, artemin, persephin, netrin, cardiotrophin-1, stem cell factor, midkine, pleiotrophin, a saposin, a semaporin, leukemia inhibitory factor, and the like.

Exemplary therapeutic antibodies or fragments that may be transported across the BBB or other TfR-containing cell membrane as a heterologous biologically active molecule of the invention include but are not limited to: anti-Abeta, anti-HER2, anti-EGF, anti-nogo A, anti-TRAIL (tumor necrosis factor-related apoptosis-inducing ligand), anti-alpha-synuclein, anti-htt, anti-prion, anti-West Nile virus and the like.

Exemplary enzymes that may be transported across the BBB or other TfR-containing cell membrane as a heterologous biologically active molecule of the invention include but are not limited to: alpha-L-iduronidase, iduronate-2-sulfatase, N-acetyl-galactosamine-6-sulfatase, arylsulfatase B, acid alpha-glucosidase, and acid sphingomyelinase.

Also, included as exemplary biologically active molecules are small molecules comprising chemical moieties (such as a therapeutic small molecule drugs); carbohydrates; polysaccharides; lipids; glycolipids and the like. Exemplary embodiments of such small molecule therapeutic agents include certain cancer drugs, such as daunorubicin, doxorubicin, and other cytotoxic chemical agents including microtubule inhibitors, topoisomerase inhibitors, platins, alkylating agents, and anti-metabolites all of which may beneficially be administered across the BBB at lower overall systemic doses than by IV administration. Other small molecule therapeutic agents may include corticosteroids, NSAIDs, COX-2 inhibitors, small molecule immunomodulators, non-steroidal immunosuppressants, 5-amino salicylic acid, DMARDs, hydroxychloroquine sulfate, and penicillamine. 1-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir, among others. Small molecule therapeutic agents which may be used according to the invention also include bevacizumab, cisplatin, irinotecan, methotrexate, temozolomide, taxol and zoledronate. Certain anti-inflammatory agents may be useful biologically active molecules. Fluoxetine, for example, reportedly inhibits MMP-2, MMP-9 and MMP-12 expression associated with blood-brain barrier disruption and inflammatory reactions after spinal cord injury, may be used according to the invention to protect blood-brain barrier and to inhibit deleterious inflammatory responses in spinal cord injury and central nervous system disease.

Exemplary embodiments of an imaging agent as an associated heterologous molecule include agents that comprise at least one of a metal such as a paramagnetic metal, a radionuclide such as a radioisotope, a fluorochrome or fluorophor, an energy emitting particle, a detectable dye, and an enzyme substrate.

Further examples of biologically active molecules include small molecules, including therapeutic agents, in particular those with low blood-brain barrier permeability. Some examples of these therapeutic agents include cancer drugs, such as daunorubicin, doxorubicin, and toxic chemicals which, because of the lower dosage that can be administered by this method, can now be more safely administered. For example, a therapeutic agent can include bevacizumab, irinotecan, zoledronate, temozolomide, taxol, methotrexate, and cisplatin.

In another embodiment, the therapeutic agent can include a broad-spectrum antibiotic (e.g., cefotaxime, ceftriaxone, ampicillin and vancomycin); an antiviral agent (e.g., acyclovir); acetazolamide; carbamazepine; clonazepam; clorazepate dipotassium; diazepam; divalproex sodium; ethosuximide; felbamate; fosphenytoin sodium; gabapentin; lamotrigine; levetiracetam; lorazepam; oxcarbazepine; phenobarbital; phenytoin; phenytoin sodium; pregabalin; primidone; tiagabine hydrochloride; topiramate; trimethadione; valproic acid; zonisamide; copaxone; tysabri; novantrone; donezepil HCL; rivastigmine; galantamine; memantine; levodopa; carbidopa; parlodel, permax, requip, mirapex; Symmetrel; artane; cogentin; eldepryl; and deprenyl. Antiviral compounds are also beneficial therapeutic agents that can be delivered using a TfR-specific binding moiety of the invention, especially for cases in which the virus uses TfR transport as its route of entry into infected cells.

Numerous other examples of biologically active molecules may be used in association with a TfR-specific binding moiety of the invention, appropriate selection of which will be apparent to the skilled artisan depending on the condition, disease or disorder to be treated.

Yet other examples of a biologically active molecule which may be used according to the present invention is an antigenic peptide. Antigenic peptides may provide immunological protection when imported by cells involved in an immune response. Other examples include immunosuppressive peptides (e.g., peptides that block autoreactive T cells, such peptides being known in the art).

An imaging agent, as used herein, may be any chemical substance which may be used to provide a signal or contrast in imaging. A signal enhancing domain may be an organic molecule, metal ion, salt or chelate, a particle (e.g., iron particle), or a labeled peptide, protein, glycoprotein, polymer or liposome. For example, an imaging agent may include one or more of a radionuclide, a paramagnetic metal, a fluorochrome, a dye, and an enzyme substrate.

For x-ray imaging, the imaging agent may comprise iodinated organic molecules or chelates of heavy metal ions of atomic numbers 57 to 83. In certain embodiments, the imaging agent is $I^{125}$ labeled IgG (see, e.g., M. Sovak, ed., "Radiocontrast Agents," Springer-Verlag, pp. 23-125 (1984).

For ultrasound imaging, an imaging agent may comprise gas-filled bubbles or particles or metal chelates where the metal ions have atomic numbers 21-29, 42, 44 or 57-83. See e.g., Tyler et al., Ultrasonic Imaging, 3, pp. 323-29 (1981) and D. P. Swanson, "Enhancement Agents for Ultrasound: Fundamentals," Pharmaceuticals in Medical Imaging, pp. 682-87. (1990) for other suitable compounds.

For nuclear radiopharmaceutical imaging or radiotherapy, an imaging agent may comprise a radioactive molecule. In certain embodiments, chelates of Tc, Re, Co, Cu, Au, Ag, Pb, Bi, In and Ga may be used. In certain embodiments, chelates of Tc-99m may be used. See e.g., Rayudu GVS, Radiotracers for Medical Applications, I, pp. 201 and D. P. Swanson et al., ed., Pharmaceuticals in Medical Imaging, pp. 279-644 (1990) for other suitable compounds.

For ultraviolet/visible/infrared light imaging, an imaging agent may comprise any organic or inorganic dye or any metal chelate.

For MRI, an imaging agent may comprise a metal-ligand complex of a paramagnetic form of a metal ion with atomic numbers 21-29, 42, 44, or 57-83. In certain embodiments, the paramagnetic metal is selected from: Cr(III), Cu(II), Dy(III), Er(III) and Eu(III), Fe(III), Gd(III), Ho(III), Mn(II and III), Tb(III). A variety of chelating ligands useful as MRI agents are well known in the art.

In sum, the invention includes TfR-specific conjugate comprising a TfR-specific binding moiety of the invention operably linked to a heterologous molecule which differs in biological activity from said moiety. Such operable linkages can be a covalent or non-covalent linkage and the heterologous molecule can be a growth factor, cytokine, lymphokine, cell surface antigen or an antibody or antibody fragment which binds to any of the foregoing; a chimeric antigen receptor; a cytotoxic small molecule; a biochemical pathway agonist or antagonist; a therapeutic agent or drug; a diagnostic agent such as a fluorescent molecule or other molecular marker; or a nucleic acid molecule with targeting or other regulatory properties (e.g., silencers) or which encodes a regulatory molecule for a cell.

For the avoidance of doubt, a TfR-selective binding compound includes TfR-specific binding moieties alone, as part of antibodies (or fragments thereof as described herein) or as part of conjugates.

Monitoring TfR Binding and Cell Internalization

TfR-binding activity (also referred to herein as "TfR bioactivity") may be determined by one or more assays described in the Examples herein, or by any other suitable method in the art, including well-known immunoassays, such as for example the ELISAs or variations thereon described in the Examples. Any other binding assay which directly or indirectly measures the binding of the TfR-specific binding moiety to a cell surface TfR, or alternatively, which measures the ability of a TfR-specific binding moiety, conjugate or compound comprising such a moiety of the invention to compete for binding to TfR in the presence of a different TfR binding compound (such as an anti-TfR antibody) such as by a competitive inhibition assay, may be used. Preferably, a selected assay measures the effect of a TfR-specific binding moiety or compound comprising such a moiety on its ability to transport a heterologous molecule or biomolecule across the membrane of a TfR-positive cell. In certain embodiments, the TfR-positive cell is one which transports a heterologous molecule across the blood brain barrier (BBB). In certain embodiments, the TfR-positive cell is one which transports a heterologous molecule across cells of the gastrointestinal tract. In certain embodiments, binding of the TfR binding moiety to TfR is measured by monitoring internalization of the TfR binding moiety into TfR-positive cells or cell type. In vivo assays of TfR bioactivity include, but are not limited to those described in the Examples herein.

Other test systems to assess TfR binding and functional activity include, for example: Surface plasmon resonance to determine affinity and off-rates; using radiolabeled or fluorescent tagged molecule or GFP fusion proteins in in vitro or in vivo animal studies including binding and internalization in tumor cell lines, immortalized endothelial cell lines or primary cells expressing TfR; in vitro transcytosis in capillary endothelial cells and cells lines; and permeability assay using Caco-2 and MDCK epithelial cell lines; in situ perfusion models and immunohistochemical or immunofluorescent staining of tissue sections; optical or PET animal imaging; standard PK and tissue distribution assays; and measuring one or more biological effects of a heterologous molecule (drug cargo or payload) in normal animals or disease animal models.

According to another embodiment, a TfR-specific binding moiety, conjugate or compound of the invention binds to human TfR in a standard ELISA or other similar assay with an EC50 of 300 nM or less, 100 nM or less, 10 nM or less, or 1 nM or less. Thus, a TfR selective binding compound of the invention binds to TfR, e.g., hTfR, in a standard ELISA or other similar assay with an EC50 in a range of 0.1 nM to 300 nM, 0.5 nM to 300 nM, 1 nM to 300 nM, 10 nM to 300 nM, 50 nM to 300 nM, 100 nM to 300 nM, 0.1 nM to 100 nM, 0.5 nM to 100 nM, 1 nM to 100 nM, 5 nM to 100 nM, 10 nM to 100 nM, 0.1 nM to 50 nM, 0.5 nM to 50 nM, 1 nM to 50 nM, 5 nM to 50 nM, 10 nM to 50 nM. It should be noted that strong selective binding may subsequently hinder transport across the membrane and/or release of the TfR-specific binding moiety and heterologous molecule(s) inside the TfR-positive cell. Hence, it should not be assumed that the tightest binding moieties are always ideal. One of skill in the art will be able to select an appropriate level of binding for desired transport and release of the therapeutic or diagnostic use envisioned. For example, in certain embodiments of the invention, the TfR-specific binding moiety binds to human TfR-1 with an EC50 in a range of about 0.1 nM to about 10 µM, or in a preferred embodiment, in a range of about 1 nM to about 800 nM.

In certain embodiments, the TfR compound of the invention binds to hTfR with a 5-fold, 10-fold, 20-fold, 50-fold, 100-fold, 500-fold or more higher affinity compared to its binding affinity to a cross reactive ligand. In some embodiments, a TfR selective binding compound of the invention is specific to human TfR but also binds to or cross-reacts with one or more other mammalian TfRs, e.g., with mouse TfR (UniProtKB/Swiss-Prot: P02786 TFR1).

Therapeutic versions of compounds with TfR-specific binding moieties of the invention include other molecular configurations, e.g., a VNAR monomer (i.e., a TfR-binding moiety) fused to stabilizing heterologous peptide regions, e.g., the Fc domain of an IgG or other immunoglobulin molecule, which may be expressed and then further purified as multimers, such as covalent dimmers, allowing the activity of certain such therapeutic molecules to have even greater potency, preferably by at least 2-10 fold higher potencies and different binding affinities to TfR-1. Any of the antibody or antibody-like structures contemplated by the invention can be used as therapeutics TfR bioactivity may also or alternatively be measured by TfR binding affinity, using any of a number of assays known in the art, such as a surface plasmon resonance assay (Example 5). According to another embodiment, a TfR-selective binding compound of the invention binds to human TfR in an affinity assay such as by surface plasmon resonance assay with a binding affinity of 300 nM or less, and preferably 100 nM or less, 10 nM or less, 1 nM or less or 100 pM or less. Thus, a TfR antagonist compound of the invention binds to TfR, e.g., hTfR, with an affinity constant (KA) in a range of 0.1 nM to 500 nM, 0.5 nM to 500 nM, or 1 nM to 500 nM, 0.1 nM to 250 nM, 0.5 nM to 250 nM, or 1 nM to 250 nM as measured, e.g., by surface plasmon resonance such as in a BIACore assay. In certain embodiments, a compound of the invention binds to TfR, e.g., hTfR, with an affinity constant in a range of 0.1 nM to 100 nM, 0.1 nM to 50 nM, or 0.1 nM to 10 nM, 0.5 nM to 100 nM, 0.5 nM to 50 nM, or 0.5 nM to 10 nM, or 1 nM to 100 nM, 1 nM to 50 nM or 1 nM to 0 nM, as measured, e.g., by surface plasmon resonance such as in a BIACore assay.

Pharmaceutically acceptable salts or solvates of any of the TfR-specific binding compounds of the invention are likewise within the scope of the present invention. As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type $N(R1)(R2)(R3)(R4)+$, wherein R1, R2, R3 and R4 independently will typically designate hydrogen, optionally substituted $C_{1-6}$-alkyl groups or optionally substituted $C_{2-6}$-alkenyl groups. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977).

The term "solvate" in the context of the present invention refers to a complex of defined stoichiometry formed between a solute (in casu, a peptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

In each of the sequences described above, and in each sequence described herein, a C-terminal "—OH" moiety may be substituted for a C-terminal "—NH$_2$" moiety, and vice-versa.

Each of the specific compounds of the invention (e.g., TfR binding moieties, TfR antagonist peptides and compounds), and pharmaceutically acceptable salts and solvates thereof, constitutes an individual embodiment of the invention.

Derivatives, Variants, Conjugates

The invention further provides variants of a TfR-specific binding moiety of the invention, wherein the variant differs from the recited amino acid sequence by up to 1, 2, 3, 4, 5, 6, 7, 8, 9, 10 or more amino acid residues (but by no more than that which retains 85%, 90%, 95%, 99% or more amino acid sequence identity) and/or retains TfR bioactivity. TfR bioactivity can be measured, for example, by TfR binding affinity, using any of a number of assays know in the art. In certain embodiments, a compound of the invention binds to TfR-1, e.g., hTfR-1, with an affinity constant in a range of 0.1 nM to 500 nM, 0.5 nM to 500 nM, or 1 nM to 500 nM, 0.1 nM to 250 nM, 0.5 nM to 250 nM, or 1 nM to 250 nM as measured, e.g., by surface plasmon resonance such as in a BIACore assay. In certain embodiments, a compound of the invention binds to TfR-1, e.g., hTfR-1, with an affinity constant in a range of 0.1 nM to 100 nM, 0.1 nM to 50 nM, or 0.1 nM to 10 nM, 0.5 nM to 100 nM, 0.5 nM to 50 nM, or 0.5 nM to 10 nM, or 1 nM to 100 nM, 1 nM to 50 nM or 1 nM to 10 nM, as measured, e.g., by surface plasmon resonance such as in a BIACore assay. It will be understood by one of skill in the art that amino acid residues outside of the conserved FW, CDR1 and CDR3 motifs are in general regions in which amino acid modifications may be tolerated more readily without deleteriously depleting TfR binding activity. And it will also be understood by one of skill in the art that in certain embodiments, the binding affinity to TfR is less important than the ability of the binding moiety to transport a heterologous molecule across the membrane of a TfR-positive cell, and to release a molecular cargo or a so-called drug or molecular payload within the cell.

A biologically active fragment of any of the foregoing sequences which retains TfR bioactivity is also encompassed by the present invention. Thus, in further aspects, the invention further comprises compounds having an amino acid sequence that is truncated (shortened), from the N- or C-terminus, relative to the full-length sequence of compounds of the invention. In some embodiments, the truncated compounds are truncated by up to 1, 2, 3, 4, 5, 6, 7, 8, 9, 10, 11, 12, 13, 14, 15, 16, 17, 18, 19, 20, 21, 22, 23, 24, 25 or more amino acid residues, counting from the C-terminus of a compound of the invention as disclosed above. Amino acid residue outside of the conserved VNAR framework motifs are regions in which amino acid modifications may be better tolerated without deleteriously depleting TfR binding activity.

In some embodiments, the compounds of the invention may have at least 40%, e.g., at least 45%, 50%, 55%, 60%, 65%, 70%, 75%, 80%, 85%, 90%, 95%, 96%, 97%, 98%, or 99%, 99.5%, or 99.9% amino acid sequence identity to one of the TfR selective binding compounds disclosed herein, as long as the compound retains a TfR biological activity (as measured by TfR binding affinity, EC50 or IC50) within a range described herein.

Thus, in certain, TfR specific binding compounds of the invention may comprise the amino acid sequence of any one of the compounds shown in Table 1 (see below), or a functional variant thereof that has at least about 70%, 75%, 80%, 85%, 90%, 95%, 97%, 98%, 99% or 99.5% sequence identity to any one of the compounds in Table 1. A functional variant of a polypeptide of the invention may inhibit at least one TfR bioactivity by any one of the assays disclosed herein by at least 50%, 55%, 60%, 65%, 70%, 75%, 80%, 85%, 90%, 95%, 97%, 98%, 99%, 99.5%, or 100%. In some embodiments, a TfR selective binding compound of the invention may comprise one or more amino acid substitutions, e.g., conservative amino acid substitutions, and retain TfR binding activity of at least 50%, 55%, 60%, 65%, 70%, 75%, 80%, 85%, 90%, 95%, 97%, 98%, 99%, 99.5%, or 100% compared to the binding by an unmodified TfR selective binding compound of the invention, and/or compared to binding of any other available anti-TfR antibody, such as anti-human TfR monoclonal antibody belimumab.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). Unless otherwise indicated, reference is made to the L-isomeric forms of the amino acids in question. Where appropriate, the D-isomeric form of an amino acid is indicated in the conventional manner by the prefix "D" before the conventional three-letter code (e.g. DAsp, DPhe). Non-traditional amino acid residues and analogs are also included within the scope of the present invention (e.g., homoserine, norleucine, norvaline, ornithine and the like; and methods for making them are well known in the art.

In certain embodiments, the invention further provides a TfR specific binding moiety or TfR selective binding compound comprising said binding moiety, in which there are one or more conservative amino acid substitutions introduced into the polypeptide sequence. As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids. See, for example, the table below. An example of a conservative substitution with a residue normally not found in endogenous, mammalian peptides and proteins is the conservative substitution of Arg or Lys with, for example, ornithine, canavanine, aminoethylcysteine or another basic amino acid. For further information concerning phenotypically silent substitutions in peptides and proteins, see, e.g., Bowie et al., Science 247, 1306-1310, 1990. In the scheme below are conservative substitutions of amino acids grouped by physicochemical properties. I: neutral, hydrophilic, II: acids and amides, III: basic, IV: hydrophobic, V: aromatic, bulky amino acids.

| I | II | III | IV | V |
|---|----|-----|----|---|
| A | N | H | M | F |
| S | D | R | L | Y |
| T | E | K | I | W |
| P | Q |   | V |   |
| G |   |   | C |   |

In some embodiments, a polypeptide of the invention may comprise functional fragments or variants of a TfR-specific binding moiety of the invention that have, at most, 20, 15, 10, 9, 8, 7, 6, 5, 4, 3, 2, or 1 amino acid substitutions compared to a polypeptide sequence recited herein, as long as it retains measurable biological activity alone or as a component of a TfR-selective binding compound. A polypeptide of the invention may further be with or without a signal sequence. In certain embodiments, the retained activity is at least 50% that of the TfR binding moiety according to Table 1.

In some embodiments, a polypeptide of the invention shares at least 85%, 90%, 95%, 96%, 97%, 98%, 99% or more amino acid sequence identity to any one of the amino acid sequences of FW1, FW2-3, FW4, CDR1 or CDR3 of Table 1, as long as it retains measurable biological activity alone or as a component of a TfR selective binding compound. In certain embodiments, the retained activity is at least 50% that of the TfR binding moiety according to Table 1.

TfR specific VNAR comprising compounds of the invention may optionally be conjugated (e.g., using linkers such as chemical linkers and/or linker peptides which are not usually associated with the domains being associated) to one or more additional agents which may include therapeutic and/or diagnostic agents. Such agents include but are not limited to chemotherapeutics such as cytostatic drugs, cytotoxins, radioisotopes, chelators, enzymes, nucleases, nucleic acids such as DNA, RNA or mixed nucleic acid oligonucleotides, including siRNAs, shRNAs, microRNAs, aptamers and the like; immunomodulators such as therapeutic antibodies, antibody and antibody-like fragments, inflammatory and anti-inflammatory cytokines, anti-inflammatory agents, radiotherapeutics, photoactive agents, diagnostic markers and the like. In certain embodiments, the pharmaceutically active moieties of the invention comprise at least one scFv molecule that is operably linked via a linker peptide to the C-terminus and/or N-terminus of an Fc region.

In certain embodiments, a compound of the invention comprising a TfR-specific binding moiety is multispecific, i.e., has at least one binding site that binds to a first molecule or epitope of a molecule (e.g., human TfR-1) and one or more other binding sites that bind to at least one heterologous molecule or to an epitope of either TfR-1 or another molecule. Multispecific binding molecules of the invention may comprise at least two binding sites, three binding sites, four binding sites or more. In certain embodiments, at least two binding site of a multispecific binding molecule of the invention are capable of transporting a linked molecule across the BBB.

The invention thus further provides methods of making derivatives of TfR specific VNARs of the invention using biochemical engineering techniques well known to those of skill in the art. Such derivatives include, inter alia, multivalent or multispecific molecules comprising a TfR-specific binding moiety, including immunoconjugates. A large body of art is available relating to how to make and use antibody drug conjugates. Such knowledge and skill in the art may be adapted for use with the TfR specific binding moieties and TfR selective binding compounds of the invention. See, e.g., WO2007/140371; WO2006/068867 specific to TfR; methods relating to making and/or using different ligand conjugates may be applied. In certain embodiments, the TfR selective binding moieties and TfR selective binding compounds of the present invention include covalently modified and conjugated polypeptides forms of the polypeptides (e.g., immunoadhesins, radiolabeled or fluorescently labeled compounds, and the like). Methods for peptide conjugation and for labeling polypeptides and conjugating molecules are well known in the art.

Nucleic Acid Sequences that Encode a TfR Selective Binding Moiety or TfR Antagonist Compound In one aspect, the invention provides an isolated nucleic acid which encodes a TfR specific binding moiety or compound of the invention, or a fragment or derivative thereof. The nucleic acid may include, e.g., nucleic acid sequence encoding a polypeptide at least 50%, 55%, 60%, 65%, 70%, 75%, 80%, 85%, 90%, 95%, 99% or more, identical to a polypeptide comprising one of the amino acid sequences of Table 1. The invention also provides an isolated nucleic acid molecule comprising a sequence that hybridizes under stringent conditions to a nucleic acid sequence which encodes a TfR specific binding moiety or compound of the invention, or a fragment or derivative thereof, or the antisense or complement of any such sequence.

In another aspect, the invention provides an isolated nucleic acid molecule encoding a fusion protein comprising at least two segments, wherein one of the segments comprises a polypeptide or fragment thereof having CDR 1, CDR3 or framework amino acid sequences shown in Table 1, and variants thereof according to the invention. In certain embodiments, a second segment comprises a heterologous signal polypeptide, a heterologous binding moiety, an immunoglobulin fragment such as a Fc domain, or a detectable marker.

One aspect of the invention provides isolated nucleic acid molecules that encode TfR specific binding moiety proteins or biologically active portions thereof. Also included are nucleic acid fragments sufficient for use as hybridization probes to identify TfR binding moiety encoding nucleic acids and fragments for use as polymerase chain reaction (PCR) primers for the amplification or mutation of TfR specific binding moiety encoding nucleic acid molecules.

As used herein, the term "nucleic acid molecule" is intended to include DNA molecules, RNA molecules (e.g., mRNA, shRNA, siRNA, microRNA), analogs of the DNA or RNA generated using nucleotide analogs, and derivatives, fragments and homologs thereof. The nucleic acid molecules of the invention may be single-, double-, or triple-stranded. A nucleic acid molecule of the present invention, e.g., a nucleic acid molecule encoding any one of the amino acid sequences disclosed in Table 1, or a complement of any of these nucleotide sequences, may be isolated using sequence information provided herein and well known molecular biological techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., CURRENT PROTOCOLS IN MOLECULAR BIOLOGY, John Wiley & Sons, New York, N.Y., 1993).

A nucleic acid molecule of the invention may be amplified using any form of nucleic acid template and appropriate oligonucleotide primers according to standard PCR amplification techniques. Amplified nucleic acid may be cloned into an appropriate vector and characterized, e.g., by restriction analysis or DNA sequencing. Furthermore, oligonucleotides corresponding to nucleotide sequences that encode a TfR selective binding moiety or compound of the invention may be prepared by standard synthetic techniques, e.g., using an automated DNA synthesizer.

The term "oligonucleotide" as used herein refers to a series of covalently linked nucleotide (or nucleoside residues, including ribonucleoside or deoxyribonucleoside residues) wherein the oligonucleotide has a sufficient number of nucleotide bases to be used in a PCR reaction. Oligonucleotides comprise portions of a nucleic acid sequence having at least about 10 nucleotides and as many as 50 nucleotides, preferably about 15 nucleotides to 30 nucleotides. Oligonucleotides may be chemically synthesized and may be used as probes. A short oligonucleotide sequence may be used to amplify, confirm, or reveal the presence of an identical, similar or complementary DNA or RNA in a particular cell or tissue.

Derivatives or analogs of the nucleic acid molecules (or proteins) of the invention include, inter alia, nucleic acid (or polypeptide) molecules having regions that are substantially homologous to the nucleic acid molecules or proteins of the invention, e.g., by at least about 45%, 50%, 70%, 80%, 95%, 98%, or even 99% identity (with a preferred identity of 80-99%) over a nucleic acid or amino acid sequence of the same size or when compared to an aligned sequence in which the alignment is done by a computer homology program known in the art. A percent identity for any candidate nucleic acid or polypeptide relative to a reference nucleic acid or polypeptide may be determined by aligning a reference sequence to one or more test sequences using, for example, the computer program ClustalW (version 1.83, default parameters), which enable nucleic acid or polypeptide sequence alignments across their entire lengths (global alignment) or across a specified length. The number of identical matches in such a ClustalW alignment is divided by the length of the reference sequence and multiplied by 100.

Also included are nucleic acid molecules capable of hybridizing to the complement of a sequence encoding the proteins of the invention under stringent or moderately stringent conditions. See e.g. Ausubel, et al., CURRENT PROTOCOLS IN MOLECULAR BIOLOGY, John Wiley & Sons, New York, N.Y., 1993, and below. An exemplary program is the GAP program (Wisconsin Sequence Analysis Package, Version 8 for UNIX, Genetics Computer Group, University Research Park, Madison, Wis.) using the default settings, which uses the algorithm of Smith and Waterman (1981) Adv. Appl. Math. 2:482489). Derivatives and analogs may be full length or other than full length, if the derivative or analog contains a modified nucleic acid or amino acid, as described below.

Stringent conditions are known to those skilled in the art and may be found in CURRENT PROTOCOLS IN MOLECULAR BIOLOGY, John Wiley & Sons, N.Y. (1989), 6.3.1-6.3.6. In certain embodiments, stringent conditions typically permit sequences at least about 65%, 70%, 75%, 85%, 90%, 95%, 98%, or 99% homologous to each other to remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. The term "stringent hybridization conditions" as used herein refers to conditions under which a nucleic acid probe, primer or oligonucleotide will hybridize to its target sequence, but only negligibly or not at all to other nucleic acid sequences. Stringent conditions are sequence- and length-dependent, and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide.

Methods of Producing TfR Specific VNAR Binding Moieties and Compounds Comprising Them.

The compounds of the invention may be manufactured by standard synthetic methods, by use of recombinant expression systems, or by any other suitable method. Thus, the compounds may be synthesized in a number of ways, including, e.g., methods comprising: (1) synthesizing a polypeptide or polypeptide component of a TfR specific binding compound using standard solid-phase or liquid-phase methodology, either stepwise or by fragment assembly, and isolating and purifying the final peptide compound product; (2) expressing a nucleic acid construct that encodes a polypeptide or polypeptide component of a TfR specific binding compound in a host cell and recovering the expression product from the host cell or host cell culture; or (3) cell-free in vitro expression of a nucleic acid construct encoding a polypeptide or polypeptide component of a TfR specific binding compound, and recovering the expression product; or by any combination of the methods of (1), (2) or (3) to obtain fragments of the peptide component, subsequently joining (e.g., ligating) the fragments to obtain the peptide component, and recovering the peptide component.

It may be preferable to synthesize a polypeptide or polypeptide component of a TfR-specific binding compound of the invention by means of solid-phase or liquid-phase peptide synthesis. Compounds of the invention may suitably be manufactured by standard synthetic methods. Thus, peptides may be synthesized by, e.g., methods comprising synthesizing the peptide by standard solid-phase or liquid-phase methodology, either stepwise or by fragment assembly, and isolating and purifying the final peptide product. In this context, reference may be made to WO1998/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a TfR specific binding compound of the invention according to above recited methods; a nucleic acid molecule encoding part or all of a polypeptide of the invention, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

TfR specific binding compounds of the invention may be prepared using recombinant techniques well known in the art. In general, methods for producing polypeptides by culturing host cells transformed or transfected with a vector comprising the encoding nucleic acid and recovering the polypeptide from cell culture are described in, e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995).

A nucleic acid encoding a desired polypeptide may be inserted into a replication vector for further cloning (amplification) of the DNA or for expression of the nucleic acid into RNA and protein. A multitude of cloning and expression vectors are publicly available.

Expression vectors capable of directing transient or stable expression of genes to which they are operably linked are well known in the art. The vector components generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

Any suitable host cell may be used to produce TfR specific binding compounds of the invention. Host cells may be cells stably or transiently transfected, transformed, transduced or infected with one or more expression vectors which drive expression of a polypeptide of the invention. Suitable host cells for cloning or expressing nucleic acids of the invention include prokaryote, yeast, or higher eukaryote cells. Eukaryotic microbes such as filamentous fungi yeast, *Arabidopsis*, and other plant and animal eukaryotic host cells that may be grown in liquid culture are suitable cloning or expression hosts for vectors. Suitable host cells for the expression of glycosylated polypeptides may also be derived from multicellular organisms.

Creation and isolation of host cell lines producing a TfR-specific binding moiety, conjugate or compound of the invention can be accomplished using standard techniques known in the art. Mammalian cells are preferred host cells for expression of peptides. Particularly useful mammalian cells include, inter alia, HEK 293, NSO, DG-44, and CHO cells, but any other suitable host cell may be used according to the invention. Preferably, the TfR-specific moieties, conjugates or compounds are secreted into the medium in which the host cells are cultured, from which the TfR-specific binding moieties, conjugates or compounds may be recovered or purified.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed.

Such procedures include, inter alia, fractionation (e.g., size separation by gel filtration or charge separation by ion-exchange column); ethanol precipitation; Protein A Sepharose columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a TfR-specific binding moiety, conjugate or compound of the invention.

Methods of Detection

In certain embodiments, the TfR specific binding compounds of the invention may be used to detect and quantify levels of TfR, or cells that express TfR. This can be achieved, for example, by contacting a test sample (such as an in vitro sample) and a control sample with a TfR specific binding moiety of the invention, or a compound comprising it, under conditions which permit formation of a complex between the compound and TfR, or between TfR and an anti-TfR antibody, or both. Any bound TfR complexes are detected and/or quantified in TfR specific VNAR containing samples and control samples.

Accordingly, the invention further provides methods for detecting the presence of TfR or TfR antibodies in a sample, or measuring the amount of either of the foregoing, comprising contacting the sample, and preferably a control sample, with a TfR-binding compound of the invention under conditions that permit complex formation between the TfR binding moiety of the compound and TfR, e.g., human TfR. Formation or inhibition of formation of a TfR-binding compound/TfR complex is then detected and/or quantified. A variety of tests can be designed based on features of binding or competition for binding. For example, the presence of TfR in a test sample may be detected directly, or may be detected and quantified based on the ability to compete for binding of TfR by a TfR-binding moiety, conjugate or compound. In general, the difference in complex formation between a test sample and a control sample is indicative of a binding interaction.

Methods of Treatment Using TfR Binding Moieties and Compositions

The present invention provides a TfR binding moiety or TfR specific binding compound for use, alone or in combination with one or more additional therapeutic agents in a pharmaceutical composition, for treatment or prophylaxis of conditions, diseases and disorders responsive to modulation (such as inhibiting or blocking) of the interaction between TfR and its in vivo ligands.

In certain embodiments, a TfR specific binding moiety or a conjugate or drug delivery vehicle comprising such a binding moiety is administered in combination with at least one additional agent that mediates blood-brain barrier transport, such as an agent comprising a receptor binding domain of an apolipoprotein such as a receptor binding domain of ApoA, ApoB, ApoC, ApoD, ApoE, ApoE2, ApoE3 or ApoE4, and any combination thereof. Any one of a number of other molecules which mediate transport of heterologous molecules across the blood brain barrier may be used in combination with the TfR specific binding moiety comprising agents of the invention, including, e.g., IgG, YY (PYY), neuropeptide Y (NPY), corticotropin releasing factor (CRF), and urocortin. Certain viral glycoproteins (e.g., rabies virus glycoprotein (RVG) peptide) and antibodies and antibody fragments may also be used in this regard.

Combination therapies may include co-administration of agents or alternate administrations which result in a combination therapy within the patient based on duration of the therapeutic agent(s) or their biological effects in the patient.

In certain embodiments, a therapeutic agent transported across the BBB in association with a TfR-specific binding moiety of the invention is effective in treating a brain or CNS disease, condition, injury or disorder, such as, for example, neurodegenerative diseases, neuronal injury, inflammation or damage, and brain cancers, spinal cord injury (SCI) and traumatic brain injury (TBI). In certain embodiments, a brain disorder is selected from epilepsy, meningitis, encephalitis including HIV Encephalitis, progressive multifocal leukoencephalopathy, neuromyelitis optica, multiple sclerosis, late-stage neurological trypanosomiasis, amyotrophic lateral sclerosis (ALS), progressive bulbar palsy (PBP), primary lateral sclerosis (PLS), progressive muscular atrophy (PMA), Alzheimer's disease, Parkinson's disease, Huntington's disease, De Vivo disease, and any type of tumor, cancer or hyperproliferative disease in the brain or CNS.

In certain embodiments, a therapeutic agent transported across a hTfR-containing membrane in association with a TfR-specific binding moiety of the invention is effective in treating a condition, disease or disorder associated with the GI tract or one which will otherwise benefit from drug delivery across an epithelial membrane of the gut mediated by hTfR transport.

The invention in certain embodiments provides methods of treatment or prevention of a TfR associated disorder, the method comprising the step of administering to a subject (e.g., a patient) in need thereof a therapeutically effective amount of the TfR specific binding compound or pharmaceutical composition comprising a TfR binding compound of the invention, as described herein. As used herein, an "effective amount," a "therapeutically effective amount" or an "effective dose" is an amount of a composition (e.g., a therapeutic composition or agent) that produces at least one desired therapeutic effect in a subject, such as preventing or treating a target condition or beneficially alleviating a symptom associated with the condition.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, PA, 2005.

Additionally, for some embodiments specificity for TfR1 is an important feature for a BBB carrier because off target binding to TfR2 could have undesirable safety and/or PK consequences. The expression of TFR2 is restricted to hepatocytes and erythroid precursors (Silvestri et al., Front Pharmacol. 2014 May 7; 5:93). Interference with transferrin binding to TfR2, which is a component of the erythropoietin receptor complex, could disrupt normal erythropoiesis (Forejtnikova et al., Blood. 2010 Dec. 9; 116(24):5357-67). Additionally, high levels of TfR2 expressed in the liver may be responsible for the rapid clearance and short half life of some cross-reacting TfR antibodies (Boado et al., Biotechnol Bioeng. 2009 Mar. 1; 102(4):1251-8). VNAR antibodies to TfR1 are highly specific and exhibit the same long half-life as IgG.

Pharmaceutical Compositions

The present invention further provides pharmaceutical compositions comprising a TfR-specific binding moiety of the invention or compound, or a pharmaceutically acceptable salt or solvate thereof, according to the invention, together with a pharmaceutically acceptable carrier, excipient or vehicle.

Accordingly, the present invention further provides a pharmaceutical composition comprising a TfR-specific binding moiety of the invention or compound comprising a TfR-specific binding moiety, as well as variant and derivative compounds comprising a TfR-specific binding moiety of the invention. Certain embodiments of the pharmaceutical compositions of the invention are described in further detail below.

The present invention also provides pharmaceutical compositions comprising a TfR-specific binding moiety or a TfR-specific binding compound for use in treating, ameliorating or preventing one or more diseases, conditions, disorders or symptoms relating to B cells and immunoglobulin production, as described in further detail below. Each such disease, condition, disorder or symptom is envisioned to be a separate embodiment with respect to uses of a pharmaceutical composition according to the invention.

Formulations, Administration and Dosing

TfR specific binding compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to the salt of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, PA, U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

An acceptable route of administration may refer to any administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

In another aspect, the present invention provides a composition, e.g., a pharmaceutical composition, comprising one or a combination of different TfR specific binding compounds of the invention, or a VNAR sequence containing, TfR specific binding region thereof, or an ester, salt or amide of any of the foregoing, and at least one pharmaceutically acceptable carrier. Such compositions may include one or more different BAFF specific binding moieties or compounds in combination to produce an immunoconjugate or multi-specific molecule comprising at least one TfR specific binding moiety. For example, a pharmaceutical composition of the invention may comprise a combination of TfR specific binding moieties which bind to different epitopes of TfR or which otherwise have complementary biological activities.

Pharmaceutical compositions of the invention may be administered alone or in combination with one or more other therapeutic or diagnostic agents. A combination therapy may include a TfR specific binding compound of the present invention combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

As used herein, "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the TfR specific binding moiety comprising compound or component may be coated in a material or materials intended to protect the compound from the action of acids and other natural inactivating conditions to which the active TfR binding moiety may encounter when administered to a subject by a particular route of administration.

As above, a compound of the invention may encompass one or more pharmaceutically acceptable salts. As used herein a "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N, N'-dibenzylethylenediamine, N-methylglucamine, chloroprocaine, choline, diethanolamine, ethylenediamine, procaine and the like.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants.

TfR selective binding moieties and compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

Exemplary pharmaceutically acceptable carriers include sterile aqueous solutions or dispersions and sterile powders for the extemporaneous preparation of sterile injectable solutions or dispersion. Such media and reagents for pharmaceutically active substances are known in the art. The pharmaceutical compositions of the invention may include any conventional media or agent unless any is incompatible with the active TfR specific binding compound. Supplementary active compounds may further be incorporated into the compositions.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a TfR specific binding moiety (or a TfR binding compound comprising such a moiety) in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a TfR selective binding moiety or composition of the invention is administered by, e.g., intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of active ingredient which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens may be adjusted to provide the optimum desired response (e.g., a therapeutic response). For example, a single bolus may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect in association with the required pharmaceutical carrier. The specification for the dosage unit forms of the invention depend on the specific characteristics of the active compound and the particular therapeutic effect(s) to be achieved, taking into consideration and the treatment and sensitivity of any individual patient.

For administration of a TfR selective binding moiety or compound, the dosage range will generally be from about 0.0001 to 100 mg/kg, and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular subject, e.g., patient. TfR specific binding compounds will typically be administered on multiple occasions. Intervals between single dosages can be, for example, 2-5 days, weekly, monthly, every two or three months, every six months, or yearly. Intervals between administrations can also be irregular, based on regulating blood levels of TfR specific binding compound to the target TfR ligand in the subject or patient. In some methods, dosage is adjusted to achieve a plasma antagonist concentration of about 1-1000 µg/ml and in some methods about 25-300 µg/ml. Dosage regimens for a TfR specific binding compound of the invention include intravenous administration of 1 mg/kg body weight or 3 mg/kg body weight with the compound administered every two to four weeks for six dosages, then every three months at 3 mg/kg body weight or 1 mg/kg body weight.

In certain embodiments, two or more TfR specific binding compounds with different binding properties may be administered simultaneously or sequentially, in which case the dosage of each administered compound may be adjusted to fall within the ranges described herein.

In certain embodiments, a TfR specific binding compound of the invention may be administered as a sustained release formulation, in which case less frequent administration is required. Dosage and frequency vary depending on the half-life of the TfR specific binding compound in the subject or patient. The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of the TfR specific binding compound alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular TfR specific binding compound or composition employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject or patient being treated, and similar factors well known in the medical arts.

Administration of a "therapeutically effective dosage" of a TfR-binding compound compound of the invention may result in a decrease in severity of disease symptoms, an increase in frequency and duration of disease symptom-free periods, or a prevention of impairment or disability due to the disease affliction.

A TfR specific binding compound or composition of the present invention may be administered via one or more routes of administration, using one or more of a variety of methods known in the art. As will be appreciated by the skilled worker, the route and/or mode of administration will vary depending upon the desired results. Routes of administration for TfR specific binding compounds or compositions of the invention include, e.g., intravenous, intramuscular, intradermal, intraperitoneal, subcutaneous, spinal or other parenteral routes of administration, for example by injection or infusion. The phrase "parenteral administration" as used herein refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

In other embodiments, a TfR specific binding compound or composition of the invention may be administered by a non-parenteral route, such as a topical, epidermal or mucosal route of administration, for example, intranasally, orally, vaginally, rectally, sublingually or topically.

As described elsewhere herein, an active TfR specific binding compound may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compounds or compositions of the invention may be administered with one or more of a variety of medical devices known in the art. For example, in one embodiment, a therapeutic TfR specific binding composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the TfR specific binding compound or composition of the invention may be formulated to ensure a desired distribution in vivo. For example, the blood-brain barrier (BBB) excludes many highly hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 and the like.

Kits for Detecting or Quantifying TfR in a Sample

Also within the scope of the invention are kits comprising at least one TfR specific binding moiety or TfR specific binding compound or composition of the invention, and optionally, instructions for use. Kits may be useful for quantifying TfR or TfR specific antibodies in a sample, or may be useful for detection of TfR, such as in diagnostics methods. The kit may further or alternatively comprise at least one nucleic acid encoding a TfR specific binding moiety of the invention. A kit of the invention may optionally comprise at least one additional reagent (e.g., standards, markers and the like). Kits typically include a label indicating the intended use of the contents of the kit. The kit may further comprise reagents and other tools for measuring TfR in a sample or in a subject, or for diagnosing whether a patient belongs to a group that responds to a TfR-specific binding compound which makes use of a compound, composition or related method of the invention as described herein.

Delivery Devices and Further Kits

In certain embodiments, the invention relates to a device comprising one or more TfR specific binding compounds of the invention, or pharmaceutically acceptable salts or solvates thereof, for delivery to a subject. Thus, one or more compounds of the invention or pharmaceutically acceptable salts or solvates thereof can be administered to a patient in accordance with the present invention via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising one or more peptides, or pharmaceutically acceptable salts or solvates thereof, of the invention. In other embodiments, the kit comprises one or more pharmaceutical compositions comprising one or more peptides or pharmaceutically acceptable salts or solvates thereof. In certain embodiments, the kit further comprises packaging and/or instructions for use.

While some embodiments of the invention have been described byway of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

EXAMPLES

The following examples demonstrate certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

Example 1. General Methods

A1. Phage Display Selection of VNARs Having TfR-Binding Properties

The phagemid vector used for both phage display and monomeric VNAR expression is pOsD2, a modified version of pSEX81 (Progen) in which a 6xHis tag (SEQ ID NO: 483), a FLAG tag, and an amber stop codon were inserted between the VNAR (inserted into SfiI sites) and the full-length PIII protein of the M13 phage (the PCT '166 appln.).

Three different semi-synthetic VNAR libraries were panned including a wobbegong shark library OSX-2 (complexity ~6.8×10$^9$ CFU) constructed as previously described (Nuttall et al., Mol Immunol. 2001 August; 38(4):313-26) and the OSX-3 and OSX-4 synthetic libraries (described in the PCT '166 appln.). The phagemid vector used for both phage display and monomeric VNAR expression is pOsD2, a modified version of pSEX81 (Progen) in which a 6xHis tag (SEQ ID NO: 483), a FLAG tag, and an amber stop codon were inserted between the VNAR (inserted into SfiI sites) and the full-length PIII protein of the M13 phage (the PCT '166 appln.). The 6xHis tag (SEQ ID NO: 483) does not normally form part of a VNAR but can optionally be retained.

Phage library panning was performed essentially as described in (Griffiths et al. 1994, EMBO J., 13:3245-3260). Briefly, human Transferrin Receptor TfR-1 (Sino Biological) was immobilized on Nunc Maxisorp 96-well plates and exposed to an excess (about 100 times the library size) of phage rescued from the library. After a 1.5-hour incubation at room temperature, unbound particles were removed by washing, first in PBS-0.1% Tween and then in PBS. The bound phage were subsequently eluted with triethylamine (100 mM) and quickly neutralized in Tris (pH 7.5). Eluted particles were then used to infect *E. coli* ER2738. A portion of the culture was used to estimate the titer of eluted phage (by counting the number of antibiotic-resistant colonies), and the rest of the culture was infected with M13KO7 helper phage to produce phage for the next round of selection. Up to four rounds of selection were performed using increasingly stringent conditions consisting in progressively reducing the coated target protein concentration at every round (50, 5.0, 2.5, and 1 µg/mL respectively), and increasing the washing steps from 10 to 20.

Phage populations were tested for specificity to the target protein by polyclonal phage ELISA. Briefly 1×10$^{12}$ phage were incubated in Nunc Maxisorp 96-well plates coated at 1 µg/mL with TfR-1 or HSA (Sigma) as a negative control. After incubating at room temperature for one hour, the unbound particles were removed by washing the wells three times in first in PBS-0.1% Tween-20. Bound bacteriophage was then detected using a specific anti-M13 antibody (GE).

After selection rounds three and four, individual clones were picked and grown in 96-well format. Human TfR-1 output clones were grown in 2XTY until mid-log phase was reached. M13KO7 helper phage was then added (>1×10$^{10}$ helper phage/well) and the infection was allowed to proceed for 30 minutes at 37° C. The medium was then exchanged for Kanamycin-containing 2XTY and the culture was incubated overnight at 30° C., 250 rpm. The culture was then spun down and the phage-enriched supernatant was collected.

Periplasmic protein and phage supernatants were directly tested in a binding ELISA. Nunc Maxisorp 96-well plates were coated at 1 µg/mL with hTfR-1 or HSA as a negative control. Periplasmic fractions and phage supernatants were pre-blocked in PBS-0.1% Tween+2.5% milk before being exposed to the coated surface. After washing in PBS-0.1% Tween, bound molecules were detected using a peroxidase-conjugated anti-FLAG antibody (Sigma) for monomeric VNARs, and using a peroxidase conjugated anti-M13 antibody for the phage. Absorbance at 450 nm was recorded using an Envision multiwell reader (Perkin Elmer) and specific clones were selected using the criteria that their signal on the target protein must be at least four times superior to their respective signal on HSA. The DNA sequence of positive clones was determined as previously described in the PCT '166 appln. and those with unique CDR3 sequences were selected for further characterization.

A2. NGS Selection of VNARs Having TfR-Binding Properties

Novel TfR1-binding VNARs were also identified by next generation sequencing (NGS) without generating phage display libraries. Sharks were immunized with recombinant mouse TfR1 ectodomain (0.25 mg) emulsified in complete Freund's adjuvant in the lateral fin. Animals received intravenous boosts with recombinant human TfR1 ectodomain (0.25 mg) in PBS into the caudal vein. Buffy coats were prepared from blood recovered before and 4 weeks after the last boost and the cells lysed in RNAlater (Qiagen). Total RNA was isolated and cDNA synthesized by reverse transcription using

```
Tm (5'-TACAAATGTGGTGTACAGCAT)
and

Sec (5'-TAGTACGACCTGAAACATTAAC) primers.

Subsequently, VNAR sequences
were amplified by PCR using
Fw (5'-GCTCGAGTGGACCAAACACCG), Rv1 (5'-GCATTCACAGTCACGACAGTGCCACCTC),
and Rv2 (5'-GCATTCACAGTCACGGCAGTGCCATCTC) primers
(SEQ ID NOS. 406-410, respectively).
```

The resultant DNA was sequenced with MiSeq System (Illumina) in the 2×250 bp pair-end configuration. The sequencing reads were processed using a combination of software for clustering and comparing nucleotide sequences including PANDAseg, CD-HIT, R and in-house written scripts. VNARs were selected which fulfilled all of the following three criteria: a) their abundance determined in the Week 4 sample had to be at least 10 higher than abundance determined in sample before the boost; b) the relative abundance score in Week 4 had to be at least 100; and c) the sequence did not contain any stop codons. VNARs that met these criteria were selected and cloned into a bacterial expression vector for functional testing.

B. Expression and Purification of Monomeric VNARs

Selected target antigen-binding clones were expressed at larger scale in order to purify monomeric VNARs for biochemical analysis. Cultures (500 mL) were grown in auto-induction medium (Novagen) and periplasmic fraction was extracted by osmotic shock by resuspending the bacteria in TES buffer (50 mM Tris, 1 mM EDTA, 20% Sucrose w/v) mixed with an equal volume of TES diluted 1:5 in water. After 30 minutes on ice, the lysate was clarified by centrifugation and the salt concentrations were adjusted to 500 mM NaCl and 10 mM imidazole in 1×PBS. The periplasmic fraction was then purified on Nickel-Sepharose resin (Qiagen), washed in 1×PBS, 10 mM imidazole, 500 mM NaCl, and then eluted in 1×PBS, 500 mM imidazole, 500 mM NaCl. The purified protein was then buffer-exchanged against PBS and concentrated by centrifugation with Vivaspin 20 filters (Sartorius, MWCO 5000). Endotoxin was subsequently removed from the protein sample using VivaPure Q mini column (Sartorius) and the protein was sterile filtered (0.22 µm). After estimating the protein concentration using Bradford reagent (Pierce), the purified protein was frozen in aliquots.

C. Expression and Purification of VNAR-Fc Fusions

Selected VNARs were produced in CHO cells as fusions to the N-terminus of the IgG-Fc fragment via a (Gly)4-Ser linker (SEQ ID NO: 484). Tissue culture supernatants containing the VNAR-Fc were purified using Protein A affinity chromatography. Samples were added to a Mab Select Sure column (GE), washed with 20 mM phosphate, 150 mM NaCl, pH 7.4 and eluted with 0.1 M glycine-HCl, pH 3. Eluted samples were neutralised with 1 M Tris, pH 8 and then buffer-exchanged against PBS and concentrated by centrifugation with Vivaspin 20 filters (Sartorius, MWCO 10,000) and then sterile filtered (0.22 µm). Protein concentration was determined by absorbance measured at 280 nm. Binding EC50 values were determined as for monomers with the exception of the use of an anti-Fc peroxidase conjugate as a detection antibody.

D. Determining Biochemical EC50 Values

The biochemical EC50 (equilibrium constant, the concentration at which the ratio of bound to unbound is 50:50) of selected clones was determined by serially diluting purified monomeric VNARs or VNAR-Fc fusion proteins in blocking buffer (PBS-0.1% Tween+2.5% milk) and exposing it to preblocked Nunc Maxisorp 96-well plates coated at 1 µg/mL with hTfR-1. After washing in PBS-0.1% Tween-20, bound VNARs were detected using a peroxidase-conjugated anti-FLAG antibody (Sigma). Absorbance at 450 nm was recorded using an Envision multiwell reader (Perkin Elmer) and EC50s were calculated by fitting curves (non-linear regression) using GraphPad Prism®.

Polyclonal phage ELISA were performed on VNAR selection outputs. Phage ($1 \times 10^{12}$) from each round's input were incubated in microwells coated with hTfR-1 or HSA. After washing, bound phage was detected with a specific anti-M13 antibody as described above. A selective increase in phage binders to hTfR-1 relative to the negative controls (HSA) occurred after 3 rounds of panning.

EC50 binding curves of selected clones binding to immobilized TfR-1 were performed. HSA-1B8 is a non-specific VNAR used as a negative control. Monomeric VNARs that internalized into either mouse or human cells when expressed as VNAR-Fc fusion proteins were selected for a range of binding potencies to recombinant human (A) or recombinant mouse (B).

Example 2. Additional Selections for TfR-1-Binding VNARs

Libraries were also selected for pH-sensitivity by binding the phage to plates coated with human Tf-1, washing at pH 7.2 and eluting the bound phage with buffer at pH 5.2 for 2-3 rounds of panning.

Additionally, 2-3 rounds of panning were performed by internalization using TfR-1 expressing cell lines as previously described with minor modifications (Poul et al., J Mol Biol. 2000 Sep. 1; 301(5):1149-61). Libraries were enriched by a single round of solid-phase panning on rhTfR-1 prior to cell-based selections. A negative selection was carried out for 60 min. at 4° C. using adherent MX-1 human breast cancer cells (Cell Lines Service GmbH) prior to adding the deplete library to either mouse bEnd.3 (ATCC, CRL-2299) or human SKOV 3 cells (ATCC, HTB-77). To recover phage from within the cell, surface-bound phages were removed with low pH glycine and trypsin before lysing the cells in 100 mM triethylamine. Recovered phages were rapidly neutralized with 1M Tris (pH=7.4) before E. coli infection.

Each input phage population was tested for specific TfR-1 binding by polyclonal phage ELISA using an HRP-labelled anti-M13 monoclonal antibody (GE Life Sciences). Briefly, $10^{12}$ phages were incubated in Maxisorp 96 well plates coated at 1 µg/mL with either rhTfR-1 or negative control human serum albumin (HSA, Sigma) or hen egg lysozyme (HEL, Sigma). After a 2-hour incubation at room temperature, the unbound particles were removed by washing the wells three times in PBS-0.1% Tween-20. Bound bacteriophage was then detected by phage ELISA using an HRP-labelled anti-M13 monoclonal antibody. Bound anti-M13 was detected with the TMB substrate and the absorbance was read at 450 nm after the reaction was quenched with HCl. Additionally, the VNAR binding in periplasmic extracts was assessed by protein ELISA using an HRP-conjugate anti-FLAG M2 antibody (Sigma).

Example 3. Sequence Analysis of TfR-1-Binding VNARs

VNAR inserts were sequenced by the dye termination method with an automated sequencer (Applied Biosystems) their corresponding amino acid aligned using Clustal W 2.0 and Clustal X 2.0 programs (Larkin et al., Bioinformatics 2007 Nov. 1; 23(21):2947-8). Framework and CDR regions were identified by reference to known VNAR structures and unique and related clones were identified by amino acid sequence of the CDR3 and CDR1 regions.

Example 4. Expression and Purification of Monomeric VNARs

VNARs were purified from 500 mL bacterial cultures which were grown in auto-induction medium (Novagen) and periplasmic fractions were extracted by osmotic shock by resuspending bacteria in TES buffer (50 mM Tris, 1 mM EDTA, 20% Sucrose) mixed with an equal volume of TES diluted 1:5 in water. After 30 minutes on ice, lysates were clarified by centrifugation and the salt concentrations were adjusted to 500 mM NaCl and 10 mM imidazole in 1×PBS. Periplasmic extracts were then purified with Nickel-Sepharose resin (Qiagen), washed in 1×PBS, 10 mM imidazole, 500 mM NaCl, and then eluted in 1×PBS, 500 mM imidazole, 500 mM NaCl. The purified protein was then buffer-exchanged against PBS and concentrated by centrifugation with Vivaspin 20 filters (Sartorius, MWCO 5000). Endotoxin was removed using VivaPure Q mini column (Sartorius) and the protein was sterile filtered (0.22 µm). After estimating the protein concentration using Bradford reagent (Pierce), the purified protein was stored in frozen aliquots. EC50 binding curves of purified VNAR monomers to immobilized to human or mouse TfR-1 (1 Dg/ml) were determined by standard protein ELISA an HRP-conjugate anti-FLAG M2 antibody. For pH binding sensitivity testing, purified monomer was bound at pH7 and then washed 3 times for 3 min at either pH5.2 or pH7.2.

Example 5. Cellular ELISA Screening

Human adenocarcinoma SKOV3 cells were seeded in sterile 96-well plates (Greiner) in growth medium 36 hours before analysis. At approximately 80% confluence, cells were treated with either VNAR-expressing phage, periplasmic lysate or purified VNAR monomers for 1 hour at 4° C. After washing with PBS the cells were fixed with 4% paraformaldehyde for 20 minutes at room temperature. VNAR binding was detect by incubation for 1 hour at 4° C. with an HRP-labelled anti-M13 monoclonal antibody (GE Life Sciences) for phage or an HRP-conjugate anti-FLAG M2 antibody (Sigma) for periplasmic extracts or purified VNAR monomers. Binding of the OKT9 anti-human TfR-1 antibody used as positive control was detected with an HRP-labelled anti-Mouse IgG antibody. After washing with PBS, TMB substrate was added and the absorbance at 450 nm in each well was determined after 10 minutes using an Envision plate reader.

Example 6. Endocytosis Screening by Indirect Immunofluorescent Staining

TfR-1 expressing mouse bEnd.3 cells and human SKOV3 cells were seeded in Lab-Tek II Chamber Slide (Nunc) slides to achieve approximately 80% confluence at the time of analysis. VNAR monomers were applied at 1-5 µM in cell culture medium (100 µl/well) and incubated 1 hour either on ice to inhibit vesicle formation or 37° C. to allow endocytosis to occur. The cells were washed 3 times with 200 µl of 3% FBS in PBS (v/v) and fixed with 100 µl of 4% paraformaldehyde in PBS for 20 minutes at room temperature. After permeabilization with 0.1% Triton X-100 in PBS for 20 minutes, the cells were incubated with a mouse anti-FLAG antibody diluted 1:5000 (Sigma) for one hour at room temperature. After three washes in 3% FBS/PBS, the primary antibody was detected with anti-mouse IgG conjugated with AlexaFluor-A555 (Life Technologies) using the same conditions. The VNAR 5A7 specific for HEL (Dooley et al., Mol Immunol. 2003 September; 40(1):25-33.) was used as a negative control. VNAR-Fc fusion proteins were detected with goat Anti-human IgG Fc conjugated with DyLight550 (abcam). The anti-human TfR-1 mouse monoclonal antibody OKT9 and the anti-mouse TfR-1 rat monoclonal antibody R17217 (eBioscience) were used as a positive control appropriate species and isotype specific fluorescent labelled antibodies were also included. The chamber slides were disassembled after staining and sealed with coverslips over mounting media containing DAPI nuclear counter-stain and analysed using a laser scanning confocal microscope.

Example 7. Brain Uptake of VNAR-Fc Fusions

A. Expression and Purification of VNAR-Fc Fusion Proteins

Selected VNARs were expressed as N-terminal fusions to the human IgG1-Fc region (CH2 and CH3 domains) using a modified pFUSE-hIgGle3-Fc2 plasmid. CHO-K1 cells (ATCC, CCL-61) were cultured in DMEM/F12 (1:1) medium (Invitrogen) supplemented with 10% FBS and penicillin (100 U/ml), streptomycin (100 µg/ml) and maintained in a humidified incubator at 37° C. and 5% $CO_2$. Cells were seeded at 50% confluence in T175 flasks and transfected 24 hours later with 50 µg of DNA using Lipofectamine 2000 (Invitrogen) following the manufacturer's protocol. Flasks were incubated overnight and the medium was replaced with 40 mL of complete medium containing ultra-low IgG serum (Invitrogen) for production of recombinant antibodies.

Post-transfection media was removed after 48 hours, filtered (0.22 µm) and mixed with Protein G Sepharose 4 Fast Flow (GE Life Sciences) overnight at 4° C. by rotation. The slurry was added to an empty column and media removed by gravity flow. The sepharose column was washed with 50 column volumes each of 150, 500, and 150 mM NaCl in 20 mM Tris (pH 7.5). Bound VNAR-Fc fusion proteins were eluted using 10 column volumes of 0.1 M Glycine-HCl (pH 2.5) and neutralized with 1M Tris pH 8. The elution buffer was then exchanged with PBS using Vivaspin 20 (5 kDa) centrifugal concentrators and the protein estimated by absorbance at 280 nm. Purified proteins were stored at −20° C. in 100 µg aliquots and once thawed maintained at 4° C. for a period of up to 2 weeks.

B. Epitope Binning

Nunc Maxisorp 96 well plates were coated at 1 µg/mL with either hTfR-1 of mTfR-1 (Sino Biological). Small-scale phage lysates of specific clones were produced as described for phage ELISA and monomeric VNARS were purified by nickel affinity chromatography. Phage lysates were pre-blocked in PBS-0.1% Tween with 2.5% milk in the presence of competitor monomeric VNARs at 2 µM final concentration before being exposed to the coated surface. After washing in PBS-0.1% Tween, bound VNARs were detected using a peroxidase-conjugated anti-M13 antibody (GE 27-9421-01). Absorbance at 450 nm was recorded using a multiwell reader.

C. Measurement of Brain Uptake

Female BALB-c mice 6-12-week-old (22-27 g) were injected with VNAR-Fc fusion proteins at 10 mg/kg into the caudal tail vein. After 24 hr, animals were sacrificed by terminal intracardiac saline perfusion under deep anesthesia with ketamine/xylazine. The brains were removed, weighed and fractionated using the capillary depletion method (Triguero et al., J Neurochem. 1990 June; 54(6):1882-8.). Briefly, brains were homogenized in 3 volumes of ice-cold buffer [10 mM HEPES, 140 mM NaCl, 4 mM KCl, 2.8 mM CaCl2), 1 mM MgSO4, 1 mM NaH2PO4, 10 mM glucose; (volume×3 brain weight)] with five strokes in a dounce homogenizer. An equal volume of ice-cold 26% dextran (MW=60.000, Sigma) was added and the tissue further homogenized with another five strokes. The endothelial cell-enriched pellet and the supernatant containing brain parenchyma and interstitial fluid were separated by centrifugation at 5,400×g for 15 minutes at 4° C. The VNAR-Fc concentration was then measured by ELISA in supernatant, pellet and serum samples.

The activity of alkaline phosphatase was used to monitor capillary contamination of the parenchymal supernatant (Moos and Morgan J Neurochem. 2001 October; 79(1):119-29). In brief, 100 µl aliquot of the suspensions of pellets were added to a 0.9 mL of buffer [50 mM MgCl2, 5 mM CaCl2, 100 mM KCl, 5 mM p-nitrophenyl phosphate, and 100 mM Tris (pH 9.0)] and incubated for 20 minutes at 37° C. After the addition of 0.2 mL 5 mM NaOH, any insoluble material was removed by spinning for 10 minutes at 3,000 g. Absorbance was determined at 420 nm and activity converted to nM per minute per mg protein using the activity of purified alkaline phosphatase (Sigma P-7640).

Example 8. Anti-TfR1 VNAR Bispecific Molecules: Expression and Characterization

To test the ability of anti-TfR1 VNARs to increase the brain penetration of a monoclonal antibody, we generated a series of fusion molecules using anti-BACE1 antibody fragments. The VNAR F02 to TfR-1 was fused to different parts of the antibody molecule to create a series of bispecific molecules as follows (FIG. 12). The following constructs were produced using available reagents and standard methods of recombinant DNA construction:

F02 was fused to the C-terminus of the Heavy Chain via a $(G_4S)_3$ linker (SEQ ID NO: 481), either as a bivalent fusion (α-BACE C-ter HC Bivalent fusion) or as a monovalent fusion using the knob-into-hole technology (α-BACE C-ter HC Monovalent fusion).

F02 was fused to either the N-(α-BACE N-ter LC fusion) or C-terminus (α-BACE C-ter LC fusion) of the Light Chain via a $(G_4S)_3$ linker (SEQ ID NO: 481).

F02 was fused to the N-terminus of the Heavy Chain via a $(G_4S)_3$ linker (SEQ ID NO: 481), either as a bivalent fusion (α-BACE N-ter HC Bivalent fusion) or as a monovalent fusion (α-BACE N-ter HC Monovalent fusion) using the knob-into-hole technology.

The anti-BACE1 variable region was converted to a single chain variable fragment (scFv) using an 18 amino acid linker and fused to the C-terminus of a Fc molecule, which was itself fused in N-terminus to F02 (hFc-α-BACE ScFv). A hybrid molecule was generated by replacing one of the two Fabs of the anti-BACE1 antibody by F02, which was fused to the hinge via a $(G_4S)_3$ linker (SEQ ID NO: 481) (αBACE Ig Hybrid).

A. Expression and Purification of Bi-Specific Molecules

Fusion proteins were cloned and expressed in CHO cells. Post-transfection media was filtered (0.22 μm) and captured on pre-equilibrated (20 mM Phosphate Buffer pH 7.4, 150 mM NaCl) Mab Select Sure columns (Protein A ligand, GE) using an AKTA Express. The resin was washed with 10 column volumes of equilibration buffer and bound molecules were eluted using 5 column volumes of 0.1 M Glycine-HCl (pH 2.9) and neutralized with 1M Tris pH 8. The elution buffer was then exchanged with PBS using Vivaspin 20 (5 kDa) centrifugal concentrators and the protein estimated by absorbance at 280 nm.

Gel electrophoresis of the purified proteins revealed that the samples displayed the expected band pattern in reducing condition, and that no aberrant migration was observed in non-reducing conditions (FIG. 13), suggesting that the bispecific molecules were correctly assembled. Further analysis of the purified samples was performed by analytical gel filtration. Purified protein (200 μg) was loaded on a Superdex™200 10/300GL column (Code No. 17-5175-01) and run at 0.3 mL/min in [20 mM Sodium Phosphate, 150 mM NaCl pH7.4]. The elution profiles revealed that no significant aggregation was present in the purified samples and the bispecific molecules were produced as designed.

B. Binding of Bispecific Molecules to Recombinant TfR1 and BACE1

To test whether the bispecific molecules retained binding to both transferrin receptor and BACE1, the purified proteins were titrated against hTfR, mTfR, or BACE1 adsorbed to the solid phase of an ELISA plate. Binding was measured with an HRP-labelled anti-human-Fc antibody. The results in Table 3 below showed that all molecules retained efficient binding to both TfR and BACE1. Only the scFv had a significantly decreased potency from 0.5 to 76 nM.

TABLE 3

|  | hTfR EC50 (M) | mTfR EC50 (M) | BACE1 EC50 (M) |
| --- | --- | --- | --- |
| αBACE Ab | — | — | 4.425E−10 |
| F02-hFc | 2.63E−08 | 3.433E−08 | — |
| F02-αBACE C-ter HC fusion BIVALENT | 3.49E−08 | 7.416E−08 | 7.665E−10 |
| F02-αBACE C-ter HC KiH MONOVALENT | 1.72E−07 | 2.927E−07 | 7.149E−10 |
| F02-αBACE N-ter HC fusion BIVALENT | 1.34E−08 | 2.244E−08 | 1.176E−09 |
| F02-αBACE N-ter HC KiH MONOVALENT | 3.94E−08 | 1.052E−07 | 5.00E−10 |
| F02-αBACE C-ter LC fusion | 8.7E−08 | 3.223E−07 | 4.434E−10 |
| F02-αBACE N-ter LC fusion | 1.45E−08 | 2.693E−08 | 5.408E−10 |
| F02-αBACE/Ig Hybrid | 1.84E−07 | 4.718E−07 | 4.13E−09 |
| F02-αBACE scFv | 3.09E−08 | 6.647E−08 | 7.618E−08 |

C. Brain Uptake of Mono and Bi-Specific Molecules to TfR1 and BACE1

The purified bispecific molecules were injected into tail vein of female BALB-c mice (6-12 week old, 22-27 g) at 10 mg/kg. The mice were perfused with saline 18 hr later and brain homogenates were prepared by lysing the brain on ice in [50 mM Tris/HCl pH 7.5, 150 mM NaCl, 10% Glycerol, 1% Triton X-100, 1 mM EDTA, proteinase inhibitors]. After clarification of the lysate, the amount of antibody that was transported into the brain was determined by Fc-capture ELISA. As shown in FIG. 14, the brain penetration of different bi-specific molecules was not equivalent. Three molecules (hFc-α-BACE-ScFv, αBACE/Ig Hybrid, and α-BACE C-ter LC fusion) showed a significantly increased brain uptake (three- to five-fold) as compared to the anti-BACE1 antibody.

An antibody to the apical domain of the TfR1 was found to crosslink the receptor leading to lysosomal degradation and cell death (Ng et a, Blood 2006 Oct. 15; 108(8):2745-54). Similarly, a monovalent binding to the TfR1 was crucial for transporting cargo across the BBB whereas a bivalent binding mode lead to lysosomal sorting (Niewoehner et al, Neuron. 2014 Jan. 8; 81(1):49-60). To compare mono- and bi-specific transport, groups of mice received the parental (BACE1) or antibody (monovlaent) or variant (divalent) at 10 mg/kg, IV and brain were fractionated after cardiac perfusion 18 hours later. Serum antibody concentrations were the same for all three forms of the BACE1 antibody, but both monovalent and bivalent forms of the TfR1 bispecific antibodies were found at higher levels in the brain parenchyma (Par.) and capillaries (Cap.). Antibody levels in serum and brain tissue were measured using the anti-human IgG ELISA (FIG. 16).

Figure 16:
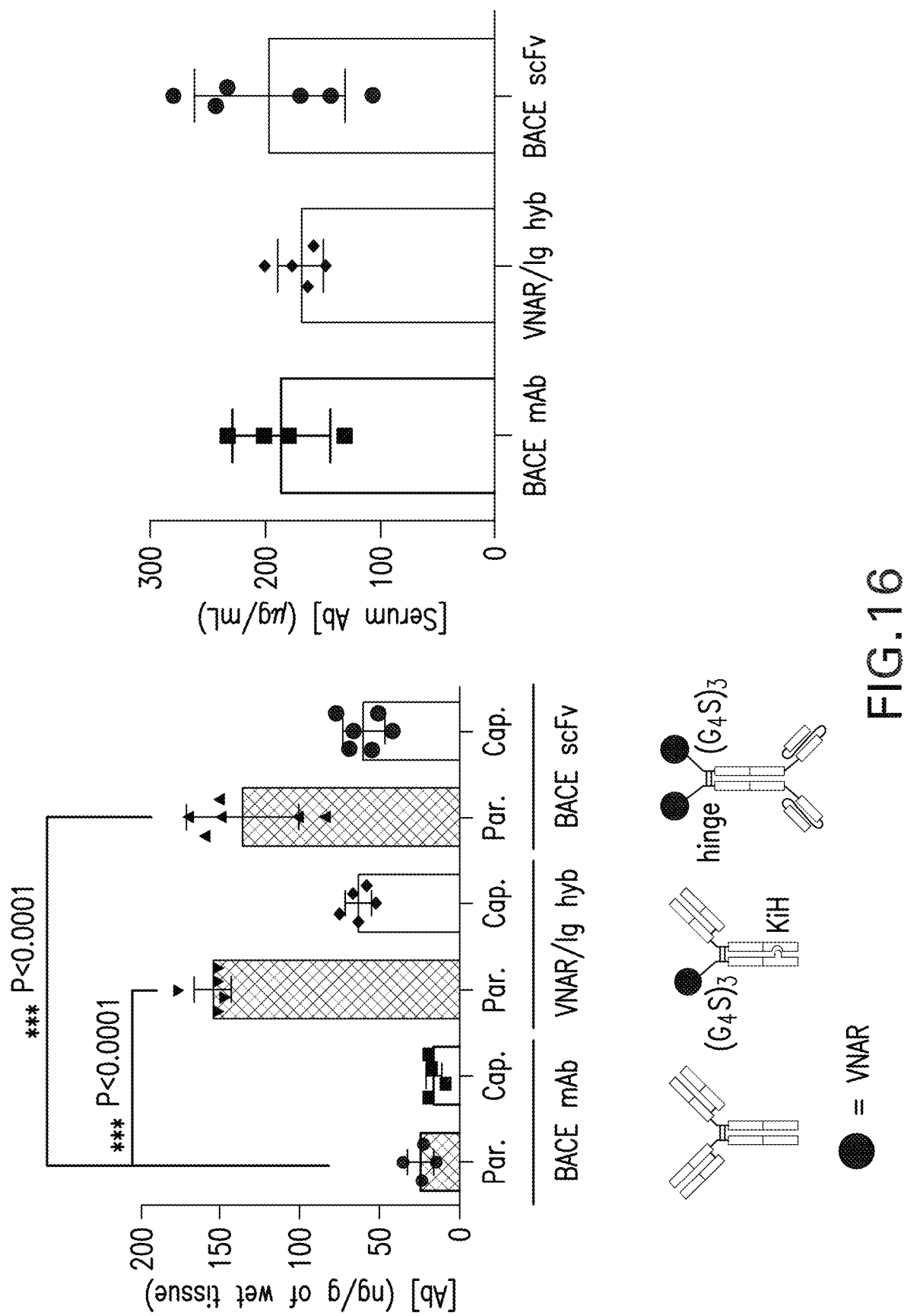
FIG. 16. Brain uptake of monovalent and divalent TfR1/BACE1 bispecific antibodies. Groups of mice received the parental or antibody or variant at 10 mg/kg, IV and brain were fractionated after cardiac perfusion 18 hours later. Serum antibody concentrations were the same for all three forms of the BACE1 antibody, but both monovalent and bivalent forms of the TfR1 bispecific antibodies were found at higher levels in the brain parenchyma (Par.) and capillaries (Cap.). Figure discloses "$(G_4S)_3$," SEQ ID NO: 481.

A distinguishing feature of VNAR carrier is that it functions equally well in monovalent and bivalent formats for transporting cargo across the BBB (FIG. 16). Affinity for TfR1 does not appear crucial since the Ig hybrid and scFv with affinities of 66 and 470 nM, respectively (Table 3) accumulated in the brain to equal levels.

D. Bispecific Anti-TfR1 VNAR Fusions have Functional Activity in the Brain

In order to demonstrate that the three anti-TfR VNAR bi-specific molecules shown to penetrate the BBB also deliver functional activity of a conjugate payload molecule (here, BACE1), The level of Abeta (40) was measured in the brain lysate of the same bispecific molecule-treated mice using a commercial detection kit (human/rat Amyloid (40) ELISA kit (Wako #294-62501). Results from two independent experiments showed that the anti-TfR VNAR-Fc fusion molecule having no anti-BACE1 moiety did not reduce the brain Abeta levels, whereas both N- and C-terminal light chain fusions, and the Ig/hybrid and the scFv-fusions of anti-TfR VNAR with anti-BACE1 moieties had a significant effect on the Abeta (40) level, reducing it by 20-30%, whereas the BACE1 antibody had no effect (FIG. 15).

E. Anti-TfR1 BACE1 Fusions do not Reduce TfR-1 Levels in the Brain

Figure 17:
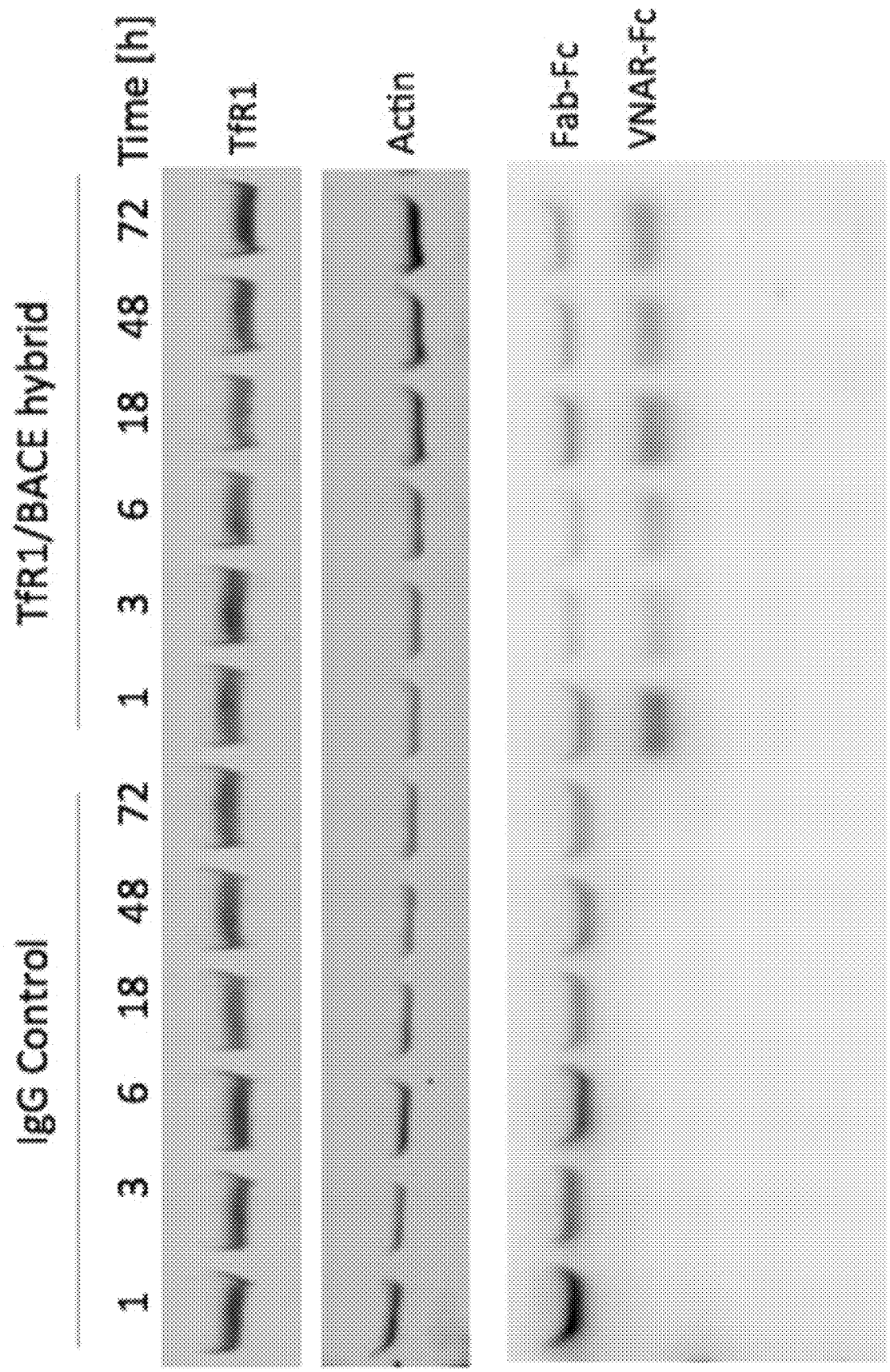
FIG. 17. TfR1 levels in the brain are not affected by exposure to an anti-TfR1 bispecific antibody. Western blots are shown of brain extracts and corresponding serum samples of mice treated with 10 mg/kg of either a control IgG or the anti-TfR1/BACE1 VNAR/Ig hybrid.

A bispecific anti-TfR/Bace1 that binds with high affinity to TfR1 (~20 nM) was found to cause a reduction in brain TfR levels by targeting the receptor to the lysosomes for degradation whereas a low affinity version of the same antibody (~600 nM) transcytosed without receptor degradation (Bien-Li et al., J Exp Med. 2014 Feb. 10; 211(2):233-44). A similar bispecific TfR1/BACE1 hybrid antibody was produced using a high affinity VNAR to TfR (~5 nM) that traverses the BBB and effectively reduces brain A levels, but without evidence of a reduction in brain TfR1 levels over a 72 hrs period despite continued serum exposure (FIG. 17).

Briefly, Western blots of brain extracts and corresponding serum samples of mice treated with 10 mg/kg of either a control IgG or the anti-TfR/BACE1 VNAR/Ig hybrid. Quantification of band intensities from 3 mice using Image Studio Lite (LiCor) showed that there was not a significant difference in the levels of TfR1 with either antibody treatment over 72 hours (not shown). Both the IgG and VNAR/Ig hybrid appeared stable in serum over the same period. Denatured IgG runs as a single band composed of two Fab-Fc chains whereas the hybrid is composed of one Fab-Fc and one lower molecular weight VNAR-Fc.

Example 15. Binding Specificity of Bivalent VNAR Fc Fusion Proteins

Figure 18:
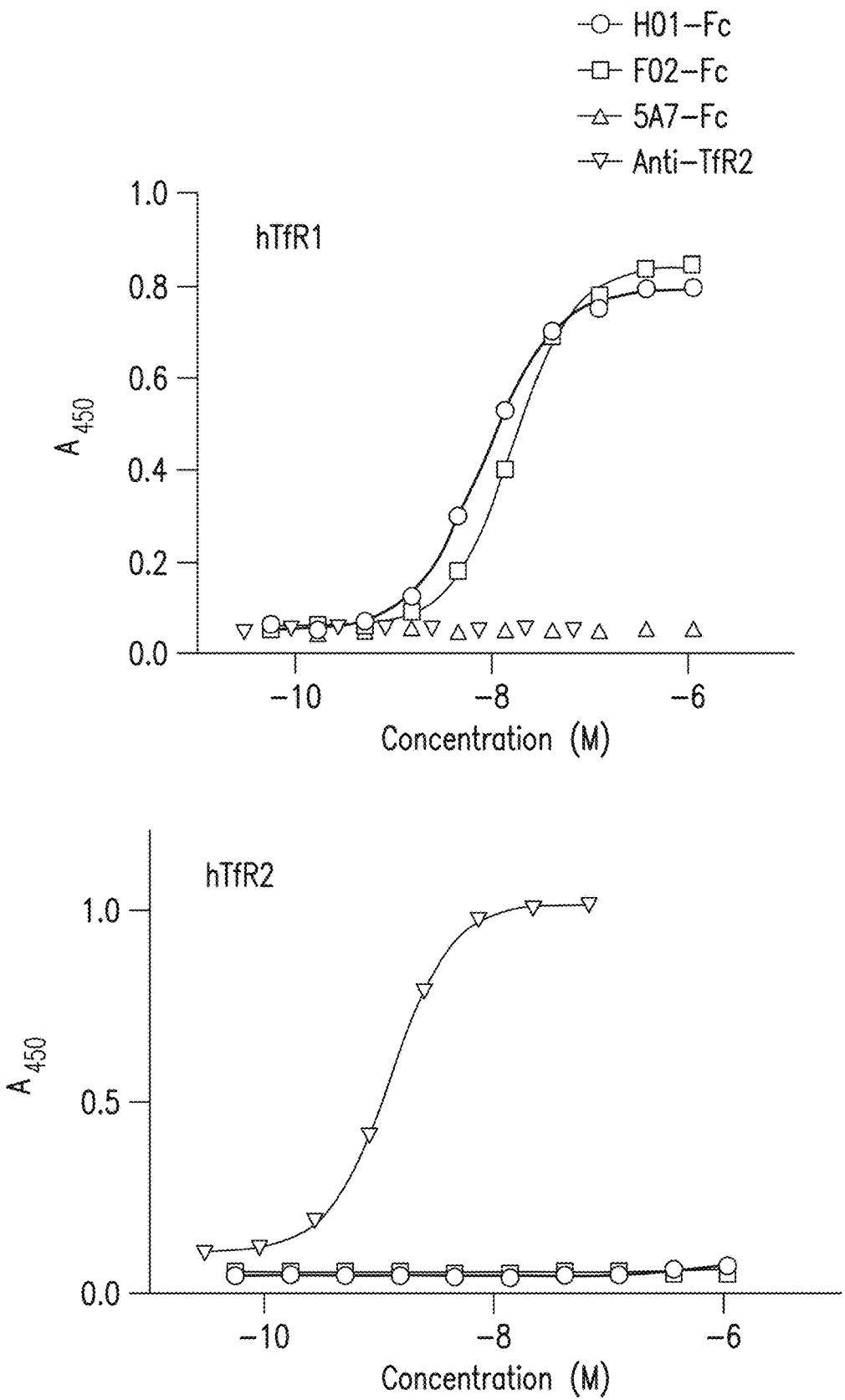
FIG. 18. Binding specificity of bivalent VNAR-Fc fusion proteins for TfR1. The left panel shows binding curves for H01-Fc and F02-Fc to human TfR-1 and that neither the negative VNAR control 5A7-Fc nor an anti-TfR-2 antibody bind to human TfR-1. The right panel shows a binding curve for the anti-TfR-2 antibody to human TfR-2 and that none of H01-Fc, F02-Fc or 5A7-Fc bind human TfR-2.

The binding specificity of H01-Fc and F02-Fc for hTfR-1 and hTfR-2 were determined by an ELISA as described in Example 1D. Anti-TfR-2 was used as a positive control for TfR-2 binding. The negative VNAR control 5A7-Fc did not bind either receptor. Both H01-Fc nor F02 Fc bound hTfR-1 with high specificity (~100 nM) and neither bound hTfR-2 (FIG. 18).

Example 16. Epitope Mapping of Tfr1-Binding VNARs by Mass-Spectrometry

To determine the epitope of three non-competing VNARs (F02, A07 and H01) on the hTfR-1 antigen with high resolution, antibody/antigen complexes were incubated with deuterated cross-linkers and subjected to multi-enzymatic proteolytic cleavage (Bich et al., Anal. Chem., 2010, 82(1): 172-179). After enrichment of the cross-linked peptides by nano-liquid chromatography (UltiMate 3000, Dionex), the samples were analysed by high-resolution mass spectrometry (LTQ Orbitrap XL, Thermo Scientific) and the data generated were processed using XQuest and Stavrox software.

Figure 19:
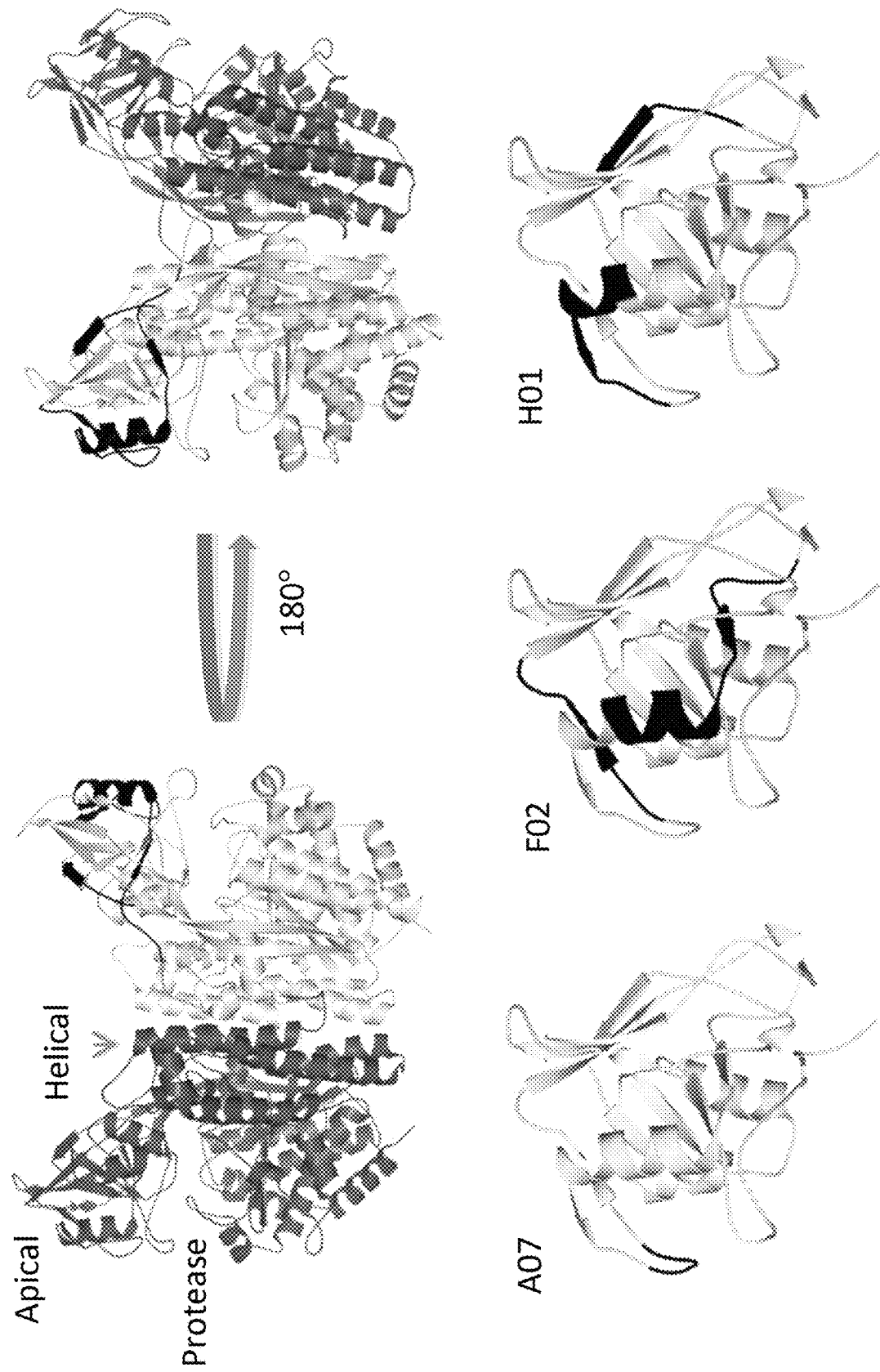
FIG. 19. Epitope coverage of VNARs to the human TfR1. Top: Ribbon diagram of the human TfR-1 dimer (light & dark grey) with highlighted regions (black) in the apical domain where VNARs cross-linked to the receptor. Bottom: Enlarged apical domain showing the specific epitope for three different VNARs (A07, F02 and H01) that did not compete with each other for binding the receptor.

FIG. 19 shows an enlarged view of the apical domain of human TfR1 with the regions where the three respective VNARs were cross-linked to the receptor highlighted (black) on the ribbon structure (grey). This region does not directly interact with transferrin (edged of the space-filling structure) as shown by previous co-crystallization studies.

Two interaction interfaces were identified for VNAR F02 that included the following amino acid sequences in human Tfr1 (G:94717625) (SEQ ID NOS. 411 and 412, respectively):

$S^{327}GLPNIPVQTISRAAAEK^{44}$ $S^{361}TCRMVTSES^{370}$

Two interaction interfaces were identified For VNAR H01 that included the following amino acid sequences in human Tfr1 (SEQ ID NOS. 413 and 414, respectively):

$K^{224}AATVT^{229}$ $K^{344}LFGNMEGDCPS^{55}$

One interaction interface was identified for VNAR A07 that included the following amino acid sequence in human Tfr1 (SEQ ID NO. 415):

$S^{355}DWKTDS^{361}$

Example 17. Anti-TfR1 VNARs that can Carry an Antibody into the Brain

Figure 20A:
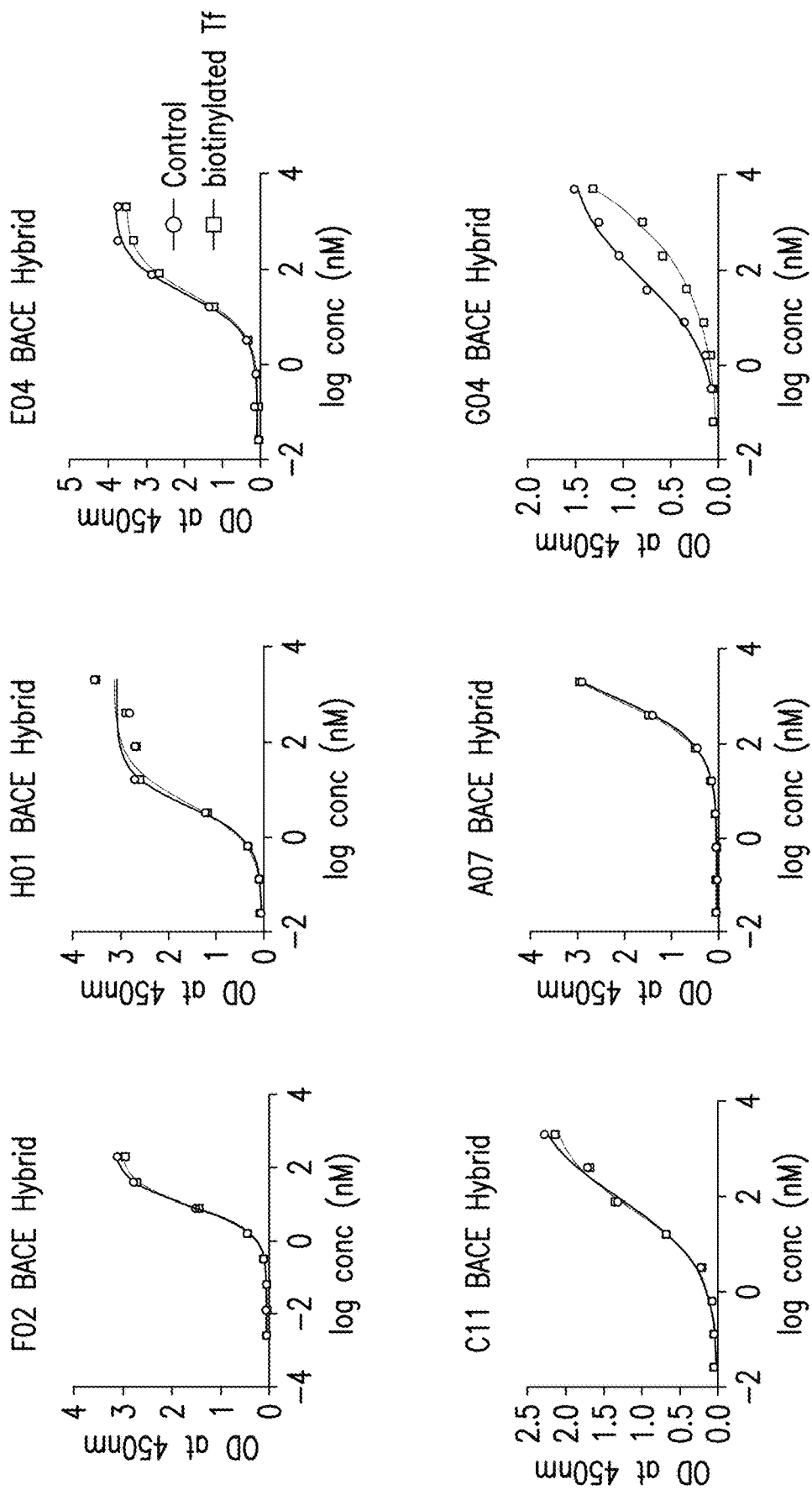
FIG. 20A and FIG. 20B. Lack of transferrin (Tf) competition of six different VNARs configured as anti-TfR1/BACE1 bispecifics. ELISA binding curves to recombinant human TfR1 were generated with (squares) or without (circles) pre-blocking with 10 µM biotinylated human transferrin (Tf) (FIG. 20A). Only G04 competed with Tf for TfR1 binding as reported for the monoclonal antibody 42/6 (FIG. 20B).
Figure 20B:
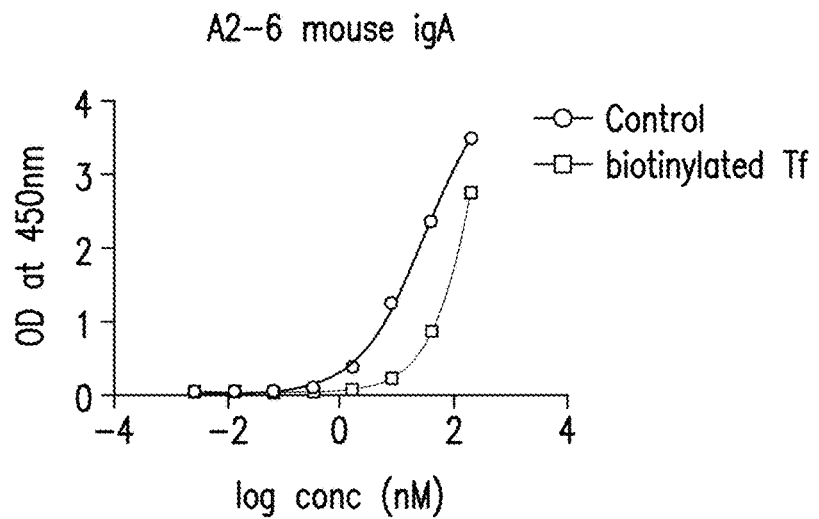
Figure 21:
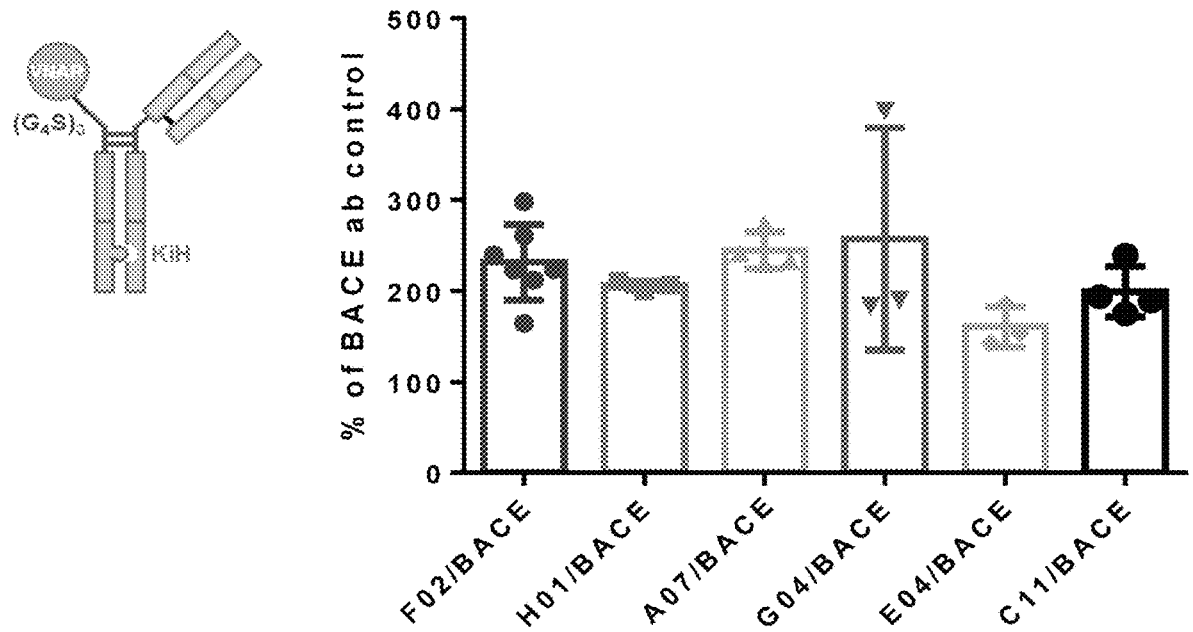
FIG. 21. Brain uptake of various anti-TfR1/BACE1 bispecific antibodies. Mice were injected with 10 mg/kg antibodies (IV) and 18 hours later antibody levels were measured in perfused brains by ELISA. Brain uptake of all the bispecific antibodies was significantly greater than of unmodified parental BACE1 antibody (P<0.001). Figure discloses "$(G_4S)_3$," SEQ ID NO: 481.

Six representative VNARs to TfR-1 were configured as BACE1 bispecifics to further explore the effect of TfR1 binding affinity and epitope on brain uptake. Binding potencies to human TfR-1 ranged from 3 nM to 3 µM and from 25 to 450 nM for mouse TfR-1 whereas the potency for BACE1 was nearly identical for all the hybrid antibodies (Table 4). Only one of the VNARs (G04) competed with transferrin for binding to the receptor (FIG. 20). Despite differences in epitope binding and affinity, all of the VNARs were similarly effective in carrying an antibody cargo across the BBB (FIG. 21), although G04 may be considered undesirable for chronic administration since it competes with transferrin.

These results collectively show that multiple VNARs can bind with high specificity to TfR1 without cross reacting with its nearest homologue or interfering with its endogenous ligand and can also effectively carry a large molecular cargo across the BBB and into the brain. Hence, the VNAR domains that have been shown to cross the BBB and/or carry cargo across the BBB are A07, F02, H01, C11, E04 and G04.

TABLE 4

Comparative EC50s (nM) of bispecific TfR1/BACE1 hybrid antibodies configured with six different VNARs that bind different epitopes on TfR1.

| | G04-BACE1 | E04-BACE1 | A07-BACE1 | C11-BACE1 | H01-BACE1 | F02-BACE1 | F02-Fc |
|---|---|---|---|---|---|---|---|
| hTfR1 | 3876.0 | 103.7 | 840.3 | 137.9 | 2.8 | 42.8 | 9.0 |
| mTfR1 | 450.7 | 146.1 | 272.0 | 178.4 | 25.6 | 93.8 | 34.2 |
| BACE1 | 2.1 | 2.1 | 3.2 | 3.0 | 2.6 | 2.6 | — |

Example 18. Identification of hTfR1 Binders from NGS of RNA

Novel TfR1 binding VNARs were also identified by NGS after immunization. To generate VNARs with species cross reactivity, sharks were primed with mouse TfR1 in adjuvant by i.m. injection and then boosted with human TfR1, i.v. as described in Example A2.

RNAs encoding VNARs were amplified by RT-PCR from lymphocyte samples taken weekly after the boost and the corresponding cDNA sequences were determined using the Illumina MiSeq next generation sequencing platform. VNARs were selected for analysis which fulfilled all the following three criteria: a) their abundance determined in the Week 4 sample had to be at least 10 higher than abundance determined in sample before the boost; b) the relative abundance score in Week 4 had to be at least 100; and c) the sequence did not contain any stop codons. In many cases, just a single VNAR sequence was amplified while in other cases, a family of related sequences was enriched after the boost although one member increased preferentially. These sequences are provided in Table 1.

Example 19. Competitive Binding for the F02 Epitope

The family of antibodies that compete with F02 for binding to TfR-1 are defined by competition for the same or overlapping epitope on TfR1. Using competitive binding experiments as generally described in Example 7B, the VNAR domains found that compete for the same epitope as F02 are C02, G02, A03, H11 and C11.

What is claimed is:

1. A transferrin receptor (TfR)-specific conjugate comprising a heterologous molecule operably linked to a TfR-specific binding moiety, wherein said TfR-specific binding moiety comprises a Type 2 VNAR domain capable of specifically binding to human TfR-1, wherein said moiety is capable of cross reacting with mouse TfR-1, and wherein said VNAR domain comprises or consists essentially of a VNAR scaffold with any one CDR1 peptide of SEQ ID NOS. 422, 423, 424, 426, 427, 429 or 434 in combination with any one CDR3 peptide of SEQ ID NOS. 189, 214, 215, 218, 226, 235, 237, 240 or 250.

2. The conjugate of claim 1, wherein said CDR1 peptide has an amino acid sequence of SEQ. ID NO. 422 and said CDR3 peptide has an amino acid sequence of SEQ. ID NO. 189.

3. The conjugate of claim 1, wherein said CDR1 peptide has the amino acid sequence of SEQ. ID NO. 429 and said CDR3 peptide has the amino acid sequence of SEQ. ID NO. 214.

4. The conjugate of claim 1, wherein said CDR1 peptide has an amino acid sequence of SEQ. ID NO. 427 and said CDR3 peptide has an amino acid sequence of SEQ. ID NO. 215.

5. The conjugate of claim 1, wherein said CDR1 peptide has an amino acid sequence of SEQ. ID NO. 426 and said CDR3 peptide has an amino acid sequence of SEQ. ID NO. 218.

6. The conjugate of claim 1, wherein said CDR1 peptide has an amino acid sequence of SEQ. ID NO. 426 and said CDR3 peptide has an amino acid sequence of SEQ. ID NO. 226.

7. The conjugate of claim 1, wherein said CDR1 peptide has an amino acid sequence of SEQ. ID NO. 423 and said CDR3 peptide has an amino acid sequence of SEQ. ID NO. 235.

8. The conjugate of claim 1, wherein said CDR1 peptide has an amino acid sequence of SEQ. ID NO. 434 and said CDR3 peptide has an amino acid sequence of SEQ. ID NO. 237.

9. The conjugate of claim 1, wherein said CDR1 peptide has an amino acid sequence of SEQ. ID NO. 424 and said CDR3 peptide has an amino acid sequence of SEQ. ID NO. 240.

10. The conjugate of claim 1, wherein said CDR1 peptide has an amino acid sequence of SEQ. ID NO. 427 and said CDR3 peptide has an amino acid sequence of SEQ. ID NO. 250.

11. The conjugate of claim 1, wherein said moiety is the VNAR domain E04 (SEQ ID NO. 7), F02 (SEQ ID NO. 30), A03 (SEQ ID NO. 31), H11 (SEQ ID NO. 34), C02 (SEQ ID NO. 42), H01 (SEQ ID NO. 51), C11 (SEQ ID NO. 53), G04 (SEQ ID NO. 56) or G02 (SEQ ID NO. 66).

12. The conjugate of claim 1, wherein said molecule and said moiety are operably linked by a covalent or non-covalent linkage.

13. The conjugate of claim 12, wherein the heterologous molecule is a growth factor, cytokine, lymphokine, cell surface antigen or an antibody or antibody fragment which binds to any of the foregoing; a chimeric antigen receptor; a cytotoxic small molecule; a biochemical pathway agonist or antagonist; a therapeutic agent or drug; a diagnostic agent such as a fluorescent molecule or other molecular marker; or a nucleic acid molecule with regulatory properties or which encodes a regulatory molecule for a cell.

* * * * *

SEQUENCE LISTING

<160> NUMBER OF SEQ ID NOS: 484

<210> SEQ ID NO 1
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Ser Asn Val Phe Cys Ile Ile Asp Gly Glu Leu Glu Asp Val
                85                  90                  95

Tyr Gly Gly Gly Thr Val Val Thr Val Asn Ala Ala Ser Gly Ala
            100                 105                 110

<210> SEQ ID NO 2
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Ala Arg Val Asp Gln Thr Pro Gln Thr Ile Ile Lys Glu Thr Gly Glu
1               5                   10                  15

Ser Leu Thr Ile Asn Cys Val Leu Arg Asp Asn Asn Cys Asp Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Ser Asn Val Phe Cys Ile Ile Asp Gly Leu Glu Asp Val
                85                  90                  95

Tyr Gly Gly Gly Thr Val Val Thr Val Asn Ala Ala Ser Gly Ala
            100                 105                 110
```

<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Met Ala Gln Ala Ala Arg Val Asp Gln Thr Pro Arg Ile Ala Thr Lys
1               5                   10                  15

Glu Thr Gly Glu Ser Leu Thr Ile Asn Cys Val Leu Arg Asp Asn Asn
            20                  25                  30

Cys Ala Leu Pro Ser Thr Asn Trp Tyr Arg Thr Lys Leu Gly Ser Thr
        35                  40                  45

Lys Glu Gln Thr Ile Ser Ile Gly Gly Arg Tyr Ser Glu Thr Val Asp
    50                  55                  60

Glu Gly Ser Asn Ser Ala Ser Leu Thr Ile Arg Asp Leu Arg Val Glu
65                  70                  75                  80

Asp Ser Gly Thr Tyr Lys Cys Lys Ala Asp Tyr Trp Cys Asp Pro Met
                85                  90                  95

Arg Ala Pro Gly Leu Phe Gly Arg Lys Glu Ala Gly Thr Val Leu
            100                 105                 110

Thr Val Lys Glu Ala Ser Gly Ala
        115                 120
```

<210> SEQ ID NO 4
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Met Ala Gln Ala Ala Arg Val Asp Gln Thr Pro Arg Ile Ala Thr Lys
1               5                   10                  15

Glu Thr Gly Glu Ser Leu Thr Ile Asn Cys Val Leu Arg Asp Ser Asn
            20                  25                  30

Cys Ala Leu Pro Ser Thr Asn Trp Tyr Arg Thr Lys Leu Gly Ser Thr
        35                  40                  45
```

Lys Glu Gln Thr Ile Ser Ile Gly Gly Arg Tyr Ser Glu Thr Val Asp
            50                  55                  60

Glu Gly Ser Asn Ser Ala Ser Leu Thr Ile Arg Asp Leu Arg Val Glu
65                  70                  75                  80

Asp Ser Gly Thr Tyr Lys Cys Lys Ala Glu Thr Asn Cys His Ile Phe
                85                  90                  95

Tyr Gln Phe Pro Lys Asp Glu Gly Ala Gly Thr Val Leu Thr Val Lys
            100                 105                 110

Glu Ala Ser Gly Ala
        115

<210> SEQ ID NO 5
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Ala Gly
            20                  25                  30

Ser Thr Tyr Trp Tyr Arg Lys Lys Ser Gly Ser Thr Asn Glu Val Arg
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys His Val Glu Thr Pro Tyr Asp Cys Pro Glu Leu Asn Trp
                85                  90                  95

Trp Asp Val Tyr Gly Gly Thr Val Val Thr Val Asn Ala Ala Ser
            100                 105                 110

Gly Ala

<210> SEQ ID NO 6
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Ala Ser
            20                  25                  30

Ser Arg Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys His Val Glu Thr Pro Tyr Asp Cys Pro Glu Leu Asn Trp

```
                    85                  90                  95

Trp Asp Val Tyr Gly Gly Gly Thr Val Val Thr Val Asn Ala Ala Ser
                100                 105                 110

Gly Ala

<210> SEQ ID NO 7
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Arg Cys Ala Ala Ser
                20                  25                  30

Ser Arg Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys His Val Glu Thr Pro Tyr Asp Cys Pro Glu Leu Asn Trp
                85                  90                  95

Trp Asp Val Tyr Gly Gly Gly Thr Val Val Thr Val Asn Ala Ala Ser
                100                 105                 110

Gly Ala

<210> SEQ ID NO 8
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Ala Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys His Val Gln Thr Pro Tyr Asp Cys Pro Glu Leu Asn Trp
                85                  90                  95

Trp Asp Val Tyr Gly Gly Gly Thr Val Val Thr Val Asn Ala Ala Ser
                100                 105                 110

Gly Ala

<210> SEQ ID NO 9
```

```
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys His Val Arg Thr Pro Tyr Asp Cys Pro Glu Leu Asn Trp
                85                  90                  95

Trp Asp Val Tyr Gly Gly Gly Thr Val Val Thr Val Asn Ala Ala Ser
            100                 105                 110

Gly Ala

<210> SEQ ID NO 10
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys His Val Thr Thr Pro Tyr Asp Cys Pro Glu Leu Asn Trp
                85                  90                  95

Trp Asp Val Tyr Gly Gly Gly Thr Ala Val Thr Val Asn Ala Ala Ser
            100                 105                 110

Gly Ala

<210> SEQ ID NO 11
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11
```

```
Ala Arg Val Asp Gln Thr Pro Arg Ile Ala Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Asn Trp Tyr Arg Thr Lys Leu Gly Ser Thr Lys Glu Gln Thr
            35                  40                  45

Ile Ser Ile Gly Gly Arg Tyr Ser Glu Thr Val Asp Glu Gly Ser Asn
        50                  55                  60

Ser Ala Ser Leu Thr Ile Arg Asp Leu Arg Val Glu Asp Ser Gly Thr
65                  70                  75                  80

Tyr Lys Cys Lys Ala Ile Cys Asp Ile Phe Thr Tyr Tyr Gly
                85                  90                  95

Ser Trp Glu Gly Ala Gly Thr Val Leu Thr Val Lys Glu Ala Ser Gly
                100                 105                 110

Ala
```

```
<210> SEQ ID NO 12
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

```
Ala Arg Val Asp Gln Thr Pro Arg Ile Ala Thr Lys Glu Thr Gly Glu
1               5                   10                  15

Ser Leu Thr Ile Asn Cys Val Leu Arg Asp Asn Asn Cys Ala Leu Pro
                20                  25                  30

Ser Thr Asn Trp Tyr Arg Thr Lys Leu Gly Ser Thr Lys Glu Gln Thr
            35                  40                  45

Ile Ser Ile Gly Gly Arg Tyr Ser Glu Thr Val Asp Glu Gly Ser Asn
        50                  55                  60

Ser Ala Ser Leu Thr Ile Arg Asp Leu Arg Val Glu Asp Ser Gly Thr
65                  70                  75                  80

Tyr Lys Cys Lys Ala Ile Asp Tyr Cys Leu Ser Trp Tyr Arg Ser Ile
                85                  90                  95

Asn Leu Glu Gly Ala Gly Thr Val Leu Thr Val Lys Glu Ala Ser Gly
                100                 105                 110

Ala
```

```
<210> SEQ ID NO 13
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13
```

```
Ala Arg Val Asp Gln Thr Pro Arg Ile Ala Thr Lys Glu Thr Gly Glu
1               5                   10                  15

Ser Leu Thr Ile Asn Cys Val Leu Arg Asp Asn Asn Cys Ala Leu Pro
                20                  25                  30

Ser Thr Asn Trp Tyr Arg Thr Lys Leu Gly Ser Thr Lys Glu Gln Thr
            35                  40                  45
```

```
Ile Ser Ile Gly Gly Arg Tyr Ser Glu Thr Val Asp Glu Gly Ser Asn
    50                  55                  60

Ser Ala Ser Leu Thr Ile Arg Asp Leu Arg Val Glu Asp Ser Gly Thr
65                  70                  75                  80

Tyr Lys Cys Lys Ala Pro Ser Phe Asp Pro Leu Asn Tyr Cys Tyr Ile
                85                  90                  95

Trp Arg Arg Thr Thr Glu Gly Ala Gly Thr Val Leu Thr Val Lys Glu
                100                 105                 110

Ala Ser Gly Ala
        115

<210> SEQ ID NO 14
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr Tyr Trp Tyr Arg Lys Lys Ser Gly Ser Thr Asn Glu Glu Arg
            35                  40                  45

Ile Ser Ala Gly Gly Arg Tyr Val Glu Thr Val Asn Ser Arg Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Ser Pro Pro Leu Val Ala Gly Val Leu Asn Cys
                85                  90                  95

Tyr Asp Ile Tyr Gly Gly Thr Ala Val Thr Val Asn Ala Ala Ser
                100                 105                 110

Gly Ala

<210> SEQ ID NO 15
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Pro
                20                  25                  30

Asn Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Ser Ser Pro Gln Leu Gly Phe Tyr Asp Cys
```

```
              85                  90                  95
Gly His Trp Ile Asp Val Tyr Gly Gly Gly Thr Val Val Thr Val Asn
              100                 105                 110

Ala Ala Ser Gly Ala
            115

<210> SEQ ID NO 16
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ala Ser Tyr Ala Leu Gly
                20                  25                  30

Ser Ala Tyr Trp Tyr Arg Lys Lys Ser Gly Ser Thr Asn Glu Glu Ser
            35                  40                  45

Ile Leu Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Phe His Ile Ala Gly Thr Asp Met Ala Glu Leu
                85                  90                  95

Val Tyr Asp Val Tyr Gly Gly Gly Thr Val Val Thr Val Asn Ala Ala
            100                 105                 110

Ser Gly Ala
        115

<210> SEQ ID NO 17
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ala Arg Val Asp Gln Thr Pro Arg Ile Ala Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Asn Trp Tyr Arg Thr Lys Leu Gly Ser Thr Lys Glu Gln Thr
            35                  40                  45

Ile Ser Ile Gly Gly Arg Tyr Ser Glu Thr Val Asp Glu Gly Ser Asn
        50                  55                  60

Ser Ala Ser Leu Thr Ile Arg Asp Leu Arg Val Glu Asp Ser Gly Thr
65                  70                  75                  80

Tyr Lys Cys Lys Ala Val Leu Val Pro Ala His Gly Asp Cys Ser Ala
                85                  90                  95

Trp Ser Leu Trp Val Gly Val Glu Gly Ala Gly Thr Val Leu Thr Val
            100                 105                 110

Lys Glu Ala Ser Gly Ala
        115
```

<210> SEQ ID NO 18
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

```
Ala Arg Val Asp Gln Thr Pro Gln Thr Ile Thr Lys Glu Thr Gly Glu
1               5                   10                  15

Ser Leu Thr Met Tyr Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Ser Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Leu Val Arg Leu Gly Trp Tyr Glu Tyr Cys Pro Val Leu
                85                  90                  95

Gly Gly Val Tyr Asp Val Tyr Gly Gly Thr Ala Val Thr Val Asn
            100                 105                 110

Ala Ala Ser Gly Ala
        115
```

<210> SEQ ID NO 19
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Ala Arg Val Asp Gln Thr Pro Arg Ile Ala Thr Lys Glu Thr Gly Glu
1               5                   10                  15

Ser Leu Thr Ile Asn Cys Val Leu Arg Asp Asn Asn Cys Ala Leu Pro
            20                  25                  30

Ser Thr Asn Trp Tyr Arg Thr Lys Leu Gly Ser Thr Lys Glu Gln Thr
        35                  40                  45

Ile Ser Ile Gly Gly Arg Tyr Ser Glu Thr Val Asp Glu Gly Ser Asn
    50                  55                  60

Ser Ala Ser Leu Thr Ile Arg Asp Leu Arg Val Glu Asp Ser Gly Thr
65                  70                  75                  80

Tyr Lys Cys Lys Ala Val Ser Trp Cys Thr Arg His Thr Met Trp Asn
                85                  90                  95

Trp Tyr Thr Val His Glu Gly Ala Gly Thr Val Leu Thr Val Lys Glu
            100                 105                 110

Ala Ser Gly Ala
        115
```

<210> SEQ ID NO 20
<211> LENGTH: 116
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 20

Ala Arg Val Asp Gln Thr Pro Arg Ile Ala Thr Lys Glu Thr Gly Glu
1               5                   10                  15

Ser Leu Thr Ile Asn Cys Val Leu Arg Asp Asn Asn Cys Ala Leu Pro
            20                  25                  30

Ser Thr Asn Trp Tyr Arg Thr Lys Leu Gly Ser Thr Lys Glu Gln Thr
        35                  40                  45

Ile Ser Ile Gly Gly Arg Tyr Ser Glu Thr Val Asp Glu Gly Ser Asn
50                  55                  60

Ser Ala Ser Leu Thr Ile Arg Asp Leu Arg Val Glu Asp Ser Gly Thr
65                  70                  75                  80

Tyr Lys Cys Lys Ala Trp Tyr Trp His Met Ser Ser Asp Cys Leu
                85                  90                  95

Ser Gly Tyr Ser Tyr Glu Gly Ala Gly Thr Val Leu Thr Val Lys Glu
            100                 105                 110

Ala Ser Gly Ala
        115

<210> SEQ ID NO 21
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asp Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Tyr Ala Met Thr Ala Asn Trp Trp Cys Asp Val
                85                  90                  95

Tyr Gly Gly Gly Thr Val Val Thr Val Asn Ala Ala Ser Gly Ala
            100                 105                 110

<210> SEQ ID NO 22
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asp Cys Ala Leu Ser
```

```
                    20                  25                  30
Ser Thr His Trp Tyr Arg Lys Lys Ser Gly Ser Thr Asn Glu Glu Ser
            35                  40                  45

Ile Trp Lys Gly Gly Arg Tyr Val Glu Thr Val Asn Ser Gly Ser Lys
 50                      55                  60

Ser Phe Ser Leu Arg Ile Asn Asp Leu Thr Val Glu Asp Ser Gly Thr
 65                      70                  75                  80

Tyr Arg Cys Asn Val Tyr Ala Met Thr Ala Asn Trp Trp Cys Asp Val
                    85                  90                  95

Tyr Gly Gly Gly Thr Val Val Thr Val Asn Ala Ala Ser Gly Ala
                100                 105                 110
```

<210> SEQ ID NO 23
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Arg Asp Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                      55                  60

Ser Phe Ser Leu Arg Ile Asn Asp Leu Thr Thr Glu Asp Ser Gly Thr
 65                      70                  75                  80

Tyr Arg Cys Asn Val Tyr Ala Met Thr Ala Asn Trp Trp Cys Asp Val
                    85                  90                  95

Tyr Gly Gly Gly Thr Val Val Thr Val Asn Ala Ala Ser Gly Ala
                100                 105                 110
```

<210> SEQ ID NO 24
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Arg Asp Cys Ala Leu Ser
                20                  25                  30

Ser Thr Tyr Trp Tyr Arg Lys Lys Ser Gly Ser Ser Asn Glu Glu Ser
            35                  40                  45

Ile Ser Lys Gly Gly Arg Tyr Val Glu Thr Val Asn Ser Gly Ser Lys
 50                      55                  60

Ser Phe Ser Leu Arg Ile Asn Asp Leu Thr Val Glu Asp Ser Gly Thr
 65                      70                  75                  80

Tyr Arg Cys Asn Val Tyr Ala Met Thr Ala Asn Trp Trp Cys Asp Val
                    85                  90                  95
```

Tyr Gly Gly Gly Thr Ala Val Thr Val Asn Ala Ala Ser Gly Ala
            100                 105                 110

<210> SEQ ID NO 25
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ala Arg Val Asp Gln Thr Pro Gln Thr Ile Thr Lys Glu Thr Gly Glu
1               5                   10                  15

Ser Leu Thr Ile Asn Cys Val Leu Arg Asp Arg Asp Cys Ala Leu Ser
            20                  25                  30

Ser Thr Tyr Trp Tyr Arg Lys Lys Ser Gly Ser Ser Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Ala Met Thr Ala Asn Trp Trp Cys Asp Val
                85                  90                  95

Tyr Gly Gly Gly Thr Val Val Thr Val Asn Ala Ala Ser Gly Ala
            100                 105                 110

<210> SEQ ID NO 26
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ala Arg Val Asp Gln Thr Pro Gln Thr Ile Thr Lys Glu Thr Gly Glu
1               5                   10                  15

Ser Leu Thr Ile Asn Cys Val Leu Arg Asp Glu Asp Cys Ala Leu Ser
            20                  25                  30

Ser Thr Tyr Trp Tyr His Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Ile Tyr Gly Leu Thr Ala Asn Trp Trp Cys Asp Val
                85                  90                  95

Tyr Gly Gly Gly Thr Val Val Thr Val Asn Ala Ala Ser Gly Ala
            100                 105                 110

<210> SEQ ID NO 27
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asp Cys Thr Leu Ser
            20                  25                  30

Ser Thr Tyr Trp Tyr Arg Lys Lys Ser Gly Ser Thr Asn Glu Glu Arg
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Ala Met Thr Arg Asn Trp Trp Cys Asp Val
                85                  90                  95

Tyr Gly Asp Gly Thr Ala Val Thr Val Asn Ala Ala Ser Gly Ala
                100                 105                 110

<210> SEQ ID NO 28
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asp Cys Thr Leu Ser
            20                  25                  30

Ser Thr Tyr Trp Tyr Arg Lys Lys Ser Gly Ser Thr Asn Glu Glu Arg
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Ala Met Thr Arg Asn Trp Trp Cys Asp Val
                85                  90                  95

Tyr Gly Gly Gly Thr Val Val Thr Val Asn Ala Ala Ser Gly Ala
                100                 105                 110

<210> SEQ ID NO 29
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Ala Arg Val Asp Gln Thr Pro Gln Thr Ile Thr Lys Glu Thr Gly Glu
1               5                   10                  15

Ser Leu Thr Ile Asn Cys Val Leu Arg Asp Arg Asp Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys

```
                    50                  55                  60

Ser Phe Ser Leu Arg Ile Asn Asp Leu Thr Val Glu Asp Ser Gly Thr
 65                  70                  75                  80

Tyr Arg Cys Asn Val Tyr Ser Met Thr Ala Asn Trp Trp Cys Asp Val
                     85                  90                  95

Tyr Gly Gly Gly Thr Val Val Thr Val Asn Ala Ala Ser Gly Ala
                100                 105                 110

<210> SEQ ID NO 30
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ala Arg Val Asp Gln Thr Pro Gln Thr Ile Thr Lys Glu Thr Gly Glu
  1               5                  10                  15

Ser Leu Thr Ile Asn Cys Val Leu Arg Asp Asn Asp Cys Thr Leu Ser
                 20                  25                  30

Ser Thr His Trp Tyr Arg Lys Lys Ser Gly Ser Thr Asn Glu Glu Arg
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Ala Met Thr Arg Asn Trp Trp Cys Asp Val
                     85                  90                  95

Tyr Gly Gly Gly Thr Val Val Thr Val Asn Ala Ala Ser Gly Ala
                100                 105                 110

<210> SEQ ID NO 31
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Ala Arg Val Asp Gln Thr Pro Gln Thr Ile Thr Lys Glu Thr Gly Glu
  1               5                  10                  15

Ser Leu Thr Ile Asn Cys Val Leu Arg Asp Arg Asp Cys Ala Leu Ser
                 20                  25                  30

Ser Thr His Trp Tyr Arg Lys Lys Ser Gly Ser Thr Asn Glu Glu Ser
             35                  40                  45

Ile Pro Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Ser Leu Thr Ala Asn Trp Trp Cys Asp Val
                     85                  90                  95

Tyr Gly Gly Gly Thr Val Val Thr Val Asn Ala Ala Ser Gly Ala
                100                 105                 110

<210> SEQ ID NO 32
```

<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Ala Tyr Trp Tyr Arg Lys Lys Ser Gly Ser Thr Asn Glu Glu Ser
        35                  40                  45

Ile Ser Ala Gly Gly Arg Tyr Val Glu Thr Val Asn Lys Gly Ser Lys
    50                  55                  60

Ser Phe Ser Leu Thr Ile Asn Asp Leu Thr Val Glu Asp Asn Gly Thr
65                  70                  75                  80

Tyr Arg Cys Asn Ile Tyr Ala Arg Glu Asp Thr Trp Tyr Gly Ser Arg
                85                  90                  95

Asp Cys Gly Leu Gly Asp Val Tyr Gly Gly Thr Val Val Thr Val
            100                 105                 110

Asn Ala Ala Ser Gly Ala
        115

<210> SEQ ID NO 33
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 33

Ala Arg Val Asp Gln Thr Pro Arg Ile Ala Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Asn Trp Tyr Arg Thr Lys Leu Gly Ser Thr Lys Glu Gln Thr
        35                  40                  45

Ile Ser Ile Gly Gly Arg Tyr Ser Glu Thr Val Asp Glu Gly Ser Asn
    50                  55                  60

Ser Ala Ser Leu Thr Ile Arg Asp Leu Arg Val Glu Asp Ser Gly Thr
65                  70                  75                  80

Tyr Lys Cys Lys Ala Tyr Asp Tyr Cys Leu His Trp Phe His Pro Tyr
                85                  90                  95

Val Ile Glu Gly Ala Gly Thr Val Leu Thr Val Lys Glu Ala Ser Gly
            100                 105                 110

Ala

<210> SEQ ID NO 34
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

-continued

<400> SEQUENCE: 34

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asp Cys Ala Leu Ser
            20                  25                  30

Ser Thr Tyr Trp Tyr Arg Lys Lys Ser Gly Ser Thr Asn Glu Glu Arg
        35                  40                  45

Met Thr Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Tyr Gly Leu Val Asp Cys Ala Ser Gly Met Asn
                85                  90                  95

Trp Ile Asp Val Tyr Gly Gly Thr Val Val Thr Val Asn Ala Ala
            100                 105                 110

Ser Gly Ala
        115

<210> SEQ ID NO 35
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Pro Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Tyr Gly Leu Val Asp Cys Gly Ser Gly Met Asn
                85                  90                  95

Trp Ile Asp Val Tyr Gly Gly Thr Ala Val Thr Val Asn Ala Ala
            100                 105                 110

Ser Gly Ala
        115

<210> SEQ ID NO 36
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Pro Leu Ser
            20                  25                  30

-continued

```
Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Gly Leu Val Asp Cys Gly Ser Gly Met Asn
                 85                  90                  95

Trp Ile Asp Val Tyr Gly Gly Thr Val Val Thr Val Asn Ala Ala
                100                 105                 110

Ser Gly Ala
        115

<210> SEQ ID NO 37
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Asn Asp Cys Ala Leu Ser
                20                  25                  30

Ser Thr Tyr Trp Tyr Arg Lys Lys Ser Gly Ser Thr Asn Glu Glu Arg
        35                  40                  45

Met Thr Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Gly Leu Val Asp Cys Ala Ser Gly Met Asn
                 85                  90                  95

Trp Ile Asp Val Tyr Gly Gly Thr Val Val Thr Val Asn Ala Ala
                100                 105                 110

Ser Gly Ala
        115

<210> SEQ ID NO 38
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Asn Thr Tyr Trp Tyr Arg Lys Lys Gln Gly Ser His His Glu Glu Ser
        35                  40                  45

Ile Ser Lys Gly Gly Arg Tyr Val Glu Thr Val Asn Ser Gly Ser Lys
 50                  55                  60
```

```
Ser Phe Ser Leu Arg Ile Asn Asp Leu Thr Val Glu Asp Ser Gly Thr
 65                  70                  75                  80

Tyr Arg Cys Asn Val Tyr Gly Val Ile Glu Cys Arg Tyr Glu Gly Met
                 85                  90                  95

Asn Trp Phe Asp Val Tyr Gly Asp Gly Thr Ala Val Thr Val Asn Ala
            100                 105                 110

Ala Ser Gly Ala
        115

<210> SEQ ID NO 39
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Asn Thr Tyr Trp Tyr Arg Lys Lys Ser Gly Ser His His Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Gly Val Ile Glu Cys Arg Tyr Glu Gly Met
                 85                  90                  95

Asn Trp Phe Asp Val Tyr Gly Asp Gly Thr Ala Val Thr Val Asn Ala
            100                 105                 110

Ala Ser Gly Ala
        115

<210> SEQ ID NO 40
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Asn Thr Tyr Trp Tyr Arg Lys Lys Ser Gly Ser His His Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Gly Val Ile Glu Cys Arg Tyr Glu Gly Met
                 85                  90                  95

Asn Trp Phe Asp Val Tyr Gly Gly Gly Thr Val Val Thr Val Asn Ala
```

Ala Ser Gly Ala
        115

<210> SEQ ID NO 41
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Pro Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Asn Ile Ala Val Met Cys Asn Asp Tyr Val
                85                  90                  95

Arg Tyr Trp Thr Asp Val Tyr Gly Gly Gly Thr Val Val Thr Val Asn
            100                 105                 110

Ala Ala Ser Gly Ala
        115

<210> SEQ ID NO 42
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asp Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Gln Pro Pro Ser Thr Glu Ser Leu Tyr Trp
                85                  90                  95

Cys Asp Val Tyr Gly Gly Gly Thr Ala Val Thr Val Asn Ala Ala Ser
            100                 105                 110

Gly Ala

<210> SEQ ID NO 43
<211> LENGTH: 114

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43
```

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asp Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Leu Asp Ser Gly Thr
65                  70                  75                  80

Tyr Arg Cys Asn Val Tyr Gln Pro Pro Ser Thr Glu Ser Leu Tyr Trp
                85                  90                  95

Cys Asp Val Tyr Gly Gly Gly Thr Val Val Thr Val Asn Ala Ala Ser
            100                 105                 110

Gly Ala

```
<210> SEQ ID NO 44
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44
```

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asp Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Ser Gly Pro Ser Tyr Asp Gln Leu Phe Trp
                85                  90                  95

Cys Asp Val Tyr Gly Asp Gly Thr Ala Val Thr Val Asn Ala Ala Ser
            100                 105                 110

Gly Ala

```
<210> SEQ ID NO 45
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45
```

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asp Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Tyr Ser Gly Pro Ser Tyr Asp Gln Leu Phe Trp
                85                  90                  95

Cys Asp Val Tyr Gly Gly Gly Thr Ala Val Thr Val Asn Ala Ala Ser
                100                 105                 110

Gly Ala

<210> SEQ ID NO 46
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asp Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Tyr Ser Gly Pro Ser Tyr Asp Gln Leu Phe Trp
                85                  90                  95

Cys Asp Val Tyr Gly Gly Gly Thr Val Val Thr Val Asn Ala Ala Ser
                100                 105                 110

Gly Ala

<210> SEQ ID NO 47
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Ser Gly Pro Ser Tyr Asp Gln Leu Phe Trp
                 85                  90                  95

Cys Asp Val Tyr Gly Asp Gly Thr Ala Val Thr Val Asn Ala Ala Ser
                100                 105                 110

Gly Ala

<210> SEQ ID NO 48
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Ala Arg Val Asp Gln Thr Pro Gln Thr Ile Thr Lys Glu Thr Gly Glu
 1                5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Ser Thr Pro Ser Tyr Asp Gln Leu Tyr Trp
                 85                  90                  95

Cys Asp Val Tyr Gly Asp Gly Thr Ala Val Thr Val Asn Ala Ala Ser
                100                 105                 110

Gly Ala

<210> SEQ ID NO 49
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ala Arg Val Asp Gln Thr Pro Gln Thr Ile Thr Lys Glu Thr Gly Glu
 1                5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Ser Thr Pro Ser Tyr Asp Gln Leu Tyr Trp
                 85                  90                  95

```
Cys Asp Val Tyr Gly Gly Gly Thr Ala Val Thr Val Asn Ala Ala Ser
            100                 105                 110
Gly Ala

<210> SEQ ID NO 50
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Val Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Val Pro Pro Gly Tyr Asp Cys Asn Tyr Trp
                85                  90                  95

Met Asp Val Tyr Gly Gly Gly Thr Val Val Thr Val Asn Ala Ala Ser
            100                 105                 110

Gly Ala

<210> SEQ ID NO 51
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Lys Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Trp His Asp Leu Val Trp Ser Val Cys Thr Thr
                85                  90                  95

Asp Val Tyr Gly Gly Gly Thr Val Val Thr Val Asn Ala Ala Ser Gly
            100                 105                 110

Ala

<210> SEQ ID NO 52
<211> LENGTH: 113
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asp Cys Ala Leu Ser
            20                  25                  30

Ser Thr Tyr Trp Tyr Arg Lys Lys Ser Gly Ser Thr Lys Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Trp His Asp Leu Val Trp Ser Val Cys Thr Thr
                85                  90                  95

Asp Val Tyr Gly Gly Gly Thr Val Val Thr Val Asn Ala Ala Ser Gly
            100                 105                 110

Ala

<210> SEQ ID NO 53
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Ala Arg Val Asp Gln Thr Pro Gln Thr Ile Thr Lys Glu Thr Gly Glu
1               5                   10                  15

Ser Leu Thr Ile Asn Cys Val Leu Arg Asp Lys Asp Cys Ala Leu Ser
            20                  25                  30

Ser Thr Ser Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Ala Arg Pro Arg Pro Asp Asn Leu Asn Trp
                85                  90                  95

Cys Asp Val Tyr Gly Gly Gly Thr Ala Val Thr Val Asn Ala Ala Ser
            100                 105                 110

Gly Ala

<210> SEQ ID NO 54
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Ala Arg Val Asp Gln Thr Pro Gln Thr Ile Thr Lys Glu Thr Gly Glu
```

```
                1               5                   10                  15
            Ser Leu Thr Ile Asn Cys Val Leu Arg Asp Ser Asp Cys Ala Leu Ser
                            20                  25                  30

Ser Thr Ser Trp Tyr Arg Lys Lys Ser Gly Ser Thr Asn Glu Glu Ser
                            35                  40                  45

Ile Ser Lys Gly Gly Arg Tyr Val Glu Thr Val Asn Ser Gly Ser Lys
                            50                  55                  60

Ser Phe Ser Leu Arg Ile Asn Asp Leu Thr Val Glu Asp Ser Gly Thr
             65                 70                  75                  80

Tyr Arg Cys Asn Val Tyr Ala Arg Pro Arg Pro Asp Asn Leu Asn Trp
                            85                  90                  95

Cys Asp Val Tyr Gly Gly Gly Thr Ala Val Thr Val Asn Ala Ala Ser
                            100                 105                 110

Gly Ala

<210> SEQ ID NO 55
            <211> LENGTH: 114
            <212> TYPE: PRT
            <213> ORGANISM: Artificial Sequence
            <220> FEATURE:
            <221> NAME/KEY: source
            <223> OTHER INFORMATION: /note="Description of Artificial Sequence:
                  Synthetic polypeptide"
            <220> FEATURE:
            <221> NAME/KEY: MOD_RES
            <222> LOCATION: (80)..(80)
            <223> OTHER INFORMATION: Any amino acid

<400> SEQUENCE: 55

Ala Arg Val Asp Gln Thr Pro Gln Thr Ile Thr Lys Glu Thr Gly Glu
             1              5                   10                  15

Ser Leu Thr Ile Asn Cys Val Leu Arg Asp Ser Asn Cys Ala Ala Thr
                            20                  25                  30

Val Thr Tyr Trp Tyr Arg Lys Thr Ser Gly Ser Thr His Glu Glu Met
                            35                  40                  45

Ile Ser Lys Gly Gly Arg Tyr Val Glu Thr Phe Ser Ser Gly Ser Lys
                            50                  55                  60

Ser Phe Ser Leu Arg Ile Asn Glu Leu Thr Val Glu Asp Ser Gly Xaa
             65                 70                  75                  80

Tyr Arg Cys Asn Val Leu Arg Asp Ser Cys Tyr Asp Val Thr Asn Trp
                            85                  90                  95

Leu Glu Arg Tyr Gly Gly Gly Thr Val Val Thr Val Asn Ala Ala Ser
                            100                 105                 110

Gly Ala

<210> SEQ ID NO 56
            <211> LENGTH: 113
            <212> TYPE: PRT
            <213> ORGANISM: Artificial Sequence
            <220> FEATURE:
            <221> NAME/KEY: source
            <223> OTHER INFORMATION: /note="Description of Artificial Sequence:
                  Synthetic polypeptide"

<400> SEQUENCE: 56

Ala Arg Val Asp Gln Thr Pro Gln Thr Ile Thr Lys Glu Thr Gly Glu
             1              5                   10                  15

Ser Leu Thr Ile Asn Cys Val Leu Arg Asp Ser Ile Cys Ala Leu Ser
                            20                  25                  30
```

```
Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Glu Asn Phe Leu Leu Asp Cys Tyr Asp Trp Leu
                 85                  90                  95

Asp Val Tyr Gly Gly Gly Thr Val Thr Val Asn Ala Ala Ser Gly
                100                 105                 110

Ala
```

<210> SEQ ID NO 57
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Glu Arg His Trp Arg Ser Arg Cys Gln Arg Ala
                 85                  90                  95

Val Asp Val Tyr Gly Gly Gly Thr Ala Val Thr Val Asn Ala Ala Ser
                100                 105                 110

Gly Ala
```

<210> SEQ ID NO 58
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Val Val Glu Asp Ser Gly Thr
 65                  70                  75                  80
```

Tyr Arg Cys Lys Val Asx Leu Trp Cys Leu Cys Pro Cys Thr Val Trp
                85                  90                  95

Val Leu Gly Asp Val Tyr Gly Gly Thr Val Val Thr Val Asn Ala
            100                 105                 110

Ala Ser Gly Ala
        115

<210> SEQ ID NO 59
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Cys Gly Ile Leu Cys Cys Phe Asx Phe Asp Val
                85                  90                  95

Tyr Gly Gly Gly Thr Val Val Thr Val Asn Ala Ala Ser Gly Ala
            100                 105                 110

<210> SEQ ID NO 60
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
                20                  25                  30

Arg Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Val Val Glu Asp Ser Gly Thr
65                  70                  75                  80

Tyr Arg Cys Asn Val Thr Ala Ile Leu Ser Asx Asp Cys Gly Ala Phe
                85                  90                  95

Ala Asp Val Tyr Gly Asp Gly Thr Ala Val Thr Val Asn Ala Ala Ser
            100                 105                 110

Gly Ala

<210> SEQ ID NO 61

<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Thr Gly Leu Arg Tyr His Ser Gly Cys Arg Thr
                85                  90                  95

Gly Asp Val Tyr Gly Gly Gly Thr Ala Val Thr Val Asn Ala Ala Ser
            100                 105                 110

Gly Ala

<210> SEQ ID NO 62
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Cys Phe Gly Asx Cys Val Asn Ser Cys Gly Glu
                85                  90                  95

Ser Met Asp Val Tyr Gly Asp Gly Thr Ala Val Thr Val Asn Ala Ala
            100                 105                 110

Ser Gly Ala
        115

<210> SEQ ID NO 63
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Lys Asp Ser Gly Thr
65                  70                  75                  80

Tyr Arg Cys Asn Val Leu Arg Phe Asx Cys Val Phe His Trp Asp Val
                85                  90                  95

Tyr Gly Gly Gly Thr Val Val Thr Val Asn Ala Ala Ser Gly Ala
            100                 105                 110
```

<210> SEQ ID NO 64
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Lys Asp Ser Gly Thr
65                  70                  75                  80

Tyr Arg Cys Lys Val Arg Asp Val Val Leu Val Asx Tyr Gly Tyr Cys
                85                  90                  95

Leu Val Asp Gly Gln Asp Val Tyr Gly Gly Gly Thr Val Val Thr Val
            100                 105                 110

Asn Ala Ala Ser Gly Ala
            115
```

<210> SEQ ID NO 65
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Ala Arg Val Asp Gln Thr Pro Gln Thr Ile Thr Lys Glu Glu Gly Glu
1               5                   10                  15

Ser Leu Thr Ile Asn Cys Val Leu Arg Asp Ser Ser Ser Ala Leu Ala
            20                  25                  30

Ser Thr Ser Trp Tyr Arg Lys Lys Ser Gly Ser Thr Arg Glu Glu Thr
        35                  40                  45
```

Ile Ser Lys Gly Gly Arg Tyr Val Glu Thr Val Asn Ser Gly Ser Lys
            50                  55                  60

Ser Phe Ser Leu Arg Ile Asn Asp Leu Thr Val Glu Asp Ser Gly Thr
65                  70                  75                  80

Tyr Arg Cys Asn Val Tyr Glu Leu Val Glu Asp Thr Ser Ala Tyr Glu
                85                  90                  95

Ile Gly Val Asp Val Tyr Gly Asp Gly Thr Ala Val Thr Val Asn Ala
                100                 105                 110

Ala Ser Gly Ala
        115

<210> SEQ ID NO 66
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Ala Arg Val Asp Gln Thr Pro Gln Thr Ile Thr Lys Glu Thr Gly Glu
1               5                   10                  15

Ser Leu Thr Ile Asn Cys Val Leu Arg Asp Arg Asp Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asp Ser Gly Ser Lys
            50                  55                  60

Ser Phe Ser Leu Arg Ile Asn Asp Leu Thr Val Glu Asp Ser Gly Thr
65                  70                  75                  80

Tyr Arg Cys Asn Val Tyr Gln Ser Pro Val Gly Arg Arg Trp Trp Cys
                85                  90                  95

Asp Val Tyr Gly Gly Gly Thr Val Val Thr Val Asn Ala Ala Ser Gly
                100                 105                 110

Ala

<210> SEQ ID NO 67
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Ala Arg Val Asp Gln Thr Pro Gln Thr Ile Thr Lys Glu Thr Gly Glu
1               5                   10                  15

Ser Ser Thr Ile Asn Cys Val Ser Arg Asp Ser Asn Cys Glu Leu Ser
                20                  25                  30

Leu Thr Tyr Trp Tyr Arg Lys Lys Ser Gly Ser Thr Leu Glu Glu Ser
            35                  40                  45

Ile Ala Lys Gly Gly Arg Tyr Val Glu Thr Val Asn Ser Lys Ser Lys
            50                  55                  60

Ser Phe Ser Leu Arg Ile Asn Asp Leu Thr Val Glu Asp Ser Gly Thr
65                  70                  75                  80

Tyr Arg Cys Asn Leu Trp Tyr Arg Pro Asp Cys Glu Glu Glu Phe Asp

```
                    85                  90                  95

Val Tyr Gly Gly Gly Thr Ala Val Thr Val Asn Ala
                100                 105

<210> SEQ ID NO 68
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Ala Arg Val Asp Gln Thr Pro Gln Thr Ile Thr Lys Glu Thr Gly Glu
1               5                   10                  15

Ser Ser Thr Ile Asn Cys Val Ser Arg Asp Ser Asn Cys Glu Leu Ser
                20                  25                  30

Leu Thr Tyr Trp Tyr Arg Lys Lys Ser Gly Ser Thr Leu Glu Glu Ser
            35                  40                  45

Ile Ala Lys Gly Gly Arg Tyr Val Glu Thr Val Asn Ser Lys Ser Lys
        50                  55                  60

Ser Phe Ser Leu Arg Ile Asn Asp Leu Thr Val Glu Asp Ser Gly Thr
65                  70                  75                  80

Tyr Arg Cys Asn Leu Trp Tyr Arg Pro Asp Cys Glu Glu Glu Phe Asp
                85                  90                  95

Val Tyr Gly Gly Gly Thr Val Val Thr Val Asn Ala
                100                 105

<210> SEQ ID NO 69
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Ala Arg Val Asp Gln Thr Pro Gln Thr Ile Thr Lys Glu Thr Gly Glu
1               5                   10                  15

Ser Ser Thr Ile Asn Cys Val Ser Arg Asp Ser Asn Cys Glu Leu Ser
                20                  25                  30

Leu Thr Tyr Trp Tyr Arg Lys Lys Ser Gly Ser Thr Leu Glu Glu Ser
            35                  40                  45

Ile Ala Lys Gly Gly Arg Tyr Val Glu Thr Val Asn Ser Lys Ser Lys
        50                  55                  60

Ser Phe Ser Leu Arg Ile Asn Asp Leu Thr Val Glu Asp Ser Gly Thr
65                  70                  75                  80

Tyr Arg Cys Asn Leu Trp Tyr Arg Pro Asp Cys Glu Glu Glu Phe Asp
                85                  90                  95

Val Tyr Gly Asp Gly Thr Ala Val Thr Val Asn Ala
                100                 105

<210> SEQ ID NO 70
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                                 Synthetic polypeptide"
<220> FEATURE:
<221> NAME/KEY: MOD_RES
<222> LOCATION: (6)..(6)
<223> OTHER INFORMATION: Any amino acid

<400> SEQUENCE: 70

Ala Arg Val Asp Gln Xaa Pro Gln Thr Ile Thr Lys Glu Thr Gly Glu
1               5                   10                  15

Ser Ser Thr Ile Asn Cys Val Ser Arg Asp Ser Asn Cys Glu Leu Ser
            20                  25                  30

Leu Thr Tyr Trp Tyr Arg Lys Lys Ser Gly Ser Thr Leu Glu Glu Ser
        35                  40                  45

Ile Ala Lys Gly Gly Arg Tyr Val Glu Thr Val Asn Ser Lys Ser Lys
 50                  55                  60

Ser Phe Ser Leu Arg Ile Asn Asp Leu Thr Val Glu Asp Ser Gly Thr
65                  70                  75                  80

Tyr Arg Cys Asn Leu Trp Tyr Arg Pro Asp Cys Glu Glu Phe Asp
                85                  90                  95

Val Tyr Gly Gly Gly Thr Val Val Thr Val Asn Ala
            100                 105

<210> SEQ ID NO 71
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Ala Arg Val Asp Gln Thr Pro Gln Thr Ile Thr Lys Glu Thr Gly Glu
1               5                   10                  15

Ser Ser Thr Ile Asn Cys Ile Ser Leu Asp Ser Asn Cys Glu Leu Ser
            20                  25                  30

Leu Thr Tyr Trp Tyr Arg Lys Lys Thr Gly Ser Thr Phe Glu Glu Asn
        35                  40                  45

Ile Ala Lys Gly Gly Arg Tyr Val Glu Thr Ile Asn Ser Lys Ser Lys
 50                  55                  60

Ser Phe Ser Leu Arg Ile Asn Asp Leu Thr Val Glu Asp Ser Gly Thr
65                  70                  75                  80

Tyr Arg Cys Asn Leu Trp Tyr Arg Pro Asp Cys Glu Glu Phe Asp
                85                  90                  95

Val Tyr Gly Gly Gly Thr Ala Val Thr Val Asn Ala
            100                 105

<210> SEQ ID NO 72
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Ala Arg Val Asp Gln Thr Pro Gln Thr Ile Thr Lys Glu Thr Gly Glu
1               5                   10                  15

Ser Ser Thr Ile Asn Cys Ile Ser Leu Asp Ser Asn Cys Glu Leu Ser
            20                  25                  30
```

```
Leu Thr Tyr Trp Tyr Arg Lys Lys Thr Gly Ser Thr Phe Glu Glu Asn
        35                  40                  45

Ile Ala Lys Gly Gly Arg Tyr Val Glu Thr Ile Asn Ser Lys Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Leu Trp Tyr Arg Pro Asp Cys Glu Glu Phe Asp
                85                  90                  95

Val Tyr Gly Gly Gly Thr Val Val Thr Val Asn Ala
                100                 105

<210> SEQ ID NO 73
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (6)..(6)
<223> OTHER INFORMATION: Any amino acid

<400> SEQUENCE: 73

Ala Arg Val Asp Gln Xaa Pro Gln Thr Ile Thr Lys Glu Thr Gly Glu
 1               5                  10                  15

Ser Ser Thr Ile Asn Cys Val Leu Arg Asp Ser Asn Cys Ala Leu Ser
                20                  25                  30

Leu Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Ile Val Glu Asp Ser Gly Thr
 65                  70                  75                  80

Tyr Arg Cys Asn Ala Trp Tyr Arg Pro Asp Cys Glu Leu Asp Tyr Asp
                85                  90                  95

Val Tyr Gly Gly Gly Thr Val Val Thr Val Asn Ala
                100                 105

<210> SEQ ID NO 74
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Ala Arg Val Asp Gln Thr Pro Gln Thr Ile Thr Lys Glu Thr Gly Glu
 1               5                  10                  15

Ser Ser Thr Ile Asn Cys Val Leu Arg Asp Ser Asn Cys Ala Leu Ser
                20                  25                  30

Leu Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Ile Val Glu Asp Ser Gly Thr
 65                  70                  75                  80
```

```
Tyr Arg Cys Asn Ala Trp Tyr Arg Pro Asp Cys Glu Leu Asp Tyr Asp
                85                  90                  95

Val Tyr Gly Gly Gly Thr Ala Val Thr Val Asn Ala
            100                 105
```

<210> SEQ ID NO 75
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
                20                  25                  30

Leu Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Ile Val Glu Asp Ser Gly Thr
65                  70                  75                  80

Tyr Arg Cys Asn Ala Trp Tyr Arg Pro Asp Cys Glu Leu Asp Tyr Asp
                85                  90                  95

Val Tyr Gly Gly Gly Thr Val Val Thr Val Asn Ala
            100                 105
```

<210> SEQ ID NO 76
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
                20                  25                  30

Leu Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Ile Val Glu Asp Ser Gly Thr
65                  70                  75                  80

Tyr Arg Cys Asn Ala Trp Tyr Arg Pro Asp Cys Glu Leu Asp Tyr Asp
                85                  90                  95

Val Tyr Gly Asp Gly Thr Ala Val Thr Val Asn Ala
            100                 105
```

<210> SEQ ID NO 77
<211> LENGTH: 114
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 77

Ala Arg Val Asp Gln Thr Pro Gln Ser Ile Thr Lys Asp Ala Gly Glu
1               5                   10                  15

Ser Ser Thr Ile Asn Cys Val Leu Leu Asp Ser Asn Cys Ala Leu Glu
            20                  25                  30

Ser Thr Tyr Trp Tyr Arg Lys Lys Ser Gly Ser Ser Asn Glu Glu Thr
        35                  40                  45

Glu Ile Ser Lys Gly Gly Arg Tyr Val Glu Thr Val Asn Ser Gly Ser
50                  55                  60

Lys Ser Phe Ser Leu Lys Ile Asn Asp Leu Thr Ile Glu Asp Ser Gly
65                  70                  75                  80

Thr Phe Arg Cys Asn Ala Asn Thr Trp Gln Ala Arg His Pro Tyr Asp
                85                  90                  95

Cys Ala Glu Ser Leu Arg Val Tyr Gly Asp Gly Thr Ala Val Thr Val
            100                 105                 110

Asn Ala

<210> SEQ ID NO 78
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

Ala Arg Val Asp Gln Thr Pro Gln Ser Ile Thr Lys Asp Ala Gly Glu
1               5                   10                  15

Ser Ser Thr Ile Asn Cys Val Leu Leu Asp Ser Asn Cys Ala Leu Glu
            20                  25                  30

Ser Thr Tyr Trp Tyr Arg Lys Lys Ser Gly Ser Ser Asn Glu Glu Thr
        35                  40                  45

Glu Ile Ser Lys Gly Gly Arg Tyr Val Glu Thr Val Asn Ser Gly Ser
50                  55                  60

Lys Ser Phe Ser Leu Lys Ile Asn Asp Leu Thr Ile Glu Asp Ser Gly
65                  70                  75                  80

Thr Phe Arg Cys Asn Ala Asn Thr Trp Gln Ala Arg His Pro Tyr Asp
                85                  90                  95

Cys Ala Glu Ser Leu Arg Val Tyr Gly Gly Gly Thr Ala Val Thr Val
            100                 105                 110

Asn Ala

<210> SEQ ID NO 79
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

Ala Arg Val Asp Gln Thr Pro Gln Ser Ile Thr Lys Asp Ala Gly Glu
1               5                   10                  15

-continued

Ser Ser Thr Ile Asn Cys Val Leu Leu Asp Ser Asn Cys Ala Leu Glu
            20                  25                  30

Ser Thr Tyr Trp Tyr Arg Lys Lys Ser Gly Ser Ser Asn Glu Glu Thr
        35                  40                  45

Glu Ile Ser Lys Gly Gly Arg Tyr Val Glu Thr Val Asn Ser Gly Ser
 50                  55                  60

Lys Ser Phe Ser Leu Lys Ile Asn Asp Leu Thr Ile Glu Asp Ser Gly
65                  70                  75                  80

Thr Phe Arg Cys Asn Ala Asn Thr Trp Gln Ala Arg His Pro Tyr Asp
                85                  90                  95

Cys Ala Glu Ser Leu Arg Val Tyr Gly Gly Gly Thr Val Val Thr Val
            100                 105                 110

Asn Ala

<210> SEQ ID NO 80
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ala Arg Val Asp Gln Thr Pro Gln Thr Ile Thr Lys Glu Thr Gly Glu
1               5                   10                  15

Ser Ser Thr Ile Asn Cys Val Leu Arg Asp Thr Asn Cys Ala Leu Ser
            20                  25                  30

Ser Thr Tyr Trp Tyr Arg Gln Asn Ser Gly Ser Arg Arg Glu Glu Ser
        35                  40                  45

Ile Pro Lys Gly Gly Arg Tyr Lys Glu Thr Leu Asn Ser Gly Ser Lys
 50                  55                  60

Ser Phe Ser Leu Arg Ile Asn Asp Leu Arg Ile Glu Asp Thr Gly Thr
65                  70                  75                  80

Tyr Leu Cys Lys Ala Asp Asn Phe Ala Cys Glu Met Ala Tyr Asn Val
                85                  90                  95

Tyr Gly Gly Gly Thr Val Val Thr Val Asn Ala
            100                 105

<210> SEQ ID NO 81
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ala Arg Val Asp Gln Thr Pro Gln Thr Ile Thr Lys Glu Thr Gly Glu
1               5                   10                  15

Ser Ser Thr Leu Asn Cys Val Leu Arg Asp Ile Asn Cys Ala Leu Gln
            20                  25                  30

Val Thr Tyr Trp Ile Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
65                  70                  75                  80

-continued

```
Tyr Arg Cys Asn Val Leu Trp Gly Ser Tyr Pro Cys Asp Glu Ile Met
                85                  90                  95

His Gly Thr Ala Val Tyr Gly Gly Gly Thr Val Val Thr Val Asn Ala
            100                 105                 110
```

<210> SEQ ID NO 82
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 82

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Arg Leu Ser
                20                  25                  30

Lys Thr Tyr Trp Leu Arg Lys Lys Ser Gly Ser Leu Asn Glu Glu Asn
            35                  40                  45

Ile Ser Leu Gly Gly Arg Tyr Val Glu Thr Val Asn Ser Gly Ser Lys
        50                  55                  60

Ser Phe Ser Leu Arg Ile Asn Asp Ser Thr Val Glu Asp Ser Gly Thr
65                  70                  75                  80

Tyr Arg Cys Asn Ala Leu Pro Arg Pro Ile Ser Trp Ile Asn Cys Asp
                85                  90                  95

Asp Ser His Ala Tyr Gly Gly Gly Thr Val Val Thr Val Asn Ala
            100                 105                 110
```

<210> SEQ ID NO 83
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 83

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Gly Phe Ser
                20                  25                  30

Ser Thr Tyr Trp Tyr Arg Lys Thr Ala Thr Ser Arg Gly Glu Glu Leu
            35                  40                  45

Ile Lys Arg Gly Gly Arg Tyr Val Glu Thr Ile Asn Ser Glu Ser Lys
        50                  55                  60

Ser Phe Ser Leu Arg Ile Thr Asp Leu Thr Val Glu Asp Ser Gly Thr
65                  70                  75                  80

Tyr Arg Cys Asn Leu Val Trp Gly Trp Ser Cys Asp Val Tyr Gly Gly
                85                  90                  95

Gly Thr Val Val Thr Val Asn Ala
            100
```

<210> SEQ ID NO 84
<211> LENGTH: 104
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 84

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Gly Phe Ser
            20                  25                  30

Ser Thr Tyr Trp Tyr Arg Lys Thr Ala Thr Ser Arg Gly Glu Glu Leu
        35                  40                  45

Ile Lys Arg Gly Gly Arg Tyr Val Glu Thr Ile Asn Ser Glu Ser Lys
    50                  55                  60

Ser Phe Ser Leu Arg Ile Thr Asp Leu Thr Val Glu Asp Ser Gly Thr
65                  70                  75                  80

Tyr Arg Cys Asn Leu Val Trp Gly Trp Ser Cys Asp Val Tyr Gly Gly
                85                  90                  95

Gly Thr Ala Val Thr Val Asn Ala
            100

<210> SEQ ID NO 85
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Gly Phe Ser
            20                  25                  30

Ser Thr Tyr Trp Tyr Arg Lys Thr Ala Thr Ser Arg Gly Glu Glu Leu
        35                  40                  45

Ile Lys Arg Gly Gly Arg Tyr Val Glu Thr Ile Asn Ser Glu Ser Lys
    50                  55                  60

Ser Phe Ser Leu Arg Ile Thr Asp Leu Thr Val Glu Asp Ser Gly Thr
65                  70                  75                  80

Tyr Arg Cys Asn Leu Val Trp Gly Trp Ser Cys Asp Val Tyr Gly Asp
                85                  90                  95

Gly Thr Ala Val Thr Val Asn Ala
            100

<210> SEQ ID NO 86
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser

```
                35                  40                  45
Ile Ser Lys Gly Gly Arg Tyr Val Glu Thr Val Asn Lys Gly Ala Lys
 50                  55                  60

Ser Phe Ser Leu Arg Ile Asn Asp Leu Thr Val Glu Asp Ser Gly Thr
 65                  70                  75                  80

Tyr Arg Cys Asn Lys Gly Ala Gly Phe Phe Ala Leu Met Asn Cys Asn
                 85                  90                  95

Tyr Asp Val Tyr Gly Gly Gly Thr Val Val Thr Val Asn Ala
                100                 105                 110
```

<210> SEQ ID NO 87
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

```
Ala Arg Val Asp Gln Thr Pro Gln Thr Ile Thr Lys Glu Thr Gly Glu
  1               5                  10                  15

Ser Ser Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Arg Glu Glu Ile
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Gln Cys Asn Ala Tyr His Asp Arg His Ile Thr Lys Asn Trp Arg
                 85                  90                  95

Cys Pro Asn Leu Asp Val Tyr Gly Gly Gly Thr Val Val Thr Val Asn
                100                 105                 110

Ala
```

<210> SEQ ID NO 88
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

```
Ala Arg Val Asp Gln Thr Pro Gln Thr Ile Thr Lys Glu Thr Gly Glu
  1               5                  10                  15

Ser Ser Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Asn
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Met Thr Trp Tyr Gly Tyr Asp Cys Gly Ala Met Asn Arg
                 85                  90                  95
```

```
Asp Val Tyr Gly Gly Thr Val Val Thr Val Asn Ala
            100                 105
```

<210> SEQ ID NO 89
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Thr Thr Tyr Trp Tyr Arg Lys Thr Ser Gly Ser Ala Asn Asp Gln Ser
        35                  40                  45

Ile Ser Lys Gly Gly Arg Tyr Val Glu Thr Val Asp Tyr Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Lys Trp Gly Pro Asp Ile Asp Gly Ala Gly Tyr Gly
                85                  90                  95

Thr His Gly Cys Tyr Asp Val Tyr Gly Gly Thr Val Val Thr Val
            100                 105                 110

Asn Ala
```

<210> SEQ ID NO 90
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

```
Ala Arg Val Asp Gln Thr Pro Gln Thr Ile Thr Lys Glu Thr Gly Glu
1               5                   10                  15

Ser Ser Thr Ile Asn Cys Val Ala Arg Asp Ser Asn Cys Ala Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Ala Trp Tyr Arg Pro Asp Cys Glu Ser Asp Tyr Asp
                85                  90                  95

Val Tyr Gly Gly Gly Thr Val Val Thr Val Asn Ala
            100                 105
```

<210> SEQ ID NO 91
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 91

Ala Arg Val Asp Gln Thr Pro Gln Thr Ile Thr Lys Glu Thr Gly Glu
1               5                   10                  15

Ser Ser Thr Ile Asn Cys Val Arg Asp Ser Asn Cys Ala Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Ala Trp Tyr Arg Pro Asp Cys Glu Ser Asp Tyr Asp
                85                  90                  95

Val Tyr Gly Gly Gly Thr Ala Val Thr Val Asn Ala
            100                 105

<210> SEQ ID NO 92
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Gly Arg Tyr Gly Trp Tyr His Asp Cys Ile
                85                  90                  95

Asp Thr Gly Glu Ala Tyr Gly Gly Gly Thr Ala Val Thr Val Asn Ala
            100                 105                 110

<210> SEQ ID NO 93
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

```
Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Gly Arg Tyr Gly Trp Tyr His Asp Cys Ile
                85                  90                  95

Asp Thr Gly Glu Ala Tyr Gly Gly Gly Thr Val Val Thr Val Asn Ala
            100                 105                 110
```

<210> SEQ ID NO 94
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Gly Arg Tyr Gly Trp Tyr His Asp Cys Ile
                85                  90                  95

Asp Thr Gly Glu Ala Tyr Gly Asp Gly Thr Ala Val Thr Val Asn Ala
            100                 105                 110
```

<210> SEQ ID NO 95
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Gly Arg Tyr Gly Trp Tyr His Asp Cys Ile
                85                  90                  95

Asp Thr Gly Glu Ala Tyr Gly Gly Gly Thr Val Val Thr Val Asn Ala
            100                 105                 110
```

-continued

```
<210> SEQ ID NO 96
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Ala Arg Val Asp Gln Thr Pro Gln Thr Ile Thr Lys Glu Thr Gly Glu
1               5                   10                  15

Ser Ser Thr Ile Asn Cys Val Leu Arg Ala Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Ser Arg Ile Asn Asp Leu Thr Val Glu Asp Ser Gly Thr
65                  70                  75                  80

Tyr Arg Cys Asn Val Phe Gly Arg Tyr Gly Trp Tyr His Asp Cys Ile
                85                  90                  95

Asp Thr Gly Glu Ala Ser Gly Gly Gly Thr Val Val Thr Val Asn Ala
            100                 105                 110

<210> SEQ ID NO 97
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Ala Arg Val Asp Gln Thr Pro Gln Thr Ile Thr Lys Glu Thr Gly Glu
1               5                   10                  15

Ser Ser Thr Ile Asn Cys Val Leu Arg Ala Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Ser Arg Ile Asn Asp Leu Thr Val Glu Asp Ser Gly Thr
65                  70                  75                  80

Tyr Arg Cys Asn Val Phe Gly Arg Tyr Gly Trp Tyr His Asp Cys Ile
                85                  90                  95

Asp Thr Gly Glu Ala Ser Gly Gly Gly Thr Ala Val Thr Val Asn Ala
            100                 105                 110

<210> SEQ ID NO 98
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Ala Arg Val Asp Gln Thr Pro Gln Thr Ile Thr Lys Glu Thr Gly Glu
1               5                   10                  15
```

```
Ser Ser Thr Ile Asn Cys Val Leu Arg Asp Ser Asn Cys Ala Leu Ser
            20                  25                  30

Ser Thr Tyr Trp Tyr Arg Lys Arg Thr Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Phe Gly Arg Tyr Gly Trp Tyr His Asp Cys Ile
                 85                  90                  95

Asp Thr Gly Glu Ala Tyr Gly Gly Gly Thr Val Val Thr Val Asn Ala
            100                 105                 110
```

<210> SEQ ID NO 99
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

```
Ala Arg Val Asp Gln Thr Pro Gln Thr Ile Thr Lys Glu Thr Gly Glu
 1               5                   10                  15

Ser Ser Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Arg Val Glu Asp Ser Gly Thr
 65                  70                  75                  80

Tyr Arg Cys Asn Val Phe Gly Arg Tyr Gly Trp Tyr His Asp Cys Ile
                 85                  90                  95

Asp Thr Gly Glu Ala Tyr Gly Gly Gly Thr Val Val Thr Val Asn Ala
            100                 105                 110
```

<210> SEQ ID NO 100
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

```
Ala Arg Val Asp Gln Thr Pro Arg Ser Val Thr Lys Glu Thr Gly Glu
 1               5                   10                  15

Ser Ser Thr Ile Asn Cys Val Leu Arg Asp Ala Asn Tyr Ala Leu Gly
            20                  25                  30

Ser Thr Cys Trp Tyr Arg Lys Asn Ser Gly Ser Thr Asn Leu Glu Ser
        35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80
```

-continued

Tyr Arg Cys Gly Val Cys Thr Arg Trp Cys Pro Ser Cys Asp Glu Ser
                85                  90                  95

Cys Ser Arg Asn Phe Ala Ala Cys Gly Asp Gly Thr Ala Val Thr Val
            100                 105                 110

Asn Ala

<210> SEQ ID NO 101
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Ala Arg Val Asp Gln Thr Pro Gln Thr Ile Thr Lys Glu Thr Gly Glu
1               5                   10                  15

Ser Ser Thr Ile Asn Cys Val Leu Ser Asp Ser Arg Cys Glu Leu Ser
            20                  25                  30

Asn Thr Tyr Trp Tyr Arg Glu Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Ala Asn Ser Phe Ser Cys Glu Ser Ala Tyr Asn Val
                85                  90                  95

Tyr Gly Gly Gly Thr Val Val Thr Val Asn Ala
            100                 105

<210> SEQ ID NO 102
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Ala Arg Val Asp Gln Thr Pro Gln Thr Ile Thr Lys Glu Thr Gly Glu
1               5                   10                  15

Ser Ser Thr Ile Asn Cys Val Leu Ser Asp Ser Arg Cys Glu Leu Ser
            20                  25                  30

Asn Thr Tyr Trp Tyr Arg Glu Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Ala Asn Ser Phe Ser Cys Glu Ser Ala Tyr Asn Val
                85                  90                  95

Tyr Gly Gly Gly Thr Ala Val Thr Val Asn Ala
            100                 105

<210> SEQ ID NO 103
<211> LENGTH: 107
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 103

Ala Arg Val Asp Gln Thr Pro Gln Thr Ile Thr Lys Asp Ala Gly Glu
1               5                   10                  15

Ser Ser Thr Ile Asn Cys Val Leu Arg Asp Ser Asn Cys Ala Leu Asp
            20                  25                  30

His Thr Phe Trp Tyr Arg Lys Lys Pro Gly Ser Arg Asn Glu Glu Ser
        35                  40                  45

Ile Ser Lys Gly Gly Arg Tyr Val Glu Thr Val Tyr Ser Gly Ser Lys
    50                  55                  60

Ser Phe Ser Leu Arg Ile Asn Asp Leu Thr Val Glu Asp Ser Gly Val
65                  70                  75                  80

Phe Arg Cys Gln Val Asn Asn Phe Ala Cys Glu Ser Ala Tyr Asn Val
                85                  90                  95

Tyr Gly Gly Gly Thr Val Val Thr Val Asn Ala
                100                 105

<210> SEQ ID NO 104
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Ala Arg Val Asp Gln Thr Pro Gln Thr Ile Thr Lys Asp Ala Gly Glu
1               5                   10                  15

Ser Ser Thr Ile Asn Cys Val Leu Arg Asp Ser Asn Cys Ala Leu Asp
            20                  25                  30

His Thr Phe Trp Tyr Arg Lys Lys Pro Gly Ser Arg Asn Glu Glu Ser
        35                  40                  45

Ile Ser Lys Gly Gly Arg Tyr Val Glu Thr Val Tyr Ser Gly Ser Lys
    50                  55                  60

Ser Phe Ser Leu Arg Ile Asn Asp Leu Thr Val Glu Asp Ser Gly Val
65                  70                  75                  80

Phe Arg Cys Gln Val Asn Asn Phe Ala Cys Glu Ser Ala Tyr Asn Val
                85                  90                  95

Tyr Gly Gly Gly Thr Ala Val Thr Val Asn Ala
                100                 105

<210> SEQ ID NO 105
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Ala Arg Val Asp Gln Thr Pro Gln Thr Ile Thr Lys Glu Thr Gly Glu
1               5                   10                  15

Ser Ser Thr Ile Asn Cys Ile Leu Ser Asp Ser Asn Cys Ala Leu Ser
            20                  25                  30
```

Thr Thr His Trp His Arg Gln Lys Pro Gly Ser Arg Asn Glu Glu Asn
            35                  40                  45

Ile Pro Lys Gly Gly Arg Tyr Val Glu Thr Val Asn Tyr Arg Ser Lys
 50                  55                  60

Ser Phe Ser Leu Thr Ile Asn Asp Leu Thr Val Glu Asp Ala Asp Thr
 65                  70                  75                  80

Tyr Arg Cys Arg Ala Ser Ser Phe Ser Cys Glu Met Ala Tyr Asn Val
                 85                  90                  95

Tyr Gly Gly Gly Thr Ala Val Thr Val Asn Ala
            100                 105

<210> SEQ ID NO 106
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Ala Arg Val Asp Gln Thr Pro Gln Thr Ile Thr Lys Glu Thr Gly Glu
 1               5                   10                  15

Ser Ser Thr Ile Asn Cys Ile Leu Ser Asp Ser Asn Cys Ala Leu Ser
                20                  25                  30

Thr Thr His Trp His Arg Gln Lys Pro Gly Ser Arg Asn Glu Glu Asn
            35                  40                  45

Ile Pro Lys Gly Gly Arg Tyr Val Glu Thr Val Asn Tyr Arg Ser Lys
 50                  55                  60

Ser Phe Ser Leu Thr Ile Asn Asp Leu Thr Val Glu Asp Ala Asp Thr
 65                  70                  75                  80

Tyr Arg Cys Arg Ala Ser Ser Phe Ser Cys Glu Met Ala Tyr Asn Val
                 85                  90                  95

Tyr Gly Gly Gly Thr Val Val Thr Val Asn Ala
            100                 105

<210> SEQ ID NO 107
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Ala Arg Val Asp Gln Thr Pro Gln Thr Ile Thr Lys Glu Thr Gly Glu
 1               5                   10                  15

Ser Ser Thr Ile Asn Cys Ile Leu Ser Asp Ser Asn Cys Ala Leu Ser
                20                  25                  30

Thr Thr His Trp His Arg Gln Lys Pro Gly Ser Arg Asn Glu Glu Asn
            35                  40                  45

Ile Pro Lys Gly Gly Arg Tyr Val Glu Thr Val Asn Tyr Arg Ser Lys
 50                  55                  60

Ser Phe Ser Leu Thr Ile Asn Asp Leu Thr Val Glu Asp Ala Asp Thr
 65                  70                  75                  80

Tyr Arg Cys Arg Ala Ser Ser Phe Ser Cys Glu Met Ala Tyr Asn Val
                 85                  90                  95

Tyr Gly Asp Gly Thr Ala Val Thr Val Asn Ala

<210> SEQ ID NO 108
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 108

Ala Arg Val Asp Gln Thr Pro Gln Thr Ile Thr Lys Glu Thr Gly Glu
1               5                   10                  15
Ser Ser Thr Ile Asn Cys Ile Leu Arg Asp Ser Asn Cys Ala Leu Ser
                20                  25                  30
Thr Thr Tyr Trp Tyr Arg Gln Lys Pro Gly Ser Arg Asn Glu Glu Asn
            35                  40                  45
Ile Pro Lys Gly Gly Arg Tyr Val Glu Thr Val Asn Asn Arg Ser Lys
        50                  55                  60
Ser Phe Ser Leu Thr Ile Asn Asp Leu Thr Val Glu Asp Ala Asp Thr
65                  70                  75                  80
Tyr Arg Cys Arg Ala Ser Ser Phe Ser Cys Glu Ser Ala Tyr Asn Val
                85                  90                  95
Tyr Gly Gly Gly Thr Val Val Thr Val Asn Ala
            100                 105

<210> SEQ ID NO 109
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

Ala Arg Val Asp Gln Thr Pro Gln Thr Ile Thr Lys Glu Thr Gly Glu
1               5                   10                  15
Ser Ser Thr Ile Asn Cys Val Leu Arg Asp Ser Asn Cys Ala Leu Ser
                20                  25                  30
Ser Thr Tyr Trp Tyr Arg Lys Lys Ser Gly Ser Thr Asn Glu Glu Ser
            35                  40                  45
Ile Ser Lys Gly Gly Arg Tyr Val Glu Thr Val Asn Ser Gly Ser Lys
        50                  55                  60
Ser Phe Ser Leu Arg Ile Asn Asp Leu Thr Val Glu Asp Ser Gly Thr
65                  70                  75                  80
Tyr Arg Cys Asn Val Trp Ala Pro Tyr Asp Cys Glu Asn Trp Arg Asp
                85                  90                  95
Val Tyr Gly Gly Gly Thr Val Val Thr Val Asn Ala
            100                 105

<210> SEQ ID NO 110
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 110

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
                20                  25                  30

Asn Thr Tyr Trp Tyr Arg Leu Phe Ser Gly Ser Arg Arg Glu Glu Arg
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Arg Ile Glu Asp Thr Gly Thr
65                  70                  75                  80

Tyr Lys Cys Lys Ala Thr Asn Phe Ala Cys Glu Ser Ala Tyr Asn Val
                85                  90                  95

Tyr Gly Gly Gly Thr Ala Val Thr Val Asn Ala
            100                 105

<210> SEQ ID NO 111
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
                20                  25                  30

Asn Thr Tyr Trp Tyr Arg Leu Phe Ser Gly Ser Arg Arg Glu Glu Arg
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Arg Ile Glu Asp Thr Gly Thr
65                  70                  75                  80

Tyr Lys Cys Lys Ala Thr Asn Phe Ala Cys Glu Ser Ala Tyr Asn Val
                85                  90                  95

Tyr Gly Gly Gly Thr Val Val Thr Val Asn Ala
            100                 105

<210> SEQ ID NO 112
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Ala Arg Val Asp Gln Thr Pro Gln Thr Ile Thr Lys Glu Thr Gly Glu
1               5                   10                  15

Ser Ser Thr Ile Asn Cys Ile Leu Arg Asp Ser Asn Cys Arg Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

-continued

Ser Phe Ser Leu Arg Ile Asn Asp Leu Thr Val Glu Asp Ser Gly Thr
65                  70                  75                  80

Tyr Arg Cys Asn Val Ala Gly Met Asp Ala Arg Tyr Asp Cys Gly Ser
            85                  90                  95

Asn Trp Thr Val Tyr Gly Gly Gly Thr Val Val Thr Val Asn Ala
        100                 105                 110

<210> SEQ ID NO 113
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Ala Arg Val Asp Gln Thr Pro Arg Ser Val Thr Lys Glu Thr Gly Glu
1               5                   10                  15

Ser Ser Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Arg
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
65                  70                  75                  80

Tyr Arg Cys Ala Ser Ser Ser Trp Cys Thr Ser Leu Thr Val Thr Val
            85                  90                  95

Cys Gly Val Asp Pro Tyr Ala Val Cys Gly Asp Gly Thr Ala Val Thr
        100                 105                 110

Val Asn Ala
        115

<210> SEQ ID NO 114
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Ala Arg Val Asp Gln Thr Pro Gln Thr Ile Thr Lys Glu Thr Gly Glu
1               5                   10                  15

Ser Ser Thr Ile Ser Cys Val Leu Arg Asp Ser Pro Cys Ala Leu Thr
                20                  25                  30

Ser Val Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Thr Gly Ser Lys
        50                  55                  60

Ser Phe Ser Leu Arg Ile Asn Asp Leu Thr Val Glu Asp Ser Gly Thr
65                  70                  75                  80

Tyr Arg Cys Arg Asn Leu Gly Phe Asn Ala Arg Ala Phe Ser Glu Ala
            85                  90                  95

Gly Cys Glu Gln Tyr Gly Gly Gly Thr Val Val Thr Val Asn Ala
        100                 105                 110

```
<210> SEQ ID NO 115
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asp Cys Ala Asp Val
            20                  25                  30

Ser Ala His Trp Arg Arg Lys Lys Ser Ala Ser Thr Arg Glu Glu Val
        35                  40                  45

Ile Ser Gln Asp Gly Arg Tyr Val Glu Thr Val Asn Ser Gly Ser Lys
    50                  55                  60

Ser Phe Ser Leu Arg Ile Asn Asp Leu Arg Phe Glu Asp Ser Gly Thr
65                  70                  75                  80

Tyr Arg Cys Asn Val Arg Ala Ser Trp Asp Leu Glu Ser Tyr Cys Thr
                85                  90                  95

Gly Leu Asp Val Tyr Gly Gly Gly Thr Val Val Thr Val Asn Ala
            100                 105                 110

<210> SEQ ID NO 116
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Phe Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Trp Tyr Ser Ile Cys Ile Glu Thr Val Asp Val Tyr
                85                  90                  95

Gly Gly Gly Thr Val Val Thr Val Asn Ala
            100                 105

<210> SEQ ID NO 117
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Ala Arg Val Asp Gln Thr Pro Gln Thr Ile Thr Lys Glu Thr Gly Glu
1               5                   10                  15
```

Ser Ser Thr Ile Asn Cys Val Leu Arg Asp Ser Asn Cys Ala Trp Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Trp Tyr Ser Ile Cys Ile Glu Thr Val Asp Val Tyr
                85                  90                  95

Gly Asp Gly Thr Ala Val Thr Val Asn Ala
            100                 105

<210> SEQ ID NO 118
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Trp Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Trp Tyr Ser Ile Cys Ile Glu Thr Val Asp Val Tyr
                85                  90                  95

Gly Gly Gly Thr Val Val Thr Val Asn Ala
            100                 105

<210> SEQ ID NO 119
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Trp Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Trp Tyr Ser Ile Cys Ile Glu Thr Val Asp Val Tyr
                 85                  90                  95

Gly Gly Gly Thr Ala Val Thr Val Asn Ala
            100                 105

<210> SEQ ID NO 120
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Ala Arg Val Asp Gln Thr Pro Gln Thr Ile Thr Lys Glu Thr Gly Gly
1               5                   10                  15

Ser Ser Thr Ile Asn Cys Val Leu Arg Asp Thr Ser Cys Ala Leu Gly
            20                  25                  30

Thr Thr Tyr Trp Thr Tyr Lys Glu Ser Gly Ser Thr Asn Glu Glu Asn
        35                  40                  45

Ile Ser Val Gly Gly Arg Tyr Val Glu Thr Ile Asn Ser Gly Ser Lys
50                  55                  60

Ser Phe Ser Leu Arg Ile Asn Asp Leu Thr Leu Glu Asp Ser Gly Thr
65                  70                  75                  80

Tyr Arg Cys Lys Asn Trp Phe Asp Cys Gly Ser Gly Thr Gly Arg Leu
                85                  90                  95

Val Tyr Gly Gly Gly Thr Val Val Thr Val Asn Ala
            100                 105

<210> SEQ ID NO 121
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Ala Arg Val Asp Gln Thr Pro Gln Thr Ile Thr Lys Ser Thr Gly Glu
1               5                   10                  15

Ser Ser Thr Ile Asn Cys Val Leu Arg Asp Thr Tyr Cys Ala Leu Ser
            20                  25                  30

Asn Thr Asn Trp Tyr His Lys Lys Ser Gly Ser Thr His Glu Glu Ser
        35                  40                  45

Ile Ser Lys Gly Gly Arg Tyr Val Glu Thr Leu Asn Thr Asp Ser Lys
50                  55                  60

Ser Phe Ser Leu Arg Ile Thr Asp Leu Thr Ile Glu Asp Ser Gly Leu
65                  70                  75                  80

Tyr Arg Cys Asn Ile Tyr Gln Leu Pro Pro Ser Arg Trp Thr Thr Glu
                85                  90                  95

Cys Leu Leu Asp Leu Tyr Gly Gly Gly Thr Val Val Thr Val Asn Ala
            100                 105                 110

<210> SEQ ID NO 122
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Ala Arg Val Asp Gln Thr Pro Gln Thr Ile Thr Lys Ser Thr Gly Glu
1               5                   10                  15

Ser Ser Thr Ile Asn Cys Val Leu Arg Asp Thr Tyr Cys Ala Leu Ser
                20                  25                  30

Asn Thr Asn Trp Tyr His Lys Lys Ser Gly Ser Thr His Glu Glu Ser
            35                  40                  45

Ile Ser Lys Gly Gly Arg Tyr Val Glu Thr Leu Asn Thr Asp Ser Lys
50                  55                  60

Ser Phe Ser Leu Arg Ile Thr Asp Leu Thr Ile Glu Asp Ser Gly Leu
65                  70                  75                  80

Tyr Arg Cys Asn Ile Tyr Gln Leu Pro Pro Ser Arg Trp Thr Thr Glu
                85                  90                  95

Cys Leu Leu Asp Leu Tyr Gly Asp Gly Thr Ala Val Thr Val Asn Ala
                100                 105                 110

<210> SEQ ID NO 123
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Ala Arg Val Asp Gln Thr Pro Gln Thr Ile Thr Lys Ser Thr Gly Glu
1               5                   10                  15

Ser Ser Thr Ile Asn Cys Val Leu Arg Asp Thr Tyr Cys Ala Leu Ser
                20                  25                  30

Asn Thr Asn Trp Tyr His Lys Lys Ser Gly Ser Thr His Glu Glu Ser
            35                  40                  45

Ile Ser Lys Gly Gly Arg Tyr Val Glu Thr Leu Asn Thr Asp Ser Lys
50                  55                  60

Ser Phe Ser Leu Arg Ile Thr Asp Leu Thr Ile Glu Asp Ser Gly Leu
65                  70                  75                  80

Tyr Arg Cys Asn Ile Tyr Gln Leu Pro Pro Ser Arg Trp Thr Thr Glu
                85                  90                  95

Cys Leu Leu Asp Leu Tyr Gly Gly Thr Ala Val Thr Val Asn Ala
                100                 105                 110

<210> SEQ ID NO 124
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Ala Arg Val Asp Gln Thr Pro Lys Thr Ile Thr Lys Glu Thr Gly Glu
1               5                   10                  15

Ser Ser Thr Ile Asn Cys Val Leu Val Glu Ser Lys Tyr Pro Leu Gly
                20                  25                  30

Ser Thr Cys Trp Phe Arg Lys Arg Ser Gly Ser Thr Ser Glu Glu Ile
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Asp Glu Asp Gly Gly Thr
65                  70                  75                  80

Tyr Arg Cys Gly Gly Ser Val Leu Val Ala Glu Lys Ser Cys Asn Cys
                85                  90                  95

Thr Ser Ala Tyr Thr Glu Cys Gly Asp Gly Thr Ala Val Thr Val Asn
            100                 105                 110

Ala

<210> SEQ ID NO 125
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Ala Arg Val Asp Gln Thr Pro Arg Ser Val Thr Lys Glu Thr Gly Glu
1               5                   10                  15

Ser Ser Thr Ile Asn Cys Val Leu Arg Asp Ala Ser Tyr Ser Leu Gly
                20                  25                  30

Thr Thr Cys Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
65                  70                  75                  80

Tyr Arg Cys Gly Ala Ser Pro Pro Asp Trp Ser Cys Asp Gly Ser Cys
                85                  90                  95

Arg Leu Asp Ala Ala Cys Gly Asp Gly Thr Ala Val Thr Val Asn Ala
            100                 105                 110

<210> SEQ ID NO 126
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Ala Arg Val Asp Gln Thr Pro Arg Ser Val Thr Lys Glu Thr Gly Glu
1               5                   10                  15

Ser Ser Thr Ile Asn Cys Val Leu Arg Asp Ala Ser Tyr Gly Leu Val
                20                  25                  30

Glu Thr Cys Trp Tyr Arg Lys Lys Ser Asp Ser Thr Tyr Glu Glu Thr
            35                  40                  45

Ile Ser Lys Gly Gly Arg Tyr Val Glu Thr Val Val Ser Gly Ser Lys
 50                  55                  60

Ser Phe Ser Leu Arg Ile Asn Asp Leu Thr Val Glu Asp Gly Gly Thr
65                  70                  75                  80

Tyr Arg Cys Gly Val Arg Cys Ala Val Arg Leu Gly Tyr Ser Gly Cys
                85                  90                  95

Ser Gly Thr Tyr Ala Thr Cys Gly Asp Gly Thr Ala Val Thr Val Asn

Ala

<210> SEQ ID NO 127
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 127

Ala Arg Val Asp Gln Thr Pro Gln Thr Ile Thr Lys Leu Glu Gly Glu
1               5                   10                  15

Ser Ser Thr Ile Asn Cys Val Leu Arg Asp Asn Asn Cys Gly Leu Ser
            20                  25                  30

Asp Thr His Trp Phe Tyr Lys Arg Ser Gly Ser Val His Glu Glu Lys
        35                  40                  45

Ile Ser Lys Gly Gly Arg Tyr Val Glu Thr Val Asn Ser Arg Ser Lys
    50                  55                  60

Ser Phe Ser Leu Arg Ile Asn Asp Leu Thr Val Glu Asp Ser Gly Thr
65                  70                  75                  80

Tyr Arg Cys Asn Gly Lys Gly Gln Cys Phe Val Ser Gly Gly Ser Thr
                85                  90                  95

Leu Pro Tyr Asn Glu Tyr Gly Gly Gly Thr Ala Val Thr Val Asn Ala
            100                 105                 110

<210> SEQ ID NO 128
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 128

Ala Arg Val Asp Gln Thr Pro Gln Thr Ile Thr Lys Leu Glu Gly Glu
1               5                   10                  15

Ser Ser Thr Ile Asn Cys Val Leu Arg Asp Asn Asn Cys Gly Leu Ser
            20                  25                  30

Asp Thr His Trp Phe Tyr Lys Arg Ser Gly Ser Val His Glu Glu Lys
        35                  40                  45

Ile Ser Lys Gly Gly Arg Tyr Val Glu Thr Val Asn Ser Arg Ser Lys
    50                  55                  60

Ser Phe Ser Leu Arg Ile Asn Asp Leu Thr Val Glu Asp Ser Gly Thr
65                  70                  75                  80

Tyr Arg Cys Asn Gly Lys Gly Gln Cys Phe Val Ser Gly Gly Ser Thr
                85                  90                  95

Leu Pro Tyr Asn Glu Tyr Gly Gly Gly Thr Val Val Thr Val Asn Ala
            100                 105                 110

<210> SEQ ID NO 129
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

```
<400> SEQUENCE: 129

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Tyr Arg Lys Lys Ser Gly Pro Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Glu Ser Val Cys Arg Tyr Arg Gly Glu Ser
                85                  90                  95

Glu Val Asp Val Tyr Gly Gly Gly Thr Val Val Thr Val Asn Ala
            100                 105                 110

<210> SEQ ID NO 130
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Tyr Arg Lys Lys Ser Gly Pro Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Phe Glu Ser Val Cys Arg Tyr Arg Gly Glu Ser
                85                  90                  95

Glu Val Asp Val Tyr Gly Gly Gly Thr Ala Val Thr Val Asn Ala
            100                 105                 110

<210> SEQ ID NO 131
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Tyr Arg Lys Lys Ser Gly Pro Thr Asn Glu Glu Ser
        35                  40                  45

Ile Ser Lys Gly Gly Arg Tyr Val Glu Thr Val Asn Ser Gly Ser Lys
```

```
                      50                  55                  60
Ser Phe Ser Leu Arg Ile Asn Asp Leu Thr Val Glu Asp Ser Gly Thr
 65                  70                  75                  80

Tyr Arg Cys Asn Val Phe Glu Ser Val Cys Arg Tyr Arg Gly Glu Ser
                     85                  90                  95

Glu Val Asp Val Tyr Gly Asp Gly Thr Ala Val Thr Val Asn Ala
                100                 105                 110

<210> SEQ ID NO 132
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Ala Arg Val Asp Gln Thr Pro Gln Thr Ile Thr Lys Glu Thr Gly Glu
 1                   5                  10                  15

Ser Ser Thr Ile Asn Cys Val Leu Arg Asp Thr Asn Cys Ala Leu Ser
                    20                  25                  30

Pro Thr Asn Trp Tyr Arg Lys Lys Ser Gly Ser Thr Asn Glu Glu Ser
                    35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Arg Gly Thr
 65                  70                  75                  80

Tyr Arg Cys Asn Val Tyr Ser Pro Asp Asp Cys Thr Asp Tyr Asn Tyr
                     85                  90                  95

Asp Val Tyr Gly Gly Gly Thr Ala Val Thr Val Asn Ala
                100                 105

<210> SEQ ID NO 133
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Ala Arg Val Asp Gln Thr Pro Gln Thr Ile Thr Lys Glu Thr Gly Glu
 1                   5                  10                  15

Ser Ser Thr Ile Asn Cys Val Leu Arg Asp Thr Asn Cys Ala Leu Ser
                    20                  25                  30

Pro Thr Asn Trp Tyr Arg Lys Lys Ser Gly Ser Thr Asn Glu Glu Ser
                    35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Arg Gly Thr
 65                  70                  75                  80

Tyr Arg Cys Asn Val Tyr Ser Pro Asp Asp Cys Thr Asp Tyr Asn Tyr
                     85                  90                  95

Asp Val Tyr Gly Gly Gly Thr Val Val Thr Val Asn Ala
                100                 105

<210> SEQ ID NO 134
```

```
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134
```

Ala Arg Val Asp Gln Thr Pro Arg Ser Val Thr Lys Glu Thr Gly Glu
1               5                   10                  15

Ser Ser Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Trp Cys Gly Leu Pro Asp Tyr Arg Ser Trp Gly
                85                  90                  95

Ala Arg Ala Ala Cys Gly Asp Gly Thr Ala Val Thr Val Asn Ala
            100                 105                 110

```
<210> SEQ ID NO 135
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135
```

Ala Arg Val Asp Gln Thr Pro Gln Thr Ile Thr Lys Glu Thr Gly Glu
1               5                   10                  15

Ser Ser Thr Ile Asn Cys Val Ile Arg Asp Gly Thr Cys Ala Phe Ala
            20                  25                  30

Ser Thr Phe Trp Tyr Arg Asn Lys Gln Gly Ser Thr Asn Glu Glu Asn
        35                  40                  45

Ile Ser Lys Gly Gly Arg Tyr Val Glu Thr Val Asn Lys Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Ala Ala Ser Val Cys Ala Pro Arg Leu Phe Glu Thr
                85                  90                  95

Lys Asp Val Ile Gly Gly Thr Ala Val Thr Val Asn Ala
            100                 105                 110

```
<210> SEQ ID NO 136
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136
```

Ala Arg Val Asp Gln Thr Pro Gln Thr Ile Thr Lys Glu Thr Gly Glu
1               5                   10                  15

```
Ser Ser Thr Ile Asn Cys Val Ile Arg Asp Gly Thr Cys Ala Phe Ala
            20                  25                  30

Ser Thr Phe Trp Tyr Arg Asn Lys Gln Gly Ser Thr Asn Glu Glu Asn
        35                  40                  45

Ile Ser Lys Gly Gly Arg Tyr Val Glu Thr Val Asn Lys Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Ala Ala Ser Val Cys Ala Pro Arg Leu Phe Glu Thr
                85                  90                  95

Lys Asp Val Ile Gly Gly Thr Val Val Thr Val Asn Ala
            100                 105                 110

<210> SEQ ID NO 137
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Phe Trp Tyr Arg Lys Ile Ser Gly Ser Arg Asn Glu Asp Leu
        35                  40                  45

Ile Ser Lys Ser Gly Arg Tyr Val Glu Thr Val Asn Ser Val Ala Lys
    50                  55                  60

Ser Phe Ser Leu Arg Ile Asn Asp Leu Thr Val Lys Asp Thr Gly Thr
65                  70                  75                  80

Tyr Arg Cys Asn Val Phe Ser Trp Cys Asp Asp Ser Ser Asp Leu Asp
                85                  90                  95

Val Tyr Gly Gly Gly Thr Val Val Thr Val Asn Ala
            100                 105

<210> SEQ ID NO 138
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Ala Arg Val Asp Gln Thr Pro Arg Ser Val Thr Lys Glu Thr Gly Glu
1               5                   10                  15

Ser Ser Thr Ile Asn Cys Val Leu Arg Asp Ala Gly Trp Arg Ser Gly
            20                  25                  30

Ser Thr Cys Trp Tyr Arg Lys Lys Ser Asp Ser Thr Asn Glu Glu Ser
        35                  40                  45

Ile Ser Glu Gly Gly Arg Tyr Val Glu Thr Val Asn Ser Gly Ser Asn
    50                  55                  60

Thr Phe Ser Leu Arg Ile Asn Asp Leu Thr Val Glu Asp Gly Gly Thr
65                  70                  75                  80

Tyr Leu Cys Gly Ala Ser Leu Pro Glu Trp Gly Cys Ser Val Tyr Cys
```

```
                85                  90                  95
Arg Leu Asp Ala Ala Cys Gly Asp Gly Thr Ala Val Thr Val Asn Ala
            100                 105                 110

<210> SEQ ID NO 139
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Glu Cys Ala Leu Ser
                20                  25                  30

Ser Thr Tyr Trp Tyr Arg Lys Lys Ser Gly Ser Thr Ser Glu Glu Asn
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Ala Asn Tyr Asp Cys Phe Arg Arg Ile Glu Leu
                85                  90                  95

Arg Asn Phe Tyr Asp Arg Tyr Gly Gly Gly Thr Val Val Thr Val Asn
            100                 105                 110

Ala

<210> SEQ ID NO 140
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Ala Arg Val Asp Gln Thr Pro Gln Thr Ile Thr Lys Glu Thr Gly Asp
1               5                   10                  15

Ser Ser Thr Ile Asn Cys Val Leu Arg Asp Ser Asn Cys Asp Leu Thr
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asp Asp Leu Arg Val Glu Asp Ser Gly Thr
65                  70                  75                  80

Tyr Arg Cys Ala Val Tyr Gly Ser Val Cys Tyr Glu Ile Arg Thr Gly
                85                  90                  95

Gln Phe Gly Asp Gly Thr Ala Val Thr Val Asn Ala
            100                 105

<210> SEQ ID NO 141
<211> LENGTH: 108
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 141

Ala Arg Val Asp Gln Thr Pro Gln Thr Ile Thr Lys Glu Thr Gly Asp
1               5                   10                  15

Ser Ser Thr Ile Asn Cys Val Leu Arg Asp Ser Asn Cys Asp Leu Thr
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asp Asp Leu Arg Val Glu Asp Ser Gly Thr
65                  70                  75                  80

Tyr Arg Cys Ala Val Tyr Gly Ser Val Cys Tyr Glu Ile Arg Thr Gly
                85                  90                  95

Gln Phe Gly Gly Gly Thr Val Val Thr Val Asn Ala
            100                 105

<210> SEQ ID NO 142
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Ala Arg Val Asp Gln Thr Pro Gln Thr Ile Thr Lys Glu Thr Gly Asp
1               5                   10                  15

Ser Ser Thr Ile Asn Cys Val Leu Arg Asp Ser Asn Cys Asp Leu Thr
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asp Asp Leu Arg Val Glu Asp Ser Gly Thr
65                  70                  75                  80

Tyr Arg Cys Ala Val Tyr Gly Ser Val Cys Tyr Glu Ile Arg Thr Gly
                85                  90                  95

Gln Phe Gly Gly Gly Thr Ala Val Thr Val Asn Ala
            100                 105

<210> SEQ ID NO 143
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Asn Thr Tyr Trp Tyr Arg Lys Lys Ser Gly Ser Thr Asn Glu Glu Asn

```
                35                  40                  45
Ile Ser Lys Ala Gly Arg Tyr Ala Arg Tyr Val Glu Thr Gly Asp Ser
 50                  55                  60

Gly Ser Lys Ser Phe Ser Leu Arg Ile Asn Asp Leu Thr Val Glu Asp
 65                  70                  75                  80

Ser Gly Thr Phe Arg Cys Asn Ala Phe Ser Trp Gly Cys Pro Asn
                 85                  90                  95

Pro Phe Asp Ile Tyr Gly Gly Thr Ala Val Thr Val Asn Ala
                100                 105                 110

<210> SEQ ID NO 144
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Ala Arg Val Asp Gln Thr Pro Gln Thr Ile Thr Lys Glu Thr Gly Glu
 1               5                  10                  15

Ser Ser Thr Ile Asn Cys Val Leu Arg Asp Ser Asn Cys Ala Leu Ser
                20                  25                  30

Asn Thr Tyr Trp Tyr Arg Lys Lys Ser Gly Ser Thr Asn Glu Glu Asn
                35                  40                  45

Ile Ser Lys Ala Gly Arg Tyr Ala Arg Tyr Val Glu Thr Gly Asp Ser
 50                  55                  60

Gly Ser Lys Ser Phe Ser Leu Arg Ile Asn Asp Leu Thr Val Glu Ser
 65                  70                  75                  80

Gly Thr Phe Arg Cys Asn Ala Phe Ser Trp Gly Cys Pro Asn Pro
                 85                  90                  95

Phe Asp Ile Tyr Gly Gly Gly Thr Val Val Thr Val Asn Ala
                100                 105                 110

<210> SEQ ID NO 145
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Ala Arg Val Asp Gln Thr Pro Gln Arg Ile Thr Lys Glu Thr Gly Glu
 1               5                  10                  15

Ser Ser Thr Ile Asn Cys Val Leu Arg Asp Ser Lys Cys Ala Leu Ser
                20                  25                  30

Asp Thr Tyr Trp Tyr Arg Lys Lys Ser Gly Ser Thr Asn Glu Glu Lys
                35                  40                  45

Ile Ser Lys Gly Gly Arg Tyr Val Glu Thr Thr Ile Ser Gly Arg Ser
 50                  55                  60

Ser Phe Ser Leu Arg Ile Tyr Asp Leu Thr Val Glu Asp Ser Gly Thr
 65                  70                  75                  80

Tyr Arg Cys Asn Thr Val Tyr Val Trp Arg Gly Ser His Tyr His Gln
                 85                  90                  95

Glu Leu Ala Cys Asp Tyr Asp Val Ser Gly Gly Thr Val Val Thr
                100                 105                 110
```

Val Asn Ala
        115

<210> SEQ ID NO 146
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Ala Arg Val Asp Gln Thr Pro Gln Arg Ile Thr Lys Glu Thr Gly Glu
1               5                   10                  15

Ser Ser Thr Ile Asn Cys Val Leu Arg Asp Ser Lys Cys Ala Leu Ser
            20                  25                  30

Asp Thr Tyr Trp Tyr Arg Lys Lys Ser Gly Ser Thr Asn Glu Glu Lys
        35                  40                  45

Ile Ser Lys Gly Gly Arg Tyr Val Glu Thr Thr Ile Ser Gly Arg Ser
    50                  55                  60

Ser Phe Ser Leu Arg Ile Tyr Asp Leu Thr Val Glu Asp Ser Gly Thr
65                  70                  75                  80

Tyr Arg Cys Asn Thr Val Tyr Val Trp Arg Gly Ser His Tyr His Gln
                85                  90                  95

Glu Leu Ala Cys Asp Tyr Asp Val Ser Gly Gly Thr Ala Val Thr
            100                 105                 110

Val Asn Ala
        115

<210> SEQ ID NO 147
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Ala Arg Val Asp Gln Thr Pro Arg Ser Val Thr Lys Glu Thr Gly Glu
1               5                   10                  15

Ser Ser Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly His Ser Trp Leu Glu Ser Cys Asp Tyr Arg Pro Cys
                85                  90                  95

Ser Asp Tyr Ala Ala Cys Gly Asp Gly Thr Ala Val Thr Val Asn Ala
            100                 105                 110

<210> SEQ ID NO 148
<211> LENGTH: 111
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 148

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asp Cys Ala Leu Ser
            20                  25                  30

Ser Thr Tyr Trp Tyr Arg Lys Val Ser Gly Ser Thr Asn Glu Glu Ser
        35                  40                  45

Ile Ser Ile Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Thr Leu Val Trp Cys Gly Met Ala Gly Met Gly Trp
                85                  90                  95

Ser Pro Asp Val Ser Gly Gly Gly Thr Val Val Thr Val Asn Ala
            100                 105                 110

<210> SEQ ID NO 149
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Ala Arg Val Asp Gln Thr Pro Gln Thr Ile Thr Lys Glu Thr Gly Glu
1               5                   10                  15

Ser Ser Thr Ile Asn Cys Val Leu Val Asp Thr Asp Cys Ala Leu Ala
            20                  25                  30

Val Thr Tyr Trp His Arg Lys Lys Leu Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Asn Gly Thr
65                  70                  75                  80

Tyr Arg Cys Ala Val Arg Arg Ala Glu Lys Lys Gly Gly Asp Cys Thr
                85                  90                  95

Leu Asn Tyr His Ala Phe Gly Gly Thr Val Val Thr Val Asn Ala
            100                 105                 110

<210> SEQ ID NO 150
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150

Ala Arg Val Asp Gln Thr Pro Gln Thr Ile Thr Lys Glu Thr Gly Glu
1               5                   10                  15

Ser Ser Thr Ile Asn Cys Val Leu Leu Asp Thr Asn Cys Pro Met Pro
            20                  25                  30

Val Ala Tyr Trp Tyr Arg Lys Lys Ala Gly Ser Arg Arg Glu Glu Arg

```
                35                  40                  45
Ile Ser Lys Gly Gly Arg Tyr Val Glu Thr Val Asn Ser Gly Arg Leu
 50                  55                  60

Ser Phe Ser Leu Arg Ile Asn Asp Leu Thr Val Glu Asp Ser Gly Lys
 65                  70                  75                  80

Tyr Arg Cys Asn Ala Tyr Ser Phe Ile Gly Val Asp Ser Cys Asp Trp
                 85                  90                  95

Asp Ile Tyr Gly Asp Gly Thr Ala Val Thr Val Asn Ala
            100                 105
```

<210> SEQ ID NO 151
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 151

```
Ala Arg Val Asp Gln Thr Pro Gln Thr Ile Thr Lys Glu Thr Gly Glu
 1               5                  10                  15

Ser Ser Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Trp Gly Ile Ala Gly Val Val Cys Arg Glu Val
                 85                  90                  95

Asn Trp Gly Gly Gln Tyr Asp Val Tyr Gly Gly Gly Thr Val Val Thr
            100                 105                 110

Val Asn Ala
        115
```

<210> SEQ ID NO 152
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 152

```
Ala Arg Val Asp Gln Thr Pro Gln Thr Ile Thr Lys Glu Thr Gly Glu
 1               5                  10                  15

Ser Ser Thr Ile Asn Cys Val Leu Leu Asp Thr Asn Cys Pro Met Pro
                20                  25                  30

Val Ala Tyr Trp Tyr Arg Lys Lys Ala Gly Ser Arg Arg Glu Glu Arg
             35                  40                  45

Ile Ser Lys Gly Gly Arg Tyr Val Glu Thr Val Asn Ser Gly Arg Leu
 50                  55                  60

Ser Phe Ser Leu Arg Ile Asn Asp Leu Thr Val Glu Asp Ser Gly Lys
 65                  70                  75                  80

Tyr Arg Cys Asn Ala Tyr Ser Phe Ile Gly Val Asp Ser Cys Asp Trp
                 85                  90                  95
```

```
Asp Ile Tyr Gly Asp Gly Thr Val Val Thr Val Asn Ala Val Lys Gly
                100                 105                 110

Gly Gly Thr Val Val Thr Val Asn Ala
        115                 120

<210> SEQ ID NO 153
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Ala Arg Val Asp Gln Thr Pro Gln Thr Ile Thr Lys Glu Thr Gly Glu
1               5                   10                  15

Ser Ser Thr Ile Asn Cys Val Leu Arg Ala Arg Asp Cys Gly Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ile Gly Ser Lys
    50                  55                  60

Ser Phe Ser Leu Arg Ile Asn Asp Leu Thr Ser Glu Asp Ser Gly Thr
65                  70                  75                  80

Tyr Arg Cys Asn Val Phe Gly Tyr Cys Pro Val Ser Gly Val Glu Ile
                85                  90                  95

Val Gly Val Tyr Gly Gly Gly Thr Val Val Thr Val Asn Ala
                100                 105                 110

<210> SEQ ID NO 154
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Ala Arg Val Asp Gln Thr Pro Gln Thr Ile Thr Lys Glu Thr Gly Glu
1               5                   10                  15

Ser Ser Thr Ile Asn Cys Val Leu Arg Ala Arg Asp Cys Gly Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ile Gly Ser Lys
    50                  55                  60

Ser Phe Ser Leu Arg Ile Asn Asp Leu Thr Ser Glu Asp Ser Gly Thr
65                  70                  75                  80

Tyr Arg Cys Asn Val Phe Gly Tyr Cys Pro Val Ser Gly Val Glu Ile
                85                  90                  95

Val Gly Val Tyr Gly Gly Gly Thr Ala Val Thr Val Asn Ala
                100                 105                 110

<210> SEQ ID NO 155
<211> LENGTH: 112
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 155

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Leu Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Tyr His Arg Trp Cys Thr Met Gly Thr Gly Gly
                85                  90                  95

Pro Gly Tyr Asp Val Tyr Gly Gly Gly Thr Val Val Thr Val Asn Ala
            100                 105                 110

<210> SEQ ID NO 156
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Leu Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Tyr His Arg Trp Cys Thr Met Gly Thr Gly Gly
                85                  90                  95

Pro Gly Tyr Asp Val Tyr Gly Gly Gly Thr Ala Val Thr Val Asn Ala
            100                 105                 110

<210> SEQ ID NO 157
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Ala Arg Val Asp Gln Thr Pro Gln Thr Ile Thr Lys Gln Thr Gly Glu
1               5                   10                  15

Ser Ser Thr Ile Asn Cys Val Leu Arg Asp Arg Asn Cys Ala Phe Met
            20                  25                  30

Ser Thr Asp Trp Tyr Arg Lys Lys Ser Gly Ser Thr His Glu Glu Ser

```
                35                  40                  45
Ile Ser Lys Gly Gly Arg Tyr Val Glu Thr Val Arg Glu Ser Lys
 50                  55                  60

Ser Gly Ser Leu Arg Ile Thr Asp Leu Thr Val Glu Asp Ser Gly Asn
 65                  70                  75                  80

Tyr Arg Cys Lys Ile Tyr Ser Arg Thr Gly Asp Leu Glu Gly Pro Leu
                 85                  90                  95

Asn Trp Cys Pro Glu Ile Tyr Gly Gly Thr Val Val Thr Val Asn
                100                 105                 110

Ala
```

<210> SEQ ID NO 158
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

```
Ala Arg Val Asp Gln Thr Pro Gln Thr Ile Thr Lys Glu Thr Gly Glu
 1               5                  10                  15

Ser Ser Thr Ile Asn Cys Val Leu Arg Asp Thr Asn Cys Ala Leu Ser
                20                  25                  30

Ser Thr Tyr Trp Tyr Arg Lys Lys Ser Gly Ser Thr Asn Glu Glu Ser
                35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Arg Asn Ser Ser Lys Asp Cys Ala Ser
                 85                  90                  95

Asn Trp Asn Tyr Asp Val Arg Gly Gly Thr Val Val Thr Val Asn
                100                 105                 110

Ala
```

<210> SEQ ID NO 159
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

```
Ala Arg Val Asp Gln Thr Pro Gln Thr Ile Thr Lys Glu Thr Gly Glu
 1               5                  10                  15

Ser Ser Thr Ile Asn Cys Val Leu Arg Asp Thr Asn Cys Ala Leu Ser
                20                  25                  30

Ser Thr Tyr Trp Tyr Arg Lys Lys Ser Gly Ser Thr Asn Glu Glu Ser
                35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Tyr Arg Asn Ser Ser Thr Lys Asp Cys Ala Ser
```

```
                85                  90                  95
Asn Trp Asn Tyr Asp Val Arg Gly Gly Gly Thr Ala Val Thr Val Asn
                100                 105                 110

Ala
```

<210> SEQ ID NO 160
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
                35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Phe Pro Leu Ser Val Pro Asp Cys Gly Thr Gly
                85                  90                  95

Pro Asp Val Tyr Gly Gly Gly Thr Val Val Thr Val Asn Ala
                100                 105                 110
```

<210> SEQ ID NO 161
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 161

```
Ala Arg Val Asp Gln Thr Pro Gln Thr Ile Thr Lys Glu Thr Gly Glu
1               5                   10                  15

Ser Ser Thr Val Asn Cys Val Leu Arg Asp Ser Gly Cys Ala Leu Ser
                20                  25                  30

Ser Thr Tyr Trp Tyr Arg Lys Ser Ser Gly Ser Thr Asn Glu Glu Ser
                35                  40                  45

Ile Pro Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Ala Lys Ser Leu Tyr Tyr Pro Asp Cys Asn Asp
                85                  90                  95

Val Tyr Gly Gly Gly Thr Val Val Thr Val Asn Ala
                100                 105
```

<210> SEQ ID NO 162
<211> LENGTH: 109
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 162

Ala Arg Val Asp Gln Thr Pro Gln Thr Ile Thr Lys Glu Thr Gly Glu
1               5                   10                  15

Ser Ser Thr Ile Asn Cys Val Leu Arg Asp Thr Asn Cys Ala Ser Ser
            20                  25                  30

Leu Thr Tyr Trp Gly Arg Lys Lys Ser Gly Ser Arg Glu Glu Asn
        35                  40                  45

Ile Ser Lys Thr Gly Arg Tyr Val Glu Thr Val Asn Ser Gly Glu Lys
50                  55                  60

Ser Phe Ser Leu Thr Ile Asn Asp Leu Thr Val Glu Asp Ser Ser Thr
65                  70                  75                  80

Tyr Arg Cys Asn Val Tyr Phe Asn Asp Cys Pro Leu Arg Asn Trp Glu
                85                  90                  95

Arg Ile Tyr Gly Gly Gly Thr Val Thr Val Asn Ala
            100                 105

<210> SEQ ID NO 163
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 163

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Cys Val Ala Gly Gly Cys Thr Arg Ile Ile Asp Val
                85                  90                  95

Tyr Gly Gly Gly Thr Val Val Thr Val Asn Ala
            100                 105

<210> SEQ ID NO 164
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 164

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Glu Met Ser
            20                  25                  30

Ser Thr Asp Trp Tyr Arg Lys Lys Ser Gly Ser Thr Ser Glu Glu Ser

```
                35                  40                  45
Ile Ser Lys Gly Gly Arg Tyr Asn Glu Thr Val Asn Thr Gly Ser Lys
 50                  55                  60
Ser Ser Ser Leu Arg Ile Asn Asp Leu Leu Val Glu Asp Ser Gly Thr
65                  70                  75                  80
Tyr Arg Cys Thr Val Lys Glu Ala Gly Gly Leu Cys Arg Lys Asn Thr
                85                  90                  95
Trp Val His Ser Gly Gly Gly Thr Val Val Thr Val Asn Ala
                100                 105                 110

<210> SEQ ID NO 165
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Ala Arg Val Asp Gln Thr Pro Arg Ser Val Thr Lys Glu Thr Gly Glu
1               5                   10                  15
Ser Ser Thr Ile Asn Cys Val Leu Arg Asp Ala Val Tyr Ala Leu Gly
                20                  25                  30
Asn Thr Cys Trp Tyr Arg Lys Lys Ser Gly Ser Thr Phe Glu Glu Ser
                35                  40                  45
Ile Ser Lys Gly Gly Arg Tyr Val Glu Thr Val Asn Ser Gly Ser Lys
 50                  55                  60
Ser Phe Ser Leu Arg Ile Asn Asp Leu Thr Val Glu Asp Gly Gly Thr
65                  70                  75                  80
Tyr Arg Cys Gly Val Ala Thr Pro Thr Gly Pro Ser Cys Ser Cys Ile
                85                  90                  95
Trp Asp Tyr Gly Ile Cys Gly Asp Gly Thr Ala Val Thr Val Asn Ala
                100                 105                 110

<210> SEQ ID NO 166
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

Ala Arg Val Asp Gln Thr Pro Gln Thr Ile Thr Lys Glu Thr Gly Glu
1               5                   10                  15
Ser Ser Thr Ile Asn Cys Val Ile Arg Asp Gly Thr Cys Ala Phe Ala
                20                  25                  30
Ser Thr Phe Trp Tyr Arg Asn Lys Gln Gly Ser Thr Asn Glu Glu Asn
                35                  40                  45
Ile Ser Lys Gly Gly Arg Tyr Val Glu Thr Val Asn Lys Gly Ser Lys
 50                  55                  60
Ser Phe Ser Leu Arg Ile Asn Asp Leu Thr Val Glu Asp Ser Gly Thr
65                  70                  75                  80
Tyr Arg Cys Lys Ala Ala Ser Val Cys Ala Pro Arg Leu Phe Thr Thr
                85                  90                  95
Lys Asp Val Tyr Gly Gly Gly Thr Ala Val Thr Val Asn Ala
                100                 105                 110
```

<210> SEQ ID NO 167
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 167

```
Ala Arg Val Asp Gln Thr Pro Gln Thr Ile Thr Lys Glu Thr Gly Glu
1               5                   10                  15

Ser Ser Thr Ile Asn Cys Val Ile Arg Asp Gly Thr Cys Ala Phe Ala
            20                  25                  30

Ser Thr Phe Trp Tyr Arg Asn Lys Gln Gly Ser Thr Asn Glu Glu Asn
        35                  40                  45

Ile Ser Lys Gly Gly Arg Tyr Val Glu Thr Val Asn Lys Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Ala Ala Ser Val Cys Ala Pro Arg Leu Phe Thr Thr
                85                  90                  95

Lys Asp Val Tyr Gly Gly Gly Thr Val Val Thr Val Asn Ala
            100                 105                 110
```

<210> SEQ ID NO 168
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 168

```
Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Asn Thr Tyr Trp Tyr Arg Lys Lys Ser Gly Ser Thr Asn Glu Glu Arg
        35                  40                  45

Ile Ser Lys Gly Gly Arg Tyr Val Glu Thr Val Asn Ser Gly Ser Ser
    50                  55                  60

Ser Phe Ser Leu Arg Ile Asn Asp Leu Thr Val Glu Asp Ser Gly Thr
65                  70                  75                  80

Tyr Arg Cys Asn Thr Lys Tyr Val Trp Tyr Gly Ser Arg Tyr His Gln
                85                  90                  95

Glu Ser Ala Cys Asp Tyr Asp Val Ser Gly Gly Gly Thr Ala Val Thr
            100                 105                 110

Val Asn Ala
        115
```

<210> SEQ ID NO 169
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 169

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Asn Thr Tyr Trp Tyr Arg Lys Lys Ser Gly Ser Thr Asn Glu Glu Arg
        35                  40                  45

Ile Ser Lys Gly Gly Arg Tyr Val Glu Thr Val Asn Ser Gly Ser Ser
    50                  55                  60

Ser Phe Ser Leu Arg Ile Asn Asp Leu Thr Val Glu Asp Ser Gly Thr
65                  70                  75                  80

Tyr Arg Cys Asn Thr Lys Tyr Val Trp Tyr Gly Ser Arg Tyr His Gln
                85                  90                  95

Glu Ser Ala Cys Asp Tyr Asp Val Ser Gly Gly Thr Val Val Thr
            100                 105                 110

Val Asn Ala
        115

<210> SEQ ID NO 170
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Ser Cys Asp Ser Ser
            20                  25                  30

Arg Thr Tyr Trp Tyr Arg Lys Lys Ser Gly Ser Thr Lys Glu Glu Ser
        35                  40                  45

Ile Ser Lys Gly Gly Arg Tyr Val Glu Thr Val Asn Ser Gly Leu Lys
    50                  55                  60

Ser Phe Ser Leu Arg Ile Asn Asp Leu Thr Val Glu Asp Ser Gly Thr
65                  70                  75                  80

Tyr Arg Cys Asn Ala Phe Asn Thr Gly Val Arg Cys Asp Arg Ala Pro
                85                  90                  95

Val Asp Val Tyr Gly Gly Gly Thr Ala Val Thr Val Asn Ala
            100                 105                 110

<210> SEQ ID NO 171
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Ser Cys Asp Ser Ser
            20                  25                  30

Arg Thr Tyr Trp Tyr Arg Lys Lys Ser Gly Ser Thr Lys Glu Glu Ser

```
                35                  40                  45

Ile Ser Lys Gly Gly Arg Tyr Val Glu Thr Val Asn Ser Gly Leu Lys
 50                  55                  60

Ser Phe Ser Leu Arg Ile Asn Asp Leu Thr Val Glu Asp Ser Gly Thr
 65                  70                  75                  80

Tyr Arg Cys Asn Ala Phe Asn Thr Gly Val Arg Cys Asp Arg Ala Pro
                 85                  90                  95

Val Asp Val Tyr Gly Gly Gly Thr Val Val Thr Val Asn Ala
            100                 105                 110
```

<210> SEQ ID NO 172
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

```
Ala Arg Val Asp Gln Thr Pro Gln Thr Ile Thr Lys Glu Thr Gly Glu
 1                   5                  10                  15

Ser Leu Thr Ile Asn Cys Val Leu Leu Asp Ser Asn Cys Ala Leu Ser
                 20                  25                  30

Ser Ala Tyr Trp Tyr Arg Lys Lys Ser Gly Ser Thr Asn Glu Glu Asn
             35                  40                  45

Ile Ser Lys Ala Gly Arg Tyr Pro Arg Tyr Val Glu Thr Val Asn Ser
 50                  55                  60

Gly Ser Lys Ser Phe Ser Leu Arg Ile Asn Asp Leu Thr Val Glu Asp
 65                  70                  75                  80

Ala Gly Thr Tyr Arg Cys Asn Val Phe Ser Trp Gly Gly Cys Pro Thr
                 85                  90                  95

Ala Phe Asp Val Tyr Gly Gly Gly Thr Ala Val Thr Val Asn Ala
            100                 105                 110
```

<210> SEQ ID NO 173
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

```
Ala Arg Val Asp Gln Thr Pro Gln Thr Ile Thr Lys Glu Thr Gly Glu
 1                   5                  10                  15

Ser Leu Thr Ile Asn Cys Val Leu Leu Asp Ser Asn Cys Ala Leu Ser
                 20                  25                  30

Ser Ala Tyr Trp Tyr Arg Lys Lys Ser Gly Ser Thr Asn Glu Glu Asn
             35                  40                  45

Ile Ser Lys Ala Gly Arg Tyr Pro Arg Tyr Val Glu Thr Val Asn Ser
 50                  55                  60

Gly Ser Lys Ser Phe Ser Leu Arg Ile Asn Asp Leu Thr Val Glu Asp
 65                  70                  75                  80

Ala Gly Thr Tyr Arg Cys Asn Val Phe Ser Trp Gly Gly Cys Pro Thr
                 85                  90                  95

Ala Phe Asp Val Tyr Gly Gly Gly Thr Val Val Thr Val Asn Ala
            100                 105                 110
```

<210> SEQ ID NO 174
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 174

Ala Arg Val Asp Gln Thr Pro Gln Thr Ile Arg Lys Val Thr Gly Glu
1               5                   10                  15

Ser Ser Thr Ile Asn Cys Val Ile Gln Asp Ser Lys Cys Arg Leu Ser
            20                  25                  30

Asp Thr His Trp Trp Arg Lys Ala Pro Gly Ser Thr Asn Glu Glu Arg
        35                  40                  45

Ile Ser Lys Gly Gly Arg Tyr Ile Glu Thr Val Asn Ser Ala Leu Lys
    50                  55                  60

Ser Phe Ser Ser Arg Ile Asn Asp Leu Arg Val Glu Asp Ser Gly Thr
65                  70                  75                  80

Tyr Arg Cys Asn Val Leu Ser Trp Arg Asp Ala Val Ser Asn Cys Asp
                85                  90                  95

Val Ala Gly Gly Gly Thr Val Val Thr Val Asn Ala
            100                 105

<210> SEQ ID NO 175
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 175

Ala Arg Val Asp Gln Thr Pro Gln Thr Ile Arg Lys Val Thr Gly Glu
1               5                   10                  15

Ser Ser Thr Ile Asn Cys Val Ile Gln Asp Ser Lys Cys Arg Leu Ser
            20                  25                  30

Asp Thr His Trp Trp Arg Lys Ala Pro Gly Ser Thr Asn Glu Glu Arg
        35                  40                  45

Ile Ser Lys Gly Gly Arg Tyr Ile Glu Thr Val Asn Ser Ala Leu Lys
    50                  55                  60

Ser Phe Ser Ser Arg Ile Asn Asp Leu Arg Val Glu Asp Ser Gly Thr
65                  70                  75                  80

Tyr Arg Cys Asn Val Leu Ser Trp Arg Asp Ala Val Ser Asn Cys Asp
                85                  90                  95

Val Ala Gly Gly Gly Thr Ala Val Thr Val Asn Ala
            100                 105

<210> SEQ ID NO 176
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 176

```
Ala Arg Val Asp Gln Thr Pro Arg Ser Val Thr Lys Glu Thr Gly Glu
1               5                   10                  15

Ser Ser Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Pro His Trp Leu Lys Gly Cys Arg Val Cys Ser
                85                  90                  95

Trp Asn Gly Ala Ala Ala Cys Gly Asp Gly Thr Ala Val Thr Val Asn
                100                 105                 110

Ala

<210> SEQ ID NO 177
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Lys Cys Ala Leu Ser
                20                  25                  30

Asp Thr Tyr Trp Tyr Arg Lys Lys Ser Gly Ser Thr Asn Glu Glu Ser
            35                  40                  45

Ile Ser Arg Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Thr Gly Gly Phe Cys Leu Ser Gly Phe Ala Leu Tyr
                85                  90                  95

Gly Gly Gly Thr Val Val Thr Val Asn Ala
                100                 105

<210> SEQ ID NO 178
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Ala Arg Val Asp Gln Thr Pro Gln Thr Ile Thr Lys Glu Thr Gly Glu
1               5                   10                  15

Ser Ser Thr Ile Asn Cys Val Leu Arg Glu Ser Lys Cys Ala Leu Ser
                20                  25                  30

Thr Thr Tyr Trp His Arg Lys Lys Ser Gly Ser Arg Asp Glu Glu Ser
            35                  40                  45

Ile Ser Leu Gly Gly Arg Tyr Val Glu Thr Val Asn Arg Gly Ser Lys
    50                  55                  60
```

```
Ser Phe Ser Leu Arg Ile Asn Gly Leu Thr Val Glu Asp Ser Gly Thr
 65                  70                  75                  80

Tyr Arg Cys Asn Ile Phe Asn Asp Cys Ala Thr Thr Val Tyr Glu Ser
                 85                  90                  95

Asp Ala Phe Gly Gly Gly Thr Val Val Thr Val Asn Ala
                100                 105
```

<210> SEQ ID NO 179
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 179

```
Ala Arg Val Asp Gln Thr Pro Gln Thr Ile Thr Lys Glu Thr Gly Glu
  1               5                  10                  15

Ser Ser Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Ser Pro Asn Cys Trp Leu Thr Lys Arg Thr Gly
                 85                  90                  95

Ser Tyr Val Tyr Gly Gly Gly Thr Val Val Thr Val Asn Ala
                100                 105                 110
```

<210> SEQ ID NO 180
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 180

```
Ala Arg Val Asp Gln Thr Pro Gln Thr Ile Thr Lys Glu Thr Gly Glu
  1               5                  10                  15

Ser Ser Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Pro Gln Gln Val Tyr Cys Arg His Glu Gln Asp Trp
                 85                  90                  95

His Asp Val Tyr Gly Gly Gly Thr Val Val Thr Val Asn Ala
                100                 105                 110
```

<210> SEQ ID NO 181
<211> LENGTH: 108

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181
```

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ser
            20                  25                  30

Lys Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys Thr Ala Tyr Asp Cys Ser His Trp Arg Ser Ile Gly
                85                  90                  95

Val Tyr Gly Gly Gly Thr Val Val Thr Val Asn Ala
                100                 105

```
<210> SEQ ID NO 182
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182
```

Ala Arg Val Asp Gln Thr Pro Gln Thr Ile Thr Lys Glu Thr Gly Glu
1               5                   10                  15

Ser Ser Thr Ile Asn Cys Val Leu Ser Asp Ser Asn Cys Ala Leu Ala
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Ala Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Pro Gln Thr Glu Tyr Cys Arg His Glu Gln Asp Phe
                85                  90                  95

Tyr Asp Val Tyr Gly Gly Gly Thr Val Val Thr Val Asn Ala
                100                 105                 110

```
<210> SEQ ID NO 183
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183
```

Ala Arg Val Asp Gln Thr Pro Gln Thr Ile Thr Lys Glu Thr Gly Glu
1               5                   10                  15

Ser Ser Thr Ile Asn Cys Val Leu Arg Asp Ser Asn Cys Ala Leu Ala

```
                    20                  25                  30
Ser Thr Tyr Trp Tyr Arg Lys Lys Ser Gly Ser Thr Asn Glu Glu Asn
                35                  40                  45

Ile Ser Lys Gly Gly Arg Tyr Val Glu Thr Val Asn Ser Gly Ser Lys
         50                  55                  60

Ser Phe Ser Leu Arg Ile Asn Asp Leu Thr Val Glu Asp Ser Gly Thr
 65                  70                  75                  80

Tyr Arg Cys Asn Val Ala Asn Tyr Asp Cys Phe Arg Arg Ile Glu Leu
                 85                  90                  95

Trp Asn Phe Tyr Asp Arg Tyr Gly Gly Gly Thr Val Val Thr Val Asn
                100                 105                 110

Ala
```

<210> SEQ ID NO 184
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 184

```
Ala Arg Val Asp Gln Thr Pro Gln Thr Ile Thr Gln Glu Thr Gly Glu
 1               5                  10                  15

Ser Ser Thr Ile Asn Cys Val Leu Arg Asp Ser Lys Cys Val Phe Ala
                20                  25                  30

Ser Thr Tyr Trp His Arg Asn Lys Ser Gly Ser Thr Asn Glu Glu Ser
                35                  40                  45

Ile Ser Lys Gly Gly Arg Tyr Val Glu Thr Val Asn Lys Gly Ser Lys
         50                  55                  60

Ser Phe Ser Leu Arg Ile Asn Asp Leu Thr Val Glu Asp Ser Gly Thr
 65                  70                  75                  80

Tyr Arg Cys Ser Leu Ala Ser Val Cys Pro Pro Arg Leu Phe Glu Ser
                 85                  90                  95

Glu Tyr Val Tyr Gly Gly Gly Thr Val Val Thr Val Asn Ala
                100                 105                 110
```

<210> SEQ ID NO 185
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 185

```
Phe Cys Ile Ile Asp Gly Glu Leu Glu Asp Val
 1               5                  10
```

<210> SEQ ID NO 186
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 186

```
Val Phe Cys Ile Ile Asp Gly Glu Leu Glu Asp Val
1               5                   10
```

<210> SEQ ID NO 187
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

```
Asp Tyr Trp Cys Asp Pro Met Arg Ala Pro Gly Leu Phe Gly Arg Lys
1               5                   10                  15
```

<210> SEQ ID NO 188
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

```
Glu Thr Asn Cys His Ile Phe Tyr Gln Phe Pro Lys Asp
1               5                   10
```

<210> SEQ ID NO 189
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

```
Glu Thr Pro Tyr Asp Cys Pro Glu Leu Asn Trp Trp Asp Val
1               5                   10
```

<210> SEQ ID NO 190
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

```
Glu Thr Pro Tyr Asp Cys Pro Glu Leu Asn Trp Trp Asp Val
1               5                   10
```

<210> SEQ ID NO 191
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

```
Glu Thr Pro Tyr Asp Cys Pro Glu Leu Asn Trp Trp Asp Val
1               5                   10
```

```
<210> SEQ ID NO 192
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Gln Thr Pro Tyr Asp Cys Pro Glu Leu Asn Trp Trp Asp Val
1               5                   10

<210> SEQ ID NO 193
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Arg Thr Pro Tyr Asp Cys Pro Glu Leu Asn Trp Trp Asp Val
1               5                   10

<210> SEQ ID NO 194
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Thr Thr Pro Tyr Asp Cys Pro Glu Leu Asn Trp Trp Asp Val
1               5                   10

<210> SEQ ID NO 195
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Ile Cys Asp Ile Phe Thr Tyr Tyr Tyr Gly Thr Ser Trp
1               5                   10

<210> SEQ ID NO 196
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Ile Asp Tyr Cys Leu Ser Trp Tyr Arg Ser Ile Asn Leu
1               5                   10

<210> SEQ ID NO 197
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 197

Pro Ser Phe Asp Pro Leu Asn Tyr Cys Tyr Ile Trp Arg Arg Thr Thr
1               5                   10                  15

<210> SEQ ID NO 198
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Ser Pro Pro Leu Val Ala Gly Val Leu Asn Cys Tyr Asp Ile
1               5                   10

<210> SEQ ID NO 199
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Ser Ser Pro Gln Leu Gly Phe Tyr Asp Cys Gly His Trp Ile Asp Val
1               5                   10                  15

<210> SEQ ID NO 200
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Val Phe His Ile Ala Gly Thr Asp Met Ala Glu Leu Val Tyr Asp Val
1               5                   10                  15

<210> SEQ ID NO 201
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Val Leu Val Pro Ala His Gly Asp Cys Ser Ala Trp Ser Leu Trp Val
1               5                   10                  15

Gly Val

<210> SEQ ID NO 202
<211> LENGTH: 18
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 202

Val Arg Leu Gly Trp Tyr Glu Tyr Cys Pro Val Leu Gly Gly Val Tyr
1               5                   10                  15

Asp Val

<210> SEQ ID NO 203
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Val Ser Trp Cys Thr Arg His Thr Met Trp Asn Trp Tyr Thr Val His
1               5                   10                  15

<210> SEQ ID NO 204
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Trp Tyr Trp His Met Ser Ser Ser Asp Cys Leu Ser Gly Tyr Ser Tyr
1               5                   10                  15

<210> SEQ ID NO 205
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Tyr Ala Met Thr Ala Asn Trp Trp Cys Asp Val
1               5                   10

<210> SEQ ID NO 206
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Tyr Ala Met Thr Ala Asn Trp Trp Cys Asp Val
1               5                   10

<210> SEQ ID NO 207
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Tyr Ala Met Thr Ala Asn Trp Trp Cys Asp Val
1               5                   10

<210> SEQ ID NO 208
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Tyr Ala Met Thr Ala Asn Trp Trp Cys Asp Val
1               5                   10

<210> SEQ ID NO 209
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Tyr Ala Met Thr Ala Asn Trp Trp Cys Asp Val
1               5                   10

<210> SEQ ID NO 210
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Tyr Gly Leu Thr Ala Asn Trp Trp Cys Asp Val
1               5                   10

<210> SEQ ID NO 211
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Tyr Ala Met Thr Arg Asn Trp Trp Cys Asp Val
1               5                   10

<210> SEQ ID NO 212
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Tyr Ala Met Thr Arg Asn Trp Trp Cys Asp Val

-continued

```
<210> SEQ ID NO 213
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Tyr Ser Met Thr Ala Asn Trp Trp Cys Asp Val
1               5                   10

<210> SEQ ID NO 214
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Tyr Ala Met Thr Arg Asn Trp Trp Cys Asp Val
1               5                   10

<210> SEQ ID NO 215
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Tyr Ser Leu Thr Ala Asn Trp Trp Cys Asp Val
1               5                   10

<210> SEQ ID NO 216
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Tyr Ala Arg Glu Asp Thr Trp Tyr Gly Ser Arg Asp Cys Gly Leu Gly
1               5                   10                  15

Asp Val

<210> SEQ ID NO 217
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Tyr Asp Tyr Cys Leu His Trp Phe His Pro Tyr Val Ile
1               5                   10
```

<210> SEQ ID NO 218
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Val Tyr Gly Leu Val Asp Cys Ala Ser Gly Met Asn Trp Ile Asp Val
1               5                   10                  15

<210> SEQ ID NO 219
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Tyr Gly Leu Val Asp Cys Gly Ser Gly Met Asn Trp Ile Asp Val
1               5                   10                  15

<210> SEQ ID NO 220
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Tyr Gly Leu Val Asp Cys Gly Ser Gly Met Asn Trp Ile Asp Val
1               5                   10                  15

<210> SEQ ID NO 221
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Tyr Gly Leu Val Asp Cys Ala Ser Gly Met Asn Trp Ile Asp Val
1               5                   10                  15

<210> SEQ ID NO 222
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Tyr Gly Val Ile Glu Cys Arg Tyr Glu Gly Met Asn Trp Phe Asp Val
1               5                   10                  15

<210> SEQ ID NO 223
<211> LENGTH: 16
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Tyr Gly Val Ile Glu Cys Arg Tyr Glu Gly Met Asn Trp Phe Asp Val
1               5                   10                  15

<210> SEQ ID NO 224
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Tyr Gly Val Ile Glu Cys Arg Tyr Glu Gly Met Asn Trp Phe Asp Val
1               5                   10                  15

<210> SEQ ID NO 225
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Tyr Asn Ile Ala Val Met Cys Asn Asp Tyr Val Arg Tyr Trp Thr Asp
1               5                   10                  15

Val

<210> SEQ ID NO 226
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Tyr Gln Pro Pro Ser Thr Glu Ser Leu Tyr Trp Cys Asp Val
1               5                   10

<210> SEQ ID NO 227
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Tyr Gln Pro Pro Ser Thr Glu Ser Leu Tyr Trp Cys Asp Val
1               5                   10

<210> SEQ ID NO 228
<211> LENGTH: 14
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 228

Tyr Ser Gly Pro Ser Tyr Asp Gln Leu Phe Trp Cys Asp Val
1               5                   10

<210> SEQ ID NO 229
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Tyr Ser Gly Pro Ser Tyr Asp Gln Leu Phe Trp Cys Asp Val
1               5                   10

<210> SEQ ID NO 230
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Tyr Ser Gly Pro Ser Tyr Asp Gln Leu Phe Trp Cys Asp Val
1               5                   10

<210> SEQ ID NO 231
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Tyr Ser Gly Pro Ser Tyr Asp Gln Leu Phe Trp Cys Asp Val
1               5                   10

<210> SEQ ID NO 232
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Tyr Ser Thr Pro Ser Tyr Asp Gln Leu Tyr Trp Cys Asp Val
1               5                   10

<210> SEQ ID NO 233
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 233

Tyr Ser Thr Pro Ser Tyr Asp Gln Leu Tyr Trp Cys Asp Val
1               5                   10

<210> SEQ ID NO 234
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Tyr Val Pro Pro Gly Tyr Asp Cys Asn Tyr Trp Met Asp Val
1               5                   10

<210> SEQ ID NO 235
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Trp His Asp Leu Val Trp Ser Val Cys Thr Thr Asp Val
1               5                   10

<210> SEQ ID NO 236
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Trp His Asp Leu Val Trp Ser Val Cys Thr Thr Asp Val
1               5                   10

<210> SEQ ID NO 237
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Tyr Ala Arg Pro Arg Pro Asp Asn Leu Asn Trp Cys Asp Val
1               5                   10

<210> SEQ ID NO 238
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Tyr Ala Arg Pro Arg Pro Asp Asn Leu Asn Trp Cys Asp Val
1               5                   10
```

```
<210> SEQ ID NO 239
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Leu Arg Asp Ser Cys Tyr Asp Val Thr Asn Trp Leu Glu Arg
1               5                   10

<210> SEQ ID NO 240
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Glu Asn Phe Leu Leu Asp Cys Tyr Asp Trp Leu Asp Val
1               5                   10

<210> SEQ ID NO 241
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Glu Arg His Trp Arg Ser Arg Cys Gln Arg Ala Val Asp Val
1               5                   10

<210> SEQ ID NO 242
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Asx Leu Trp Cys Leu Cys Pro Cys Thr Val Trp Val Leu Gly Asp Val
1               5                   10                  15

<210> SEQ ID NO 243
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Cys Gly Ile Leu Cys Cys Phe Asx Phe Asp Val
1               5                   10

<210> SEQ ID NO 244
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Thr Ala Ile Leu Ser Asx Asp Cys Gly Ala Phe Ala Asp Val
1               5                   10

<210> SEQ ID NO 245
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Thr Gly Leu Arg Tyr His Ser Gly Cys Arg Thr Gly Asp Val
1               5                   10

<210> SEQ ID NO 246
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Cys Phe Gly Asx Cys Val Asn Ser Cys Gly Glu Ser Met Asp Val
1               5                   10                  15

<210> SEQ ID NO 247
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Leu Arg Phe Asx Cys Val Phe His Trp Asp Val
1               5                   10

<210> SEQ ID NO 248
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Arg Asp Val Val Leu Val Asx Tyr Gly Tyr Cys Leu Val Asp Gly Gln
1               5                   10                  15

Asp Val

<210> SEQ ID NO 249
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 249

Tyr Glu Leu Val Glu Asp Thr Ser Ala Tyr Glu Ile Gly Val Asp Val
1               5                   10                  15

<210> SEQ ID NO 250
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Tyr Gln Ser Pro Val Gly Arg Arg Trp Trp Cys Asp Val
1               5                   10

<210> SEQ ID NO 251
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Trp Tyr Arg Pro Asp Cys Glu Glu Glu Phe Asp Val
1               5                   10

<210> SEQ ID NO 252
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Trp Tyr Arg Pro Asp Cys Glu Glu Glu Phe Asp Val
1               5                   10

<210> SEQ ID NO 253
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Trp Tyr Arg Pro Asp Cys Glu Glu Glu Phe Asp Val
1               5                   10

<210> SEQ ID NO 254
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 254

Trp Tyr Arg Pro Asp Cys Glu Glu Glu Phe Asp Val
1               5                   10

<210> SEQ ID NO 255
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Trp Tyr Arg Pro Asp Cys Glu Glu Glu Phe Asp Val
1               5                   10

<210> SEQ ID NO 256
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Trp Tyr Arg Pro Asp Cys Glu Glu Glu Phe Asp Val
1               5                   10

<210> SEQ ID NO 257
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Trp Tyr Arg Pro Asp Cys Glu Leu Asp Tyr Asp Val
1               5                   10

<210> SEQ ID NO 258
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Trp Tyr Arg Pro Asp Cys Glu Leu Asp Tyr Asp Val
1               5                   10

<210> SEQ ID NO 259
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Trp Tyr Arg Pro Asp Cys Glu Leu Asp Tyr Asp Val

```
<210> SEQ ID NO 260
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Trp Tyr Arg Pro Asp Cys Glu Leu Asp Tyr Asp Val
1               5                   10

<210> SEQ ID NO 261
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Asn Thr Trp Gln Ala Arg His Pro Tyr Asp Cys Ala Glu Ser Leu Arg
1               5                   10                  15

Val

<210> SEQ ID NO 262
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Asn Thr Trp Gln Ala Arg His Pro Tyr Asp Cys Ala Glu Ser Leu Arg
1               5                   10                  15

Val

<210> SEQ ID NO 263
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Asn Thr Trp Gln Ala Arg His Pro Tyr Asp Cys Ala Glu Ser Leu Arg
1               5                   10                  15

Val

<210> SEQ ID NO 264
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264
```

```
Asp Asn Phe Ala Cys Glu Met Ala Tyr Asn Val
1               5                   10

<210> SEQ ID NO 265
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Leu Trp Gly Ser Tyr Pro Cys Asp Glu Ile Met His Gly Thr Ala Val
1               5                   10                  15

<210> SEQ ID NO 266
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Leu Pro Arg Pro Ile Ser Trp Ile Asn Cys Asp Asp Ser His Ala
1               5                   10                  15

<210> SEQ ID NO 267
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Val Trp Gly Trp Ser Cys Asp Val
1               5

<210> SEQ ID NO 268
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Val Trp Gly Trp Ser Cys Asp Val
1               5

<210> SEQ ID NO 269
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Val Trp Gly Trp Ser Cys Asp Val
1               5
```

-continued

```
<210> SEQ ID NO 270
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Gly Ala Gly Phe Phe Ala Leu Met Asn Cys Asn Tyr Asp Val
1               5                   10

<210> SEQ ID NO 271
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Tyr His Asp Arg His Ile Thr Lys Asn Trp Arg Cys Pro Asn Leu Asp
1               5                   10                  15

Val

<210> SEQ ID NO 272
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Trp Tyr Gly Tyr Asp Cys Gly Ala Met Asn Arg Asp Val
1               5                   10

<210> SEQ ID NO 273
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Trp Gly Pro Asp Ile Asp Gly Ala Gly Tyr Gly Thr His Gly Cys Tyr
1               5                   10                  15

Asp Val

<210> SEQ ID NO 274
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Trp Tyr Arg Pro Asp Cys Glu Ser Asp Tyr Asp Val
1               5                   10
```

<210> SEQ ID NO 275
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Trp Tyr Arg Pro Asp Cys Glu Ser Asp Tyr Asp Val
1               5                   10

<210> SEQ ID NO 276
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Phe Gly Arg Tyr Gly Trp Tyr His Asp Cys Ile Asp Thr Gly Glu Ala
1               5                   10                  15

<210> SEQ ID NO 277
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Phe Gly Arg Tyr Gly Trp Tyr His Asp Cys Ile Asp Thr Gly Glu Ala
1               5                   10                  15

<210> SEQ ID NO 278
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Phe Gly Arg Tyr Gly Trp Tyr His Asp Cys Ile Asp Thr Gly Glu Ala
1               5                   10                  15

<210> SEQ ID NO 279
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Phe Gly Arg Tyr Gly Trp Tyr His Asp Cys Ile Asp Thr Gly Glu Ala
1               5                   10                  15

<210> SEQ ID NO 280
<211> LENGTH: 16
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Phe Gly Arg Tyr Gly Trp Tyr His Asp Cys Ile Asp Thr Gly Glu Ala
1               5                   10                  15

<210> SEQ ID NO 281
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Phe Gly Arg Tyr Gly Trp Tyr His Asp Cys Ile Asp Thr Gly Glu Ala
1               5                   10                  15

<210> SEQ ID NO 282
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Phe Gly Arg Tyr Gly Trp Tyr His Asp Cys Ile Asp Thr Gly Glu Ala
1               5                   10                  15

<210> SEQ ID NO 283
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Phe Gly Arg Tyr Gly Trp Tyr His Asp Cys Ile Asp Thr Gly Glu Ala
1               5                   10                  15

<210> SEQ ID NO 284
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Cys Thr Arg Trp Cys Pro Ser Cys Asp Glu Ser Cys Ser Arg Asn Phe
1               5                   10                  15

Ala Ala Cys

<210> SEQ ID NO 285
<211> LENGTH: 11
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 285

Asn Ser Phe Ser Cys Glu Ser Ala Tyr Asn Val
1               5                   10

<210> SEQ ID NO 286
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Asn Ser Phe Ser Cys Glu Ser Ala Tyr Asn Val
1               5                   10

<210> SEQ ID NO 287
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Asn Asn Phe Ala Cys Glu Ser Ala Tyr Asn Val
1               5                   10

<210> SEQ ID NO 288
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Asn Asn Phe Ala Cys Glu Ser Ala Tyr Asn Val
1               5                   10

<210> SEQ ID NO 289
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Ser Ser Phe Ser Cys Glu Met Ala Tyr Asn Val
1               5                   10

<210> SEQ ID NO 290
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 290

Ser Ser Phe Ser Cys Glu Met Ala Tyr Asn Val
1               5                   10

<210> SEQ ID NO 291
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Ser Ser Phe Ser Cys Glu Met Ala Tyr Asn Val
1               5                   10

<210> SEQ ID NO 292
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Ser Ser Phe Ser Cys Glu Ser Ala Tyr Asn Val
1               5                   10

<210> SEQ ID NO 293
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Trp Ala Pro Tyr Asp Cys Glu Asn Trp Arg Asp Val
1               5                   10

<210> SEQ ID NO 294
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Thr Asn Phe Ala Cys Glu Ser Ala Tyr Asn Val
1               5                   10

<210> SEQ ID NO 295
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Thr Asn Phe Ala Cys Glu Ser Ala Tyr Asn Val
1               5                   10
```

```
<210> SEQ ID NO 296
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Val Ala Gly Met Asp Ala Arg Tyr Asp Cys Gly Ser Asn Trp Thr Val
1               5                   10                  15

<210> SEQ ID NO 297
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Ser Ser Trp Cys Thr Ser Leu Thr Val Thr Val Cys Gly Val Asp Pro
1               5                   10                  15

Tyr Ala Val Cys
            20

<210> SEQ ID NO 298
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Gly Phe Asn Ala Arg Ala Phe Ser Glu Ala Gly Cys Glu Gln
1               5                   10

<210> SEQ ID NO 299
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Arg Ala Ser Trp Asp Leu Glu Ser Tyr Cys Thr Gly Leu Asp Val
1               5                   10                  15

<210> SEQ ID NO 300
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Trp Tyr Ser Ile Cys Ile Glu Thr Val Asp Val
1               5                   10
```

```
<210> SEQ ID NO 301
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Tyr Ser Ile Cys Ile Glu Thr Val Asp Val
1               5                   10

<210> SEQ ID NO 302
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Tyr Ser Ile Cys Ile Glu Thr Val Asp Val
1               5                   10

<210> SEQ ID NO 303
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Tyr Ser Ile Cys Ile Glu Thr Val Asp Val
1               5                   10

<210> SEQ ID NO 304
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Trp Phe Asp Cys Gly Ser Gly Thr Gly Arg Leu Val
1               5                   10

<210> SEQ ID NO 305
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Tyr Gln Leu Pro Pro Ser Arg Trp Thr Thr Glu Cys Leu Leu Asp Leu
1               5                   10                  15

<210> SEQ ID NO 306
<211> LENGTH: 16
<212> TYPE: PRT
```

-continued

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Tyr Gln Leu Pro Pro Ser Arg Trp Thr Thr Glu Cys Leu Leu Asp Leu
1               5                   10                  15

<210> SEQ ID NO 307
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Tyr Gln Leu Pro Pro Ser Arg Trp Thr Thr Glu Cys Leu Leu Asp Leu
1               5                   10                  15

<210> SEQ ID NO 308
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Ser Val Leu Val Ala Glu Lys Ser Cys Asn Cys Thr Ser Ala Tyr Thr
1               5                   10                  15

Glu Cys

<210> SEQ ID NO 309
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Ser Pro Pro Asp Trp Ser Cys Asp Gly Ser Cys Arg Leu Asp Ala Ala
1               5                   10                  15

Cys

<210> SEQ ID NO 310
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Arg Cys Ala Val Arg Leu Gly Tyr Ser Gly Cys Ser Gly Thr Tyr Ala
1               5                   10                  15

Thr Cys

<210> SEQ ID NO 311
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Lys Gly Gln Cys Phe Val Ser Gly Gly Ser Thr Leu Pro Tyr Asn Glu
1               5                   10                  15

<210> SEQ ID NO 312
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Lys Gly Gln Cys Phe Val Ser Gly Gly Ser Thr Leu Pro Tyr Asn Glu
1               5                   10                  15

<210> SEQ ID NO 313
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Phe Glu Ser Val Cys Arg Tyr Arg Gly Glu Ser Glu Val Asp Val
1               5                   10                  15

<210> SEQ ID NO 314
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Phe Glu Ser Val Cys Arg Tyr Arg Gly Glu Ser Glu Val Asp Val
1               5                   10                  15

<210> SEQ ID NO 315
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Phe Glu Ser Val Cys Arg Tyr Arg Gly Glu Ser Glu Val Asp Val
1               5                   10                  15

<210> SEQ ID NO 316
<211> LENGTH: 13
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 316

Tyr Ser Pro Asp Asp Cys Thr Asp Tyr Asn Tyr Asp Val
1               5                   10

<210> SEQ ID NO 317
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Tyr Ser Pro Asp Asp Cys Thr Asp Tyr Asn Tyr Asp Val
1               5                   10

<210> SEQ ID NO 318
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Trp Cys Gly Leu Pro Asp Tyr Arg Ser Trp Gly Ala Arg Ala Ala Cys
1               5                   10                  15

<210> SEQ ID NO 319
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Ala Ser Val Cys Ala Pro Arg Leu Phe Glu Thr Lys Asp Val
1               5                   10

<210> SEQ ID NO 320
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Ala Ser Val Cys Ala Pro Arg Leu Phe Glu Thr Lys Asp Val
1               5                   10

<210> SEQ ID NO 321
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 321

Phe Ser Trp Cys Asp Asp Ser Ser Asp Leu Asp Val
1               5                   10

<210> SEQ ID NO 322
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Ser Leu Pro Glu Trp Gly Cys Ser Val Tyr Cys Arg Leu Asp Ala Ala
1               5                   10                  15

Cys

<210> SEQ ID NO 323
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Ala Asn Tyr Asp Cys Phe Arg Arg Ile Glu Leu Arg Asn Phe Tyr Asp
1               5                   10                  15

Arg

<210> SEQ ID NO 324
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Tyr Gly Ser Val Cys Tyr Glu Ile Arg Thr Gly Gln
1               5                   10

<210> SEQ ID NO 325
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Tyr Gly Ser Val Cys Tyr Glu Ile Arg Thr Gly Gln
1               5                   10

<210> SEQ ID NO 326
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 326

Tyr Gly Ser Val Cys Tyr Glu Ile Arg Thr Gly Gln
1               5                   10

<210> SEQ ID NO 327
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Phe Ser Trp Gly Gly Cys Pro Asn Pro Phe Asp Ile
1               5                   10

<210> SEQ ID NO 328
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Phe Ser Trp Gly Gly Cys Pro Asn Pro Phe Asp Ile
1               5                   10

<210> SEQ ID NO 329
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Val Tyr Val Trp Arg Gly Ser His Tyr His Gln Glu Leu Ala Cys Asp
1               5                   10                  15

Tyr Asp Val

<210> SEQ ID NO 330
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Val Tyr Val Trp Arg Gly Ser His Tyr His Gln Glu Leu Ala Cys Asp
1               5                   10                  15

Tyr Asp Val

<210> SEQ ID NO 331
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 331

Ser Trp Leu Glu Ser Cys Asp Tyr Arg Pro Cys Ser Asp Tyr Ala Ala
1               5                   10                  15

Cys

<210> SEQ ID NO 332
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Leu Val Trp Cys Gly Met Ala Gly Met Gly Trp Ser Pro Asp Val
1               5                   10                  15

<210> SEQ ID NO 333
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Arg Arg Ala Glu Lys Lys Gly Gly Asp Cys Thr Leu Asn Tyr His Ala
1               5                   10                  15

<210> SEQ ID NO 334
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Tyr Ser Phe Ile Gly Val Asp Ser Cys Asp Trp Asp Ile
1               5                   10

<210> SEQ ID NO 335
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Trp Gly Ile Ala Gly Val Val Cys Arg Glu Val Asn Trp Gly Gly Gln
1               5                   10                  15

Tyr Asp Val

<210> SEQ ID NO 336
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 336

Tyr Ser Phe Ile Gly Val Asp Ser Cys Asp Trp Asp Ile Tyr Gly Asp
1               5                   10                  15

Gly Thr Val Val Thr Val Asn Ala Val Lys
            20                  25

<210> SEQ ID NO 337
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Phe Gly Tyr Cys Pro Val Ser Gly Val Glu Ile Val Gly Val
1               5                   10

<210> SEQ ID NO 338
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

Phe Gly Tyr Cys Pro Val Ser Gly Val Glu Ile Val Gly Val
1               5                   10

<210> SEQ ID NO 339
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Tyr His Arg Trp Cys Thr Met Gly Thr Gly Gly Pro Gly Tyr Asp Val
1               5                   10                  15

<210> SEQ ID NO 340
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Tyr His Arg Trp Cys Thr Met Gly Thr Gly Gly Pro Gly Tyr Asp Val
1               5                   10                  15

<210> SEQ ID NO 341
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341
```

Tyr Ser Arg Thr Gly Asp Leu Glu Gly Pro Leu Asn Trp Cys Pro Glu
1               5                   10                  15

Ile

<210> SEQ ID NO 342
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Tyr Arg Asn Ser Ser Thr Lys Asp Cys Ala Ser Asn Trp Asn Tyr Asp
1               5                   10                  15

Val

<210> SEQ ID NO 343
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Tyr Arg Asn Ser Ser Thr Lys Asp Cys Ala Ser Asn Trp Asn Tyr Asp
1               5                   10                  15

Val

<210> SEQ ID NO 344
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Phe Pro Leu Ser Val Pro Asp Cys Gly Thr Gly Pro Asp Val
1               5                   10

<210> SEQ ID NO 345
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Ala Lys Ser Leu Tyr Tyr Pro Asp Cys Asn Asp Val
1               5                   10

<210> SEQ ID NO 346
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

<400> SEQUENCE: 346

Tyr Phe Asn Asp Cys Pro Leu Arg Asn Trp Glu Arg Ile
1               5                   10

<210> SEQ ID NO 347
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Cys Val Ala Gly Gly Cys Thr Arg Ile Ile Asp Val
1               5                   10

<210> SEQ ID NO 348
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Lys Glu Ala Gly Gly Leu Cys Arg Lys Asn Thr Trp Val His
1               5                   10

<210> SEQ ID NO 349
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Ala Thr Pro Thr Gly Pro Ser Cys Ser Cys Ile Trp Asp Tyr Gly Ile
1               5                   10                  15

Cys

<210> SEQ ID NO 350
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Ala Ser Val Cys Ala Pro Arg Leu Phe Thr Thr Lys Asp Val
1               5                   10

<210> SEQ ID NO 351
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

```
Ala Ser Val Cys Ala Pro Arg Leu Phe Thr Thr Lys Asp Val
1               5                   10
```

<210> SEQ ID NO 352
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

```
Lys Tyr Val Trp Tyr Gly Ser Arg Tyr His Gln Glu Ser Ala Cys Asp
1               5                   10                  15

Tyr Asp Val
```

<210> SEQ ID NO 353
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

```
Lys Tyr Val Trp Tyr Gly Ser Arg Tyr His Gln Glu Ser Ala Cys Asp
1               5                   10                  15

Tyr Asp Val
```

<210> SEQ ID NO 354
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

```
Phe Asn Thr Gly Val Arg Cys Asp Arg Ala Pro Val Asp Val
1               5                   10
```

<210> SEQ ID NO 355
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

```
Phe Asn Thr Gly Val Arg Cys Asp Arg Ala Pro Val Asp Val
1               5                   10
```

<210> SEQ ID NO 356
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

```
Phe Ser Trp Gly Gly Cys Pro Thr Ala Phe Asp Val
1               5                   10
```

<210> SEQ ID NO 357
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 357

```
Phe Ser Trp Gly Gly Cys Pro Thr Ala Phe Asp Val
1               5                   10
```

<210> SEQ ID NO 358
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

```
Leu Ser Trp Arg Asp Ala Val Ser Asn Cys Asp Val
1               5                   10
```

<210> SEQ ID NO 359
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

```
Leu Ser Trp Arg Asp Ala Val Ser Asn Cys Asp Val
1               5                   10
```

<210> SEQ ID NO 360
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

```
Pro His Trp Leu Lys Gly Cys Arg Val Cys Ser Trp Asn Gly Ala Ala
1               5                   10                  15

Ala Cys
```

<210> SEQ ID NO 361
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

```
Gly Gly Phe Cys Leu Ser Gly Phe Ala Leu
```

```
<210> SEQ ID NO 362
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Phe Asn Asp Cys Ala Thr Thr Val Tyr Glu Ser Asp Ala
1               5                   10

<210> SEQ ID NO 363
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Ser Pro Asn Cys Trp Leu Thr Lys Arg Thr Gly Ser Tyr Val
1               5                   10

<210> SEQ ID NO 364
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Gln Gln Val Tyr Cys Arg His Glu Gln Asp Trp His Asp Val
1               5                   10

<210> SEQ ID NO 365
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Ala Tyr Asp Cys Ser His Trp Arg Ser Ile Gly Val
1               5                   10

<210> SEQ ID NO 366
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Gln Thr Glu Tyr Cys Arg His Glu Gln Asp Phe Tyr Asp Val
1               5                   10

<210> SEQ ID NO 367
```

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Ala Asn Tyr Asp Cys Phe Arg Arg Ile Glu Leu Trp Asn Phe Tyr Asp
1               5                   10                  15

Arg

<210> SEQ ID NO 368
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

Ala Ser Val Cys Pro Pro Arg Leu Phe Glu Ser Glu Tyr Val
1               5                   10

<210> SEQ ID NO 369
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Phe Cys Ile Ile Asp Gly Glu Leu Glu Asp Val
1               5                   10

<210> SEQ ID NO 370
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

Asp Tyr Trp Cys Asp Pro Met Arg Ala Pro Gly Leu Phe Gly Arg Lys
1               5                   10                  15

<210> SEQ ID NO 371
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Glu Thr Asn Cys His Ile Phe Tyr Gln Phe Pro Lys Asp
1               5                   10

<210> SEQ ID NO 372
<211> LENGTH: 14
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Glu Thr Pro Tyr Asp Cys Pro Glu Leu Asn Trp Trp Asp Val
1               5                   10

<210> SEQ ID NO 373
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Ile Cys Asp Ile Phe Thr Tyr Tyr Tyr Gly Thr Ser Trp
1               5                   10

<210> SEQ ID NO 374
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Ile Asp Tyr Cys Leu Ser Trp Tyr Arg Ser Ile Asn Leu
1               5                   10

<210> SEQ ID NO 375
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Pro Ser Phe Asp Pro Leu Asn Tyr Cys Tyr Ile Trp Arg Arg Thr Thr
1               5                   10                  15

<210> SEQ ID NO 376
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Ser Pro Pro Leu Val Ala Gly Val Leu Asn Cys Tyr Asp Ile
1               5                   10

<210> SEQ ID NO 377
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 377

Ser Ser Pro Gln Leu Gly Phe Tyr Asp Cys Gly His Trp Ile Asp Val
1               5                   10                  15

<210> SEQ ID NO 378
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Val Phe His Ile Ala Gly Thr Asp Met Ala Glu Leu Val Tyr Asp Val
1               5                   10                  15

<210> SEQ ID NO 379
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Val Leu Val Pro Ala His Gly Asp Cys Ser Ala Trp Ser Leu Trp Val
1               5                   10                  15

Gly Val

<210> SEQ ID NO 380
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 380

Val Arg Leu Gly Trp Tyr Glu Tyr Cys Pro Val Leu Gly Gly Val Tyr
1               5                   10                  15

Asp Val

<210> SEQ ID NO 381
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Val Ser Trp Cys Thr Arg His Thr Met Trp Asn Trp Tyr Thr Val His
1               5                   10                  15

<210> SEQ ID NO 382
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 382

Trp Tyr Trp His Met Ser Ser Ser Asp Cys Leu Ser Gly Tyr Ser Tyr
1               5                   10                  15

<210> SEQ ID NO 383
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Tyr Ala Met Thr Ala Asn Trp Trp Cys Asp Val
1               5                   10

<210> SEQ ID NO 384
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 384

Tyr Ala Arg Glu Asp Thr Trp Tyr Gly Ser Arg Asp Cys Gly Leu Gly
1               5                   10                  15

Asp Val

<210> SEQ ID NO 385
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 385

Tyr Asp Tyr Cys Leu His Trp Phe His Pro Tyr Val Ile
1               5                   10

<210> SEQ ID NO 386
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 386

Tyr Gly Leu Val Asp Cys Gly Ser Gly Met Asn Trp Ile Asp Val
1               5                   10                  15

<210> SEQ ID NO 387
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 387

Tyr Gly Val Ile Glu Cys Arg Tyr Glu Gly Met Asn Trp Phe Asp Val
1               5                   10                  15

<210> SEQ ID NO 388
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 388

Tyr Asn Ile Ala Val Met Cys Asn Asp Tyr Val Arg Tyr Trp Thr Asp
1               5                   10                  15

Val

<210> SEQ ID NO 389
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 389

Tyr Gln Lys Pro Ser Phe Glu Ser Leu Tyr Trp Cys Asp Val
1               5                   10

<210> SEQ ID NO 390
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 390

Tyr Ser Gly Pro Ser Tyr Asp Gln Leu Phe Trp Cys Asp Val
1               5                   10

<210> SEQ ID NO 391
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 391

Tyr Val Pro Pro Gly Tyr Asp Cys Asn Tyr Trp Met Asp Val
1               5                   10

<210> SEQ ID NO 392
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392
```

```
Trp His Asp Leu Val Trp Ser Val Cys Thr Thr Asp Val
1               5                   10
```

<210> SEQ ID NO 393
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 393

```
Tyr Ala Arg Pro Arg Pro Asp Asn Leu Asn Trp Cys Asp Val
1               5                   10
```

<210> SEQ ID NO 394
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

```
Leu Arg Asp Ser Cys Tyr Asp Val Thr Asn Trp Leu Glu Arg
1               5                   10
```

<210> SEQ ID NO 395
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

```
Glu Asn Phe Leu Leu Asp Cys Tyr Asp Trp Leu Asp Val
1               5                   10
```

<210> SEQ ID NO 396
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

```
Glu Arg His Trp Arg Ser Arg Cys Gln Arg Ala Val Asp Val
1               5                   10
```

<210> SEQ ID NO 397
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

```
Asx Leu Trp Cys Leu Cys Pro Cys Thr Val Trp Val Leu Gly Asp Val
1               5                   10                  15
```

```
<210> SEQ ID NO 398
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Cys Gly Ile Leu Cys Cys Phe Asx Phe Asp Val
1               5                   10

<210> SEQ ID NO 399
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

Thr Ala Ile Leu Ser Asx Asp Cys Gly Ala Phe Ala Asp Val
1               5                   10

<210> SEQ ID NO 400
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Thr Gly Leu Arg Tyr His Ser Gly Cys Arg Thr Gly Asp Val
1               5                   10

<210> SEQ ID NO 401
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 401

Cys Phe Gly Asx Cys Val Asn Ser Cys Gly Glu Ser Met Asp Val
1               5                   10                  15

<210> SEQ ID NO 402
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Leu Arg Phe Asx Cys Val Phe His Trp Asp Val
1               5                   10

<210> SEQ ID NO 403
<211> LENGTH: 18
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 403

Arg Asp Val Val Leu Val Asx Tyr Gly Tyr Cys Leu Val Asp Gly Gln
1               5                   10                  15

Asp Val

<210> SEQ ID NO 404
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 404

Tyr Glu Leu Val Glu Asp Thr Ser Ala Tyr Glu Ile Gly Val Asp Val
1               5                   10                  15

<210> SEQ ID NO 405
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 405

Tyr Gln Ser Pro Val Gly Arg Arg Trp Trp Cys Asp Val
1               5                   10

<210> SEQ ID NO 406
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 406
tacaaatgtg gtgtacagca t                                             21

<210> SEQ ID NO 407
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 407
tagtacgacc tgaaacatta ac                                            22

<210> SEQ ID NO 408
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 408
gctcgagtgg accaaacacc g                                        21

<210> SEQ ID NO 409
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 409
gcattcacag tcacgacagt gccacctc                                 28

<210> SEQ ID NO 410
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 410
gcattcacag tcacggcagt gccatctc                                 28

<210> SEQ ID NO 411
<211> LENGTH: 18
<212> TYPE: PRT
<213> ORGANISM: Homo sapiens

<400> SEQUENCE: 411

Ser Gly Leu Pro Asn Ile Pro Val Gln Thr Ile Ser Arg Ala Ala Ala
1               5                   10                  15

Glu Lys

<210> SEQ ID NO 412
<211> LENGTH: 10
<212> TYPE: PRT
<213> ORGANISM: Homo sapiens

<400> SEQUENCE: 412

Ser Thr Cys Arg Met Val Thr Ser Glu Ser
1               5                   10

<210> SEQ ID NO 413
<211> LENGTH: 6
<212> TYPE: PRT
<213> ORGANISM: Homo sapiens

<400> SEQUENCE: 413

Lys Ala Ala Thr Val Thr
1               5

<210> SEQ ID NO 414
<211> LENGTH: 12
<212> TYPE: PRT
<213> ORGANISM: Homo sapiens

<400> SEQUENCE: 414

Lys Leu Phe Gly Asn Met Glu Gly Asp Cys Pro Ser
1               5                   10

```
<210> SEQ ID NO 415
<211> LENGTH: 7
<212> TYPE: PRT
<213> ORGANISM: Homo sapiens

<400> SEQUENCE: 415

Ser Asp Trp Lys Thr Asp Ser
1               5

<210> SEQ ID NO 416
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 416

Asp Ser Asn Cys Asp Leu Ser
1               5

<210> SEQ ID NO 417
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 417

Asp Asn Asn Cys Asp Leu Ser
1               5

<210> SEQ ID NO 418
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 418

Asp Asn Asn Cys Ala Leu Pro
1               5

<210> SEQ ID NO 419
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 419

Asp Ser Asn Cys Ala Leu Pro
1               5

<210> SEQ ID NO 420
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 420

Asp Ser Asn Cys Ala Ala Gly
1               5

<210> SEQ ID NO 421
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 421

Asp Ser Asn Cys Ala Ala Ser
1               5

<210> SEQ ID NO 422
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 422

Asp Ser Arg Cys Ala Ala Ser
1               5

<210> SEQ ID NO 423
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 423

Asp Ser Asn Cys Ala Leu Ser
1               5

<210> SEQ ID NO 424
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 424

Asp Ser Ile Cys Ala Leu Ser
1               5

<210> SEQ ID NO 425
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 425

```
Asp Ala Ser Tyr Ala Leu Gly
1               5
```

<210> SEQ ID NO 426
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 426

```
Asp Asn Asp Cys Ala Leu Ser
1               5
```

<210> SEQ ID NO 427
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 427

```
Asp Arg Asp Cys Ala Leu Ser
1               5
```

<210> SEQ ID NO 428
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 428

```
Asp Glu Asp Cys Ala Leu Ser
1               5
```

<210> SEQ ID NO 429
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 429

```
Asp Asn Asp Cys Thr Leu Ser
1               5
```

<210> SEQ ID NO 430
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 430

```
Asp Asn Asn Cys Pro Leu Ser
1               5
```

```
<210> SEQ ID NO 431
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 431

Asp Asn Asn Cys Ala Leu Ser
1               5

<210> SEQ ID NO 432
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 432

Asp Ser Asn Cys Pro Leu Ser
1               5

<210> SEQ ID NO 433
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 433

Asp Ser Asp Cys Ala Leu Ser
1               5

<210> SEQ ID NO 434
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 434

Asp Lys Asp Cys Ala Leu Ser
1               5

<210> SEQ ID NO 435
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 435

Asp Ser Asn Cys Ala Ala Thr
1               5

<210> SEQ ID NO 436
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 436

Asp Ser Ser Ser Ala Leu Ala Ser
1               5

<210> SEQ ID NO 437
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 437

Asp Ser Asn Cys Glu Leu Ser
1               5

<210> SEQ ID NO 438
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 438

Asp Ser Asn Cys Ala Leu Glu
1               5

<210> SEQ ID NO 439
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 439

Asp Ser Asn Cys Ala Leu Glu Ser
1               5

<210> SEQ ID NO 440
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 440

Asp Thr Asn Cys Ala Leu Ser
1               5

<210> SEQ ID NO 441
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 441

Asp Ile Asn Cys Ala Leu Gln
1               5

<210> SEQ ID NO 442
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 442

Asp Ser Asn Cys Arg Leu Ser
1               5

<210> SEQ ID NO 443
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 443

Asp Ser Asn Cys Gly Phe Ser
1               5

<210> SEQ ID NO 444
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 444

Ala Ser Asn Cys Ala Leu Ser
1               5

<210> SEQ ID NO 445
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 445

Asp Ala Asn Tyr Ala Leu Gly
1               5

<210> SEQ ID NO 446
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 446

Asp Ser Arg Cys Glu Leu Ser
```

```
1               5
```

<210> SEQ ID NO 447
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 447

```
Asp Ser Asn Cys Ala Leu Asp
1               5
```

<210> SEQ ID NO 448
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 448

```
Asp Ser Pro Cys Ala Leu Thr
1               5
```

<210> SEQ ID NO 449
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 449

```
Asp Ser Asp Cys Ala Asp Val
1               5
```

<210> SEQ ID NO 450
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 450

```
Asp Ser Asn Cys Ala Phe Ser
1               5
```

<210> SEQ ID NO 451
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 451

```
Asp Ser Asn Cys Ala Trp Ser
1               5
```

<210> SEQ ID NO 452

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 452

Asp Thr Ser Cys Ala Leu Gly
1               5

<210> SEQ ID NO 453
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 453

Asp Thr Tyr Cys Ala Leu Ser
1               5

<210> SEQ ID NO 454
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 454

Glu Ser Lys Tyr Pro Leu Gly
1               5

<210> SEQ ID NO 455
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 455

Asp Ala Ser Tyr Ser Leu Gly
1               5

<210> SEQ ID NO 456
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 456

Asp Ala Ser Tyr Gly Leu Val
1               5

<210> SEQ ID NO 457
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 457

Asp Asn Asn Cys Gly Leu Ser
1               5

<210> SEQ ID NO 458
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 458

Asp Gly Thr Cys Ala Phe Ala
1               5

<210> SEQ ID NO 459
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 459

Asp Ala Gly Trp Arg Ser Gly
1               5

<210> SEQ ID NO 460
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 460

Asp Ser Glu Cys Ala Leu Ser
1               5

<210> SEQ ID NO 461
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 461

Asp Ser Asn Cys Asp Leu Thr
1               5

<210> SEQ ID NO 462
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 462

Asp Ser Lys Cys Ala Leu Ser
1               5

<210> SEQ ID NO 463
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 463

Asp Thr Asp Cys Ala Leu Ala
1               5

<210> SEQ ID NO 464
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 464

Asp Thr Asn Cys Pro Met Pro
1               5

<210> SEQ ID NO 465
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 465

Ala Arg Asp Cys Gly Leu Ser
1               5

<210> SEQ ID NO 466
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 466

Asp Arg Asn Cys Ala Phe Met
1               5

<210> SEQ ID NO 467
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 467

Asp Ser Gly Cys Ala Leu Ser
1               5
```

```
<210> SEQ ID NO 468
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 468

Asp Thr Asn Cys Ala Ser Ser
1               5

<210> SEQ ID NO 469
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 469

Asp Ser Asn Cys Glu Met Ser
1               5

<210> SEQ ID NO 470
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 470

Asp Ala Val Tyr Ala Leu Gly
1               5

<210> SEQ ID NO 471
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 471

Asp Ser Ser Cys Asp Ser
1               5

<210> SEQ ID NO 472
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 472

Asp Ser Lys Cys Arg Leu Ser
1               5

<210> SEQ ID NO 473
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 473

Glu Ser Lys Cys Ala Leu Ser
1               5

<210> SEQ ID NO 474
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 474

Asp Ser Asn Cys Ala Leu Ala
1               5

<210> SEQ ID NO 475
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 475

Asp Ser Lys Cys Val Phe Ala
1               5

<210> SEQ ID NO 476
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 476

Asp Asn Tyr Cys Pro Leu Ser
1               5

<210> SEQ ID NO 477
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 477

Asp Arg Ala Cys Ala Leu Leu
1               5

<210> SEQ ID NO 478
<211> LENGTH: 7
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 478

Asp Ser Val Cys Ala Leu Ser
1               5

<210> SEQ ID NO 479
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 479

Asp Thr Ala Cys Ala Leu Asp
1               5

<210> SEQ ID NO 480
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 480

Arg Ala Cys Ala Leu Leu Asn
1               5

<210> SEQ ID NO 481
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 481

Gly Gly Gly Gly Ser Gly Gly Gly Gly Ser Gly Gly Gly Gly Ser
1               5                   10                  15

<210> SEQ ID NO 482
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Lys" or "Asn" or "Arg" or "Ser" or
      "Thr"
<220> FEATURE:
<221> NAME/KEY: VARIANT
<222> LOCATION: (3)..(3)
<223> OTHER INFORMATION: /replace="Asp" or "Ile" or "Asn" or "Ser" or
      "Val" or "Tyr"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: VARIANT
<222> LOCATION: (5)..(5)

```
<223> OTHER INFORMATION: /replace="Asp" or "Pro" or "Arg" or "Thr"
<220> FEATURE:
<221> NAME/KEY: VARIANT
<222> LOCATION: (6)..(6)
<223> OTHER INFORMATION: /replace="Leu"
<220> FEATURE:
<221> NAME/KEY: VARIANT
<222> LOCATION: (7)..(7)
<223> OTHER INFORMATION: /replace="Gly" or "Leu" or "Ser" or "Pro" or
      "Thr"
<220> FEATURE:
<221> NAME/KEY: misc_feature
<222> LOCATION: (1)..(7)
<223> OTHER INFORMATION: /note="Variant residues given in the sequence
      have no preference with respect to those in the annotations
      for variant positions"

<400> SEQUENCE: 482

Asp Ala Ala Cys Ala Ala Asp
1               5

<210> SEQ ID NO 483
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 483

His His His His His His
1               5

<210> SEQ ID NO 484
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 484

Gly Gly Gly Gly Ser
1               5
```